(12) United States Patent
Pascual et al.

(10) Patent No.: US 7,608,395 B2
(45) Date of Patent: Oct. 27, 2009

(54) SYSTEMIC LUPUS ERYTHEMATOSUS DIAGNOSTIC ASSAY

(75) Inventors: Maria Virginia Pascual, Dallas, TX (US); Jacques F. Banchereau, Dallas, TX (US); Lynda B. Bennett, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 94 days.

(21) Appl. No.: 11/228,586

(22) Filed: Sep. 15, 2005

(65) Prior Publication Data

US 2007/0059717 A1 Mar. 15, 2007

(51) Int. Cl.
C12Q 1/68 (2006.01)
C12P 19/34 (2006.01)
C07H 21/02 (2006.01)
C07H 21/04 (2006.01)

(52) U.S. Cl. .................... 435/6; 435/7.1; 435/91.2; 536/23.5; 536/24.31

(58) Field of Classification Search .............. None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,227,437 A | 10/1980 | Inloes et al. | |
| 4,275,149 A | 6/1981 | Litman et al. | |
| 4,366,241 A | 12/1982 | Tom et al. | |
| 4,603,102 A | 7/1986 | Himmelmann et al. | |
| 4,682,195 A | 7/1987 | Yilmaz | |
| 4,683,202 A | 7/1987 | Mullis | |
| 4,695,188 A | 9/1987 | Pulkkinen | |
| 5,310,952 A | 5/1994 | Heveling | |
| 5,322,770 A | 6/1994 | Gelfand | |
| 5,399,491 A | 3/1995 | Kacian et al. | |
| 5,405,783 A | 4/1995 | Pirrung et al. | |
| 5,412,087 A | 5/1995 | McGall et al. | |
| 5,427,202 A | 6/1995 | Behring et al. | |
| 5,445,934 A | 8/1995 | Fodor et al. | |
| 5,578,832 A | 11/1996 | Trulson et al. | |
| 5,631,734 A | 5/1997 | Stern et al. | |
| 5,795,716 A | 8/1998 | Chee et al. | |
| 6,040,138 A | 3/2000 | Lockhart et al. | |
| 6,391,550 B1 | 5/2002 | Lockhart et al. | |
| 6,596,501 B2 * | 7/2003 | Roth ............... 435/7.21 | |
| 2003/0148298 A1 | 8/2003 | O'Toole et al. | |
| 2004/0033498 A1 | 2/2004 | Behrens et al. | |
| 2004/0241726 A1 | 12/2004 | Liew et al. | |

FOREIGN PATENT DOCUMENTS

| | | |
|---|---|---|
| EP | 0 320 308 B1 | 6/1989 |
| WO | 95/20681 A1 | 8/1995 |
| WO | 97/10365 A1 | 3/1997 |
| WO | 03/016476 A | 2/2003 |

OTHER PUBLICATIONS

Liu et al . Clinical Immunology. 2004. 112: 225-230.*
Coleman, R.A. Drug Discovery Today. 2003. 8: 233-235.*
GeneCard Database for DNAPTP6/LOC2601, available via URL <genecards.org/cgi-bin/carddisp.pl?gene=LOC26010>.*
GeneCard Database for DNAPTP6/LOC2601, available via URL <genecards.org/cgi-bin/carddisp.pl?gene=PAFAH1B>.*
GeneCard Database for DNAPTP6/LOC2601, available via URL <genecards.org/cgi-bin/carddisp.pl?gene=TDRD7>.*
GeneCard Database for DNAPTP6/LOC2601, available via URL <genecards.org/cgi-bin/carddisp.pl?gene=GPR84>.*
GeneCard Database for DNAPTP6/LOC2601, available via URL <genecards.org/cgi-bin/carddisp.pl?gene=GTPBP2>.*
GeneCard Database for DNAPTP6/LOC2601φ available via URL <genecards.org/cgi-bin/carddisp.pl?gene=B4GALT5>.*
GeneCard Database for DNAPTP6/LOC2601, available via URL <genecards.org/cgi-bin/carddisp.pl?gene=FRAT2>.*
International Search Report and Written Opinion for PCT/US2006/036320 dated Aug. 20, 2007.
National Center for Biotechnology Information. National Library of Medicine, NIH (Bethesda, MD, USA). GenBank Accession No. AW292752, Jan. 16, 2000.
Affymetrix, GeneChip Human Genome U1333 Arrays. 2003.
Arce et al., "Increased Frequency of Pre-germinal Center B Cells and Plasma Cell Precursors in the Blood of Children with Systemic Lupus Erythematosus," J Immunol (2001), 167:2361-2369.

(Continued)

*Primary Examiner*—Carla Myers
(74) *Attorney, Agent, or Firm*—Edwin S. Flores; Chainey P. Singleton; Chalker Flores, LLP

(57) ABSTRACT

The present invention provides compositions and methods for aiding in the diagnosis, monitoring and prognosis of SLE in a subject and for identifying potential therapeutic agents to treat and/or ameliorate the symptoms associated with SLE. Accordingly, embodiments of the invention are directed to methods of identifying the gene expression profile of a suitable sample by screening for the presence of a differentially expressed SLE-associated gene isolated from a sample containing or suspected of containing a cell that can differentially express an SLE-associated gene.

15 Claims, 2 Drawing Sheets

OTHER PUBLICATIONS

Bennett, et al., "Interferon and Granulopoiesis Signatures in Systemic Lupus Erythematosus Blood," J. Exp. Med. (2003), 197:711-723.

Baechler, et al., "Interferon-inducible gene expression signature in peripheral blood cells of patients with severe lupus," Proc. Natl. Acad. Sci. USA (2003), 100:2610-2615.

Hardin, J.A., "Directing Autoimmunity to Nucleoprotein Particles: The Impact of Dendritic Cells and Interferon α in Lupus," J. Exp. Med. (2003), 185:1101-1111.

Tibshirani et al., "Diagnosis of multiple cancer types by shrunken centroids of gene expression." Proc. Natl. Acad. Sci. USA (2002), 99:6567-6572.

Supplementary European Search Report for EP 06814874.1 dated May 4, 2009.

Alcorta, D., et al., "Microarray Studies of Gene Expression in Circulating Leukocytes in Kidney Disease," Exp Nephrol (2002), 10:139-149.

Franchin, G., et al., "Pathogenesis of SLE: implications for rational therapy," Drug Discovery Today: Disease Mechanisms (2004), 1:303-308.

Pereira, E., et al., "Immunosuppressive therapy modulates T lymphocyte gene expression in patients with systemic lupus erythematosus," Immunology (2004), 113:99-105.

* cited by examiner

SYSTEMIC LUPUS ERYTHEMATOSUS DIAGNOSTIC ASSAY

STATEMENT AS TO FEDERALLY SPONSORED RESEARCH

Funding for the work described herein was provided in part by the National Institutes of Health grant no. RFP N01-AI-05412. The federal government may have certain rights in the invention.

TECHNICAL FIELD OF INVENTION

This invention relates to expression profiles for the diagnosis, prognosis, monitoring and therapeutic management of patients with Systemic Lupus Erythematosus (SLE).

BACKGROUND OF THE INVENTION

Systemic lupus erythematosus (SLE) is an autoimmune disease clinically characterized by a waxing and waning course and by involvement of multiple organs including skin, kidneys and central nervous system (Kammer G M and Tsokos G C Eds. (1999) Lupus: Molecular and Cellular Pathogenesis 1st Ed, Human Press, N.J.; Lahita R G Ed. (1999) Systemic Lupus Erythromatosus, 3rd Ed, Academic Press, Amsterdams. The overall prevalence of SLE is about one in 2000, and about one in 700 Caucasian women develops SLE during her life time. Lahita R G (1999) supra. In the United States alone, over half a million people have SLE, and most are women in their childbearing years (Hardin J A (2003) J. Exp. Med. 185:1101-1111).

There is no single criteria to diagnose SLE. The American College of Rheumatology has developed 11 criteria to diagnose SLE, which span the clinical spectrum of SLE in aspects of skin, systemic, and laboratory tests. These criteria include malar rash, discoid rash, sensitivity to sun light, oral ulcers, arthritis, serositis, kidney and central nervous system inflammation, blood alterations, and the presence of antinuclear antibodies. A patient must meet four of these criteria in order to be classified as a SLE patient. (Tan et al. (1982) Arthritis Rheumatol. 25:1271-1277, the contents of which are incorporated by reference.) SLE is usually confirmed by tests including, but not limited to, blood tests to detect anti-nuclear antibodies; blood and urine tests to assess kidney function; complement tests to detect the presence of low levels of complement that are often associated with SLE; a sedimentation rate (ESR) or C-reactive protein (CRP) to measure inflammation levels; X-rays to assess lung damage and EKGs to assess heart damage.

Designing successful randomized controlled trials in SLE poses many challenges because it is a relapsing, remitting disease, with multiorgan system involvement ranging from mild to life threatening manifestations. While it is possible to identify serologic and immunologic abnormalities which characterize active disease, it has not previously been possible to treat expectantly, nor to initiate prophylactic, potentially preventative interventions on the basis of these markers. In addition, it has been difficult to correlate alterations in biologic markers with clinical outcome, especially when signs and symptoms are intermittent and broadly variable between patients. Accordingly, it would be useful to be able correlate gene expression profiles with prognosis and efficacy of therapeutic intervention.

The applicants generated previously expression profiles of SLE patients and controls using microarray technology. In the prior studies, it was found that 210 genes were up-regulated and 141 genes were down-regulated when PBMCs were isolated from 30 pediatric SLE patients (an auto-immune disease) as compared to healthy controls and patients with juvenile chronic arthritis (an auto-inflammatory disease). Fourteen of 15 genes showing the greatest differential expression were interferon (IFN) regulated (Bennett et al. (2003) J. Exp. Med. 197:711-723). Baechler et al. (2003 Proc. Natl. Acad. Sci. USA 100:2610-2615 and U.S. 2004/0033498), identified 161 genes, 23 of which are IFN-inducible, that were differentially expressed by at least 1.5 fold in peripheral blood mononuclear cells (PBMCs) isolated from 48 adult SLE patients compared to healthy adult controls. The IFN gene expression signature in SLE patients was correlated with disease severity. However, neither of these studies examined correlations between gene expression and the likelihood to develop renal disease in SLE patients.

The standard therapy for SLE is administration of the steroid glucocorticoid, a general immune response inhibitor. It can be used to relieve symptoms; however, no cure for SLE is currently available. Low dose p.o. prednisone at a level less than 0.5 mg/kg/day is usually given. Unfortunately, this therapy is insufficient to keep children in remission, and flaring of the disease is frequent. Flares can be controlled with high dose glucocorticoid via intravenous pulses at 30 mg methylprednisolone/kg/day for 3 consecutive days. However, steroid treatment at high dosage can present severe side effects for patients, especially pediatric patients.

Up to 25% of all SLE cases start before the age of 18 years. Children with SLE typically have more severe symptoms. Approximately 70% of pediatric SLE patients develop kidney involvement leading to renal failure, and 18% of children with SLE progress towards death. Lahita R G (1999) supra. Because pediatric SLE patients may develop life-threatening renal involvement, they are often treated aggressively with steroids, resulting in harmful or unwanted side effects which are typically more serious in children than in adults. Accordingly, the ability to predict the likelihood that an individual patient will develop renal disease would make it possible to reduce the dose of steroids or other treatments in those children who are unlikely to develop renal involvement, or to tailor other treatment plans according to the predicted outcome. Therefore, there is an unmet and urgent medical need for diagnostic methods that will predict the likelihood of renal involvement, as well as to diagnose SLE, distinguish SLE gene expression profiles from profiles of patients infected with influenza, and to monitor disease progression and treatment. This invention satisfies these needs and provides related advantages as well.

SUMMARY OF THE INVENTION

The present invention provides compositions and methods for aiding in the diagnosis, prognosis and disease monitoring of SLE in a subject and for evaluating potential therapeutic agents to treat and/or ameliorate the symptoms associated with SLE. Embodiments of the invention are directed to methods of identifying the gene expression profile of a suitable sample by screening for the presence of one or more differentially expressed SLE-associated genes in a sample containing or suspected of containing a cell that can differentially express an SLE-associated gene, These cells include, but are not limited to, peripheral blood mononuclear cells, neutrophils and granulocytes obtained from the subject.

Detection of differentially expressed SLE-associated genes can be by any appropriate method, including for example, detecting the quantity of mRNA transcribed from a gene identified in Table 1A, 1B 2A, 2B, 3A, 3B and/or 4, or the quantity of the polypeptide or protein encoded by the gene. These methods can be performed on a sample by sample basis or modified for high throughput analysis. Additionally, databases containing quantitative full or partial transcripts or protein sequences isolated from a cell sample can be searched and analyzed for the presence and amount of transcript or expressed polypeptide product. The methods are particularly useful for diagnosing. SLE and for predicting which SLE patients, especially pediatric SLE patients, are likely to develop renal involvement. In addition, the methods are useful to distinguish a patient with SLE from patients without SLE and patients with fibromyalgia or viral infection.

Thus, in one aspect, the invention provides a method for predicting whether a mammal suffering from systemic lupus erythematosus (SLE) is likely to develop renal involvement, by determining whether or not the mammal contains one or more cells that express at least 1 gene listed in Table 1A by at least 50% less and/or at least 1 gene listed in Table 1B by at least two-fold more than one or more controls, and predicting that the mammal suffering from SLE is likely to develop renal involvement if the mammal contains the cell, or predicting that the mammal is not likely to develop renal involvement if the cell is not identified.

Alternatively, the invention provides a method for predicting whether a mammal suffering from systemic lupus erythematosus (SLE) is likely to develop renal involvement, by providing a plurality of reference expression profiles, each associated with a likelihood that an SLE patient will develop renal disease; providing a subject expression profile generated from at least one cell and/or sample from a mammalian subject; and selecting the reference expression profile most similar to the subject expression profile, to associate a likelihood of the developing renal disease with the subject; wherein, the subject expression profile and the reference expression profiles represent the level of expression of at least one gene listed in Table 1A and/or Table 1B.

In another aspect, the invention provides a method for diagnosing systemic lupus erythematosus (SLE), including the steps of determining whether or not a mammal contains one or more cells that express at least 375 genes listed in Table 2A by at least 50% less, and/or in Table 2B to an extent at least two-fold more, than one or more controls; and diagnosing the mammal as having SLE if the mammal contains the one or more cells or diagnosing the mammal as not having SLE if the cells are not identified.

Alternatively, the invention provides a method for diagnosing systemic lupus erythematosus (SLE), by providing a plurality of reference expression profiles, each associated with the presence or absence of SLE, and optionally with the severity of SLE; providing a subject expression profile generated from one or more cells or other sample from a mammalian subject; and selecting the reference expression profile most similar to the subject expression profile, to thereby diagnose the presence or absence of SLE in the subject, and optionally the severity of SLE in the subject; wherein, the subject expression profile and the reference expression profiles represent the level of expression of at least 375 genes listed in Table 2A and/or Table 2B.

In still another aspect, the invention provides a method for distinguishing a mammal suffering from systemic lupus erythematosus (SLE) as compared to a mammal not suffering from SLE and having a viral infection, determining whether or not the mammal contains a cell that expresses at least 1 gene listed in Table 3A by at least 50% less, and/or at least 1 gene listed in Table 3B by at least two-fold greater, than one or more control cells; and diagnosing the mammal as having SLE if the mammal contains the cell(s) or as not having SLE if the cell(s) are not identified.

In still another aspect, the invention provides a method for diagnosing systemic lupus erythematosus (SLE), by providing a plurality of reference expression profiles, each associated with the presence or absence of SLE, and optionally with the severity of SLE; providing a subject expression profile generated from one or more cells or other sample from a mammalian subject; and selecting the reference expression profile most similar to the subject expression profile, to thereby diagnose the presence or absence of SLE in the subject, and optionally the severity of SLE in the subject; wherein, the subject expression profile and the reference expression profiles represent the level of expression of one or more genes listed in Table 3A and/or Table 3B.

In another aspect, the invention provides a method of diagnosing system lupus erythematosus (SLE), by determining whether a mammal contains one or more cells that express at least one gene selected from Table 4 to an extent at least two-fold greater than one or more controls; and diagnosing the mammal as having SLE if the mammal contains the one or more cells, or as not having SLE if the cells are not identified.

In an additional aspect, the invention provides a method of determining the severity of SLE, including the steps of determining the extent to which one or more cells from a mammal suffering from SLE over express one or more genes selected from Table 4 as compared to one or more controls; and correlating the severity of the disease with the extent of over expression.

In still another aspect, the invention provides a method for diagnosing systemic lupus erythematosus (SLE) and/or determining the severity thereof, by providing a plurality of reference expression profiles, each associated with the presence or absence of SLE, and optionally with the severity of SLE; providing a subject expression profile generated from one or more cells or other sample from a mammalian subject; and selecting the reference expression profile most similar to the subject expression profile, to thereby diagnose the presence or absence of SLE in the subject, and optionally the severity of SLE in the subject; wherein, the subject expression profile and the reference expression profiles represent the level of expression of at least 1 gene listed in Table 4.

In a further aspect, the invention provides a method for monitoring disease state in an adult subject having systemic lupus erythematosus, by comparing the level of expression of at least one gene selected from Table 4 in one or more cells or other sample from the mammal at a first time point to the level of expression in one or more cells or other sample from the mammal at a second time point; and correlating a decrease in the degree of expression of genes in Table 4 at the second time point as compared to the first time point with an improvement in the mammals disease state, and/or correlating an increase in the degree of expression of genes in Table 4 at the second time point as compared to the first time point with an increase in the severity of the mammals disease state.

In a further aspect, the invention provides a diagnostic composition using nucleic acids selected from the group consisting of: a) at least 10 polynucleotides that hybridize under stringent conditions to a different gene of Table 1A and/or Table 1B; b) at least 375 polynucleotides that hybridize under stringent conditions to a different gene identified in Table 2A and/or Table 2B, c) at least 10 polynucleotides that hybridize under stringent conditions to a different gene of Table 3A and/or Table 3B; d) at least 2 polynucleotides that hybridize under stringent conditions to a different gene of Table 4; wherein the nucleic acids include at least 40% of the polynucleotides in the composition.

The diagnostic compositions of the inventions are useful in the diagnosis, prognosis and monitoring of SLE. Thus, the invention provides a method for detecting a systemic lupus erythematosus (SLE) profile in a suitable sample by contacting the suitable sample with a diagnostic composition described above under conditions that are favorable to the recognition of one or more nucleic acids identified in Table 1A, 1B, 2A, 2B, 2C, 3A, 3B or 4, by the polynucleotides and detecting the location and identity of nucleic acids recognized by the polynucleotides, thereby detecting the presence or absence of an SLE profile.

Another aspect of the invention is a screen to identify therapeutic agents that treat or ameliorate the symptoms of SLE. The method includes contacting the cell(s) previously identified as possessing this genotype with an effective amount of a potential agent and assaying for reversal or correction of the genotype of the progeny of the cell or the cell(s).

The present invention also includes compositions, kits and methods for identifying a human subject predisposed to systemic lupus erythematosus comprising determining the expression level one or more genes listed in Table 1A (160 down regulated genes) by at least 50% less; one or more genes listed in Table 1B (185 up regulated genes) by at least two-fold more than one or more controls; or combinations thereof. Another embodiment of the present invention includes comparing one or more reference expression profiles associated with likelihood that an SLE patient will develop renal disease to the expression profile obtained from a subject, wherein the subject expression profile and the reference profiles represent the level of expression of one or more genes listed in Table 1A and/or Table 1B. The expression profile may be obtained from one or more blood cells, e.g., peripheral blood mononuclear cells (PBMCs), monocytes, dendritic cells, immature neutrophils, mature neutrophils, granulocytes, B cells, T cells. The subject may even be a pediatric subject.

Another method for diagnosing systemic lupus erythematosus (SLE) includes determining alone or in combination the expression level of one or more genes selected from the 375 genes listed in Table 2A by at least 50% less and one or more genes selected from Table 2B to an extent at least two-fold more than one or more controls; wherein the presence or absence of the one or more genes are used to diagnose SLE.

Another method for diagnosing systemic lupus erythematosus (SLE) includes determining alone or in combination the expression level of one or more genes selected from the 10 genes listed in Table 3A by at least 50% less and one or more genes selected from Table 3B to an extent at least two-fold more than one or more controls; wherein the presence or absence of the one or more genes are used to diagnose SLE.

Another method for diagnosing systemic lupus erythematosus (SLE) includes determining whether a mammal contains one or more cells that express at least one gene selected from Table 4 to an extent at least two-fold greater than one or more controls and diagnosing the mammal as having SLE if the mammal contains the one or more cells, or as not having SLE if the cell is not identified.

A diagnostic array for systemic lupus erythematosus may include one or more of the following includes: at least 10 probes that hybridize under stringent conditions to one or more polynucleotides listed Table 1A and/or Table 1B; at least 375 probes that hybridize under stringent conditions to one or more polynucleotides listed in Table 2A and/or Table 2B; at least 10 probes that hybridize under stringent conditions to one or more polynucleotides listed Table 3A and/or Table 3B; and at least 2 probes that hybridize under stringent conditions to one or more polynucleotides listed Table 4, mixtures and combinations thereof. The polynucleotides may be probes, amplification primers, and/or are attached to an array in a pre-determined location.

A kit may also include an array with at least 10 probes that hybridize under stringent conditions to a polynucleotide of Table 1A and/or Table 1B; at least 375 probes that hybridize under stringent conditions to a polynucleotide of Table 2A and/or Table 2B; at least 10 probes that hybridize under stringent conditions to a polynucleotide of Table 3A and/or Table 3B; at least 2 probes that hybridize under stringent conditions to a polynucleotide of Table 4, mixtures and combinations thereof; and instructions for determining the identity of each polynucleotide and its location in the array.

Yet another invention includes a method for detecting a systemic lupus erythematosus (SLE) profile in a suitable sample by contacting the suitable sample under conditions that are favorable to the recognition of one or more nucleic acids identified in Table 1A, 1B, 2A, 2B, 2C, 3A, 3B or 4 and detecting the location and identity of nucleic acids recognized by the polynucleotides, thereby detecting the presence or absence of an SLE profile. The method may further includes the step of gathering a control diagnostic or a control profile selected from the group of indications consisting of a normal healthy control, an influenza infection, SLE subjects with renal involvement, and SLE subjects without renal involvement. A control is from the profile determined for a subject prior to therapeutic intervention. The method may also include a therapeutic intervention a candidate therapeutic agent selected from interferon alpha (IFN-α) inhibitors, corticosteroids, nonsteroidal immune suppressants, antimalarials, and nonsteroidal anti-inflamatory drugs.

Yet another method of the present invention is a computer implemented method for determining the genotype of a sample by obtaining a plurality of sample probe intensities from a patient suspected of having SLE; diagnosing systemic lupus erythematosus based upon the sample probe intensities; and calculating linear correlation coefficient between the sample probe intensities and reference probe intensities; and accepting the tentative genotype as the genotype of the sample if the linear correlation coefficient is greater than a threshold value. Probes for use with the invention may include one or more probes that hybridize under stringent conditions to a polynucleotide of Table 1A and/or Table 1B; one or more that hybridize under stringent conditions to a different nucleic acid molecule identified in Table 2A and/or Table 2B, one or more 10 probes that hybridize under stringent conditions to a polynucleotide of Table 3A and/or Table 3B; one or more probes that hybridize under stringent conditions to a polynucleotide of Table 4; and mixtures and combinations thereof. One specific gene may be C1 ORF 29 (Affymetrix ID 204439 at). Yet another specific examples of probes includes one or more genes selected from:

| Accession No. | Database | Gene |
|---|---|---|
| NM_019096 | GenBank | GTPBP2 |
| AK002064.1 | GenBank | DNAPTP6 |
| AF237762 | GenBank | GPR84 |
| NM_004776.1 | GenBank | B4GALT5 |
| AB045118.1 | GenBank | FRAT2 |
| L13386.1 | GenBank | PAFAH1B1. |

BRIEF DESCRIPTION OF THE FIGURES

For a more complete understanding of the features and advantages of the present invention, reference is now made to the detailed description of the invention along with the accompanying figures and in which.

DETAILED DESCRIPTION OF THE INVENTION

Figure 1:
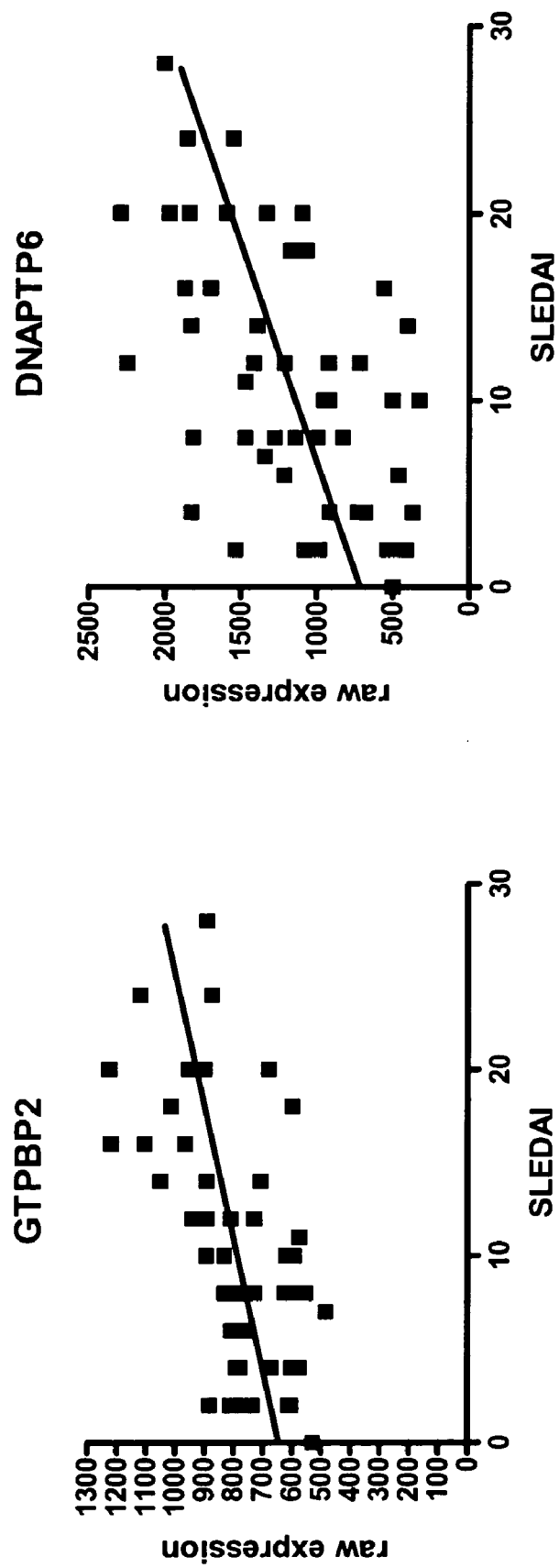
FIG. 1 shows the correlation between SLEDAI index and the level of expression of IFN-regulated genes newly associated with SLE: GTPBP2, and DNAPTP6.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The practice of the present invention will employ, unless otherwise indicated, conventional techniques of immunology, molecular biology, microbiology, cell biology and recombinant DNA, which are within the skill of the art. See e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL and ANIMAL CELL CULTURE (R. I. Freshney, ed. (1987)).

As used herein, "amplification" refers to nucleic acid amplification procedures using primers and nucleic acid polymerase that generate multiple copies of a target nucleic acid sequence. Such amplification reactions are known to those of skill in the art, and include, but are not limited to, the polymerase chain reaction (PCR, see U.S. Pat. Nos. 4,682,195, 4,683,202 and 4,965,188), RT-PCR (see U.S. Pat. Nos. 5,322,770 and 5,310,652) the ligase chain reaction (LCR, see EP 0 320 308), NASBA or similar reactions such as TMA described in U.S. Pat. No. 5,399,491 and gap LCR (GLCR, see U.S. Pat. No. 5,427,202). If the nucleic acid target is RNA, RNA may first be copied into a complementary DNA strand using a reverse transcriptase (see U.S. Pat. Nos. 5,322,770 and 5,310,652).

As used herein, the terms "polynucleotide" and "nucleic acid" are used interchangeably to refer polynucleotides of any length, either deoxyribonucleotides or ribonucleotides or analogs (e.g., inosine, 7-deazaguanosine, etc.) thereof. "Oligonucleotides" refer to polynucleotides of less than 100 nucleotides in length, preferably less than 50 nucleotides in length, and most preferably about 10-30 nucleotides in length. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can include modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "gene" refers to a polynucleotide containing at least one open reading frame (ORF) that is capable of encoding a particular polypeptide or protein after being transcribed and translated, and to fragments of such polynucleotides. Any of the polynucleotides sequences described herein, or fragments thereof, may be used to identify larger fragments or full-length coding sequences of the gene with which they are associated. Methods of isolating larger fragment sequences are known to those of skill in the art. Tables 1A, 1B, 2A, 2B, 2C, 3A, 3B and 4 list the accession number and name of SLE-associated human genes, relevant sequences incorporated in their entirety (or portions thereof) herein by reference. As used herein, "gene" refers to the human gene referenced in the table, fragments and allelic variants thereof, as well as non-human homolog thereof. The accession number is linked to the sequences of the listed genes. These sequences can be used to identify allelic variants and non-human homologs by searching existing databases or by comparison to new sequences.

As used herein, the term a "gene product," or "gene expression product" refer to the amino acid (e.g., peptide or polypeptide) generated when a gene is transcribed and translated.

The term "polypeptide" is used interchangeably with the term "protein" and in its broadest sense refers to a compound of two or more subunit amino acids linked by peptide bonds. A peptide of three or more amino acids is commonly called an oligopeptide if the peptide chain is short. If the peptide chain is long, the peptide is commonly called a polypeptide or a protein.

As used herein, the term "isolated" refers to the separation, isolation and/or purification away from constituents, cellular and otherwise, in which the polynucleotide, peptide, polypeptide, protein, antibody or fragment(s) thereof, are normally associated with in nature. In one aspect of this invention, an isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart. In addition, a "concentrated", "separated" or "diluted" polynucleotide, peptide, polypeptide, protein, antibody or fragment(s) thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody or fragment(s) thereof, which differs from the naturally occurring counterpart in its primary sequence or for example, by its glycosylation pattern, need not be present in its isolated form since it is distinguishable from its naturally occurring counterpart by its primary sequence or, alternatively, by another characteristic such as glycosylation pattern. Thus, a non-naturally occurring polynucleotide is provided as a separate embodiment from the isolated naturally occurring polynucleotide.

A "probe" when used in the context of polynucleotide manipulation refers to a polynucleotide, preferably an oligonucleotide, that is provided as a reagent to detect a target polynucleotide, potentially present in a sample of interest, by hybridizing with the target. In one embodiment, a probe is a nucleic acid attached to a substrate (e.g., a microarray). In some instances, a probe may include a label, either before or subsequent to the hybridization reaction. Suitable labels include, but are not limited to radioisotopes, fluorochromes, chemiluminescent compounds, dyes and proteins, including enzymes.

A "primer" is an oligonucleotide, generally with a free 3'—OH group that binds to a target or "template" potentially present in a sample of interest by hybridizing with the target and, thereafter, promoting polymerization of a polynucleotide complementary to the target. A "polymerase chain reaction" ("PCR") is a type of amplification reaction in which replicate copies are made of a target polynucleotide using a "pair of primers" or a "set of primers" consisting of an "upstream" and a "downstream" primer and a catalyst of polymerization, such as a DNA polymerase and, typically, a thermally-stable polymerase enzyme. Methods for PCR are well-known in the art, and taught, for example in "PCR: A PRACTICAL APPROACH" (M. MacPherson et al., IRL Press at Oxford University Press (1991)). All processes of producing replicate copies of a polynucleotide, such as PCR or gene cloning, are collectively referred to herein as "replication" or amplification." A primer can also be used as a probe in hybridization reactions, such as Southern or Northern blot analyses. Sambrook et al., supra.

The term "cDNA" refers to complementary DNA that is initially made by reverse transcribing mRNA molecules present in a cell or organism into a complementary DNA with an enzyme such as reverse transcriptase.

As used herein, "expression" refers to the process by which polynucleotides are transcribed into mRNA and/or the process by which the mRNA transcript is subsequently translated into peptides, polypeptides or proteins. If the polynucleotide is derived from genomic DNA, expression may include splicing of the mRNA in a eukaryotic cell. "Differentially expressed" as applied to a gene, refers to the differential production of the mRNA transcribed from the gene and/or translated from the mRNA transcript into the protein product. The difference in gene expression between similar cell types from different subjects may be compared, or the difference in gene expression at a first and second time point in the same subject can be compared. In addition, the expression profile of a subject can be compared to a stored reference expression profile. A differentially expressed gene may be over-expressed or under-expressed as compared to the expression level of a normal or control cell. However, as used herein, differentially over-expressed is used to refer to a change in the expressed level of at least 2.0 fold, at least 2.25 fold, at least 2.5 fold or, at least 3 fold, at least 3.5 fold, at least 4 fold, at least 5-fold, or at least 10 fold, greater than that in the control cell, tissue or other biological sample. The 3004 transcripts disclosed herein were identified as being differentially expressed by statistical comparisons between the healthy and SLE groups using both parametric (Welch's approximate t-test) and non-parametric (Mann-Whitney U-test) methods ($p<0.0001$).

As used herein, a "level 2-fold more than 'X'" refers to the level is 2X. As used herein differentially under-expressed refers to expression at a level at least 50% less, at least 60%, at least 70%, at least 80%, at least 90% or at least 95% less than that in the control cell or tissue. For example, a "level 75% less than 'X'" refers to a level that is 0.25X. The term "differentially expressed" also refers to nucleotide and/or protein sequences in a cell or tissue which are expressed where silent in a control cell or not expressed where expressed in a control cell.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels, microarrays and chips. As used herein, "solid support" also includes synthetic antigen-presenting matrices, cells and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412, 087; and 5,445,934. Using this method, the probes are synthesized on a derivatized glass surface also known as chip arrays. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding or in any other sequence-specific manner. The complex may include two strands forming a duplex structure, three or more strands forming a multi-stranded complex, a single self-hybridizing strand or any combination of these. A hybridization reaction may constitute a step in a more extensive process, such as the initiation of a PCR reaction or the enzymatic cleavage of a polynucleotide by a ribozyme.

Hybridization reactions can be performed under conditions of different "stringency". As an example, a low stringency hybridization reaction is carried out at about 400 C in 10×SSC or a solution of equivalent ionic strength/temperature. A moderate stringency hybridization can be performed at about 500 C in 6×SSC, and a high stringency hybridization reaction can be performed at about 600 C in 1×SSC. Stringent conditions may also be achieved with the addition of destabilizing agents (e.g., formamide and the like). Preferably, stringent hybridization conditions are those commonly used in microarray experiments, such as hybridization in 100 mM MES pH 6.5-6.7, 1M [$Na^+$], 20 mM EDTA, 0.01% Tween-20, 10% DMSO, 0.1 mg/ml herring sperm DNA, 0.5 mg/ml BSA at 45° C. for 16 hours, followed by one or more first washes in 6×SSPE, 0.01% Tween-20 at 25° C., and then one or more second washes in 100 mM MES pH 6.5-6.7, 0.1M [Na$^+$], 0.01% Tween-20 at 50° C.

As used herein, the phrase "hybridizing specifically to" refers to the binding, duplexing or hybridizing of a molecule only to particular target nucleotide sequences under stringent conditions when one or more of the target sequences are present in a complex mixture, such as, but not limited to, total cellular RNA or mRNA. Some mismatch is allowed, so that a probe may hybridize specifically to both the target sequence (e.g., a portion of a sequence referred to in the Tables herein, or to an allelic variant thereof, or to a region of a non-human homolog that is conserved between species. It is apparent that the probe would need to be selected such that it would hybridize to a targeted region of allelic variant or non-human homolog that is highly homologous (e.g., at least 80% homologous) with the corresponding region of the human genes identified in the Tables herein. The genes listed in the Tables herein are human genes, however, probes and arrays can be prepared to specifically detect and quantify the expression of non-human homologs of the genes when the subject is a non-human mammal.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" "Homology" (the degree that one polynucleotide is identical to another), is quantifiable in terms of the proportion of bases in opposing strands that are expected to form hydrogen bonding with each other, according to generally accepted base-pairing rules. "Homology" is the degree that one polynucleotide is identical to another.

A polynucleotide or polynucleotide region (or a polypeptide or polypeptide region) has a certain percentage (for example, 80%, 85%, 90% or 95% or greater) of "sequence identity" to another sequence when aligned and that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Default parameters may be used for alignment. One alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/cgi-bin/BLAST.

An "effective amount" is an amount sufficient to effect beneficial or desired results such as prevention or treatment. An effective amount can be administered in one or more administrations, applications or dosages.

A "subject," "individual" or "patient" is used interchangeably herein, which refers to a human that may be afflicted with SLE. In one embodiment, the human is a pediatric subject. By pediatric is meant less than 18 years of age. A "control" is an alternative subject or sample used in an experiment for comparison purpose. The term "control" as used herein in reference to determining whether a gene in Table 1A, Table 1B, Table 2A, Table 2B, Table 3A, Table 3B and/or Table 4, or an allelic variant thereof, is over or under expressed, refers to one or more negative controls, such that the control sample in which gene expression is analyzed is from one or more mammals that do not have SLE. Preferably, the control is from the same species as the subject. In addition, it is preferable to determine the levels of gene expression from the same cell type or types in both the subject and the controls. One or more controls may be used. If more than one control is used, the level expressed in the controls is preferably the average or median level of expression of a gene in the controls. Any number of controls may be used. In one example, at least 10, 20, 30, 40, or at least 50 controls are used. The level of gene expression in a control may be determined at or around the same time that the level of gene expression is determined in a subject. Alternatively, the level expression of a control may be previously determined and stored for subsequent comparison. In another embodiment, the expression level in a subject may be determined and stored prior to determination of the expression level in one or more controls.

The present invention relates to compositions and methods for diagnosis, prognosis, monitoring and treatment of human Systemic Lupus Erythematosus (SLE). In particular, the present invention provides a composition of agents that correlate to a signature profile of SLE. The composition is useful to determine the likelihood of developing renal involvement and to monitor the disease state or treatment efficacy in a SLE subject.

The inventors have identified 160 down-regulated genes (Table 1A) and 185 up-regulated genes (Table 1B) in SLE patients who are likely to develop renal involvement. These genes were identified by monitoring the expression of these genes in SLE patients over the course of approximately 3 years, and comparing the expression over this time period in patients that progressed to renal involvement to the expression in those patients who did not progress to renal involvement. As used herein, the term "renal involvement" refers to: a) the presence of blood, protein and/or casts by urine analysis; b) abnormal parameters of renal function; c) abnormal renal biopsy. Patients likely to develop renal disease can then be treated more aggressively than those patients who are unlikely to develop renal involvement.

Table 1A. 160 genes that are down-regulated in SLE patients who are likely to progress to renal involvement.

TABLE 1A

| Affy ID | Common | Genbank |
|---|---|---|
| 241751_at | OFD1 | AW292752 |
| 227867_at |  | AA005361 |
| 219700_at | TEM7 | NM_020405 |
| 203288_at | KIAA0355 | NM_014686 |
| 228512_at |  | AW138833 |
| 211339_s_at | ITK | D13720.1 |
| 39582_at |  | AL050166 |
| 205254_x_at | TCF7 | AW027359 |
| 227178_at |  | AI652861 |
| 223450_s_at | COG3 | AF332595.1 |
| 217800_s_at | NDFIP1 | NM_030571 |
| 221897_at | TRIM52 | AA205660 |
| 214220_s_at | ALMS1 | AW003635 |
| 201153_s_at | MBNL1 | NM_021038 |
| 200000_s_at | PRPF8 | NM_006445 |
| 1729_at | TRADD | L41690 |
| 222125_s_at | PH-4 | BC000580.1 |
| 217838_s_at | EVL | NM_016337 |
| 227796_at | FLJ34231 | AW157773 |

TABLE 1A-continued

| Affy ID | Common | Genbank |
|---|---|---|
| 201018_at | EIF1A | BE542684 |
| 222661_at | FLJ10283 | AA528017 |
| 229854_at | OBSCN | AW614056 |
| 218674_at | FLJ13611 | NM_024941 |
| 202880_s_at | PSCD1 | NM_004762 |
| 244375_at | | AW873606 |
| 217911_s_at | BAG3 | NM_004281 |
| 206695_x_at | ZNF43 | NM_003423 |
| 206095_s_at | FUSIP1 | NM_006625 |
| 235679_at | | AI598222 |
| 214202_at | | N21364 |
| 209105_at | NCOA1 | U19179.1 |
| 212370_x_at | KIAA0592 | AL080183.1 |
| 233186_s_at | BANP | AK001039.1 |
| 223002_s_at | XRN2 | AL136841.1 |
| 214946_x_at | FLJ10824 | AV728658 |
| 202355_s_at | GTF2F1 | BC000120.1 |
| 210686_x_at | SLC25A16 | BC001407.1 |
| 206385_s_at | ANK3 | NM_020987 |
| 227173_s_at | BACH2 | AW450901 |
| 205934_at | PLCL1 | NM_006226 |
| 222488_at | DCTN4 | BE218028 |
| 223440_at | FLJ12076 | BC004556.1 |
| 201662_s_at | FACL3 | D89053.1 |
| 203704_s_at | RREB1 | AW118862 |
| 202832_at | GCC185 | NM_014635 |
| 217952_x_at | PHF3 | AW189430 |
| 201084_s_at | BTF | NM_014739 |
| 204512_at | HIVEP1 | NM_002114 |
| 204739_at | CENPC1 | NM_001812 |
| 202171_at | | NM_007146.1 |
| 235756_at | | AW802645 |
| 204847_at | ZNF-U69274 | NM_014415 |
| 214847_s_at | C6orf9 | BG111168 |
| 200099_s_at | | AL356115 |
| 212842_x_at | RANBP2L1 | AL043571 |
| 235434_at | SREBF2 | AI984541 |
| 234788_x_at | | AK024819.1 |
| 217906_at | KLHDC2 | NM_014315 |
| 218348_s_at | HSPC055 | NM_014153 |
| 219394_at | PGS1 | NM_024419 |
| 213198_at | | AL117643.1 |
| 221492_s_at | APG3 | AF202092.1 |
| 208935_s_at | LGALS8 | L78132.1 |
| 235566_at | | AW591660 |
| 200033_at | DDX5 | NM_004396 |
| 229265_at | SKI | AA927480 |
| 236016_at | | AI702962 |
| 208760_at | | NM_003345.1 |
| 219988_s_at | FLJ10597 | NM_018150 |
| 213864_s_at | NAP1L1 | AI985751 |
| 203818_s_at | SF3A3 | NM_006802 |
| 214790_at | SUSP1 | AK001406.1 |
| 209033_s_at | DYRK1A | D86550.1 |
| 218098_at | | NM_006420.1 |
| 218079_s_at | LZK1 | NM_024835 |
| 217742_s_at | WAC | NM_016628 |
| 218852_at | C14orf10 | NM_017917 |
| 209034_at | PROL2 | AF279899.1 |
| 223140_s_at | DDX36 | AF217190.1 |
| 205270_s_at | LCP2 | NM_005565 |
| 210817_s_at | NDP52 | BC004130.1 |
| 217732_s_at | ITM2B | AF092128.1 |
| 225505_s_at | C20orf81 | NM_022760.1 |
| 228905_at | | BE672700 |
| 212675_s_at | KIAA0582 | AB011154.1 |
| 208933_s_at | FLJ10359 | AI659005 |
| 218346_s_at | PA26 | NM_014454 |
| 213295_at | | AA555096 |
| 228370_at | SNURF | BE114870 |
| 217945_at | BTBD1 | NM_025238 |
| 39650_s_at | KIAA0435 | AB007895 |
| 201556_s_at | VAMP3 | BC002737.1 |
| 218084_x_at | FXYD5 | NM_014164 |
| 226895_at | GEMIN7 | AWI34798 |
| 214792_x_at | VAMP2 | AI955119 |
| 235125_x_at | | AI078279 |

TABLE 1A-continued

| Affy ID | Common | Genbank |
|---|---|---|
| 227345_at | | AI738556 |
| 221741_s_at | dJ963E22.1 | AL096828 |
| 231449_at | | AV700626 |
| 200613_at | AP2M1 | NM_004068 |
| 225703_at | KIAA1545 | AL583509 |
| 226951_at | | AI741415 |
| 204193_at | CHKL | NM_005198 |
| 211383_s_at | KIAA0982 | AL136827.1 |
| 201071_x_at | SF3B1 | NM_012433 |
| 214753_at | | AW084068 |
| 235444_at | | AI417897 |
| 224938_at | | AU144387 |
| 219966_x_at | BANP | NM_017869 |
| 60528_at | PLA2G4B | N71116 |
| 238378_at | | C14394 |
| 200912_s_at | EIF4A2 | NM_001967 |
| 226062_x_at | FLJ11280 | AB037811.1 |
| 226680_at | PEGASUS | BF056303 |
| 211185_s_at | FLJ14753 | AF130099.1 |
| 206015_s_at | KIAA1041 | NM_014947 |
| 225224_at | DKFZP566G1424 | AL034550 |
| 204791_at | NR2C1 | NM_003297 |
| 218552_at | FLJ10948 | NM_018281 |
| 202419_at | FVT1 | NM_002035 |
| 201166_s_at | PUM1 | NM_014676 |
| 211946_s_at | KIAA1096 | AL096857.1 |
| 209654_at | KIAA0947 | BC004902.1 |
| 218432_at | FBXO3 | NM_012175 |
| 212276_at | LPIN1 | D80010.1 |
| 220924_s_at | SLC38A2 | NM_018976 |
| 235848_x_at | | N35250 |
| 218754_at | FLJ23323 | NM_024654 |
| 229317_at | | BG231980 |
| 219711_at | FLJ20070 | NM_017652 |
| 201023_at | TAF7 | NM_005642 |
| 202969_at | | Y09216.1 |
| 203310_at | STXBP3 | NM_007269 |
| 212267_at | KIAA0261 | D87450.1 |
| 213567_at | | BF431965 |
| 202423_at | RUNXBP2 | NM_006766 |
| 231039_at | | BE549532 |
| 228423_at | | AI887898 |
| 244598_at | | W72060 |
| 202775_s_at | SFRS8 | NM_004592 |
| 202646_s_at | NRAS | AA167775 |
| 209481_at | SNRK | AF226044.1 |
| 226744_at | MGC3329 | BG284386 |
| 219817_at | LOC51275 | NM_016534 |
| 212042_x_at | RPL7 | BG389744 |
| 208113_x_at | PABPC3 | NM_030979 |
| 241825_at | | AI265967 |
| 218528_s_at | RNF38 | NM_022781 |
| 238829_at | | AI540253 |
| 222251_s_at | GMEB2 | AL133646.1 |
| 47773_at | KIAA1332 | AA836114 |
| 200858_s_at | RPS8 | NM_001012 |
| 209022_at | STAG2 | AK026678.1 |
| 212781_at | RBBP6 | AK026954.1 |
| 211666_x_at | RPL3 | L22453.1 |
| 224763_at | | AL137450.1 |
| 225958_at | M6PR | AI554106 |
| 222307_at | LOC282997 | AI695595 |
| 201653_at | CNIH | NM_005776 |
| 200847_s_at | MGC8721 | NM_016127 |

Table 1B. 185 genes that are up-regulated in SLE patients who are likely to progress to renal involvement.

TABLE 1B

| Affy ID | Common | Genbank |
|---|---|---|
| 211643_x_at | IGKC | L14457.1 |
| 216853_x_at | IGLJ3 | AF234255.1 |
| 223565_at | PACAP | AF151024.1 |

TABLE 1B-continued

| Affy ID | Common | Genbank |
|---|---|---|
| 214777_at | IGKC | BG482805 |
| 221286_s_at | PACAP | NM_016459 |
| 214768_x_at | IGKC | BG540628 |
| 216207_x_at | IGKV1D-13 | AW408194 |
| 215176_x_at | IGKC | AW404894 |
| 202411_at | IFI27 | NM_005532 |
| 209773_s_at | RRM2 | BC001886.1 |
| 211649_x_at | | L14456.1 |
| 224789_at | KIAA1892 | AL555107 |
| 217480_x_at | IGKV1OR15-118 | M20812 |
| 228377_at | KIAA1384 | AB037805.1 |
| 216401_x_at | IGKV | AJ408433 |
| 218585_s_at | RAMP | NM_016448 |
| 222528_s_at | MSCP | BG251467 |
| 205692_s_at | CD38 | NM_001775 |
| 201292_at | TOP2A | NM_001067.1 |
| 201890_at | RRM2 | NM_001034.1 |
| 202655_at | ARMET | NM_006010 |
| 204444_at | KIF11 | NM_004523 |
| 220306_at | FLJ20202 | NM_017709 |
| 223381_at | CDCA1 | AF326731.1 |
| 222529_at | MSCP | BG251467 |
| 205436_s_at | H2AFX | NM_002105 |
| 222411_s_at | SSR3 | AW087870 |
| 211647_x_at | | L14454.1 |
| 207434_at | FXYD2 | NM_021603 |
| 209340_at | UAP1 | S73498.1 |
| 202503_s_at | KIAA0101 | NM_014736 |
| 203554_x_at | PTTG1 | NM_004219 |
| 202083_s_at | SEC14L1 | NM_003003.1 |
| 218039_at | ANKT | NM_016359 |
| 222039_at | LOC146909 | AA292789 |
| 209030_s_at | IGSF4 | NM_014333.1 |
| 204170_s_at | CKS2 | NM_001827 |
| 224428_s_at | CDCA7 | AY029179.1 |
| 207165_at | HMMR | NM_012485 |
| 230645_at | MGC20553 | BF110588 |
| 226936_at | | BG492359 |
| 204767_s_at | FEN1 | BC000323.1 |
| 235113_at | PPIL5 | AA742244 |
| 208103_s_at | ANP32E | NM_030920 |
| 212021_s_at | MKI67 | BF001806 |
| 228273_at | | BG165011 |
| 209457_at | DUSP5 | U16996.1 |
| 202667_s_at | HKE4 | NM_006979 |
| 226085_at | | AA181060 |
| 217755_at | HN1 | NM_016185 |
| 206364_at | KIF14 | NM_014875 |
| 223086_x_at | MRPL51 | AF151075.1 |
| 223054_at | DNAJB11 | BC001144.1 |
| 200039_at | PSMB2 | NM_002794 |
| 202954_at | UBE2C | NM_007019 |
| 225686_at | | AK022820.1 |
| 202589_at | TYMS | NM_001071 |
| 205632_s_at | PIP5K1B | NM_003558 |
| 203046_s_at | TIMELESS | NM_003920 |
| 201204_s_at | | AI921320 |
| 213007_at | FLJ10719 | BG478677 |
| 220684_at | TBX21 | NM_013351 |
| 229893_at | | BF589413 |
| 204531_s_at | BRCA1 | NM_007295 |
| 200968_s_at | PPIB | NM_000942 |
| 224596_at | CDW92 | NM_022109.1 |
| 204007_at | FCGR3A | J04162.1 |
| 225171_at | MacGAP | AK002195.1 |
| 228607_at | | AI651594 |
| 229097_at | | AI813331 |
| 222532_at | APMCF1 | BF983948 |
| 225890_at | C20orf72 | AI678096 |
| 211048_s_at | ERP70 | BC006344.1 |
| 209152_s_at | TCF3 | M31523.1 |
| 225083_at | LOC112495 | AL536986 |
| 200967_at | PPIB | NM_000942 |
| 202082_s_at | SEC14L1 | NM_003003.1 |
| 208527_x_at | HIST1H2BE | NM_003523 |
| 222600_s_at | FLJ10808 | NM_018227.1 |
| 204559_s_at | LSM7 | NM_016199 |
| 224683_at | FBXO18 | BE961916 |
| 205967_at | HIST1H4C | NM_003542 |
| 213811_x_at | TCF3 | BG393795 |
| 218662_s_at | HCAP-G | NM_022346 |
| 224511_s_at | MGC14353 | BC006405.1 |
| 223252_at | MGC2641 | BC000755.1 |
| 207389_at | GP1BA | NM_000173 |
| 213688_at | CALM1 | N25325 |
| 219512_at | C20orf172 | NM_024918 |
| 204613_at | PLCG2 | NM_002661 |
| 213399_x_at | RPN2 | AI560720 |
| 219618_at | IRAK4 | NM_016123 |
| 218875_s_at | FBXO5 | NM_012177 |
| 203658_at | SLC25A20 | BC001689.1 |
| 200679_x_at | HMGB1 | BE311760 |
| 230942_at | CKLFSF5 | AI147740 |
| 222702_x_at | CRIPT | BF540954 |
| 208941_s_at | SPS | BC000941.1 |
| 225404_at | LOC113444 | R75637 |
| 202534_x_at | DHFR | NM_000791 |
| 233588_x_at | HKE2 | BE561798 |
| 202839_s_at | NDUFB7 | NM_004146 |
| 214798_at | | AW291664 |
| 222029_x_at | HKE2 | NM_014260.1 |
| 223191_at | LOC51241 | AF151037.1 |
| 207223_s_at | ROD1 | NM_005156 |
| 209709_s_at | HMMR | U29343.1 |
| 235353_at | KIAA0746 | AI887866 |
| 201277_s_at | HNRPAB | NM_004499 |
| 218357_s_at | TIMM8B | NM_012459 |
| 223370_at | PLEKHA3 | AF286162.1 |
| 203136_at | RABAC1 | NM_006423 |
| 226024_at | MURR1 | BG481459 |
| 224577_at | KIAA1181 | AB033007.1 |
| 204146_at | PIR51 | BE966146 |
| 225143_at | EIF3S10 | BG179991 |
| 229074_at | EHD4 | AI692267 |
| 201622_at | p100 | NM_014390 |
| 235341_at | | AL119957 |
| 212350_at | TBC1D1 | AB029031.1 |
| 217772_s_at | MTCH2 | NM_014342 |
| 218680_x_at | HYPK | NM_016400 |
| 229803_at | NUDT3 | AI347000 |
| 210224_at | HLALS | AF031469.1 |
| 213734_at | WSB2 | BG260658 |
| 222654_at | FLJ20421 | AW295105 |
| 234926_s_at | C20orf43 | AK026118.1 |
| 210378_s_at | SSNA1 | BC004118.1 |
| 207508_at | ATP5G3 | NM_001689 |
| 202779_s_at | E2-EPF | NM_014501 |
| 201202_at | PCNA | NM_002592 |
| 202461_at | EIF2B2 | NM_014239 |
| 213748_at | KIAA0298 | AW271713 |
| 225552_x_at | AKIP | AI991669 |
| 202070_s_at | IDH3A | NM_005530 |
| 202875_s_at | PBX2 | BE397715 |
| 224217_s_at | FAF1 | AF094700.1 |
| 222518_at | ARFGEF2 | NM_006420.1 |
| 213629_x_at | MT1F | BF246115 |
| 209477_at | EMD | BC000738.1 |
| 204079_at | TPST2 | NM_003595 |
| 203168_at | CREBL1 | NM_004381 |
| 203225_s_at | FLJ11149 | NM_018339 |
| 232103_at | BPNT1 | AI439695 |
| 211769_x_at | TDE1 | BC006088.1 |
| 219801_at | MGC10520 | NM_030580 |
| 218302_at | PEN-2 | NM_018468 |
| 227259_at | CD47 | BF439618 |
| 202110_at | COX7B | NM_001866 |
| 204226_at | STAU2 | NM_014393 |
| 206445_s_at | HRMT1L2 | NM_001536 |
| 218391_at | EAP30 | NM_007241 |
| 229067_at | | BF977829 |
| 203484_at | SEC61G | NM_014302 |
| 204033_at | TRIP13 | NM_004237 |
| 215691_x_at | LOC51668 | AV702994 |

TABLE 1B-continued

| Affy ID | Common | Genbank |
|---|---|---|
| 209836_x_at | MGC5178 | AF060511.1 |
| 202347_s_at | HIP2 | AB022435.1 |
| 224160_s_at | NPD002 | BC001817.1 |
| 212119_at | TC10 | BF348067 |
| 209162_s_at | PRPF4 | U82756.1 |
| 225695_at | | BG497776 |
| 204048_s_at | KIAA0680 | NM_014721.1 |
| 235577_at | | AL036451 |
| 225100_at | | AK025697.1 |
| 201155_s_at | MFN2 | NM_014874 |
| 227133_at | LOC139231 | BE856541 |
| 202001_s_at | NDUFA6 | NM_002490 |
| 204282_s_at | FARS1 | NM_006567 |
| 209391_at | DPM2 | AF061729.1 |
| 223059_s_at | MGC11034 | BC004872.1 |
| 223179_at | MGC10500 | BC005009.1 |
| 212492_s_at | KIAA0876 | AW237172 |
| 225674_at | BAP29 | AK000878.1 |
| 218250_s_at | CNOT7 | NM_013354 |
| 226765_at | SPTBN1 | AA971514 |
| 233559_s_at | FENS-1 | AK023415.1 |
| 229021_at | | AI052257 |
| 225309_at | PHE5A | AL008582 |
| 63825_at | MAGED1 | AI557319 |
| 205072_s_at | XRCC4 | NM_022406 |
| 238909_at | | BF126155 |
| 227740_at | KIS | AW173222 |
| 227454_at | KIAA1361 | AB037782.1 |
| 208727_s_at | CDC42 | BC002711.1 |

Long term is has been found that out of 53 SLE patients identified using the present invention there was no Renal Disease (RD) in 10 patients; RD at blood draw=29 (one not used for RD analysis); no RD at blood draw, but RD developed since=7; no RD at blood draw, no follow-up=2; RD uncertain=5.

Using the PAM package (Prediction Analysis of Microarrays) [described in Tibshirani et. al. (2002) Diagnosis of multiple cancer types by shrunken centroids of gene expression. PNAS 99: 6567-6572], a minimum of 99 probe sets predicted from the patients who had no renal disease at the time of blood draw those who later developed renal disease with a 100% accuracy. 37 probe sets predicted later renal disease onset with 86% accuracy (6/7 patients predicted correctly). The Tables of genes disclosed herein list the name of the gene, and an annotation to the database where the sequence of the gene can be found. Determination of the level of gene expression can include determining the level of mRNA expression or the level of protein expression. Levels of expression can be based on de novo expression or on steady state levels of an mRNA transcript or protein. As used herein, detection of gene expression includes detection of expression of sequences identical to those in the referenced annotation and fragments thereof, as well as to allelic variants and homologs of the genes listed in the Tables and fragments thereof. Methods for determining the sequences of such allelic variants and homologs are known to those of skill in the art. Gene expression can be detected in cells, cell extracts, tissues and tissue extracts or other biological sample. Detection of gene expression in a tissue or tissue extract would be included in the meaning of determining whether one or more cells over- or under-expresses a gene. In addition, it can be inferred that a subject contains at least one cell that over- or under-expresses a protein if increased or decreased levels of that protein are found extracellularly in biological samples (e.g., plasma, serum, urine, etc.) obtained from a subject. As used herein, if the tested cells, tissues, or other samples do not differentially express the relevant gene(s), then "the one or more cells are not identified."

As used herein, a patient suspected of having SLE has at least 4 of the 11 criteria established by the ACR: malar rash, discoid rash, sensitivity to sun light, oral ulcers, arthritis, serositis, kidney and central nervous system inflammation, blood alterations, the presence of antinuclear antibodies (ANA), anti-dsDNA and anti-phospholipid/cardiolipin antibodies. One gene was found to be upregulated in 50/53 pediatric SLE patients, namely, C1 ORF 29 (Affymetrix ID 204439_at).

In one embodiment, the methods of the invention include determining whether or not the mammal contains one or more cells that express at least 1 gene listed in Table 1A (160 down regulated genes) by at least 75% less and/or at least 1 gene listed in Table 1B (185 up regulated genes) by at least four-fold more than one or more controls. In yet a further aspect, the method may include determining whether the patient has cells that differentially express at least 5, 10, 20, 30, 40, 50, 60, 70, 80, 90, 100, 110, 115, or at least 160 of the genes of Table 1A by at least 50% less or at least 75% less than the control, and/or at least 5, 10, 20, 30, 40, 50, 60, 70, 80, 90, 100, 110, 120, 130, 140, 150, 160, 170 or at least 185 genes of Table 1B by at least two-fold more, or at least four-fold more than the control.

As an alternative to comparing the level of expression of genes listed in Table 1A and/or 1B in a mammalian subject with the expression levels in one or more controls, the level of expression in the subject can be compared to a plurality of reference expression profiles associated with a likelihood of an SLE patient to develop renal involvement. Thus, the invention provides a method for predicting whether a mammal suffering from systemic lupus erythematosus (SLE) is likely to develop renal involvement, by providing a plurality of reference expression profiles, each associated with likelihood that an SLE patient will develop renal disease; providing a subject expression profile generated from one or more cells or other sample from a mammalian subject; and selecting the reference expression profile most similar to the subject expression profile, to associate a likelihood of the developing renal disease with the subject, wherein, the subject expression profile and the reference expression profiles represent the level of expression of at least one gene listed in Table 1A and/or Table 1B.

By expression profile is meant the level of expression of one or more of the human genes listed in the appropriate table herein, or of an allelic variant or homolog (i.e., a non-human homolog) of one of these genes. The level of expression can be represented in any convenient form. As a non-limiting example, the level of expression of a gene could be stored as a number representing the absolute or relative amount of label detected upon the binding of a labeled mRNA or cDNA to a probe on an immobilized surface, such as a microarray. The number could represent the level of expression of a gene detected in a single sample, or an average or median of the levels of expression detected in multiple samples. The expression profile may contain a value representing the expression of one gene, or a plurality of values representing the levels of expression of multiple genes (e.g., 160 genes listed in Table 1A and 185 genes listed in Table 1B).

A reference expression profile associates the level of expression of one or more genes with a further value, such as a likelihood of an SLE patient to develop renal disease, presence or absence of SLE, severity of SLE, absence or SLE coupled with the presence of flu or fibromyalgia, etc. The likelihood could be a percent likelihood, or simply "more likely that not", or "not likely", etc.

Methods of comparing reference expression profiles to a subject expression profile, and evaluating the similarity thereof, are known to those of skill in the art. We can use global gene expression arrays or custom gene expression arrays. There are several programs available to compare gene expression profiles, including GeneSpring and Spotfire. These programs use various statistical algorithms to compare expression patterns. Real time RT-PCR is a method that can be used to compare expression levels of transcripts in a subject's cells to a reference expression profile. For the purposes of determining the reference profile most similar to the subject expression profile, the expression of genes in the reference profile can be ignored where a corresponding level of gene expression in the subject is not determined.

Previously, Bennett et al. (2003) identified 210 up-regulated and 141 down-regulated genes in SLE patients as compared to controls. Similarly, Baechler et al. (2003) identified 47 down-regulated and 123 up-regulated genes in SLE patients as compared to controls. The inventors have broadened these studies of differential gene expression in SLE patients as compared to controls, and list 3004 SLE-associated genes in Tables 2A and 2B. Table 2A lists 1,751 genes that are down-regulated in SLE patients by at least one-fold as compared to the control, while Table 2B lists 1,253 genes that are up-regulated in SLE patients by at least one-fold as compared to controls.

TABLE 2A

| Affymetrix ID | Common | Genbank |
|---|---|---|
| 90610_at | LRRN1 | AI654857 |
| 227878_s_at | MGC10974 | AI245026 |
| 223318_s_at | MGC10974 | BC004393.1 |
| 224664_at | | AK023981.1 |
| 226845_s_at | LOC150678 | AL036350 |
| 229874_x_at | | BE865517 |
| 229429_x_at | | AA863228 |
| 228987_at | | AA156238 |
| 226466_s_at | MGC29729 | AL544688 |
| 201216_at | C12orf8 | NM_006817 |
| 200792_at | G22P1 | NM_001469 |
| 228710_at | | BE905157 |
| 226413_at | | AA044705 |
| 227447_at | PPAP2A | AA525163 |
| 222448_s_at | UMP-CMPK | AF112216.1 |
| 222431_at | SPIN | AL136719.1 |
| 231896_s_at | DENR | AF103800.1 |
| 224688_at | | BE962299 |
| 225439_at | CML66 | BC000967.2 |
| 235014_at | LOC147727 | BF345728 |
| 210949_s_at | EIF3S8 | BC000533.1 |
| 200652_at | SSR2 | NM_003145 |
| 201064_s_at | PABPC4 | NM_003819 |
| 224479_s_at | MRPL45 | BC006235.1 |
| 64432_at | LOC51275 | W05463 |
| 229949_at | DKFZP434A0131 | AA554827 |
| 64418_at | | AI472320 |
| 243764_at | | AW085312 |
| 243154_at | | AA215381 |
| 231940_at | KIAA1615 | AI369933 |
| 215307_at | | AL109722.1 |
| 204793_at | GASP | NM_014710 |
| 228841_at | | AW299250 |
| 201054_at | HNRPA0 | BE966599 |
| 212846_at | KIAA0179 | D80001.1 |
| 209974_s_at | BUB3 | AF047473.1 |
| 202741_at | PRKACB | AA130247 |
| 227867_at | | AA005361 |
| 221648_s_at | | AK025651.1 |
| 221558_s_at | LEF1 | AF288571.1 |
| 219528_s_at | BCL11B | NM_022898 |

TABLE 2A-continued

| Affymetrix ID | Common | Genbank |
|---|---|---|
| 200965_s_at | ABLIM1 | NM_006720 |
| 205255_x_at | TCF7 | NM_003202 |
| 213193_x_at | TRB@ | AL559122 |
| 210915_x_at | TRB@ | M15564.1 |
| 211796_s_at | TRB@ | AF043179.1 |
| 211005_at | LAT | AF036906.1 |
| 204891_s_at | LCK | NM_005356 |
| 217950_at | NOSIP | NM_015953 |
| 205804_s_at | DJ434O14.3 | NM_025228 |
| 221601_s_at | TOSO | AI084226 |
| 204352_at | TRAF5 | NM_004619 |
| 203723_at | ITPKB | NM_002221 |
| 226272_at | | N25986 |
| 218918_at | MAN1C1 | NM_020379 |
| 203386_at | TBC1D4 | AI650848 |
| 218532_s_at | FLJ20152 | NM_019000 |
| 212538_at | zizimin1 | AL576253 |
| 201656_at | ITGA6 | NM_000210 |
| 205961_s_at | PSIP2 | NM_004682 |
| 203387_s_at | TBC1D4 | NM_014832 |
| 226247_at | PLEKHA1 | AI346026 |
| 212406_at | MYT1 | AB028973.1 |
| 205006_s_at | NMT2 | NM_004808 |
| 205005_s_at | NMT2 | AW293531 |
| 213564_x_at | LDHB | BE042354 |
| 201030_x_at | LDHB | NM_002300 |
| 212675_s_at | KIAA0582 | AB011154.1 |
| 209068_at | HNRPDL | D89678.1 |
| 223162_s_at | | AF116707.1 |
| 211929_at | | BE867771 |
| 235046_at | | AA456099 |
| 212641_at | HIVEP2 | AL023584 |
| 236198_at | | AW292872 |
| 212672_at | | U82828 |
| 223358_s_at | | AW269834 |
| 218490_s_at | ZNF302 | NM_018443 |
| 215785_s_at | CYFIP2 | AL161999.1 |
| 201892_s_at | IMPDH2 | NM_000884 |
| 206337_at | CCR7 | NM_001838 |
| 207339_s_at | LTB | NM_002341 |
| 227754_at | | AV700815 |
| 226635_at | | BG170478 |
| 218263_s_at | LOC58486 | NM_021211 |
| 203804_s_at | OA48-18 | NM_006107 |
| 213743_at | CCNT2 | BE674119 |
| 225180_at | FLJ00166 | W73788 |
| 225477_s_at | MRPS25 | AL138444 |
| 204773_at | IL11RA | NM_004512 |
| 217895_at | FLJ20758 | NM_017952 |
| 210858_x_at | ATM | U26455.1 |
| 208442_s_at | ATM | NM_000051 |
| 203408_s_at | SATB1 | NM_002971 |
| 241365_at | | AA002140 |
| 235085_at | DKFZp761P0423 | BF739767 |
| 224518_s_at | MGC13105 | BC006436.1 |
| 225159_s_at | EG1 | AW614072 |
| 227796_at | FLJ34231 | AW157773 |
| 236583_at | | AA286867 |
| 238043_at | | AI913123 |
| 225361_x_at | LOC159090 | AI341165 |
| 222673_x_at | LOC159090 | AI582192 |
| 226816_s_at | KIAA1143 | AI745170 |
| 213720_s_at | SMARCA4 | AI831675 |
| 232161_x_at | | AK025546.1 |
| 218003_s_at | FKBP3 | NM_002013 |
| 202591_s_at | SSBP1 | NM_003143 |
| 201855_s_at | KIAA0431 | NM_015251 |
| 212145_at | MRPS27 | D87453.1 |
| 240344_x_at | | AA424065 |
| 209153_s_at | TCF3 | M31523.1 |
| 224763_at | | AL137450.1 |
| 221726_at | RPL22 | BE250348 |
| 211938_at | PRO1843 | BF247371 |
| 217969_at | C11orf2 | NM_013265 |
| 217719_at | EIF3S6IP | NM_016091 |
| 218253_s_at | LGTN | NM_006893 |

TABLE 2A-continued

| Affymetrix ID | Common | Genbank |
|---|---|---|
| 217846_at | QARS | NM_005051 |
| 210027_s_at | APEX1 | M80261.1 |
| 212018_s_at | DKFZP564M182 | AK025446.1 |
| 201922_at | YR-29 | NM_014886 |
| 213864_s_at | NAP1L1 | AI985751 |
| 212967_x_at | NAP1L1 | AW148801 |
| 208752_x_at | NAP1L1 | AI888672 |
| 208754_s_at | NAP1L1 | AL162068.1 |
| 211954_at | KPNB3 | NM_002271.1 |
| 242292_at | MGC34827 | H12084 |
| 212690_at | KIAA0725 | AB018268.1 |
| 222824_at | SEC61A2 | AW237290 |
| 227261_at | KLF12 | AA020010 |
| 226254_s_at | KIAA1430 | AI912523 |
| 204890_s_at | LCK | U07236.1 |
| 230003_at | | AW779917 |
| 226148_at | HSPC063 | AU144305 |
| 225845_at | | BG253884 |
| 227087_at | | AA126419 |
| 226116_at | | BF064224 |
| 229145_at | LOC119504 | AA541762 |
| 227639_at | | AI275605 |
| 223269_at | MGC3200 | BC004355.1 |
| 229220_x_at | | AI249173 |
| 226641_at | | AU157224 |
| 228029_at | KIAA1982 | AW513477 |
| 227026_at | HSMPP8 | AI016714 |
| 225886_at | | AA156797 |
| 223282_at | SDCCAG33 | W60810 |
| 229891_x_at | LSR7 | AI630799 |
| 225629_s_at | KIAA1538 | AI669498 |
| 228760_at | B2M | AV725947 |
| 218699_at | RAB7L1 | BG338251 |
| 212918_at | FLJ22028 | BF219234 |
| 210116_at | SH2D1A | AF072930.1 |
| 212486_s_at | | N20923 |
| 202136_at | BS69 | BE250417 |
| 201877_s_at | PPP2R5C | NM_002719 |
| 224833_at | ETS1 | BE218980 |
| 224579_at | | AK024263.1 |
| 202365_at | MGC5139 | BC004815.1 |
| 209421_at | MSH2 | U04045.1 |
| 212313_at | MGC29816 | BC004344.1 |
| 209827_s_at | IL16 | NM_004513.1 |
| 204328_at | EVER1 | NM_007267 |
| 217729_s_at | AES | NM_001130 |
| 214032_at | ZAP70 | AI817942 |
| 222557_at | STMN3 | AL353715 |
| 227686_at | MGC15763 | BE465433 |
| 224060_s_at | CGI-30 | AF157319.1 |
| 212893_at | DKFZP564I052 | AL080063.1 |
| 225856_at | | BF512028 |
| 235587_at | LOC202781 | BG400596 |
| 228549_at | | AI491983 |
| 213539_at | CD3D | NM_000732.1 |
| 205831_at | CD2 | NM_001767 |
| 209670_at | TRA@ | M12959.1 |
| 210038_at | | AL137145 |
| 206761_at | TACTILE | NM_005816 |
| 225112_at | | BF245400 |
| 223287_s_at | FOXP1 | AF146696.1 |
| 217802_s_at | NUCKS | NM_022731 |
| 209711_at | UGTREL7 | N80922 |
| 208662_s_at | TTC3 | D84294.1 |
| 221509_at | DENR | AB014731.1 |
| 201753_s_at | ADD3 | NM_019903 |
| 218667_at | PJA1 | NM_022368 |
| 212917_x_at | FLJ22028 | BF219234 |
| 203497_at | PPARBP | NM_004774 |
| 212677_s_at | | AB011154.1 |
| 213958_at | CD6 | AW134823 |
| 202969_at | | Y09216.1 |
| 202968_s_at | DYRK2 | Y09216.1 |
| 209604_s_at | GATA3 | BC003070.1 |
| 212594_at | PDCD4 | N92498 |
| 212637_s_at | WWP1 | BF131791 |
| 201177_s_at | UBA2 | NM_005499 |
| 201486_at | RCN2 | NM_002902 |
| 205541_s_at | GSPT2 | NM_018094 |
| 206042_x_at | SNURF | NM_022804 |
| 201522_x_at | SNRPN | NM_003097 |
| 217988_at | HEI10 | NM_021178 |
| 217870_s_at | UMP-CMPK | NM_016308 |
| 214709_s_at | KTN1 | Z22551.1 |
| 200915_x_at | KTN1 | NM_004986 |
| 211727_s_at | COX11 | BC005895.1 |
| 203285_s_at | HS2ST1 | NM_012262 |
| 232004_at | | AK001846.1 |
| 202524_s_at | SPOCK2 | NM_014767 |
| 218545_at | FLJ11088 | NM_018318 |
| 32541_at | calcineurin A catalytic subunit, calmodulin-dependent protein phosphatase catalytic subunit, CaM-PrP catalytic subunit | S46622 |
| 207000_s_at | PPP3CC | NM_005605 |
| 201092_at | RBBP7 | NM_002893 |
| 228370_at | SNURF | BF114870 |
| 205259_at | NR3C2 | NM_000901 |
| 223092_at | ANKH | AF274753.1 |
| 228843_at | KIAA1337 | AI824171 |
| 46665_at | SEMA4C | AI949392 |
| 203413_at | NELL2 | NM_006159 |
| 243363_at | LEF1 | AA992805 |
| 231798_at | NOG | AL575177 |
| 214081_at | TEM7 | AF070526.1 |
| 204612_at | PKIA | NM_006823 |
| 227670_at | ZNF75A | N74222 |
| 235725_at | | AW055351 |
| 229629_at | | AI923633 |
| 202491_s_at | IKBKAP | NM_003640 |
| 224759_s_at | MGC17943 | AK001731.1 |
| 222715_s_at | AP1GBP1 | BE856321 |
| 36553_at | CRIP2 | AA669799 |
| 229686_at | LOC286530 | AI436587 |
| 217286_s_at | | BC001805.1 |
| 218572_at | HSPC134 | NM_014169 |
| 209539_at | ARHGEF6 | D25304.1 |
| 209143_s_at | CLNS1A | AF005422.1 |
| 202757_at | COBRA1 | NM_015456 |
| 226496_at | FLJ22611 | BG291039 |
| 225457_at | DKFZP564I1171 | BF528646 |
| 229253_at | CTMP | AI184512 |
| 40189_at | set | M93651 |
| 200631_s_at | SET | NM_003011 |
| 213047_x_at | SET | AI278616 |
| 239122_at | | AI638155 |
| 235457_at | | AI769569 |
| 218428_s_at | REV1L | NM_016316 |
| 221691_x_at | NPM1 | AB042278.1 |
| 215136_s_at | OIP2 | AL050353.1 |
| 202144_s_at | ADSL | NM_000026 |
| 210097_s_at | RARG-1 | AF130102.1 |
| 202521_at | CTCF | NM_006565 |
| 218395_at | FLJ13433 | NM_022496 |
| 209422_at | C20orf104 | AL109965 |
| 228174_at | | AI832363 |
| 232909_s_at | | AU146870 |
| 229844_at | | AI699465 |
| 224838_at | FOXP1 | AK026898.1 |
| 224711_at | | AK025731.1 |
| 227979_at | | AU152162 |
| 222490_at | RPC5 | AK023160.1 |
| 225310_at | | AI928344 |
| 228007_at | | AL133101.1 |
| 227077_at | | BF432328 |
| 222317_at | PDE3B | AA888858 |
| 214582_at | PDE3B | NM_000753.1 |
| 212709_at | NUP160 | D83781.1 |
| 238523_at | C16orf44 | BF941204 |
| 206059_at | ZNF91 | NM_003430 |

TABLE 2A-continued

| Affymetrix ID | Common | Genbank |
|---|---|---|
| 216945_x_at | PASK | U79240.1 |
| 213534_s_at | PASK | D50925.1 |
| 206545_at | CD28 | NM_006139 |
| 202268_s_at | APPBP1 | NM_003905 |
| 241871_at | CAMK4 | AL529104 |
| 214369_s_at | RASGRP2 | AI688812 |
| 208206_s_at | RASGRP2 | NM_005825 |
| 228722_at | HRMT1L1 | AI928367 |
| 229322_at | PPP2R5E | BF529715 |
| 222895_s_at | BCL11B | AA918317 |
| 219571_s_at | GIOT-3 | NM_016265 |
| 208661_s_at | TTC3 | D84294.1 |
| 212332_at | RBL2 | NM_005611.1 |
| 201606_s_at | PWP1 | BE796924 |
| 221046_s_at | HSPC135 | NM_014170 |
| 218142_s_at | LOC51185 | NM_016302 |
| 212462_at | MORF | AF113514.1 |
| 221559_s_at | MGC2488 | BC000229.1 |
| 228049_x_at | | AA523172 |
| 237333_at | SYNCOILIN | T90771 |
| 227884_at | | AW296067 |
| 221499_s_at | NPEPL1 | AF008936.1 |
| 221264_s_at | AF311304 | NM_031214 |
| 213189_at | DKFZp667G2110 | AL574514 |
| 219700_at | TEM7 | NM_020405 |
| 216111_x_at | hPMSR3 | U38979 |
| 203579_s_at | SLC7A6 | NM_003983.1 |
| 233068_at | | AK023264.1 |
| 215275_at | | AW963138 |
| 202978_at | ZF | NM_021212.1 |
| 213666_at | 6-Sep | AK026589.1 |
| 217506_at | | H49382 |
| 202724_s_at | FOXO1A | NM_002015 |
| 218437_s_at | LZTFL1 | NM_020347 |
| 203939_at | NT5E | NM_002526 |
| 221645_s_at | ZNF83 | M27877.1 |
| 213064_at | FLJ11806 | N64802 |
| 203569_at | OFD1 | NM_003611 |
| 231853_at | TUBD1 | AK022771.1 |
| 222164_at | | AU145411 |
| 221593_s_at | VRP | BC001663.1 |
| 212773_s_at | TOMM20-PENDING | BG165094 |
| 219155_at | RDGBB | NM_012417 |
| 221588_x_at | ALDH6A1 | AF130089.1 |
| 217092_x_at | | AL031589 |
| 217266_at | | Z97353 |
| 217336_at | dJ858M22.1 | AL118510 |
| 221493_at | TSPYL | AL136629.1 |
| 212239_at | | M61906.1 |
| 209112_at | CDKN1B | BC001971.1 |
| 212920_at | | AV682285 |
| 209323_at | PRKRIR | AF081567.1 |
| 214800_x_at | BTF3 | R83000 |
| 200608_s_at | RAD21 | NM_006265 |
| 211698_at | CRI1 | AF349444.1 |
| 201153_s_at | MBNL1 | NM_021038 |
| 208753_s_at | NAP1L1 | BC002387.1 |
| 204528_s_at | NAP1L1 | NM_004537 |
| 209674_at | CRY1 | D83702.1 |
| 209064_x_at | PAIP1 | AL136920.1 |
| 208051_s_at | PAIP1 | NM_006451 |
| 209481_at | SNRK | AF226044.1 |
| 219029_at | FLJ21657 | NM_022483 |
| 212928_at | KIAA0721 | AL050331 |
| 217851_s_at | C20orf45 | NM_016045 |
| 218499_at | MST4 | NM_016542 |
| 201260_s_at | SYPL | NM_006754 |
| 214678_x_at | ZFX | R51161 |
| 213786_at | TAX1BP1 | AI935415 |
| 213750_at | | AA928506 |
| 208796_s_at | CCNG1 | BC000196.1 |
| 211761_s_at | SIP | BC005975.1 |
| 221931_s_at | SEC13L | AV701173 |
| 221589_s_at | ALDH6A1 | AF130089.1 |
| 217707_x_at | SMARCA2 | AI535683 |
| 206542_s_at | SMARCA2 | AV725365 |
| 219351_at | SEDL | NM_014563 |
| 209602_s_at | GATA3 | AI796169 |
| 231817_at | KIAA1350 | H25097 |
| 231124_x_at | | AI524095 |
| 224367_at | DJ79P11.1 | AF251053.1 |
| 229070_at | MGC12335 | AA470369 |
| 224196_x_at | CGI-30 | AF161492.1 |
| 223671_x_at | CGI-30 | AF248965.1 |
| 218005_at | ZNF22 | AA744771 |
| 205089_at | ZNF7 | NM_003416 |
| 202227_s_at | BRD8 | NM_006696 |
| 202983_at | SMARCA3 | AI760760 |
| 216221_s_at | PUM2 | D87078.2 |
| 203575_at | CSNK2A2 | NM_001896 |
| 228109_at | | AI912976 |
| 204917_s_at | MLLT3 | AV756536 |
| 235199_at | | AI969697 |
| 215440_s_at | FLJ10097 | AL523320 |
| 32042_at | APK1 antigen | S72904 |
| 235695_at | | AI051236 |
| 227158_at | MGC9912 | AU149257 |
| 212352_s_at | TMP21 | BE780075 |
| 226532_at | | AL563613 |
| 225716_at | | AI357639 |
| 223155_at | DKFZP564D1378 | AL136681.1 |
| 225036_at | | BF969806 |
| 223177_at | MGC24302 | AL515061 |
| 225509_at | LOC56757 | AI862477 |
| 218491_s_at | THY28 | NM_014174 |
| 232024_at | HIMAP2 | AI431931 |
| 210502_s_at | PPIE | AF042386.1 |
| 227637_at | TFCP2 | AV712694 |
| 226688_at | DKFZp313N0621 | AW003508 |
| 228856_at | MGC2474 | AV698149 |
| 212904_at | KIAA1185 | AB033011.1 |
| 201327_s_at | CCT6A | NM_001762 |
| 201209_at | HDAC1 | NM_004964 |
| 222103_at | ATF1 | AI434345 |
| 204155_s_at | KIAA0999 | AA044154 |
| 207996_s_at | C18orf1 | NM_004338 |
| 238649_at | | AA815089 |
| 230350_at | | AA503360 |
| 213090_s_at | TAF4 | AI744029 |
| 204552_at | | AA355179 |
| 228039_at | | AI765169 |
| 229614_at | LOC162967 | AI277652 |
| 201518_at | CBX1 | NM_006807 |
| 221514_at | SDCCAG16 | BC001149.1 |
| 225501_at | MGC14797 | AK027039.1 |
| 225030_at | LOC91272 | AA824341 |
| 209846_s_at | BTN3A2 | BC002832.1 |
| 204820_s_at | BTN3A3 | NM_006994 |
| 226339_at | TRUB1 | AW500239 |
| 217726_at | COPZ1 | NM_016057 |
| 215772_x_at | SUCLG2 | AL050226.1 |
| 212459_x_at | SUCLG2 | BF593940 |
| 214835_s_at | SUCLG2 | AF131748.1 |
| 228446_at | KIAA2026 | BF062203 |
| 226943_at | RAI1 | BF984830 |
| 204839_at | POP5 | NM_015918 |
| 235964_x_at | SAMHD1 | AA603344 |
| 224621_at | MAPK1 | AA129773 |
| 235529_at | SAMHD1 | BF437747 |
| 201637_s_at | FXR1 | NM_005087 |
| 201326_at | CCT6A | BE737030 |
| 201036_s_at | HADHSC | NM_005327 |
| 218373_at | FTS | NM_022476 |
| 208848_at | ADH5 | M30471.1 |
| 211105_s_at | NFATC1 | U80918.1 |
| 34210_at | CDW52 | N90866 |
| 202747_s_at | ITM2A | NM_004867 |
| 202746_at | ITM2A; E25A | AL021786 |
| 243968_x_at | FCRH1 | AI572979 |
| 217979_at | NET-6 | NM_014399 |
| 235372_at | FREB | AW575245 |
| 221969_at | PAX5 | BF510692 |

TABLE 2A-continued

| Affymetrix ID | Common | Genbank |
|---|---|---|
| 227224_at | FLJ25604 | AW003297 |
| 202732_at | PKIG | NM_007066 |
| 222285_at | IGHG3 | AW134608 |
| 227198_at | | AW085505 |
| 230509_at | FLJ13952 | BF528605 |
| 206983_at | CCR6 | NM_004367 |
| 226878_at | | AL581873 |
| 226550_at | | AI672159 |
| 227173_s_at | BACH2 | AW450901 |
| 222891_s_at | BCL11A | AI912275 |
| 226223_at | PAWR | AI189509 |
| 236280_at | | AI225238 |
| 210279_s_at | GPR18 | AF261135.1 |
| 204642_at | EDG1 | NM_001400 |
| 223477_s_at | FLJ38663 | AF061733.1 |
| 214779_s_at | DJ1042K10.2 | R51077 |
| 219315_s_at | FLJ20898 | NM_024600 |
| 212400_at | | AL043266 |
| 52940_at | SIGIRR | AA085764 |
| 214049_x_at | CD7 | AI829961 |
| 210463_at | FLJ20244 | BC002492.1 |
| 204153_s_at | MFNG | NM_002405 |
| 203314_at | PGPL | NM_012227 |
| 224910_at | LOC91012 | AL575747 |
| 219812_at | MGC2463 | NM_024070 |
| 210039_at | PRKCQ | L01087.1 |
| 210031_at | CD3Z | J04132.1 |
| 206118_at | STAT4 | NM_003151 |
| 235124_at | | BE502930 |
| 218538_s_at | MRS2L | NM_020662 |
| 230178_s_at | | BE672676 |
| 225816_at | | AV646599 |
| 240806_at | | AI939308 |
| 234875_at | rpL7a | AJ224082 |
| 234873_x_at | rpL7a | AJ224080 |
| 224841_x_at | | BF316352 |
| 224741_x_at | | BG329175 |
| 224719_x_at | LOC113246 | BG339653 |
| 207040_s_at | ST13 | NM_003932 |
| 216032_s_at | SDBCAG84 | AF091085.1 |
| 234512_x_at | dJ486D24.1 | AL136226 |
| 218495_at | UXT | NM_004182 |
| 200651_at | GNB2L1 | NM_006098 |
| 210908_s_at | PFDN5 | AB055804.1 |
| 207132_x_at | PFDN5 | NM_002624 |
| 222229_x_at | | AL121871 |
| 219762_s_at | RPL36 | NM_015414 |
| 216505_x_at | | AL118502 |
| 213687_s_at | RPL35A | BE968801 |
| 216570_x_at | | AL096829 |
| 216177_at | RPL29 | AW582267 |
| 214167_s_at | RPLP0 | AA555113 |
| 208826_x_at | HINT1 | U27143.1 |
| 207721_x_at | HINT1 | NM_005340 |
| 200826_at | SNRPD2 | NM_004597 |
| 210633_x_at | KRT10 | M19156.1 |
| 207023_x_at | KRT10 | NM_000421 |
| 221775_x_at | RPL22 | BG152979 |
| 208768_x_at | RPL22 | D17652.1 |
| 212039_x_at | RPL3 | BG339228 |
| 201217_x_at | RPL3 | NM_000967 |
| 211073_x_at | RPL3 | BC006483.1 |
| 211927_x_at | | BE963164 |
| 201254_x_at | RPS6 | NM_001010 |
| 211345_x_at | EEF1G | AF119850.1 |
| 200689_x_at | EEF1G | NM_001404 |
| 211710_x_at | RPL4 | BC005817.1 |
| 201154_x_at | RPL4 | NM_000968 |
| 217740_x_at | RPL7A | NM_000972 |
| 200725_x_at | RPL10 | NM_006013 |
| 213969_x_at | RPL29 | BF683426 |
| 212537_x_at | RPL17 | BE733979 |
| 212270_x_at | RPL17 | BG168283 |
| 200674_s_at | RPL32 | NM_000994 |
| 211542_x_at | RPS10 | BC004334.1 |
| 212191_x_at | RPL13 | AW574664 |
| 208929_x_at | RPL13 | BC004954.1 |
| 213588_x_at | RPL14 | AA838274 |
| 213890_x_at | RPS16 | AI200589 |
| 200949_x_at | RPS20 | NM_001023 |
| 224003_at | RPS20 | BF184532 |
| 213377_x_at | C1S | AI799007 |
| 212391_x_at | RPS3A | AI925635 |
| 201257_x_at | RPS3A | NM_001006 |
| 200926_at | RPS23 | NM_001025 |
| 200741_s_at | RPS27 | NM_001030 |
| 213347_x_at | RPS4X | AW132023 |
| 200763_s_at | RPLP1 | NM_001003 |
| 200716_x_at | RPL13A | NM_012423 |
| 212734_x_at | RPL13 | AI186735 |
| 213356_x_at | HNRPA1 | AL568186 |
| 213414_s_at | RPS19 | BE259729 |
| 202649_x_at | RPS19 | NM_001022 |
| 200869_at | RPL18A | NM_000980 |
| 200834_s_at | RPS21 | NM_001024 |
| 221476_s_at | RPL15 | AF279903.1 |
| 221475_s_at | RPL15 | NM_002948.1 |
| 213080_x_at | RPL5 | BF214492 |
| 211666_x_at | RPL3 | L22453.1 |
| 200937_s_at | RPL5 | NM_000969 |
| 200705_s_at | EEF1B2 | NM_001959 |
| 212933_x_at | RPL13 | AA961748 |
| 217807_s_at | GLTSCR2 | NM_015710 |
| 201258_at | RPS16 | NM_001020 |
| 214042_s_at | RPL22 | AW071997 |
| 211623_s_at | FBL | M30448.1 |
| 201592_at | EIF3S3 | NM_003756 |
| 208697_s_at | EIF3S6 | BC000734.1 |
| 200715_x_at | RPL13A | BC000514.1 |
| 201812_s_at | TOM7 | NM_019059 |
| 208635_x_at | NACA | BF976260 |
| 200735_x_at | NACA | NM_005594 |
| 213941_x_at | RPS7 | AI970731 |
| 212433_x_at | RPS2 | AA630314 |
| 209134_s_at | RPS6 | BC000524.1 |
| 216342_x_at | | AL121916 |
| 220960_x_at | RPL22 | NM_000983 |
| 214143_x_at | DPP7 | AI560573 |
| 200909_s_at | RPLP2 | NM_001004 |
| 201665_x_at | RPS17 | NM_001021 |
| 216520_s_at | TPT1 | AF072098 |
| 211943_x_at | TPT1 | AL565449 |
| 200781_s_at | RPS15A | NM_001019 |
| 200717_x_at | RPL7 | NM_000971 |
| 200936_at | RPL8 | NM_000973 |
| 212042_x_at | RPL7 | BG389744 |
| 215963_x_at | | Z98200 |
| 200858_s_at | RPS8 | NM_001012 |
| 214271_x_at | RPL12 | AA281332 |
| 201406_at | RPL36A | NM_021029 |
| 212578_x_at | RPS17 | BF026595 |
| 211942_x_at | | BF979419 |
| 211939_x_at | BTF3 | X74070.1 |
| 214351_x_at | RPL13 | AA789278 |
| 214394_x_at | EEF1D | AI613383 |
| 208887_at | EIF3S4 | BC000733.1 |
| 200823_x_at | RPL29 | NM_000992 |
| 203113_s_at | EEF1D | NM_001960 |
| 217379_at | bA209A2.1 | AL121934 |
| 200888_s_at | RPL23 | NM_000978 |
| 221488_s_at | LOC51596 | AF230924.1 |
| 214214_s_at | MGC4189 | AU151801 |
| 201268_at | NME2 | NM_002512 |
| 213762_x_at | RBMX | AI452524 |
| 208646_at | RPS14 | AF116710.1 |
| 220755_s_at | C6orf48 | NM_016947 |
| 202698_x_at | COX4I1 | NM_001861 |
| 217747_s_at | RPS9 | NM_001013 |
| 221494_x_at | M9 | AF085358.1 |
| 210501_x_at | | AF119846.1 |
| 212716_s_at | M9 | AW083133 |
| 213166_x_at | | BG332462 |

TABLE 2A-continued

| Affymetrix ID | Common | Genbank |
|---|---|---|
| 212995_x_at | | BG255188 |
| 201782_s_at | AIP | NM_003977 |
| 213239_at | PIBF1 | NM_006346.1 |
| 209066_x_at | UQCRB | M26700.1 |
| 205849_at | UQCRB | NM_006294 |
| 218764_at | PRKCH | NM_024064 |
| 205790_at | SCAP1 | NM_003726 |
| 213151_s_at | CDC10 | AU157515 |
| 201022_at | DSTN | NM_006870 |
| 205376_at | INPP4B | NM_003866 |
| 229872_s_at | FLJ21308 | AA532655 |
| 225391_at | LOC93622 | AL562398 |
| 200094_at | EEF2 | AI004246 |
| 200005_at | EIF3S7 | NM_003753 |
| 200093_s_at | HINT1 | N32864 |
| 200036_s_at | RPL10A | NM_007104 |
| 200081_s_at | RPS6 | BE741754 |
| 200089_s_at | RPL4 | AI953886 |
| 217256_x_at | dJ507I15.1 | Z98950 |
| 201561_s_at | CLSTN1 | NM_014944 |
| 225240_s_at | | BF435123 |
| 228853_at | STYX | AI652546 |
| 224604_at | | AK025703.1 |
| 224935_at | EIF2S3 | BE252813 |
| 222731_at | ZDHHC2 | AI814257 |
| 227630_at | | AW274445 |
| 223231_at | CDA11 | AF212250.1 |
| 225274_at | | BF247054 |
| 222391_at | COL12A1; BA209D8.1; DJ234P15.1 | AL080250 |
| 200850_s_at | AHCYL1 | NM_006621 |
| 208873_s_at | DP1 | BC000232.1 |
| 203485_at | RTN1 | NM_021136 |
| 208630_at | HADHA | BG472176 |
| 218592_s_at | CECR5 | NM_017829 |
| 221820_s_at | MYST1 | AK024102.1 |
| 218645_at | ZNF277 | NM_021994 |
| 202232_s_at | GA17 | NM_006360 |
| 205361_s_at | PFDN4 | AI718295 |
| 202231_at | GA17 | NM_006360 |
| 213581_at | PDCD2 | BF446180 |
| 201513_at | TSN | NM_004622.1 |
| 208319_s_at | RBM3 | NM_006743 |
| 226336_at | PPIA | T62044 |
| 215096_s_at | | AU145746 |
| 209009_at | ESD | BC001169.1 |
| 225918_at | LOC146346 | AI742940 |
| 218802_at | FLJ20647 | NM_017918 |
| 238026_at | | AI458020 |
| 218421_at | CERK | NM_022766 |
| 217906_at | KLHDC2 | NM_014315 |
| 211955_at | KPNB3 | NM_002271.1 |
| 211678_s_at | ZNF313 | AF090934.1 |
| 228131_at | ASE-1 | BG111047 |
| 204521_at | HSU79274 | NM_013300 |
| 235005_at | MGC4562 | AA192361 |
| 225583_at | UXS1 | AL573637 |
| 225405_at | DKFZp762N1910 | AI151434 |
| 225554_at | ANAPC7 | AA131793 |
| 224599_at | CGGBP1 | BE501318 |
| 224163_s_at | DMAP1 | AL136657.1 |
| 227580_s_at | DKFZP434B0335 | BE616972 |
| 224593_at | DKFZp761B128 | BE965646 |
| 225876_at | DJ462O23.2 | T84558 |
| 225732_at | | AU146850 |
| 232001_at | | AW193600 |
| 228077_at | MGC3207 | AK026666.1 |
| 218735_s_at | AF020591 | AA349848 |
| 213573_at | KPNB1 | AA861608 |
| 210555_s_at | NFATC3 | U85430.1 |
| 239278_at | | AI471969 |
| 228972_at | PITPN | AI028602 |
| 227585_at | FLJ14600 | AI359136 |
| 219627_at | FLJ12700 | NM_024910 |
| 221842_s_at | ZNF131 | BE972394 |
| 218531_at | FLJ21749 | NM_025124 |
| 218517_at | Jade-1 | NM_024900 |
| 227449_at | | AI799018 |
| 226611_s_at | p30 | AA722878 |
| 216241_s_at | TCEA1 | X57198.1 |
| 208667_s_at | ST13 | U17714.1 |
| 210017_at | MALT1 | AF070528.1 |
| 230224_at | | BF446577 |
| 229083_at | | AI672356 |
| 229590_at | RPL13 | AI369389 |
| 219293_s_at | PTD004 | NM_013341 |
| 214749_s_at | FLJ20811 | AK000818.1 |
| 225478_at | MRPL19; RLX1; RPML15; MRP-L15; KIAA0104; MGC20675; RPML15 | BE783723 |
| 216305_s_at | KIAA0104 | AC005034 |
| 228099_at | MGC41917 | AI805301 |
| 209841_s_at | LRRN3 | AL442092.1 |
| 226718_at | KIAA1163 | AA001423 |
| 208944_at | TGFBR2 | D50683.1 |
| 219025_at | TEM1 | NM_020404 |
| 227877_at | | AI991103 |
| 208895_s_at | DDX18 | BC003360.1 |
| 217019_at | | AL137162 |
| 203366_at | POLG | NM_002693 |
| 202577_s_at | FLJ11126 | BC005162.1 |
| 229064_at | DSCR1L2 | BE670097 |
| 228381_at | | AV716964 |
| 212508_at | MOAP1 | AK024029.1 |
| 202595_s_at | LEPROTL1 | AF161461.1 |
| 202165_at | PPP1R2 | NM_006241.1 |
| 200666_s_at | DNAJB1 | NM_006145 |
| 200811_at | CIRBP | NM_001280 |
| 212131_at | DKFZP434D1335 | AL117499.1 |
| 214482_at | ZNF46 | NM_006977.1 |
| 221519_at | SHFM3 | AF281859.1 |
| 214177_s_at | HPIP | AI935162 |
| 213340_s_at | KIAA0495 | AB007964.1 |
| 213598_at | HSA9761 | W87688 |
| 222010_at | TCP1 | BF224073 |
| 211988_at | SMARCE1 | NM_003079.1 |
| 224968_at | MGC15407 | AL518311 |
| 225396_at | | AI928212 |
| 225295_at | KIAA1265 | AB033091.1 |
| 202408_s_at | PRPF31 | NM_015629 |
| 229264_at | | AI675152 |
| 37590_g_at | | AL109698 |
| 212706_at | CAPRI | AB011110.2 |
| 218237_s_at | SLC38A1 | NM_030674 |
| 221897_at | TRIM52 | AA205660 |
| 228571_at | | BE963438 |
| 227701_at | FLJ10188 | AK024739.1 |
| 223444_at | SENP7 | AL136599.1 |
| 225892_at | | BF438417 |
| 225517_at | PRO1914 | AW236976 |
| 224643_at | LOC133619 | AL524045 |
| 224786_at | HRIHFB2072 | AL133580.1 |
| 227361_at | HS3ST3B1 | AA780067 |
| 226016_at | CD47 | AL118798 |
| 200802_at | SARS | NM_006513 |
| 219765_at | FLJ12586 | NM_024620 |
| 239049_at | ROCK1 | BF514509 |
| 220113_x_at | POLR1B | NM_019014 |
| 214594_x_at | ATP8B1 | BG252666 |
| 220071_x_at | FLJ10460 | NM_018097 |
| 210679_x_at | | BC002629.1 |
| 207730_x_at | FLJ20700 | NM_017932 |
| 206792_x_at | PDE4C | NM_000923 |
| 217679_x_at | | AI683552 |
| 214902_x_at | | AL080232.1 |
| 217713_x_at | | AA126763 |
| 208137_x_at | MGC5384 | NM_030972 |
| 204387_x_at | MRP63 | NM_024026 |
| 218155_x_at | FLJ10534 | AK026565.1 |
| 215359_x_at | ZNF44 | AI758888 |
| 219392_x_at | FLJ11029 | NM_018304 |
| 219678_x_at | DCLRE1C | NM_022487 |

TABLE 2A-continued

| Affymetrix ID | Common | Genbank |
|---|---|---|
| 215985_at | HCGVIII-1 | X92110.1 |
| 212503_s_at | KIAA0934 | N31807 |
| 205934_at | PLCL1 | NM_006226 |
| 204992_s_at | PFN2 | NM_002628 |
| 200912_at | EIF4A2 | NM_001967 |
| 200847_s_at | MGC8721 | NM_016127 |
| 212783_at | RBBP6 | AK026954.1 |
| 217627_at | FLJ30921 | BE515346 |
| 220760_x_at | FLJ14345 | NM_024733 |
| 236267_at | JAZ | BG178775 |
| 204635_at | RPS6KA5 | NM_004755 |
| 217446_x_at | | AL080160.1 |
| 218496_at | RNASEH1 | BG534527 |
| 211009_s_at | ZNF271 | AF159567.1 |
| 228393_s_at | | BF508739 |
| 228392_at | | BF508739 |
| 214662_at | KIAA0007 | D26488.1 |
| 222243_s_at | TOB2 | AB051450.1 |
| 222204_s_at | RRN3 | AL110238.1 |
| 201517_at | NCBP2 | BC001255.1 |
| 217776_at | RDH11 | AF167438.1 |
| 202060_at | SH2BP1 | NM_014633 |
| 208296_x_at | GG2-1 | NM_014350 |
| 216321_s_at | NR3C1 | X03348.1 |
| 213000_at | KIAA0136 | AP000693 |
| 202163_s_at | CNOT8 | NM_004779 |
| 201437_s_at | EIF4E | NM_001968 |
| 214751_at | | BE541042 |
| 212536_at | ATP11B | AB023173.1 |
| 203310_at | STXBP3 | NM_007269 |
| 213145_at | | BF001666 |
| 204075_s_at | KIAA0562 | NM_014704 |
| 218528_s_at | RNF38 | NM_022781 |
| 212267_at | KIAA0261 | D87450.1 |
| 217466_x_at | | L48784 |
| 218352_at | RCBTB1 | NM_018191 |
| 209096_at | UBE2V2 | U62136.2 |
| 201424_s_at | CUL4A | NM_003589 |
| 204831_at | | R59697 |
| 204291_at | KIAA0335 | NM_014803 |
| 203801_at | MRPS14 | NM_022100.1 |
| 221891_x_at | HSPA8 | AA704004 |
| 210338_s_at | HSPA8 | AB034951.1 |
| 208687_x_at | HSPA8 | AF352832.1 |
| 206976_s_at | HSPH1 | NM_006644 |
| 221744_at | HAN11 | AK026008.1 |
| 218565_at | HSPC109 | BG223334 |
| 226153_s_at | CNOT6L | AW514857 |
| 225314_at | MGC45416 | BG291649 |
| 205677_s_at | DLEU1 | NM_005887 |
| 214615_at | P2Y10 | NM_014499.1 |
| 216547_at | | AL353681 |
| 217347_at | | Z82202 |
| 201345_s_at | UBE2D2 | NM_003339 |
| 220054_at | IL23A | NM_016584 |
| 202774_s_at | SFRS8 | AI023864 |
| 201143_s_at | EIF2S1 | BC002513.1 |
| 214519_s_at | RLN2 | NM_005059.1 |
| 217394_at | TRA@ | AE000659 |
| 244798_at | | AA398139 |
| 213567_at | | BF431965 |
| 213035_at | KIAA0379 | AI081194 |
| 205571_at | LIPT1 | NM_015929 |
| 201272_at | AKR1B1 | NM_001628 |
| 234192_s_at | | AK026487.1 |
| 214855_s_at | TULIP1 | AL050050.1 |
| 202259_s_at | CG005 | NM_014887 |
| 212205_at | H2AV | BF343852 |
| 206445_s_at | HRMT1L2 | NM_001536 |
| 203259_s_at | CGI-130 | BC001671.1 |
| 219006_s_at | HSPC125 | NM_014165 |
| 211747_s_at | LSM5 | BC005938.1 |
| 203316_s_at | SNRPE | NM_003094 |
| 221564_at | HRMT1L1 | AL570294 |
| 225619_at | FLJ30046 | AV730849 |
| 57516_at | MGC13138 | AA746290 |
| 239231_at | | BE464819 |
| 202594_at | LEPROTL1 | NM_015344 |
| 228071_at | hIAN7 | AA858297 |
| 228916_at | FLJ32343 | BE857467 |
| 226529_at | FLJ11273 | BF513060 |
| 206989_s_at | SFRS2IP | NM_004719 |
| 222028_at | ZNF45 | AI967981 |
| 202042_at | HARS | NM_002109 |
| 202217_at | C21orf33 | NM_004649 |
| 55616_at | CAB2 | AI703342 |
| 228959_at | | AI676241 |
| 224755_at | SMBP | BE621524 |
| 212560_at | | AV728268 |
| 203509_at | SORL1 | NM_003105 |
| 228416_at | | AI149508 |
| 214220_s_at | ALMS1 | AW003635 |
| 225330_at | MGC18216 | AL044092 |
| 227844_at | WBP3 | AI089932 |
| 212873_at | HA-1 | BE349017 |
| 212655_at | BDG-29 | AB011151.1 |
| 238311_at | | BF940192 |
| 238156_at | | AW205632 |
| 222244_s_at | FLJ20618 | AK000749.1 |
| 221834_at | SIAH1 | U70056 |
| 213637_at | ROK1 | BE503392 |
| 204516_at | SCA7 | BG390306 |
| 225760_at | KIAA1915 | AI302244 |
| 206828_at | TXK | NM_003328 |
| 238929_at | | N30132 |
| 218425_at | TRIAD3 | BC000787.1 |
| 205684_s_at | FLJ20686 | NM_017925 |
| 208289_s_at | EI24 | NM_004879 |
| 225409_at | | AL529672 |
| 214949_at | | AL050136.1 |
| 218050_at | BM-002 | NM_016617 |
| 228680_at | | AW340096 |
| 213474_at | FLJ32069 | AI890903 |
| 231929_at | | AI458439 |
| 50376_at | EZF-2 | AI278629 |
| 229348_at | | N30416 |
| 208745_at | ATP5L | AA917672 |
| 217961_at | FLJ20551 | NM_017875 |
| 209382_at | RPC62 | U93867.1 |
| 230479_at | | AI872374 |
| 228291_s_at | | AI806322 |
| 218642_s_at | MGC2217 | NM_024300 |
| 203494_s_at | KIAA0092 UNC84B; SUN2; | NM_014679 |
| 212144_at | KIAA0668 | AL021707 |
| 219698_s_at | FLJ23017 | NM_022840 |
| 215283_at | | U79248.1 |
| 228974_at | | AI816281 |
| 226350_at | | AU155565 |
| 64438_at | FLJ22222 | W19668 |
| 243495_s_at | | AL036450 |
| 232392_at | SFRS3 | BE927772 |
| 230820_at | SMURF2 | BF111169 |
| 228477_at | | AV707196 |
| 228993_s_at | PDCD4 | AV728606 |
| 226880_at | NUCKS | AL035851 |
| 230085_at | | AW263542 |
| 226085_at | | AA181060 |
| 201737_s_at | TEB4 | NM_005885 |
| 221419_s_at | | NM_013307 |
| 214182_at | ARF6 | AA243143 |
| 214041_x_at | RPL37A | BE857772 |
| 228204_at | PSMB4 | AA630330 |
| 204290_s_at | ALDH6A1 | NM_005589 |
| 229803_s_at | NUDT3 | AI347000 |
| 242104_at | | AA826288 |
| 223936_s_at | FOXP1 | BC005055.1 |
| 219343_at | HARC | NM_017913 |
| 218929_at | CARF | NM_017632 |
| 208184_s_at | TMEM1 | NM_003274 |
| 213152_s_at | SRP46 | AI343248 |
| 209657_s_at | HSF2 | M65217.1 |

TABLE 2A-continued

| Affymetrix ID | Common | Genbank |
|---|---|---|
| 204176_at | AB026190 | AA808694 |
| 212781_at | RBBP6 | AK026954.1 |
| 209712_at | UGTREL7 | N80922 |
| 202683_s_at | RNMT | NM_003799 |
| 213372_at | LOC152559 | AW173157 |
| 202853_s_at | RYK | NM_002958 |
| 217843_s_at | HSPC126 | NM_014166 |
| 210691_s_at | SIP | AF275803.1 |
| 203203_s_at | HRB2 | NM_007043 |
| 234975_at | | BE544748 |
| 216218_s_at | PLCL2 | AK023546.1 |
| 221268_s_at | SGPP1 | NM_030791 |
| 219767_s_at | CRYZL1 | NM_005111 |
| 212107_s_at | DDX9 | BE910323 |
| 211681_s_at | LIM | AF116705.1 |
| 206968_s_at | NFRKB | NM_006165 |
| 210257_x_at | CUL4B | AF212995.1 |
| 210568_s_at | RECQL | BC001052.1 |
| 209471_s_at | FNTA | L00634.1 |
| 202742_s_at | PRKACB | NM_002731 |
| 201151_s_at | MBNL | NM_021038.1 |
| 201946_s_at | CCT2 | AL545982 |
| 201635_s_at | FXR1 | AI990766 |
| 205882_x_at | ADD3 | AI818488 |
| 201752_s_at | ADD3 | AI763123 |
| 202479_s_at | GS3955 | BC002637.1 |
| 207627_s_at | TFCP2 | NM_005653 |
| 214359_s_at | HSPCB | AI218219 |
| 201988_s_at | CREBL2 | NM_001310.1 |
| 202089_s_at | LIV-1 | NM_012319 |
| 211937_at | EIF4B | NM_001417.1 |
| 216593_s_at | PIGCP1 | AB000359 |
| 213461_at | | AI800983 |
| 221423_s_at | SMAP-5 | NM_030799 |
| 201781_s_at | AIP | AL558532 |
| 217412_at | TRA@ | AE000659 |
| 238692_at | FLJ33957 | AL040935 |
| 213079_at | DT1P1A10 | AA223871 |
| 214666_x_at | IREB2 | AI204981 |
| 228725_x_at | HRMT1L1 | BF003112 |
| 227981_at | | AI741458 |
| 221214_s_at | DKFZP586J1624 | NM_015537 |
| 208657_s_at | MSF | AF142408.1 |
| 207556_s_at | DGKZ | NM_003646 |
| 225458_at | DKFZP564I1171 | BF528646 |
| 225628_at | MLLT6 | BE677453 |
| 222790_s_at | FLJ11220 | BE888593 |
| 221011_s_at | LBH | NM_030915 |
| 218127_at | NFYB | AI804118 |
| 218165_at | FLJ11730 | NM_022756 |
| 222789_at | FLJ11220 | BE888593 |
| 212697_at | LOC162427 | AL515874 |
| 212190_at | SERPINE2 | AL541302 |
| 213031_s_at | FLJ14888 | AF161382.1 |
| 203958_s_at | KIAA0478 | AI557467 |
| 213019_at | RANBP6 | AI123233 |
| 205324_s_at | FTSJ1 | NM_012280 |
| 218170_at | CGI-111 | NM_016048 |
| 203449_s_at | TERF1 | NM_017489 |
| 207845_s_at | APC10 | NM_014885 |
| 201017_at | EIF1A | BE542684 |
| 223189_x_at | MLL5 | AW082219 |
| 238761_at | | BE645241 |
| 222826_at | PLDN | BC004819.1 |
| 235369_at | C14orf28 | BF435952 |
| 203277_at | DFFA | NM_004401 |
| 231840_x_at | | AK000803.1 |
| 208740_at | SAP18 | NM_005870.2 |
| 218700_s_at | RAB7L1 | BC002585.1 |
| 217608_at | FLJ36754 | AW408767 |
| 204314_s_at | CREB1 | NM_004379 |
| 219056_at | FLJ11712 | NM_024570 |
| 229908_s_at | CAB56184 | BF338332 |
| 218149_s_at | DKFZp434K1210 | NM_017606 |
| 215460_x_at | BRD1 | AL080149.1 |
| 204520_x_at | BRD1 | NM_014577 |
| 212200_at | POU2F1 | AB014592.1 |
| 202832_at | GCC185 | NM_014635 |
| 201344_at | UBE2D2 | NM_003339.1 |
| 212244_at | GRINL1A | AI632774 |
| 225276_at | | AA143579 |
| 224482_s_at | | BC006240.1 |
| 214958_s_at | EVIN1 | AK021738.1 |
| 210622_x_at | CDK10 | AF153430.1 |
| 212259_s_at | HPIP | BF344265 |
| 226030_at | ACADSB | BE897866 |
| 203551_s_at | COX11 | NM_004375 |
| 210018_x_at | MALT1 | AB026118.1 |
| 225958_at | M6PR | AI554106 |
| 220206_at | FLJ23151 | NM_024772 |
| 205987_at | CD1C | NM_001765 |
| 216559_x_at | | AL050348 |
| 227221_at | | N36085 |
| 223283_s_at | SDCCAG33 | AF039698.1 |
| 224645_at | EIF4EBP2 | BG106477 |
| 217900_at | FLJ10326 | NM_018060 |
| 208669_s_at | CRI1 | AF109873.1 |
| 230779_at | | BF594371 |
| 227984_at | | BE464483 |
| 221757_at | MGC17330 | AC002073 |
| 221756_at | MGC17330 | AC002073 |
| 216033_s_at | FYN | S74774.1 |
| 210105_s_at | FYN | M14333.1 |
| 211989_at | SMARCE1 | NM_003079.1 |
| 53076_at | B4GALT7 | AI040029 |
| 222297_x_at | RPL18 | AV738806 |
| 212881_at | PIASY | NM_015897.1 |
| 208089_s_at | TDRD3 | NM_030794 |
| 207769_s_at | PQBP1 | NM_005710 |
| 219939_s_at | D1S155E | NM_007158 |
| 218277_s_at | FLJ22060 | NM_024612 |
| 203303_at | TCTE1L | NM_006520 |
| 203544_s_at | STAM | NM_003473 |
| 217833_at | | NM_006372.1 |
| 201366_at | ANXA7 | NM_004034 |
| 217340_at | | AL024509 |
| 203078_at | CUL2 | U83410.1 |
| 216348_at | | AL049693 |
| 216954_x_at | ATP5O | S77356.1 |
| 213287_s_at | KRT10; K10; KPP | X14487 |
| 208760_at | | NM_003345.1 |
| 231851_x_at | KIAA1712 | AB051499.1 |
| 203445_s_at | OS4 | NM_005730 |
| 203341_at | CBF2 | NM_005760 |
| 235432_at | FLJ35693 | BE865779 |
| 225635_s_at | | AK023696.1 |
| 211953_s_at | KPNB3 | NM_002271.1 |
| 239467_at | | AI806747 |
| 226680_at | PEGASUS | BF056303 |
| 226352_at | | BF447037 |
| 239300_at | | AI632214 |
| 233019_at | | AU145061 |
| 229384_at | | BE044193 |
| 206099_at | PRKCH | NM_006255 |
| 231713_s_at | ELP2 | NM_018255.1 |
| 228495_at | | AI880633 |
| 214061_at | MGC21654 | AI017564 |
| 221103_s_at | FLJ11142 | NM_018338 |
| 228171_s_at | DKFZP434I216 | AI056683 |
| 205087_at | DKFZP566K023 | NM_015485 |
| 209431_s_at | ZNF278 | AF254083.1 |
| 218919_at | FLJ14007 | NM_024699 |
| 212936_at | DKFZP564D172 | AI927701 |
| 212321_at | SGPL1 | AF144638.1 |
| 212824_at | FUBP3 | U69127.1 |
| 218637_at | IMPACT | NM_018439 |
| 235729_at | FLJ14457 | T93113 |
| 232167_at | SLC2A11 | BE675356 |
| 51200_at | FLJ20850 | AI744084 |
| 202880_s_at | PSCD1 | NM_004762 |
| 227811_at | FGD3 | AK000004.1 |
| 38892_at | KIAA0240 | D87077 |

TABLE 2A-continued

| Affymetrix ID | Common | Genbank |
|---|---|---|
| 209130_at | SNAP23 | BC003686.1 |
| 201833_at | HDAC2 | NM_001527 |
| 203182_s_at | SRPK2 | NM_003138 |
| 212640_at | LOC201562 | AV712602 |
| 203983_at | TSNAX | NM_005999 |
| 228548_at | | AU126086 |
| 226910_at | LOC51122 | AW008502 |
| 214857_at | | AL050035.1 |
| 228005_at | | BE677308 |
| 241299_at | | AI651969 |
| 202355_s_at | GTF2F1 | BC000120.1 |
| 65635_at | FLJ21865 | AL044097 |
| 220349_s_at | FLJ21865 | NM_022759 |
| 228662_at | | AI492369 |
| 218220_at | C12orf10 | NM_021640 |
| 201106_at | GPX4 | NM_002085 |
| 203025_at | ARD1 | NM_003491 |
| 218001_at | MRPS2 | NM_016034 |
| 218064_s_at | NAKAP95 | NM_014371 |
| 219628_at | WIG1 | NM_022470 |
| 49329_at | FLJ14360 | N38751 |
| 212946_at | KIAA0564 | AK025432.1 |
| 201307_at | FLJ10849 | AL534972 |
| 212607_at | | U79271.1 |
| 225244_at | IMAGE3451454 | AA019893 |
| 200957_s_at | SSRP1 | NM_003146 |
| 244716_x_at | MGC23244 | AI817976 |
| 218120_s_at | HMOX2 | D21243.1 |
| 226548_at | LOC112868 | AI935915 |
| 204333_at | AGA | NM_000027 |
| 217946_s_at | SAE1 | NM_016402 |
| 204985_s_at | MGC2650 | NM_024108 |
| 213109_at | KIAA0551 | N25621 |
| 210625_s_at | AKAP1 | U34074.1 |
| 210349_at | CAMK4 | L24959.1 |
| 203578_s_at | SLC7A6 | NM_003983.1 |
| 235603_at | HNRPU | N95466 |
| 212168_at | RBM12 | AB018308.1 |
| 204905_s_at | EEF1E1 | NM_004280 |
| 218100_s_at | ESRRBL1 | NM_018010 |
| 217956_s_at | MASA | NM_021204 |
| 205176_s_at | ITGB3BP | NM_014288 |
| 231234_at | | AV699565 |
| 204857_at | MAD1L1 | NM_003550 |
| 202139_at | AKR7A2 | NM_003689 |
| 219041_s_at | RIP60 | NM_014374 |
| 218518_at | C5orf5 | NM_016603 |
| 234970_at | C14orf47 | AI741469 |
| 212399_s_at | KIAA0121 | D50911.2 |
| 229814_at | | BG149337 |
| 217805_at | ILF3 | NM_004516 |
| 203179_at | GALT | NM_000155 |
| 212160_at | XPOT | AI984005 |
| 208738_x_at | SMT3H2 | AK024823.1 |
| 210970_at | IBTK | AF235049.1 |
| 234969_s_at | EPC1 | AK024117.1 |
| 234807_x_at | | AL121916 |
| 216383_at | | U52111 |
| 230490_x_at | | AI866717 |
| 227964_at | FLJ31034 | BF435621 |
| 226449_at | FLJ36090 | AI392933 |
| 222494_at | C14orf116 | AW051527 |
| 219100_at | FLJ22559 | NM_024928 |
| 225584_at | | BE880820 |
| 204000_at | GNB5 | NM_016194 |
| 200845_s_at | PRDX6 | NM_004905 |
| 227590_at | | BE501980 |
| 202261_at | TCFL1 | NM_005997 |
| 209702_at | MGC5149 | U79260.1 |
| 222517_at | AP3M1 | AA700485 |
| 228324_at | | BF031819 |
| 213416_at | ITGA4 | BG532690 |
| 237753_at | | AW504569 |
| 204651_at | | AW003022 |
| 202703_at | DUSP11 | NM_003584 |
| 204327_s_at | ZNF202 | N91520 |
| 201612_at | ALDH9A1 | NM_000696 |
| 205277_at | PRDM2 | NM_012231 |
| 234921_at | | AC007228 |
| 229725_at | | AV705292 |
| 239896_at | | AW190479 |
| 230489_at | CD5 | AI797836 |
| 227722_at | | AW043594 |
| 207283_at | DKFZp547I014 | NM_020217 |
| 228516_at | CDAN1 | AI122852 |
| 240413_at | | AI827431 |
| 220646_s_at | KLRF1 | NM_016523 |
| 205291_at | IL2RB | NM_000878 |
| 206785_s_at | KLRC2 | NM_002260 |
| 217143_s_at | TRD@ | X06557.1 |
| 216191_s_at | TRA@ | X72501.1 |
| 213830_at | TRD@ | AW007751 |
| 211597_s_at | LAGY | AB059408.1 |
| 207840_at | BY55 | NM_007053 |
| 214470_at | KLRB1 | NM_002258.1 |
| 207723_s_at | KLRC3 | NM_002261 |
| 213906_at | MYBL1 | AW592266 |
| 211685_s_at | NCALD | AF251061.1 |
| 209160_at | AKR1C3 | AB018580.1 |
| 219529_at | CLIC3 | NM_004669 |
| 230464_at | EDG8 | AI814092 |
| 205495_s_at | GNLY | NM_006433 |
| 218638_s_at | SPON2 | NM_012445 |
| 228788_at | PPIL2 | AA425358 |
| 225688_s_at | FLJ21791 | AK025444.1 |
| 205171_at | PTPN4 | NM_002830 |
| 206267_s_at | MATK | NM_002378 |
| 222000_at | | AI915947 |
| 212959_s_at | MGC4170 | AK001821.1 |
| 223228_at | DKFZp761O17121 | AL136553.1 |
| 219304_s_at | SCDGF-B | NM_025208 |
| 218568_at | FLJ10842 | NM_018238 |
| 226157_at | TFDP2 | AI569747 |
| 211984_at | | AI653730 |
| 201648_at | | AL039831 |
| 213618_at | CENTD1 | AB011152.1 |
| 229025_s_at | FLJ25059 | AW008627 |
| 227567_at | | AL524467 |
| 244024_at | ZNF21 | T67481 |
| 222146_s_at | TCF4 | AK026674.1 |
| 203753_at | TCF4 | NM_003199 |
| 212605_s_at | | W85912 |
| 203825_at | BRD3 | NM_007371 |
| 238656_at | RAD50 | AA877043 |
| 226062_x_at | FLJ11280 | AB037811.1 |
| 217810_x_at | LARS | NM_020117 |
| 218371_s_at | PSPC1 | NM_018282 |
| 218403_at | HSPC132 | NM_016399 |
| 218283_at | SS18L2 | NM_016305 |
| 214317_x_at | RPS9 | BE348997 |
| 216088_s_at | PSMA7 | AL078633 |
| 210574_s_at | NUDC | AF241788.1 |
| 200959_at | FUS | NM_004960 |
| 209538_at | ZNF32 | U69645.1 |
| 201509_at | IDH3B | NM_006899 |
| 201993_x_at | HNRPDL | NM_005463 |
| 203051_at | KIAA0945 | NM_014952 |
| 212826_s_at | SLC25A6 | AI961224 |
| 212085_at | SLC25A6 | AA916851 |
| 204102_s_at | EEF2 | NM_001961 |
| 242214_at | RPS27A | AU152194 |
| 235222_x_at | | AW675725 |
| 218573_at | MAGEH1 | NM_014061 |
| 218025_s_at | PECI | NM_006117 |
| 44040_at | KIAA1940 | AA524093 |
| 220036_s_at | LIMR | NM_018113 |
| 205192_at | MAP3K14 | NM_003954 |
| 239401_at | | AI668672 |
| 213263_s_at | MAP3K12 | AW025150 |
| 212814_at | KIAA0828 | AB020635.1 |
| 212922_s_at | HSKM-B | AF070592.1 |
| 201343_at | UBE2D2 | NM_003339.1 |

TABLE 2A-continued

| Affymetrix ID | Common | Genbank |
|---|---|---|
| 202693_s_at | STK17A | NM_004760.1 |
| 221963_x_at | | BE999967 |
| 218674_at | FLJ13611 | NM_024941 |
| 212297_at | FLJ20986 | BF218804 |
| 212588_at | PTPRC | AI809341 |
| 212132_at | DKFZP434D1335 | AL117499.1 |
| 208127_s_at | SOCS5 | NM_014011 |
| 204449_at | PDCL | NM_005388 |
| 215009_at | | U92014.1 |
| 211962_s_at | ZFP36L1 | X79067.1 |
| 213251_at | | AV712064 |
| 202250_s_at | H326 | NM_015726 |
| 201788_at | RNAHP | NM_007372 |
| 52731_at | FLJ20294 | AI359466 |
| 202692_s_at | UBTF | NM_014233 |
| 204559_s_at | LSM7 | NM_016199 |
| 235292_at | | BE875232 |
| 224919_at | MRPS6 | AL555227 |
| 223431_at | FLJ11230 | BC001818.1 |
| 200627_at | TEBP | BC003005.1 |
| 221507_at | | BG258639 |
| 208807_s_at | CHD3 | U91543.1 |
| 238520_at | | BF724270 |
| 226280_at | LAMB1 | AA133277 |
| 223455_at | | BG493862 |
| 212034_s_at | EXO70 | BE646386 |
| 227199_at | | AW027812 |
| 213815_x_at | NY-REN-24 | AI913329 |
| 202809_s_at | FLJ21919 | NM_023015 |
| 208503_s_at | ODAG | NM_021167 |
| 201837_s_at | STAF65(gamma) | AF197954.1 |
| 208424_s_at | LOC57019 | NM_020313 |
| 203073_at | COG2 | NM_007357 |
| 219603_s_at | ZNF226 | NM_015919 |
| 219443_at | C20orf13 | NM_017714 |
| 223983_s_at | DKFZP762D096 | BC004957.1 |
| 209565_at | ZNF183 | BC000832.1 |
| 205718_at | ITGB7 | NM_000889 |
| 223154_at | MRPL1 | AF212225.1 |
| 202208_s_at | ARL7 | BC001051.1 |
| 204918_s_at | MLLT3 | NM_004529 |
| 241525_at | LOC200772 | AV700191 |
| 40255_at | DDX28 | AC004531 |
| 225376_at | LOC284734 | BG480592 |
| 210418_s_at | IDH3B | AF023265.1 |
| 205055_at | ITGAE | NM_002208 |
| 224734_at | HMGB1 | BF673940 |
| 201417_at | | NM_003107.1 |
| 228239_at | C21orf51 | AA148789 |
| 201416_at | | NM_003107.1 |
| 227726_at | MGC2647 | BF057084 |
| 227640_s_at | LOC222136 | AI492167 |
| 228369_at | TNRC5 | AI262560 |
| 238768_at | | BF976290 |
| 228590_at | | AA045257 |
| 224718_at | | AK025731.1 |
| 225350_s_at | FLJ13456 | AV701229 |
| 222547_at | FLJ20373 | AL561281 |
| 217549_at | | AW574933 |
| 212886_at | DKFZP434C171 | AL080169.1 |
| 211208_s_at | CASK | AB039327.2 |
| 228155_at | MGC4248 | BF512388 |
| 224435_at | MGC4248 | BC005871.1 |
| 224709_s_at | | AF131831.1 |
| 228334_x_at | KIAA1712 | AI633734 |
| 204718_at | EPHB6 | NM_004445 |
| 226909_at | KIAA1729 | AW270138 |
| 225853_at | GNPNAT1 | BE789346 |
| 235170_at | FLJ34299 | T52999 |
| 221452_s_at | MGC1223 | NM_030969 |
| 222125_s_at | PH-4 | BC000580.1 |
| 218617_at | IPT | NM_017646 |
| 219335_at | FLJ12969 | NM_022838 |
| 206833_s_at | ACYP2 | NM_001108 |
| 207786_at | MGC4663 | NM_024514 |
| 212673_at | METAP1 | D42084.1 |
| 59999_at | HIF1AN | W37897 |
| 214259_s_at | AKR7A2 | AW074911 |
| 225967_s_at | | BF683512 |
| 49111_at | | N80935 |
| 43511_s_at | | AI201594 |
| 226656_at | CRTAP | AW024741 |
| 220307_at | CD244 | NM_016382 |
| 212224_at | ALDH1A1 | NM_000689.1 |
| 202331_at | BCKDHA | NM_000709 |
| 218271_s_at | PARL | NM_018622 |
| 212063_at | CD44 | BE903880 |
| 220750_s_at | LEPRE1 | NM_022356 |
| 206682_at | HML2 | NM_006344 |
| 219093_at | FLJ20701 | NM_017933 |
| 211734_s_at | FCER1A | BC005912.1 |
| 210982_s_at | HLA-DRA | M60333.1 |
| 208894_at | HLA-DRA | M60334.1 |
| 203932_at | HLA-DMB | NM_002118 |
| 203300_x_at | AP1S2 | NM_003916 |
| 214058_at | | M19720 |
| 203582_s_at | RAB4A | NM_004578 |
| 229588_at | ERdj5 | AA651899 |
| 218718_at | PDGFC | NM_016205 |
| 203581_at | RAB4A | BC002438.1 |
| 225553_at | | AL042817 |
| 212416_at | SCAMP1 | BF058944 |
| 229544_at | | AI690169 |
| 210567_s_at | SKP2 | BC001441.1 |
| 226692_at | | AI092931 |
| 224392_s_at | OPN3 | AF303588.1 |
| 225487_at | DKFZp434C1714 | AI720705 |
| 209263_x_at | TM4SF7 | BC000389.1 |
| 215088_s_at | | BG110532 |
| 203166_at | CFDP1 | NM_006324 |
| 226987_at | HUMAGCGB | W68720 |
| 234947_s_at | FLJ13188 | AK026630.1 |
| 225889_at | MGC17922 | BF475280 |
| 225268_at | KPNA4 | AK021602.1 |
| 222438_at | HSPC126 | AK001934.1 |
| 229355_at | UBE2D3 | AU150386 |
| 244743_x_at | ZNF138 | AA114243 |
| 221596_s_at | DKFZP564O0523 | AL136619.1 |
| 212774_at | RP58 | AJ223321 |
| 205474_at | CRLF3 | NM_015986 |
| 228961_at | FLJ35954 | R66534 |
| 225123_at | | BE883841 |
| 227636_at | | BG500677 |
| 226392_at | | AI888503 |
| 209330_s_at | HNRPD | D55674.1 |
| 201381_x_at | SIP | AF057356.1 |
| 242878_at | | BF061275 |
| 236814_at | MDM4 | AA745971 |
| 225116_at | | BG166310 |
| 224754_at | | BG431266 |
| 222024_s_at | AKAP13 | AK022014.1 |
| 230703_at | | AA001543 |
| 225956_at | LOC153222 | AL565238 |
| 201488_x_at | KHDRBS1 | BC000717.1 |
| 210162_s_at | NFATC1 | U08015.1 |
| 225916_at | ZNF131 | AA789302 |
| 231225_at | | AI568622 |
| 227402_s_at | MGC14595 | AI056895 |
| 225641_at | MEF2D | AI829724 |
| 222251_s_at | GMEB2 | AL133646.1 |
| 217952_x_at | PHF3 | AW189430 |
| 200977_s_at | TAX1BP1 | AF090891.1 |
| 217456_x_at | HLA-E | M31183.1 |
| 238431_at | | W68845 |
| 235424_at | | N66727 |
| 218905_at | FLJ20530 | NM_017864 |
| 227551_at | CGI-67 | BE856596 |
| 218539_at | FBXO34 | NM_017943 |
| 226924_at | | AI016355 |
| 226452_at | PDK1 | AU146532 |
| 204788_s_at | PPOX | NM_000309 |
| 227172_at | LOC89894 | BC000282.1 |

TABLE 2A-continued

| Affymetrix ID | Common | Genbank |
|---|---|---|
| 207734_at | LAX | NM_017773 |
| 242463_x_at | MGC5384 | AI620827 |
| 218911_at | GAS41 | NM_006530 |
| 235470_at | LSM8 | AI766279 |
| 227446_s_at | | BF445127 |
| 224364_s_at | PPIL3 | AF251049.1 |
| 212896_at | KIAA0052 | D29641.2 |
| 219644_at | NY-REN-58 | NM_016122 |
| 229312_s_at | GKAP42 | BF434321 |
| 225522_at | | AW628987 |
| 235309_at | | AA126311 |
| 216862_s_at | MTCP1 | Z24459 |
| 210212_x_at | MTCP1 | BC002600.1 |
| 214097_at | RPS21 | AW024383 |
| 213540_at | HSD17B8 | AL031228 |
| 220942_x_at | E2IG5 | NM_014367 |
| 212931_at | TCF20 | AB006630.1 |
| 205419_at | EBI2 | NM_004951 |
| 203380_x_at | SFRS5 | NM_006925 |
| 229854_at | OBSCN | AW614056 |
| 244534_at | ZRF1 | AI695743 |
| 41220_at | KIAA0991 | AB023208 |
| 241859_at | | BF593050 |
| 225346_at | LOC80298 | NM_025198.1 |
| 230739_at | | AI192379 |
| 230793_at | FLJ20048 | BE671038 |
| 227547_at | | AA824321 |
| 200597_at | EIF3S10 | BE614908 |
| 209106_at | NCOA1 | U19179.1 |
| 201876_at | PON2 | NM_000305 |
| 213725_x_at | LOC283824 | AI693140 |
| 203777_s_at | RPS6KB2 | NM_003952 |
| 202182_at | GCN5L2 | NM_021078 |
| 210653_s_at | BCKDHB | M55575.1 |
| 214252_s_at | CLN5 | AV700514 |
| 37549_g_at | B1 | U87408 |
| 226527_at | | AI569785 |
| 225549_at | | BF129093 |
| 212905_at | CSTF2T | BF732638 |
| 201139_s_at | SSB | NM_003142 |
| 223006_s_at | C9orf5 | BG402553 |
| 215690_s_at | GPAA1 | AL157437.1 |
| 211060_x_at | GPAA1 | BC006383.1 |
| 201618_x_at | GPAA1 | NM_003801 |
| 227049_at | LOC147632 | N21127 |
| 225494_at | | BG478726 |
| 224936_at | EIF2S3 | BE252813 |
| 225181_at | ELD/OSA1 | AK000921.1 |
| 219275_at | PDCD5 | NM_004708 |
| 218188_s_at | TIMM13 | NM_012458 |
| 223773_s_at | LOC85028 | AF277181.1 |
| 222848_at | FKSG14 | BC005400.1 |
| 218443_s_at | DAZAP1 | NM_018959 |
| 227451_at | | BF507383 |
| 228604_at | | AI805069 |
| 213507_s_at | KPNB1 | BG249565 |
| 235694_at | | N49233 |
| 227696_at | | AI701408 |
| 230248_x_at | | BE673759 |
| 218981_at | DC11 | NM_020186 |
| 204349_at | CRSP9 | BC005250.1 |
| 214658_at | CGI-109 | BG286537 |
| 201634_at | CYB5-M | NM_030579 |
| 206087_x_at | HFE | NM_000410 |
| 209751_s_at | SEDLP | AF291676.1 |
| 201653_at | CNIH | NM_005776 |
| 200902_at | | NM_004261 15-Sep |
| 235802_at | LOC122618 | BE676703 |
| 229063_s_at | FLJ14642 | AI912238 |
| 228240_at | KIAA1337 | AW952320 |
| 203713_s_at | LLGL2 | NM_004524 |
| 212197_x_at | KIAA0864 | AB020671.1 |
| 239287_at | | AA769410 |
| 226959_at | | AL137430.1 |
| 224516_s_at | HSPC195 | BC006428.1 |
| 231927_at | | BF671883 |
| 225768_at | NR1D2 | AI761621 |
| 223248_at | LOC83693 | AK025626.1 |
| 226255_at | ZNF-kaiso | BE302089 |
| 225117_at | DKFZP727C091 | AL137317.1 |
| 230721_at | LOC146174 | BF436957 |
| 218375_at | NUDT9 | NM_024047 |
| 207922_s_at | MAEA | NM_005882 |
| 79005_at | FLJ14251 | AA504646 |
| 59433_at | LOC286434 | N32185 |
| 32540_at | PPP3CC | AI762547 |
| 220957_at | CTAGE-1 | NM_022663 |
| 216437_at | | AK024949.1 |
| 203999_at | | NM_005639.1 |
| 214923_at | ATP6V1D | AK001155.1 |
| 214775_at | N4BP3 | AW139448 |
| 216540_at | TRA@ | X61072.1 |
| 207152_at | NTRK2 | NM_006180 |
| 202488_s_at | FXYD3 | NM_005971 |
| 202709_at | FMOD | NM_002023 |
| 213919_at | DNAJC4 | AW024467 |
| 205189_s_at | FANCC | NM_000136 |
| 215766_at | | AL096729.1 |
| 213861_s_at | DKFZP586D0919 | N67741 |
| 207041_at | MASP2 | NM_006610 |
| 204665_at | FLJ21168 | NM_025073.1 |
| 215511_at | TCF20 | U19345.1 |
| 37793_r_at | RAD51D | AF034956 |
| 203788_s_at | SEMA3C | AI962897 |
| 216049_at | RHOBTB3 | AK023621.1 |
| 209436_at | SPON1 | AB018305.1 |
| 220721_at | FLJ21941 | NM_025040 |
| 208591_s_at | PDE3B | NM_000922 |
| 208588_at | FKSG2 | NM_021631 |
| 221591_at | JIK | AF181985.1 |
| 204605_at | CGR19 | NM_006568 |
| 206900_x_at | ZNF253 | NM_021047 |
| 201677_at | ELF3 | AI937543 |
| 206910_x_at | HFL3 | NM_005666 |
| 207105_s_at | PIK3R2 | NM_005027 |
| 217052_x_at | | AK024108.1 |
| 207972_at | GLRA1 | NM_000171 |
| 78330_at | ZNF335 | AA845577 |
| 220791_x_at | SCN11A | NM_014139 |
| 203874_s_at | SMARCA1 | NM_003069 |
| 222279_at | | AI669379 |
| 201630_s_at | ACP1 | NM_004300 |
| 216497_at | | AL390738 |
| 213285_at | LOC161291 | AV691491 |
| 208832_at | E46L | AW241832 |
| 209733_at | | AL034399 |
| 205042_at | GNE | NM_005476 |
| 220048_at | EDAR | NM_022336 |
| 219731_at | | NM_024343 |
| 216751_at | | AK024879.1 |
| 205554_s_at | DNASE1L3 | NM_004944 |
| 204151_x_at | AKR1C1 | NM_001353 |
| 212590_at | RRAS2 | BG168858 |
| 222099_s_at | DKFZP434D1335 | AW593859 |
| 47530_at | NAP1 | AA748492 |
| 218287_s_at | EIF2C1 | NM_012199 |
| 209574_s_at | C18orf1 | AI349506 |
| 221087_s_at | APOL3 | NM_014349 |
| 209338_at | TFCP2 | U03494.1 |
| 202264_s_at | TOMM40 | NM_006114 |
| 202183_s_at | KIF22 | NM_007317 |
| 205661_s_at | PP591 | NM_025207 |
| 205510_s_at | FLJ10038 | NM_017976 |
| 219164_s_at | C14orf103 | NM_018036 |
| 235956_at | | AI797063 |
| 221170_at | HRH4 | AF312230.1 |
| 212468_at | SPAG9 | AB011088.1 |
| 221681_s_at | | AF094508.1 |
| 221600_s_at | PTD015 | BC002752.1 |
| 205139_s_at | UST | NM_005715 |
| 215997_s_at | CUL4B | AV694732 |
| 215948_x_at | ZNF237 | AI522311 |

TABLE 2A-continued

| Affymetrix ID | Common | Genbank |
|---|---|---|
| 203321_s_at | KIAA0863 | NM_014913.1 |
| 201917_s_at | FLJ10618 | AI694452 |
| 202526_at | MADH4 | U44378.1 |
| 218268_at | FLJ12085 | NM_022771 |
| 213052_at | PRKAR2A | BF246917 |
| 201380_at | CRTAP | NM_006371 |
| 205232_s_at | PAFAH2 | U89386.1 |
| 222122_s_at | THOC2 | BG403671 |
| 217602_at | PPIA | AI191118 |
| 217322_x_at | | AL024509 |
| 208629_s_at | HADHA | BG472176 |
| 200767_s_at | C9orf10 | NM_014612 |
| 201299_s_at | C2orf6 | NM_018221 |
| 208325_s_at | AKAP13 | NM_006738 |
| 201462_at | KIAA0193 | NM_014766 |
| 203526_s_at | APC | M74088.1 |
| 213979_s_at | CTBP1 | AA053830 |
| 208264_s_at | EIF3S1 | NM_003758 |
| 215057_at | | U66046.1 |
| 215063_x_at | | AL390149.1 |
| 210573_s_at | RPC62 | BC004424.1 |
| 215718_s_at | PHF3 | AI949220 |
| 217795_s_at | MGC3222 | W74580 |
| 202366_at | ACADS | NM_000017 |
| 206499_s_at | CHC1 | NM_001269 |
| 233779_x_at | | AK022046.1 |
| 206158_s_at | ZNF9 | NM_003418 |
| 222151_s_at | FLJ13386 | AK023738.1 |
| 205839_s_at | BZRAP1 | NM_004758 |
| 219599_at | PRO1843 | NM_018507 |
| 202554_s_at | GSTM3 | AL527430 |
| 240015_at | | AI299467 |
| 216508_x_at | WUGSC:H_NH0244E06.1 | AC007277 |
| 201611_s_at | ICMT | NM_012405 |
| 240572_at | | BF436632 |
| 200664_at | DNAJB1 | BG537255 |
| 227558_at | CBX4 | AI570531 |
| 226883_at | | T89044 |
| 227100_at | | AI569766 |
| 204120_s_at | ADK | NM_001123 |
| 215146_s_at | KIAA1043 | AB028966.1 |
| 212528_at | | AL023553 |
| 206744_s_at | ZNF237 | NM_014242 |
| 220949_s_at | MGC5242 | NM_024033 |
| 202461_at | EIF2B2 | NM_014239 |
| 212025_s_at | FLII | U80184 |
| 210417_s_at | PIK4CB | U81802.1 |
| 204252_at | CDK2 | M68520.1 |
| 221207_s_at | NBEA | NM_015678 |
| 213929_at | | AL050204.1 |
| 203790_s_at | UK114 | N54448 |
| 201725_at | C10orf7 | NM_006023 |
| 201701_s_at | PGRMC2 | NM_006320 |
| 201342_at | SNRPC | NM_003093 |
| 202105_at | IGBP1 | NM_001551 |
| 215082_at | | BF973387 |
| 221874_at | KIAA1324 | AB037745.1 |
| 238952_x_at | | BF439163 |
| 232661_s_at | DKFZP564O0523 | AF161422.1 |
| 200751_s_at | HNRPC | BE898861 |
| 205408_at | MLLT10 | NM_004641 |
| 229903_x_at | FLJ25070 | AI632212 |
| 227665_at | | BE968576 |
| 200883_at | UQCRC2 | NM_003366 |
| 225184_at | ELD/OSA1 | AK000921.1 |
| 203552_at | MAP4K5 | AW298170 |
| 202213_s_at | CUL4B | AI650819 |
| 218129_at | NFYB | NM_006166 |
| 202663_at | | AI005043 |
| 224452_s_at | MGC12966 | BC006110.1 |
| 204638_at | ACP5 | NM_001611 |
| 220252_x_at | FLJ11577 | NM_025159 |
| 203375_s_at | TPP2 | NM_003291 |
| 201748_s_at | SAFB | NM_002967 |
| 224580_at | | AK024263.1 |
| 212302_at | KIAA0252 | D87440.1 |
| 203707_at | ZNF263 | NM_005741 |
| 219177_at | BRIX | NM_018321 |
| 218314_s_at | FLJ10726 | NM_018195 |
| 240830_at | | AI300126 |
| 220952_s_at | PEPP2 | NM_019012 |
| 201025_at | IF2 | NM_015904.1 |
| 202372_at | RAB3-GAP150 | BF240652 |
| 213063_at | FLJ11806 | N64802 |
| 238823_at | WBP3 | AA481044 |
| 205562_at | RPP38 | NM_006414 |
| 207445_s_at | CCR9 | AF145439.1 |
| 227616_at | | BG481877 |
| 220985_s_at | DKFZP564A022 | NM_030954 |
| 209835_x_at | CD44 | BC004372.1 |
| 204490_s_at | CD44 | M24915.1 |
| 206621_s_at | WBSCR1 | NM_022170 |
| 201055_s_at | HNRPA0 | NM_006805 |
| 200644_at | MLP | NM_023009 |
| 244443_at | | BE247450 |
| 244219_at | | AI613089 |
| 241845_at | | BE550501 |
| 229574_at | HSU53209 | AI268231 |
| 208705_s_at | EIF5 | AL080102.1 |
| 225250_at | STIM2 | AB040915.1 |
| 228259_s_at | TIGA1 | AW590155 |
| 208094_s_at | MGC10471 | NM_030818 |
| 202573_at | CSNK1G2 | AL530441 |
| 201544_x_at | PABPN1 | BF675004 |
| 212991_at | FBXO9 | AL137520.1 |
| 215722_s_at | SNRPA1 | AJ130971.1 |
| 206036_s_at | REL | NM_002908 |
| 202439_s_at | IDS | NM_000202 |
| 228909_at | C21orf86 | AW131553 |
| 218682_s_at | SLC4A1AP | NM_018158 |
| 207071_s_at | ACO1 | NM_002197 |
| 219163_at | FLJ20079 | NM_017656 |
| 39729_at | NKEFB | L19185 |
| 217144_at | UBBP1 | X04801 |
| 212430_at | RNPC1 | AL109955 |
| 213327_s_at | USP12 | AI820101 |
| 202782_s_at | SKIP | NM_016532 |
| 224653_at | EIF4EBP2 | BG106477 |
| 218570_at | FLJ10450 | NM_018095 |
| 222129_at | MGC3035 | AK026155.1 |
| 208995_s_at | PPIG | U40763.1 |
| 236001_at | | BF446940 |
| 230376_at | | AI339915 |
| 243973_at | | R67076 |
| 229861_at | LOC117584 | N66669 |
| 213879_at | SMT3H2 | AI971724 |
| 229204_at | HP1-BP74 | BE218428 |
| 227748_at | LOC56267 | AI971694 |
| 229436_x_at | C6.1A | AI672084 |
| 225164_s_at | EIF2AK4 | AB037759.1 |
| 220761_s_at | JIK | NM_016281 |
| 224151_s_at | AK3L1 | AF183419.1 |
| 221311_x_at | DJ122O8.2 | NM_020466 |
| 212878_s_at | KNS2 | AA284075 |
| 227712_at | DJ122O8.2 | AV682940 |
| 224533_s_at | TRB@ | M77498.1 |
| 203077_s_at | MADH2 | NM_005901 |
| 213370_s_at | SFMBT | BF057298 |
| 205372_at | PLAG1 | NM_002655 |
| 240102_at | | AW024095 |
| 222875_at | DDX33 | AI720923 |
| 223117_s_at | FLJ20727 | AW025093 |
| 203279_at | EDEM | NM_014674 |
| 219433_at | BCoR | NM_017745 |
| 219854_at | ZNF14 | NM_021030 |
| 219111_s_at | MGC2835 | NM_024072 |
| 212492_s_at | KIAA0876 | AW237172 |
| 238722_x_at | | AI460037 |
| 219045_at | ARHF | NM_019034 |
| 234294_x_at | FLJ20085 | AL390164.1 |
| 218131_s_at | p66alpha | NM_017660 |
| 226133_s_at | EPI64 | AW628835 |

TABLE 2A-continued

| Affymetrix ID | Common | Genbank |
|---|---|---|
| 217775_s_at | RDH11 | NM_016026 |
| 227319_at | C16orf44 | AI693862 |
| 226402_at |  | AW055161 |
| 225982_at | UBTF | BG341575 |
| 202926_at | NAG | NM_015909 |
| 213034_at |  | AB023216.1 |
| 214848_at |  | U79277.1 |
| 230580_at |  | AI222805 |
| 217704_x_at |  | AI820796 |
| 244189_at |  | AI888657 |
| 225155_at |  | BG339050 |
| 235032_at | HSPCB | BG112118 |
| 202135_s_at | ACTR1B | NM_005735 |
| 204772_s_at | TTF1 | NM_007344 |
| 237143_at |  | AW296162 |
| 212834_at | ROK1 | AK001652.1 |
| 223871_x_at | ING5 | BC005370.1 |
| 209788_s_at | ARTS-1 | AF183569.1 |
| 235459_at |  | BF114745 |
| 215482_s_at | EIF2B4 | AJ011307 |
| 232103_at | BPNT1 | AI439695 |
| 225426_at | PPP6C | BF240782 |
| 229410_at |  | AI659219 |
| 224331_s_at | MRPL36 | AB049654.1 |
| 222530_s_at | MKKS | AF275813.1 |
| 225795_at | LOC91689 | AV751709 |
| 216591_s_at | CII-3 | AF080579 |
| 210131_x_at | SDHC | D49737.1 |
| 202004_x_at | SDHC | NM_003001 |
| 225472_at | BAT4 | AF129756 |
| 225717_at | KIAA1715 | AI814587 |
| 220083_x_at | UCHL5 | NM_016017 |
| 214037_x_at | JM1 | BF224247 |
| 229905_at |  | N92500 |
| 201563_at | SORD | L29008.1 |
| 226224_at | DKFZp434D1428 | AI798846 |
| 227410_at | FLJ90022 | AW264102 |
| 226100_at | MLL5 | AI762876 |
| 226712_at |  | BF206389 |
| 205926_at | WSX1 | NM_004843 |
| 212052_s_at | KIAA0676 | AB014576.1 |
| 225341_at | LOC80298 | NM_025198.1 |
| 238077_at | MGC27385 | T75480 |
| 227313_at | MGC40499 | AI870866 |
| 214527_s_at | PQBP1 | AB041836.1 |
| 221893_s_at | MGC20727 | N32831 |
| 234672_s_at | FLJ10407 | AL354612.1 |
| 229143_at | CNOT3 | AW449353 |
| 225455_at | STAF42 | AI760812 |
| 226665_at | DKFZp564C236 | AI986239 |
| 222315_at |  | AW972855 |
| 218150_at | ARL5 | NM_012097 |
| 238155_at |  | AI638235 |
| 230790_x_at | C14orf116 | AI589978 |
| 227001_at |  | AI096706 |
| 203243_s_at | LIM | NM_006457 |
| 218610_s_at | FLJ11151 | NM_018340 |
| 202901_x_at | CTSS | BC002642.1 |
| 210968_s_at | RTN4 | AF333336.1 |
| 214674_at | USP19 | AW451502 |
| 204949_at | ICAM3 | NM_002162 |
| 228108_at |  | AW274846 |
| 227375_at | DKFZp566D1346 | AA152232 |
| 219125_s_at | LOC55974 | NM_018845 |
| 218411_s_at | MBIP | NM_016586 |
| 203818_s_at | SF3A3 | NM_006802 |
| 214672_at | KIAA0998 | AB023215.1 |
| 228988_at | ZNF6 | AU157017 |
| 235024_at | Jade-1 | AI868315 |
| 230598_at | KIAA1387 | BF063821 |
| 225065_x_at | MGC40157 | AI826279 |
| 224871_at |  | AK025464.1 |
| 218992_at | MDS030 | NM_018465 |
| 218201_at | NDUFB2 | NM_004546 |
| 217801_at | ATP5E | NM_006886 |
| 202000_at | NDUFA6 | BC002772.1 |
| 214334_x_at | DAZAP2 | N34846 |
| 230452_at | SLC20A1 | AI939400 |
| 209899_s_at | SIAHBP1 | AF217197.1 |
| 200773_x_at | PTMA | NM_002823 |
| 231812_x_at | PHAX | AK023255.1 |
| 227181_at |  | AI203021 |
| 204045_at | TCEAL1 | NM_004780 |
| 216028_at | DKFZP564C152 | AL049980.1 |
| 208971_at | UROD | M14016.1 |
| 227035_x_at | LOC222136 | BE670798 |
| 230274_s_at | RAB5EP | BF589088 |
| 209375_at | XPC | D21089.1 |
| 200962_at |  | AI348010 |
| 217928_s_at | C11orf23 | NM_018312 |
| 226951_at |  | AI741415 |
| 204995_at | CDK5R1 | AL567411 |
| 228380_at |  | BE551193 |
| 212626_x_at | HNRPC | AA664258 |
| 233186_s_at | BANP | AK001039.1 |
| 225226_at | FLJ14743 | AB051548.1 |
| 210829_s_at |  | AF077048.1 |
| 214435_s_at | RALA | NM_005402.1 |
| 211656_x_at | HLA-DQB1 | M32577.1 |
| 204481_at | BRPF1 | NM_004634 |
| 210514_x_at | HLA-G | AF226990.2 |
| 223076_s_at | FLJ20303 | BC001041.1 |
| 211990_at | HLA-DPA1 | M27487.1 |
| 227814_at | MGC12928 | AA789329 |
| 212828_at |  | AL157424.1 |
| 209174_s_at | ANXA6 | BC000978.2 |
| 224721_at | FLJ12519 | AI917328 |
| 235300_x_at | ZNF363 | AW236209 |
| 223443_s_at | FLJ32065 | BC003669.1 |
| 217552_x_at | CR1 | AI432713 |
| 202922_at | GCLC | BF676980 |
| 202537_s_at | DKFZP564O123 | AF151842.1 |
| 223027_at | SNX9 | BF972871 |
| 227562_at |  | AI335267 |
| 49878_at | PEX16 | AA523441 |
| 228822_s_at |  | AI435036 |
| 224681_at | GNA12 | BG028884 |
| 224569_s_at |  | BG388615 |
| 207434_s_at | FXYD2 | NM_021603 |
| 219506_at | FLJ23221 | NM_024579 |
| 233605_x_at |  | AK022050.1 |
| 241962_at |  | AI332476 |
| 227546_x_at | AKIP | AI738987 |

TABLE 2B

| Affymetrix ID | Common | Genbank |
|---|---|---|
| AFFX-HUMISGF3A/M97935_MB_at | STAT1 | M97935 |
| AFFX-HUMISGF3A/M97935_MA_at | STAT1 | M97935 |
| AFFX-HUMISGF3A/M97935_3_at | STAT1 | M97935 |
| 200887_s_at | STAT1 | NM_007315 |
| 44673_at | SN | N53555 |
| 242625_at | cig5 | AW189843 |
| 213797_at | cig5 | AI337069 |
| 219863_at | CEB1 | NM_016323 |
| 204747_at | IFIT4 | NM_001549 |
| 229450_at |  | AI075407 |
| 226702_at | LOC129607 | AI742670 |
| 214453_s_at | IFI44 | NM_006417.1 |
| 204439_at | C1orf29 | NM_006820 |
| 202086_at | MX1 | NM_002462 |
| 208436_s_at | IRF7 | NM_004030 |
| 205483_s_at | G1P2 | NM_005101 |

TABLE 2B-continued

| Affymetrix ID | Common | Genbank |
|---|---|---|
| 222154_s_at | DKFZP564A2416 | AK002064.1 |
| 204994_at | MX2 | NM_002463 |
| 227609_at | EPSTI1 | AA633203 |
| 218400_at | OAS3 | NM_006187 |
| 202145_at | LY6E | NM_002346 |
| 204972_at | OAS2 | NM_016817 |
| 213294_at |  | AV755522 |
| 210797_s_at | OASL | AF063612.1 |
| 230036_at | FLJ39885 | BE669858 |
| 226603_at | FLJ39885 | BE966604 |
| 223220_s_at | BAL | AF307338.1 |
| 205552_s_at | OAS1 | NM_002534 |
| 203153_at | IFIT1 | NM_001548 |
| 228617_at |  | AA142842 |
| 227807_at |  | AI738416 |
| 202446_s_at | PLSCR1 | AI825926 |
| 219211_at | USP18 | NM_017414 |
| 228607_at |  | AI651594 |
| 209417_s_at | IFI35 | BC001356.1 |
| 235276_at | EPSTI1 | AA781795 |
| 226757_at | IFIT2 | AA131041 |
| 205660_at | OASL | NM_003733 |
| 214059_at | IFI44 | BE049439 |
| 213293_s_at | TRIM22 | AA083478 |
| 216565_x_at |  | AL121994 |
| 212203_x_at | IFITM3 | BF338947 |
| 217933_s_at | LAP3 | NM_015907 |
| 202411_at | IFI27 | NM_005532 |
| 219352_at | FLJ20637 | NM_017912 |
| 225415_at | LOC151636 | AA577672 |
| 218986_s_at | FLJ20035 | NM_017631 |
| 202869_at | OAS1 | NM_016816 |
| 204415_at | G1P3 | NM_022873 |
| 236285_at |  | AI631846 |
| 200923_at | LGALS3BP | NM_005567 |
| 228531_at | FLJ20073 | AA741307 |
| 219691_at | FLJ20073 | NM_017654 |
| 225291_at | OLD35 | AI967971 |
| 219356_s_at | HSPC177 | NM_016410 |
| 218085_at | HSPC177 | NM_015961 |
| 219209_at | MDA5 | NM_022168 |
| 203964_at | NMI | NM_004688 |
| 204211_x_at | PRKR | NM_002759 |
| 218543_s_at | FLJ22693 | NM_022750 |
| 225344_at | ERAP140 | AL035689 |
| 209593_s_at | TOR1B | AF317129.1 |
| 228152_s_at | FLJ31033 | AK023743.1 |
| 200986_at | SERPING1 | NM_000062 |
| 225929_at | KIAA1554 | AI954660 |
| 239979_at |  | BE645480 |
| 232375_at |  | AI539443 |
| 209969_s_at | STAT1 | BC002704.1 |
| 201786_s_at | ADAR | NM_001111 |
| 228230_at | PRIC285 | AL121829 |
| 201649_at | UBE2L6 | NM_004223 |
| 213361_at | PCTAIRE2BP | AW129593 |
| 201641_at | BST2 | NM_004335 |
| 203236_s_at | LGALS9 | NM_009587 |
| 242234_at | HSXIAPAF1 | AI859280 |
| 231577_s_at | GBP1 | AW014593 |
| 202269_x_at | GBP1 | BC002666.1 |
| 202307_s_at | TAP1 | NM_000593 |
| 202270_at | GBP1 | NM_002053 |
| 225636_at | STAT2 | H98105 |
| 205569_at | LAMP3 | NM_014398 |
| 206133_at | HSXIAPAF1 | NM_017523 |
| 217502_at | IFIT2 | BE888744 |
| 209762_x_at | SP110 | AF280094.1 |
| 208012_x_at | SP110 | NM_004509 |
| 214022_s_at | MGC27165 | AA749101 |
| 201601_x_at | IFITM1 | NM_003641 |
| 238327_at | ECGF1 | AI962367 |
| 204858_s_at | ECGF1 | NM_001953 |
| 205241_at | SCO2 | NM_005138 |
| 225245_x_at | H2AFJ | BG386566 |
| 224301_x_at | H2AFJ | BC003602.1 |
| 217165_x_at | MT1F | M10943 |
| 208581_x_at | MT1X | NM_005952 |
| 204326_x_at | MT1L | NM_002450 |
| 216336_x_at |  | AL031602 |
| 212185_x_at | MT2A | NM_005953.1 |
| 212859_x_at | MT1E | BF217861 |
| 211456_x_at |  | AF333388.1 |
| 222483_at | MGC4342 | AW664179 |
| 202284_s_at | CDKN1A | NM_000389 |
| 213988_s_at | SAT | BE971383 |
| 201315_at | IFITM2 | NM_006435 |
| 222986_s_at | SCOTIN | BC001463.1 |
| 208751_at | NAPA | BC001165.1 |
| 206491_s_at | NAPA | NM_003827 |
| 224701_at | KIAA1268 | AA056548 |
| 205099_s_at | CCR1 | NM_001295 |
| 219062_s_at | FLJ20281 | NM_017742 |
| 203596_s_at | RI58 | NM_012420 |
| 203595_s_at | RI58 | N47725 |
| 205875_s_at | TREX1 | NM_016381 |
| 230314_at |  | AW014557 |
| 223298_s_at | NT5C3 | AF312735.1 |
| 231455_at |  | AA768888 |
| 202430_s_at | PLSCR1 | NM_021105 |
| 203882_at | ISGF3G | NM_006084 |
| 211012_s_at | PML | BC000080.1 |
| 202068_s_at | LDLR | NM_000527 |
| 242020_s_at |  | AI925506 |
| 232666_at | OAS3 | R13458 |
| 225076_s_at | KIAA1404 | AA150460 |
| 218943_s_at | RIG-I | NM_014314 |
| 221816_s_at | NY-REN-34 | BF055474 |
| 241801_at |  | AW084937 |
| 33304_at | HEM45 | U88964 |
| 204698_at | ISG20 | NM_002201 |
| 202863_at | SP100 | NM_003113 |
| 235508_at |  | AW291023 |
| 225931_s_at | KIAA1554 | AI954660 |
| 208087_s_at | ZBP1 | NM_030776 |
| 231769_at | FBXO6 | AF129536.1 |
| 215617_at |  | AU145711 |
| 226103_at | nexilin | AF114264.1 |
| 233880_at | KIAA1554 | AL161961.1 |
| 239988_at |  | AA708470 |
| 224806_at |  | BE563152 |
| 200815_s_at | PAFAH1B1 | L13386.1 |
| 241812_at |  | AV648669 |
| 204224_s_at | GCH1 | NM_000161 |
| 222816_s_at | FLJ20281 | BE676543 |
| 241916_at |  | AI984040 |
| 228628_at |  | AI478268 |
| 204713_s_at | F5 | AA910306 |
| 203258_at | DRAP1 | NM_006442 |
| 232517_s_at | PRIC285 | AL121829 |
| 208912_s_at | CNP | BC001362.1 |
| 226390_at | STARD4 | AA628398 |
| 232787_at |  | AK023724.1 |
| 208392_x_at | SP110 | NM_004510 |
| 243934_at |  | AW139261 |
| 213497_at | DKFZP586C1619 | AL050374.1 |
| 204533_at | NYREN18 | AF300717.1 |
| 212845_at | CXCL10 | NM_001565 |
| 207614_s_at | KIAA1053 | AB028976.1 |
| 210524_s_at | CUL1 | NM_003592 |
| 204745_x_at |  | AF078844.1 |
| 38487_at | MT1G | NM_005950 |
| 200839_s_at | KIAA0246 | D87433 |
| 211135_x_at | CTSB | NM_001908 |
| 210225_x_at | LILRB3 | AF009644.1 |
| 207697_x_at | LILRB3 | AF009635.1 |
| 243099_at | LILRB2 | NM_005874 |
| 202897_at | NFAM1 | AW271350 |
| 229770_at | PTPNS1 | AB023430.1 |
| | FLJ31978 | AI041543 |

TABLE 2B-continued

| Affymetrix ID | Common | Genbank |
|---|---|---|
| 217977_at | SEPX1 | NM_016332 |
| 207677_s_at | NCF4 | NM_013416 |
| 205627_at | CDA | NM_001785 |
| 205147_x_at | NCF4 | NM_000631 |
| 218454_at | FLJ22662 | NM_024829 |
| 228497_at | FLIPT1 | AI279062 |
| 201118_at | PGD | NM_002631 |
| 205863_at | S100A12 | NM_005621 |
| 204959_at | MNDA | NM_002432 |
| 203765_at | GCA | NM_012198 |
| 212602_at | ALFY | AI806395 |
| 207275_s_at | FACL1 | NM_001995 |
| 201963_at | FACL2 | NM_021122 |
| 205568_at | AQP9 | NM_020980 |
| 204924_at | TLR2 | NM_003264 |
| 205119_s_at | FPR1 | NM_002029 |
| 214438_at | HLX1 | M60721.1 |
| 212268_at | SERPINB1 | NM_030666.1 |
| 203167_at | TIMP2 | NM_003255 |
| 221210_s_at | C1orf13 | NM_030769 |
| 217835_x_at | C20orf24 | NM_018840 |
| 200663_at | CD63 | NM_001780 |
| 226275_at |  | AI188653 |
| 222934_s_at | CLECSF9 | BC000715.1 |
| 221676_s_at | CORO1C | BC002342.1 |
| 214875_x_at | APLP2 | AW001847 |
| 208702_x_at | APLP2 | BC000373.1 |
| 211404_s_at | APLP2 | BC004371.1 |
| 208918_s_at | FLJ13052 | BC001709.1 |
| 223553_s_at | FLJ22570 | BC004564.1 |
| 208919_s_at | FLJ13052 | BC001709.1 |
| 228499_at | PFKFB4 | AL038787 |
| 216041_x_at | GRN | AK023348.1 |
| 200678_x_at | GRN | NM_002087 |
| 211284_s_at | GRN | BC000324.1 |
| 205237_at | FCN1 | NM_002003 |
| 205936_s_at | HK3 | NM_002115 |
| 202096_s_at | BZRP | NM_000714 |
| 201482_at | QSCN6 | NM_002826 |
| 240862_at | RASGRP4 | AA923524 |
| 224818_at |  | BE622952 |
| 205726_at | DIAPH2 | NM_006729 |
| 213241_at |  | AF035307.1 |
| 217763_s_at | RAB31 | NM_006868 |
| 217762_s_at | RAB31 | BE789881 |
| 212807_s_at | SORT1 | BE742268 |
| 201463_s_at | TALDO1 | NM_006755 |
| 236172_at |  | AW206817 |
| 220001_at | PADI4 | NM_012387 |
| 227929_at |  | AU151342 |
| 229101_at |  | AI963142 |
| 207809_s_at | ATP6IP1 | NM_001183 |
| 200661_at | PPGB | NM_000308 |
| 209930_s_at | NFE2 | L13974.1 |
| 223502_s_at | TNFSF13B | AF134715.1 |
| 223501_at |  | AW151360 |
| 216950_s_at |  | X14355.1 |
| 214511_x_at |  | L03419.1 |
| 219403_s_at | HPSE | NM_006665 |
| 204204_at | SLC31A2 | NM_001860 |
| 222670_s_at | MAFB | AW135013 |
| 218559_s_at | MAFB | NM_005461 |
| 206715_at | TFEC | NM_012252 |
| 210785_s_at | ICB-1 | AB035482.1 |
| 207571_x_at | C1orf38 | NM_004848 |
| 218773_s_at | PILB | NM_012228 |
| 207674_at | FCAR | NM_002000 |
| 201642_at | IFNGR2 | NM_005534 |
| 233587_s_at |  | AK022852.1 |
| 228846_at |  | AW071793 |
| 222496_s_at | FLJ20273 | AW241742 |
| 217738_at | PBEF | BF575514 |
| 205681_at | BCL2A1 | NM_004049 |
| 215001_s_at | GLUL | AL161952.1 |
| 206584_at | LY96 | NM_015364 |
| 200648_s_at | GLUL | NM_002065 |
| 202912_at | ADM | NM_001124 |
| 203574_at | NFIL3 | NM_005384 |
| 210592_s_at |  | M55580.1 |
| 216243_s_at | IL1RN | BE563442 |
| 212659_s_at | IL1RN | AW083357 |
| 212657_s_at | IL1RN | AW083357 |
| 210101_x_at | SH3GLB1 | AF257318.1 |
| 209091_s_at | SH3GLB1 | AF263293.1 |
| 205896_at | SLC22A4 | NM_003059 |
| 223145_s_at | FLJ10342 | BC000764.1 |
| 229521_at | FLJ36031 | BE466274 |
| 203041_s_at | LAMP2 | J04183.1 |
| 235054_at | FLJ31265 | BF941983 |
| 229584_at | DKFZp434H2111 | AK026776.1 |
| 219806_s_at | FN5 | NM_020179 |
| 217118_s_at | KIAA0930 | AK025608.1 |
| 212830_at | EGFL5 | BF110421 |
| 227624_at | KIAA1546 | AB046766.1 |
| 226169_at | LOC283105 | AW276572 |
| 210773_s_at | FPRL1 | U81501.1 |
| 210772_at | FPRL1 | M88107.1 |
| 215706_x_at | ZYX | BC002323.1 |
| 200808_s_at | ZYX | NM_003461 |
| 212090_at | VPS28 | AL571424 |
| 205312_at | SPI1 | NM_003120 |
| 201360_at | CST3 | NM_000099 |
| 202426_s_at | RXRA | NM_002957.2 |
| 208540_x_at | S100A11P | NM_021039 |
| 200660_at | S100A11 | NM_005620 |
| 224856_at | FKBP5 | AL122066.1 |
| 204900_x_at | SAP30 | NM_003864 |
| 204899_s_at | SAP30 | BF247098 |
| 218092_s_at | HRB | NM_004504 |
| 215049_x_at | CD163 | Z22969.1 |
| 216202_s_at | CD163 | NM_004244 |
| 203127_s_at | SPTLC2 | U15555.1 |
| 200919_at | PHC2 | BC005123.1 |
| 205403_at | IL1R2 | NM_004427 |
| 211676_s_at | IFNGR1 | NM_004633 |
| 218217_at | RISC | AF056979.1 |
| 228754_at | KIAA1719 | NM_021626 |
| 223482_at | TMPIT | BG150485 |
| 223303_at | MGC10966 | AF327923.1 |
| 200766_at | CTSD | BC004347.1 |
| 207168_s_at | H2AFY | NM_001909 |
| 200765_x_at | CTNNA1 | NM_004893 |
| 205786_s_at | ITGAM | NM_001903 |
| 209124_at | MYD88 | NM_000632 |
| 218660_at | DYSF | U70451.1 |
| 224791_at | DDEF1 | NM_003494 |
| 212606_at | ALFY | W03103 |
| 238025_at | FLJ34389 | AI806395 |
| 225447_at |  | AA706818 |
| 225095_at |  | AA613031 |
| 224414_s_at | CARD6 | W81119 |
| 201193_at | IDH1 | AF356193.1 |
| 201619_at | PRDX3 | NM_005896 |
| 204050_s_at | CLTA | NM_006793 |
| 200960_x_at | CLTA | NM_001833 |
| 222498_at | FLJ21939 | NM_007096 |
| 224983_at |  | AI809206 |
| 228019_s_at | MRPS18C | BF339821 |
| 227948_at | FRABIN | AV758614 |
| 217853_at | TEM6 | AI949549 |
| 211961_s_at | RAB7 | NM_022748 |
| 206934_at | SIRPB1 | AK000826.1 |
| 203518_at | CHS1 | NM_006065 |
| 203066_at | GALNAC4S-6ST | NM_000081 |
| 202939_at | ZMPSTE24 | NM_014863 |
| 213708_s_at | HUMGT198A | NM_005857 |
| 202441_at | KEO4 | N40555 |
| 211509_s_at | RTN4 | AL568449 |
| 226577_at |  | AB015639.1 |
|  |  | N49844 |

TABLE 2B-continued

| Affymetrix ID | Common | Genbank |
|---|---|---|
| 210275_s_at | ZNF216 | AF062347.1 |
| 226353_at | SPPL2A | AI674647 |
| 221036_s_at | PSFL | NM_031301 |
| 225032_at | FAD104 | AI141784 |
| 203234_at | UP | NM_003364 |
| 239598_s_at | FLJ20481 | AA789296 |
| 201858_s_at | PRG1 | J03223.1 |
| 238513_at | | BF905445 |
| 201020_at | YWHAH | NM_003405 |
| 200999_s_at | CKAP4 | NM_006825 |
| 200998_s_at | CKAP4 | AW029619 |
| 235536_at | | AI640483 |
| 202934_at | HK2 | AI761561 |
| 202671_s_at | PDXK | NM_003681 |
| 213532_at | LOC285148 | AI797833 |
| 212975_at | KIAA0870 | AB020677.2 |
| 202197_at | MTMR3 | NM_021090 |
| 203140_at | BCL6 | NM_001706 |
| 231644_at | | AW016812 |
| 218091_at | HRB | AI989512 |
| 212820_at | RC3 | AB020663.1 |
| 205992_s_at | IL15 | NM_000585 |
| 204249_s_at | LMO2 | NM_005574 |
| 228089_x_at | MGC3196 | H72927 |
| 224981_at | LOC124446 | AL520900 |
| 215399_s_at | OS-9 | AI683900 |
| 226071_at | DKFZP434K1772 | AF217974.1 |
| 219256_s_at | FLJ20356 | NM_018986 |
| 200709_at | FKBP1A | NM_000801 |
| 204043_at | TCN2 | NM_000355 |
| 209234_at | KIF1B | BF939474 |
| 202201_at | BLVRB | NM_000713 |
| 37028_at | GADD34 | U83981 |
| 202014_at | PPP1R15A | NM_014330 |
| 224606_at | | BG250721 |
| 202768_at | FOSB | NM_006732 |
| 201531_at | ZFP36 | NM_003407 |
| 209189_at | FOS | BC004490.1 |
| 202241_at | C8FW | NM_025195 |
| 208961_s_at | COPEB | AB017493.1 |
| 201489_at | PPIF | BC005020.1 |
| 230492_s_at | KIAA1434 | BE328402 |
| 217202_s_at | | U08626 |
| 210190_at | STX11 | AF071504.1 |
| 200798_x_at | MCL1 | NM_021960 |
| 224790_at | DDEF1 | W03103 |
| 211749_s_at | VAMP3 | BC005941.1 |
| 224898_at | FLJ21016 | AA482548 |
| 225468_at | FLJ36874 | AI761804 |
| 223309_x_at | IPLA2(GAMMA) | BG025248 |
| 203471_s_at | PLEK | NM_002664 |
| 208926_at | NEU1 | U84246.1 |
| 228648_at | LRG | AA622495 |
| 206026_s_at | TNFAIP6 | NM_007115 |
| 206025_s_at | TNFAIP6 | AW188198 |
| 202391_at | BASP1 | NM_006317 |
| 204470_at | CXCL1 | NM_001511 |
| 202193_at | LIMK2 | NM_005569 |
| 221345_at | GPR43 | NM_005306 |
| 209864_at | FRAT2 | AB045118.1 |
| 210449_x_at | MAPK14 | AF100544.1 |
| 266_s_at | CD24 | L33930 |
| 216379_x_at | CD24 | AK000168.1 |
| 209771_x_at | CD24 | AA761181 |
| 208651_x_at | CD24 | M58664.1 |
| 208650_s_at | CD24 | BG327863 |
| 231688_at | | AW337833 |
| 207329_at | MMP8 | NM_002424 |
| 211657_at | CEACAM6 | M18728.1 |
| 203757_s_at | CEACAM6 | BC005008.1 |
| 207269_at | DEFA4 | NM_001925 |
| 209369_at | ANXA3 | M63310.1 |
| 212531_at | LCN2 | NM_005564.1 |
| 206676_at | CEACAM8 | M33326.1 |
| 210244_at | CAMP | U19970.1 |
| 202018_s_at | LTF | NM_002343 |
| 205557_at | BPI | NM_001725 |
| 205513_at | TCN1 | NM_001062 |
| 206177_s_at | ARG1 | NM_000045 |
| 203021_at | SLPI | NM_003064 |
| 209498_at | CEACAM1 | X16354.1 |
| 214575_s_at | AZU1 | NM_001700.1 |
| 203949_at | MPO | NM_000250 |
| 205653_at | CTSG | NM_001911 |
| 206851_at | RNASE3 | NM_002935 |
| 209396_s_at | CHI3L1 | M80927.1 |
| 210254_at | MS4A3 | L35848.1 |
| 212768_s_at | bA209J19.1 | AL390736 |
| 224707_at | ORF1-FL49 | AL522667 |
| 221485_at | B4GALT5 | NM_004776.1 |
| 206515_at | CYP4F3 | NM_000896 |
| 203936_s_at | MMP9 | NM_004994 |
| 204351_at | S100P | NM_005980 |
| 211883_x_at | CEACAM1 | M76742.1 |
| 205033_s_at | DEFA1 | NM_004084 |
| 206697_s_at | HP | NM_005143 |
| 202286_s_at | M1S1 | J04152 |
| 235816_s_at | Rgr | AI867408 |
| 227140_at | | AI343467 |
| 235568_at | LOC199675 | BF433657 |
| 206111_at | RNASE2 | NM_002934 |
| 239108_at | | H16791 |
| 220615_s_at | FLJ10462 | NM_018099 |
| 211275_s_at | GYG | AF087942.1 |
| 201554_x_at | GYG | NM_004130 |
| 201061_s_at | STOM | M81635.1 |
| 209772_s_at | CD24 | X69397.1 |
| 204430_s_at | SLC2A5 | NM_003039 |
| 201060_x_at | STOM | AI537887 |
| 220570_at | RETN | NM_020415 |
| 224967_at | UGCG | W72338 |
| 227236_s_at | TSPAN-2 | AK022144.1 |
| 206157_at | PTX3 | NM_002852 |
| 204174_at | ALOX5AP | NM_001629 |
| 219669_at | PRV1 | NM_020406 |
| 226789_at | ARIH2 | W84421 |
| 202119_s_at | CPNE3 | NM_003909 |
| 225129_at | CPNE2 | AW170571 |
| 221523_s_at | RAGD | AL138717 |
| 217995_at | SQRDL | NM_021199 |
| 201470_at | GSTTLp28 | NM_004832 |
| 207157_s_at | GNG5 | NM_005274 |
| 200886_s_at | PGAM1 | NM_002629 |
| 200650_s_at | LDHA | NM_005566 |
| 210386_s_at | MTX1 | BC001906.1 |
| 219890_at | CLECSF5 | NM_013252 |
| 211889_x_at | CEACAM1 | D12502.1 |
| 242013_at | | BF445012 |
| 224009_at | RDHL | AF240697.1 |
| 223952_x_at | RDHL | AF240698.1 |
| 223423_at | GPCR1 | BC000181.2 |
| 209892_at | FUT4 | AF305083.1 |
| 228253_at | PRSS25 | AI917716 |
| 226968_at | KIF1B | AK023184.1 |
| 203725_at | GADD45A | NM_001924 |
| 221484_at | B4GALT5 | NM_004776.1 |
| 224973_at | C6orf37; FLJ20037 | AL078599 |
| 219938_s_at | PSTPIP2 | NM_024430 |
| 219259_at | FLJ12287 | NM_022367 |
| 213453_x_at | GAPD | BF689355 |
| 203535_at | S100A9 | NM_002965 |
| 201426_s_at | RPLP2 | AI922599 |
| 210142_x_at | FLOT1 | AF117234.1 |
| 208749_x_at | FLOT1 | AF085357.1 |
| 238439_at | MGC22805 | AI925518 |
| 201850_at | CAPG | NM_001747 |
| 203044_at | CHSY1 | NM_014918 |
| 203042_at | LAMP2 | NM_002294 |
| 208886_at | H1F0 | BC000145.1 |

TABLE 2B-continued

| Affymetrix ID | Common | Genbank |
|---|---|---|
| 224130_s_at | SRA1 | AF293026.1 |
| 217728_at | S100A6 | NM_014624 |
| 201105_at | LGALS1 | NM_002305 |
| 230322_at | NFAM1 | AI492017 |
| 210146_x_at | LILRB2 | AF004231.1 |
| 219079_at | b5 + b5R | NM_016230 |
| 200782_at | ANXA5 | NM_001154 |
| 216903_s_at | CBARA1 | AK022697.1 |
| 214151_s_at | PIGB | AU144243 |
| 226885_at | | AI743880 |
| 227769_at | GPR27 | AI703476 |
| 225941_at | MGC39820 | BE465037 |
| 225940_at | MGC39820 | BE465037 |
| 201576_s_at | GLB1 | NM_000404 |
| 200950_at | ARPC1A | NM_006409 |
| 228412_at | BAZ2B | AI991451 |
| 201200_at | CREG | NM_003851 |
| 242943_at | | AA352113 |
| 222981_s_at | RAB10 | BC000896.1 |
| 225039_at | RPE | AV699857 |
| 209970_x_at | CASP1 | M87507.1 |
| 205842_s_at | JAK2 | AF001362.1 |
| 208966_x_at | IFI16 | AF208043.1 |
| 202688_at | TNFSF10 | NM_003810 |
| 202687_s_at | TNFSF10 | U57059.1 |
| 205098_at | CCR1 | AI421071 |
| 201298_s_at | C2orf6 | BC003398.1 |
| 221786_at | XAP135 | AF055030.1 |
| 226464_at | MGC33365 | BE348597 |
| 211075_s_at | CD47 | Z25521.1 |
| 208899_x_at | ATP6V1D | AF100741.1 |
| 221449_s_at | CDA08 | NM_030790 |
| 222466_s_at | MRPL42 | AL136659.1 |
| 222793_at | RIG-I | AK023661.1 |
| 219283_at | C1GALT2 | NM_014158 |
| 235385_at | | AI935334 |
| 241752_at | SLC8A1 | AA094434 |
| 225847_at | KIAA1363 | AB037784.1 |
| 223392_s_at | KIAA1474 | BF510588 |
| 210176_at | TLR1 | AL050262.1 |
| 222833_at | | AU154202 |
| 218280_x_at | HIST2H2AA | NM_003516 |
| 214290_s_at | HIST2H2AA | AA451996 |
| 223375_at | FLJ20337 | BC002720.1 |
| 210638_s_at | FBXO9 | AF176704.1 |
| 201350_at | FLOT2 | NM_004475 |
| 225782_at | LOC253827 | BG171064 |
| 225320_at | LOC90550 | AA579630 |
| 224596_at | CDW92 | NM_022109.1 |
| 213836_s_at | KIAA1001 | AW052084 |
| 228585_at | | AI301948 |
| 218482_at | DC6 | NM_020189 |
| 235427_at | | AA418074 |
| 227129_x_at | | AW006934 |
| 225899_x_at | | AL040396 |
| 212457_at | TFE3 | AL161985.1 |
| 220066_at | CARD15 | NM_022162 |
| 214084_x_at | NCF1 | AW072388 |
| 204961_s_at | NCF1 | NM_000265 |
| 201594_s_at | PPP4R1 | NM_005134 |
| 227833_s_at | MBD6 | AW207668 |
| 227150_at | KIAA1337 | N46867 |
| 225056_at | | AB037810.1 |
| 229460_at | CED-6 | AI927605 |
| 203397_s_at | GALNT3 | BF063271 |
| 227438_at | LAK | AI760166 |
| 202530_at | MAPK14 | NM_001315 |
| 208872_s_at | DP1 | AA814140 |
| 208819_at | MEL | BC002977.1 |
| 229373_at | | AW139719 |
| 227379_at | MGC44669 | AI734993 |
| 219607_s_at | MS4A4A | NM_024021 |
| 209684_at | RIN2 | AL136924.1 |
| 201926_s_at | DAF | BC001288.1 |
| 213607_x_at | FLJ13052 | BE551347 |
| 230748_at | | AI873273 |
| 212506_at | PICALM | AL135735 |
| 205173_x_at | CD58 | NM_001779 |
| 222235_s_at | dJ19N1.1 | AL139812 |
| 220330_s_at | SAMSN1 | NM_022136 |
| 218871_x_at | GALNACT-2 | NM_018590 |
| 219157_at | KLHL2 | NM_007246 |
| 36564_at | FLJ90005 | W27419 |
| 203370_s_at | ENIGMA | NM_005451 |
| 215498_s_at | MAP2K3 | AA780381 |
| 220947_s_at | DKFZP434P1750 | NM_015527 |
| 204923_at | CXorf9 | AL023653 |
| 201155_s_at | MFN2 | NM_014874 |
| 211433_x_at | FLJ11560 | AL583909.1 |
| 202084_s_at | SEC14L1 | NM_003003 |
| 204336_s_at | RGS19 | NM_005873 |
| 208992_s_at | STAT3 | BC000627.1 |
| 203184_at | FBN2 | NM_001999 |
| 233924_s_at | SEC15L | AK002113.1 |
| 207691_x_at | ENTPD1 | NM_001776 |
| 201583_s_at | SEC23B | NM_006363 |
| 202348_s_at | DYT1 | BC000674.1 |
| 231513_at | KCNJ2 | BF111326 |
| 225492_at | | BG500396 |
| 223767_at | GPR84 | AF237762.1 |
| 212658_at | LHFPL2 | N66633 |
| 204393_s_at | ACPP | NM_001099 |
| 231029_at | AK2 | AI740541 |
| 204714_s_at | F5 | NM_000130 |
| 227184_at | | BF508702 |
| 217897_at | FXYD6 | NM_022003 |
| 201078_at | TM9SF2 | NM_004800 |
| 213503_x_at | ANXA2 | BE908217 |
| 201590_x_at | ANXA2 | NM_004039 |
| 210427_x_at | ANXA2 | BC001388.1 |
| 208683_at | CAPN2 | M23254.1 |
| 211729_x_at | BLVRA | BC005902.1 |
| 203773_x_at | BLVRA | NM_000712 |
| 225633_at | LOC147991 | BF057717 |
| 218423_x_at | HCC8 | NM_016516 |
| 212467_at | KIAA0678 | AB014578.1 |
| 204798_at | MYB | NM_005375 |
| 202794_at | INPP1 | NM_002194 |
| 226939_at | | AI202327 |
| 243931_at | CD58 | R64696 |
| 230052_s_at | TA-NFKBH | AA004799 |
| 220712_at | | NM_024984 |
| 206472_s_at | TLE3 | NM_005078 |
| 222088_s_at | SLC2A14 | AA778684 |
| 202499_s_at | SLC2A3 | NM_006931 |
| 208724_s_at | RAB1A | BC000905.1 |
| 203097_s_at | PDZ-GEF1 | NM_014247 |
| 203420_at | FAM8A1 | NM_016255 |
| 204780_s_at | TNFRSF6 | AA164751 |
| 203885_at | RAB21 | NM_014999 |
| 202906_s_at | NBS1 | AI796269 |
| 203505_at | ABCA1 | AF285167.1 |
| 203504_s_at | ABCA1 | NM_005502 |
| 218924_s_at | CTBS | NM_004388 |
| 218520_at | TBK1 | NM_013254 |
| 201898_s_at | UBE2A | AI126625 |
| 225466_at | FLJ36874 | AI761804 |
| 221490_at | UBAP1 | AL136733.1 |
| 229305_at | | AA460299 |
| 208864_s_at | TXN | AF313911.1 |
| 200985_s_at | CD59 | NM_000611 |
| 208881_x_at | IDI1 | BC005247.1 |
| 204615_x_at | IDI1 | NM_004508 |
| 208691_at | TFRC | BC001188.1 |
| 207332_s_at | TFRC | NM_003234 |
| 226758_at | CGI-59 | AA043552 |
| 227991_x_at | | BF516567 |
| 207196_s_at | TNIP1 | NM_006058 |
| 224829_at | KIAA1673 | AA772278 |
| 208901_s_at | TOP1 | J03250.1 |

TABLE 2B-continued

| Affymetrix ID | Common | Genbank |
|---|---|---|
| 222303_at | | AV700891 |
| 224578_at | DKFZp762N0610 | AB040903.1 |
| 213119_at | LOC91974 | AW058600 |
| 204613_at | PLCG2 | NM_002661 |
| 212795_at | KIAA1033 | AL137753.1 |
| 212408_at | LAP1B | AK023204.1 |
| 212397_at | RDX | AL137751.1 |
| 210044_s_at | LYL1 | BC002796.1 |
| 208898_at | ATP6V1D | AF077614.1 |
| 202228_s_at | SDFR1 | NM_017455 |
| 205844_at | VNN1 | NM_004666 |
| 232520_at | | AK023585.1 |
| 225750_at | | BE966748 |
| 225440_at | AGPAT3 | BE737251 |
| 219505_at | CECR1 | NM_017424 |
| 225661_at | LOC284829 | BF794958 |
| 222774_s_at | NETO2 | AI335263 |
| 201302_at | ANXA4 | NM_001153 |
| 201301_s_at | ANXA4 | BC000182.1 |
| 218117_at | RBX1 | NM_014248 |
| 208680_at | PRDX1 | L19184.1 |
| 213329_at | FNBP2 | AA742261 |
| 202296_s_at | RER1 | NM_007033 |
| 208270_s_at | RNPEP | NM_020216 |
| 213113_at | EEG1 | AI630178 |
| 201894_s_at | DCN | NM_001920 |
| 203761_at | SLA | NM_006748 |
| 209409_at | GRB10 | D86962.1 |
| 208709_s_at | NRD1 | U64898.1 |
| 203371_s_at | NDUFB3 | NM_002491 |
| 201186_at | LRPAP1 | NM_002337 |
| 218728_s_at | HSPC163 | NM_014184 |
| 244313_at | | AI052659 |
| 236155_at | | AW974609 |
| 227645_at | P101-PI3K | BF892532 |
| 224909_s_at | PRex1 | BF308645 |
| 227638_at | KIAA1632 | AI393091 |
| 225897_at | | AI709406 |
| 201669_s_at | MARCKS | NM_002356 |
| 204436_at | PP1628 | NM_025201 |
| 210754_s_at | LYN | M79321.1 |
| 202626_s_at | LYN | NM_002350 |
| 232349_x_at | PC326 | BF671187 |
| 213726_x_at | TUBB2 | AA515698 |
| 208977_at | TUBB2 | BC004188.1 |
| 213476_x_at | TUBB4 | AL565749 |
| 212639_x_at | K-ALPHA-1 | AL581768 |
| 209251_x_at | TUBA6 | BC004949.1 |
| 201666_at | TIMP1 | NM_003254 |
| 203814_s_at | NQO2 | NM_000904 |
| 201012_at | ANXA1 | NM_000700 |
| 217794_at | DKFZP564J157 | NM_018457 |
| 222143_s_at | FLJ22405 | AY007098.1 |
| 217930_s_at | TOLLIP | NM_019009 |
| 209467_s_at | MKNK1 | BC002755.1 |
| 200714_x_at | OS-9 | NM_006812 |
| 205020_s_at | ARL4 | NM_005738 |
| 34689_at | drn3 | AJ243797 |
| 201453_x_at | RHEB2 | NM_005614 |
| 32836_at | AGPAT1 | U56417 |
| 209117_at | WBP2 | U79458.1 |
| 235885_at | | AA810452 |
| 226188_at | HSPC159 | AK025603.1 |
| 223717_s_at | ACRBP | AB051833.1 |
| 204081_at | NRGN | NM_006176 |
| 202708_s_at | HIST2H2BE | NM_003528 |
| 235456_at | | AI810266 |
| 209911_x_at | H2BFB | BC002842.1 |
| 218999_at | FLJ11000 | NM_018295 |
| 200863_s_at | RAB11A | AI215102 |
| 206254_at | EGF | NM_001963 |
| 206049_at | SELP | NM_003005 |
| 229893_at | | BF589413 |
| 225672_at | GOLGA2 | AL514295 |
| 201758_at | TSG101 | NM_006292 |
| 236243_at | | AW070776 |
| 211628_x_at | | J04755.1 |
| 203455_s_at | SAT | NM_002970 |
| 223218_s_at | MAIL | AB037925.1 |
| 200797_s_at | MCL1 | NM_021960.1 |
| 221766_s_at | C6orf37; FLJ20037 | AL078599 |
| 202194_at | CGI-100 | AL117354 |
| 201097_s_at | ARF4 | NM_001660 |
| 242760_x_at | | AA808203 |
| 217909_s_at | TCFL4 | BF056105 |
| 203142_s_at | AP3B1 | NM_003664 |
| 209853_s_at | PSME3 | BC002684.1 |
| 200987_x_at | PSME3 | AA758755 |
| 202069_s_at | IDH3A | AI826060 |
| 208654_s_at | CD164 | AF299343.1 |
| 210317_s_at | YWHAE | U28936.1 |
| 201805_at | PRKAG1 | NM_002733 |
| 224716_at | NFKBIE | BG163267 |
| 221693_s_at | MRPS18A | AB049952.1 |
| 200757_s_at | CALU | NM_001219 |
| 233072_at | KIAA1857 | AI348745 |
| AFFX-HUMGAPDH/M33197_M_at | GAPD | M33197 |
| 200039_s_at | PSMB2 | NM_002794 |
| 200001_at | CAPNS1 | NM_001749 |
| 201119_s_at | COX8 | NM_004074 |
| 200654_at | P4HB | J02783.1 |
| 227649_s_at | | AU144000 |
| 203342_at | TIMM17B | NM_005834 |
| 64899_at | FLJ13055 | AA209463 |
| 212443_at | KIAA0540 | AB011112.2 |
| 201050_at | PLD3 | NM_012268 |
| 203254_s_at | TLN1 | NM_006289 |
| 225294_s_at | MUM2 | BG340967 |
| 201251_at | PKM2 | NM_002654 |
| 212705_x_at | TTS-2.2 | BF570210 |
| 211716_x_at | ARHGDIA | BC005851.1 |
| 201168_x_at | ARHGDIA | NM_004309 |
| 209367_at | STXBP2 | AB002559.1 |
| 203085_s_at | TGFB1 | BC000125.1 |
| 200649_s_at | NUCB1 | BC002356.1 |
| 203718_at | NTE | NM_006702 |
| 207722_s_at | BTBD2 | NM_017797 |
| 201082_s_at | DCTN1 | NM_004082 |
| 200964_at | UBE1 | NM_003334 |
| 200041_s_at | BAT1 | NM_004640 |
| 202111_at | SLC4A2 | NM_003040 |
| 204789_at | FMNL | NM_005892 |
| 201903_at | UQCRC1 | NM_003365 |
| 224916_at | | BG286973 |
| 220320_at | FLJ22570 | NM_024872 |
| 224186_s_at | FLJ12565 | AL136729.1 |
| 204805_s_at | H1FX | NM_006026 |
| 203839_s_at | ACK1 | NM_005781 |
| 36994_at | ATPL | M62762 |
| 203175_at | ARHG | NM_001665 |
| 226111_s_at | ZFP385 | BF525395 |
| 217903_at | STRN4 | NM_013403 |
| 201234_at | ILK | NM_004517 |
| 231974_at | MLL2 | AI742164 |
| 203523_at | LSP1 | NM_002339 |
| 234068_s_at | AP2A1 | AC006942 |
| 208625_s_at | EIF4G1 | AF104913.1 |
| 40850_at | FKBP38 | L37033 |
| 208677_s_at | BSG | AL550657 |
| 202041_s_at | FIBP | NM_004214 |
| 202275_at | G6PD | NM_000402 |
| 223050_s_at | FBXW5 | BC000850.1 |
| 210996_s_at | YWHAE | U43430.1 |
| 221050_s_at | GTPBP2 | NM_019096 |
| 218522_s_at | VCY2IP1 | NM_018174 |
| 205740_s_at | MGC10433 | NM_024321 |
| 201794_s_at | C1orf16 | NM_014837 |
| 224783_at | | AI024869 |

TABLE 2B-continued

Table 2B

| Affymetrix ID | Common | Genbank |
|---|---|---|
| 203729_at | EMP3 | NM_001425 |
| 202518_at | BCL7B | NM_001707 |
| 203751_x_at | JUND | NM_005354.2 |
| 212737_at | GM2A | AL513583 |
| 209616_s_at | CES1 | S73751.1 |
| 202592_at | GCN5L1 | NM_001487 |
| 227937_at |  | AA307731 |
| 220998_s_at | UNC93B1 | NM_030930 |
| 200922_at | KDELR1 | NM_006801 |
| 226144_at | KIAA1138 | AB032964.1 |
| 225753_at | FLJ32203 | AW003280 |
| 226201_at |  | AI224128 |
| 209636_at | NFKB2 | BC002844.1 |
| 202848_s_at | GPRK6 | BG423052 |
| 205142_x_at | ABCD1 | NM_000033 |
| 208829_at | TAPBP | AF029750.1 |
| 205398_s_at | MADH3 | NM_005902 |
| 201412_at | LRP10 | NM_014045 |
| 227511_at | ACTR2 | BE963280 |
| 224951_at | LOC91012 | BE348305 |
| 233571_x_at | C20orf149 | AL121829 |
| 40225_at | GAK | D88435 |
| 202281_at | GAK | NM_005255 |
| 212601_at | KIAA0399 | AB007859.2 |
| 219253_at | FAM11B | NM_024121 |
| 212099_at |  | AI263909 |
| 224800_at | FENS-1 | AK022888.1 |
| 50314_i_at | C20orf27 | AI761506 |
| 222779_at | HSA277841 | AA706815 |
| 218057_x_at | NOC4 | NM_006067 |
| 222690_s_at | FLJ10902 | AA194996 |
| 223031_s_at | DKFZp586I021 | AL136921.1 |
| 200677_at | PTTG1IP | NM_004339 |
| 222662_at | LOC286044 | W60806 |
| 218472_s_at | PELO | NM_015946 |
| 90265_at | CENTA1 | AW050627 |
| 37965_at | PARVB | AA181053 |
| 212472_at |  | BE965029 |
| 211385_x_at | SULT1A2 | U28169.1 |
| 207122_x_at | SULT1A2 | NM_001054 |
| 203615_at | SULT1A1 | NM_001055 |
| 210580_x_at | SULT1A3 | L25275.1 |
| 221866_at | TFEB | AL035588 |
| 226760_at | LOC203411 | BF666325 |
| 222654_at | FLJ20421 | AW295105 |
| 224900_at | KIAA1255 | AK025960.1 |
| 223167_s_at | USP25 | AF170562.1 |
| 220146_at | TLR7 | NM_016562 |
| 218909_at | RPS6KC1 | NM_012424 |
| 202447_at | DECR1 | NM_001359 |
| 210705_s_at | TRIM5 | AF220028.1 |
| 206553_at | OAS2 | NM_002535 |
| 209971_x_at | HRI | AI928526 |
| 201172_x_at | ATP6V0E | NM_003945 |
| 212552_at | HPCAL1 | BE617588 |
| 201798_s_at | FER1L3 | NM_013451 |
| 226002_at. | GAB1 | AK022142.1 |
| 225890_at | C20orf72 | AI678096 |
| 227854_at | FLJ10335 | BE620258 |
| 226874_at | KLHL8 | BF591270 |
| 221718_s_at | AKAP13 | M90360.1 |
| 239277_at |  | AI559696 |
| 242538_at | TFDP1 | AW007021 |
| 206335_at | GALNS | NM_000512 |
| 35254_at | fln29 | AB007447 |
| 212051_at |  | AK026913.1 |
| 209056_s_at | CDC5L | AW268817 |
| 202313_at | PPP2R2A | NM_002717 |
| 200881_s_at | DNAJA1 | NM_001539 |
| 232034_at |  | AL117607.1 |
| 243196_s_at | FLN29 | BF223703 |
| 226448_at |  | AI130705 |
| 225622_at | PAG | NM_018440.1 |
| 209536_s_at | MAGED2 | AF320070.1 |
| 230219_at | NUDE1 | AI831952 |
| 225561_at | SELT | BF692332 |
| 205698_s_at | MAP2K6 | NM_002758 |
| 232233_at | CT2; OKB1; FLIPT2; dJ261K5.1 | AL050350 |
| 223043_at | LOC51234 | AF151018.1 |
| 226646_at | KLF2 | AI831932 |
| 222887_s_at | FLJ20507 | AA034018 |
| 203043_at | ALTE | NM_004729 |
| 201484_at | SUPT4H1 | NM_003168 |
| 235234_at | FLJ36874 | AA359612 |
| 228685_at |  | AI990349 |
| 224858_at | ZDHHC5 | AB051535.1 |
| 218018_at | C21orf97 | NM_021941.1 |
| 201136_at | PLP2 | NM_002668 |
| 203437_at | C17orf35 | NM_003876 |
| 222468_at | PKD1-like | W58365 |
| 221434_s_at | DC50 | NM_031210 |
| 203974_at | FAM16AX | NM_012080 |
| 234351_x_at | TRPS1 | AK000948.1 |
| 221492_s_at | APG3 | AF202092.1 |
| 210873_x_at | APOBEC3A | U03891.2 |
| 244811_at |  | AI561173 |
| 233011_at |  | AU155094 |
| 227404_s_at | EGR1 | AI459194 |
| 201694_s_at | EGR1 | NM_001964 |
| 205249_at | EGR2 | NM_000399 |
| 219492_at | CHIC2 | NM_012110 |
| 215719_x_at | TNFRSF6 | X83493.1 |
| 212577_at | KIAA0650 | AA868754 |
| 210681_s_at | USP15 | AF153604.1 |
| 203094_at | CMT2 | NM_014628 |
| 222881_at | HPSE | AF155510.1 |
| 38710_at | FLJ20113 | AL096714 |
| 240336_at |  | AI242749 |
| 224789_at | KIAA1892 | AL555107 |
| 223649_s_at | CGI-69 | AF317711.1 |
| 223266_at | ALS2CR2 | AB038950.1 |
| 221748_s_at |  | AL046979 |
| 219672_at | ERAF | NM_016633 |
| 206834_at | HBD | NM_000519 |
| 214433_s_at | SELENBP1 | NM_003944.1 |
| 211546_x_at | SNCA | L36674.1 |
| 207827_x_at | SNCA | L36675.1 |
| 204466_s_at | SNCA | BG260394 |
| 205950_s_at | CA1 | NM_001738 |
| 201178_at | FBXO7 | NM_012179 |
| 213515_x_at | HBG2 | AI133353 |
| 204419_x_at | HBG2 | NM_000184 |
| 204848_x_at | HBG1 | NM_000559 |
| 226179_at |  | N63920 |
| 221920_s_at | MSCP | BE677761 |
| 217748_at | CGI-45 | NM_015999 |
| 209845_at | MKRN1 | AF117233.1 |
| 201285_at | MKRN1 | NM_013446 |
| 226811_at | FLJ20202 | AL046017 |
| 215438_x_at | GSPT1 | BE906054 |
| 231078_at | MSCP | H69701 |
| 208632_at | RNF10 | AL578551 |
| 202130_at | SUDD | AW006290 |
| 204187_at | GMPR | NM_006877 |
| 202974_at | MPP1 | NM_002436 |
| 228361_at |  | AL561296 |
| 209339_at | SIAH2 | U76248.1 |
| 212540_at | CDC34 | BG476661 |
| 201160_s_at | CSDA | AL556190 |
| 224891_at |  | BE888885 |
| 221675_s_at | CHPT1 | AF195624.1 |
| 225074_at | RAB2B | AA531016 |
| 202387_at | BAG1 | NM_004323 |
| 218030_at | GIT1 | NM_014030 |
| 212330_at | TFDP1 | R60866 |
| 224640_at | SPPL3 | AL514199 |
| 227935_s_at | MGC16202 | AA522681 |
| 217882_at | LOC55831 | NM_018447 |

TABLE 2B-continued

| Affymetrix ID | Common | Genbank |
|---|---|---|
| 200622_x_at | CALM3 | AV685208 |
| 217736_s_at | HRI | NM_014413 |
| 239205_s_at | CR1L | BE552138 |
| 209398_at | H1F2 | BC002649.1 |
| 227219_x_at | MAP1LC3A | BE857601 |
| 226664_at | | AL121747 |
| 222730_s_at | ZDHHC2 | AI814257 |
| 223518_at | DFFA | AF087573.1 |
| 202568_s_at | MARK3 | AI745639 |
| 223252_at | MGC2641 | BC000755.1 |
| 212383_at | ATP6V0A1 | AL096733.1 |
| 203344_s_at | RBBP8 | NM_002894 |
| 243095_at | | AW451624 |
| 244492_at | | BF357738 |
| 229907_at | | AW058634 |
| 212262_at | QKI | AF142419.1 |
| 222608_s_at | ANLN | AK023208.1 |
| 229200_at | | N40199 |
| 204308_s_at | KIAA0329 | NM_014844 |
| 225160_x_at | MGC5370 | AI952357 |
| 223302_s_at | VIK | BC004288.1 |
| 203276_at | LMNB1 | NM_005573 |
| 207467_x_at | CAST | NM_001750 |
| 209193_at | PIM1 | M24779.1 |
| 225206_s_at | LOC54516 | NM_019041.1 |
| 204255_s_at | VDR | NM_000376.1 |
| 223849_s_at | MOV10 | BC002548.1 |
| 223140_s_at | DDX36 | AF217190.1 |
| 218599_at | REC8 | NM_005132 |
| 201015_s_at | JUP | NM_021991 |
| 210859_x_at | CLN3 | AF077973.1 |
| 212285_s_at | AGRN | AF016903.1 |
| 212370_x_at | KIAA0592 | AL080183.1 |
| 211068_x_at | FLJ10824 | BC006456.1 |
| 226077_at | FLJ31951 | AL553942 |
| 244660_at | | AA746320 |
| 244481_at | AK2 | BF196523 |
| 233433_at | | AU158871 |
| 223824_at | FLJ11218 | BC005364.1 |
| 213037_x_at | STAU | AJ132258.1 |
| 207320_x_at | STAU | NM_004602 |
| 222734_at | WARS2 | BF515963 |
| 239342_at | DGKZ | AI567554 |
| 41386_i_at | KIAA0346 | AB002344 |
| 244548_at | | AI189587 |
| 244312_at | | AW195572 |
| 241893_at | | BE927766 |
| 235028_at | | BG288330 |
| 237006_at | | AA703523 |
| 229483_at | | AA760738 |
| 231109_at | | R44974 |
| 239780_at | | AA468422 |
| 242403_at | | AI459177 |
| 235847_at | | BF111312 |
| 232744_x_at | | BG485129 |
| 242471_at | | AI916641 |
| 238534_at | | AA262583 |
| 238883_at | | AW975051 |
| 239264_at | MCCC2 | AW973078 |
| 243819_at | | AU146329 |
| 241837_at | | AI289774 |
| 239331_at | | AW954199 |
| 224984_at | NFAT5 | W61007 |
| 242865_at | | AI332638 |
| 239876_at | | R37337 |
| 244026_at | | BF063657 |
| 233914_s_at | KIAA1766 | AK022478.1 |
| 227528_s_at | MLL2 | AI394529 |
| 227527_at | MLL2 | AI394529 |
| 211950_at | RBAF600 | AB007931.1 |
| 232614_at | | AU146963 |
| 233425_at | | AU147903 |
| 235680_at | | AI914925 |
| 215375_x_at | | AK023938.1 |
| 242558_at | | AW362945 |
| 244358_at | | AW372457 |
| 240038_at | | AW057518 |
| 235592_at | | AW960145 |
| 239379_at | | AW449624 |
| 236742_at | | AA132172 |
| 239555_at | | W87626 |
| 232537_x_at | | AU159474 |
| 225893_at | | AL589593 |
| 233224_at | | AL137645.1 |
| 226115_at | ELYS | AI138934 |
| 235361_at | | AW842975 |
| 238788_at | | AI475803 |
| 218397_at | FLJ10335 | NM_018062 |
| 226155_at | KIAA1600 | AB046820.1 |
| 201377_at | NICE-4 | NM_014847 |
| 218776_s_at | FLJ23375 | NM_024956 |
| 203907_s_at | KIAA0763 | NM_014869 |
| 241692_at | | AA868729 |
| 242390_at | | AI821925 |
| 204435_at | NUPL1 | NM_014778 |
| 243261_at | | BF530486 |
| 234631_at | KRTAP4-8 | AJ406940.1 |
| 233732_at | | AL137445.1 |
| 227197_at | DKFZP434D146 | AI989530 |
| 241027_at | | BE858373 |
| 243158_at | | AV700081 |
| 217839_at | TFG | NM_006070 |
| 237262_at | | AI912190 |
| 207876_s_at | FLNC | NM_001458 |
| 230386_at | | AI819394 |
| 223448_x_at | MRPS22 | AF063603.1 |
| 235479_at | | AI948598 |
| 209774_x_at | CXCL2 | M57731.1 |
| 222729_at | FBXW7 | BE551877 |
| 229097_at | | AI813331 |
| 204141_at | TUBB | NM_001069 |
| 235882_at | | BF115777 |
| 216260_at | DICER1 | AK001827.1 |
| 223797_at | | AF130079.1 |
| 220576_at | FLJ12377 | NM_024989 |
| 203241_at | UVRAG | NM_003369 |
| 239725_at | | T90703 |
| 217047_s_at | FAM13A1 | AK027138.1 |
| 202973_x_at | FAM13A1 | NM_014883 |
| 201999_s_at | TCTEL1 | NM_006519 |
| 235258_at | | AI873425 |
| 227680_at | LOC284695 | AI057121 |
| 229501_s_at | USP8 | AI393759 |
| 214684_at | MEF2A | X63381.1 |
| 209025_s_at | NSAP1 | AF037448.1 |
| 203057_s_at | PRDM2 | NM_015866.1 |
| 241596_at | NUDT10 | AL045306 |
| 235421_at | | AV713062 |
| 223846_at | FLJ21939 | BC001139.1 |
| 235175_at | GBP4 | BG260886 |
| 226269_at | | AL110252.1 |
| 209040_s_at | PSMB8 | U17496.1 |
| 212380_at | KIAA0082 | D43949.1 |
| 202255_s_at | KIAA0440 | NM_015556 |
| 238792_at | PCNX | BF209668 |
| 242035_at | | AA805681 |
| 236077_at | CAPN3 | AI671238 |
| 226274_at | | AK025562.1 |
| 228891_at | | N93399 |
| 200814_at | PSME1 | NM_006263 |
| 243_g_at | MAP4 | M64571 |
| 231241_at | MGC13114 | AW469714 |
| 230110_at | MCOLN2 | AV713773 |
| 224849_at | FLJ10890 | AK023161.1 |
| 218008_at | FLJ10099 | NM_017994 |
| 204279_at | PSMB9 | NM_002800 |
| 200620_at | C1orf8 | NM_004872 |
| 217978_s_at | HSA243666 | NM_017582 |
| 200790_at | ODC1 | NM_002539 |
| 206777_s_at | CRYBB2 | NM_000496 |

TABLE 2B-continued

Table 2B

| Affymetrix ID | Common | Genbank |
|---|---|---|
| 219953_s_at | C11orf17 | NM_020642 |
| 243601_at | | AA744124 |
| 224076_s_at | WHSC1L1 | AF255649.1 |
| 225205_at | KIF3B | AI819734 |
| 240118_at | | AI401105 |
| 235113_at | PPIL5 | AA742244 |
| 234884_x_at | | L21961.1 |
| 234764_x_at | IGL@ | U96394.1 |
| 217258_x_at | | AF043583.1 |
| 216576_x_at | | AF103529.1 |
| 215176_x_at | IGKC | AW404894 |
| 211645_x_at | IGKC | M85256.1 |
| 217148_x_at | IGLJ3 | AJ249377.1 |
| 216984_x_at | IGLJ3 | D84143.1 |
| 211798_x_at | IGLJ3 | AB001733.1 |
| 211644_x_at | IGKC | L14458.1 |
| 223565_at | PACAP | AF151024.1 |
| 216207_x_at | IGKV1D-13 | AW408194 |
| 221253_s_at | MGC3178 | NM_030810 |
| 215946_x_at | LOC91316 | AL022324 |
| 217227_x_at | IGL@ | X93006.1 |
| 224342_x_at | IGL@ | L14452.1 |
| 217179_x_at | IGL@ | X79782.1 |
| 215379_x_at | IGLJ3 | AV698647 |
| 215121_x_at | IGLJ3 | AA680302 |
| 214677_x_at | IGLJ3 | X57812.1 |
| 209138_x_at | IGLJ3 | M87790.1 |
| 214777_at | IGKC | BG482805 |
| 216853_x_at | IGLJ3 | AF234255.1 |
| 211881_x_at | IGLJ3 | AB014341.1 |
| 214768_x_at | IGKC | BG540628 |
| 234366_x_at | IGL@ | AF103591.1 |
| 217480_x_at | IGKV1OR15-118; IGKVP2; IGKV1OR118; IGKV1/OR-118; IGKV1/OR15-118 | M20812 |
| 216401_x_at | IGKV | AJ408433 |
| 216491_x_at | V4-4 | U80139 |
| 211637_x_at | IGHM | L23516.1 |
| 224795_x_at | IGKC | AW575927 |
| 211430_s_at | IGHG3 | M87789.1 |
| 217235_x_at | IGLJ3 | D84140.1 |
| 211634_x_at | IGHM | M24669.1 |
| 211633_x_at | ICAP-1A | M24668.1 |
| 211908_x_at | IGHM | M87268.1 |
| 205692_s_at | CD38 | NM_001775 |
| 201923_at | PRDX4 | NM_006406 |
| 211639_x_at | IGHM | L23518.1 |
| 216517_at | IGKV1D-8; L24; L24a; IGKV1D8 | Z00008 |
| 228323_at | AF15Q14 | BF248364 |
| 218883_s_at | FLJ23468 | NM_024629 |
| 218039_at | ANKT | NM_016359 |
| 209773_s_at | RRM2 | BC001886.1 |
| 202589_at | TYMS | NM_001071 |
| 202503_s_at | KIAA0101 | NM_014736 |
| 201890_at | RRM2 | NM_001034.1 |
| 201292_at | TOP2A | NM_001067.1 |
| 209714_s_at | CDKN3 | AF213033.1 |
| 203554_x_at | PTTG1 | NM_004219 |
| 204026_s_at | ZWINT | NM_007057 |
| 202107_s_at | MCM2 | NM_004526 |
| 222680_s_at | RAMP | AK001261.1 |
| 226099_at | ELL2 | AI924426 |
| 204170_s_at | CKS2 | NM_001827 |
| 222036_s_at | | AI859865 |
| 203213_at | CDC2 | AL524035 |
| 203755_at | BUB1B | NM_001211 |
| 200983_x_at | CD59 | NM_000611.1 |
| 209610_s_at | SLC1A4 | BF340083 |
| 201897_s_at | CKS1B | NM_001826 |
| 218350_s_at | GMNN | NM_015895 |
| 209408_at | KNSL6 | U63743.1 |
| 226936_at | | BG492359 |

TABLE 2B-continued

Table 2B

| Affymetrix ID | Common | Genbank |
|---|---|---|
| 208103_s_at | ANP32E | NM_030920 |
| 225834_at | | AL135396 |
| 201096_s_at | ARF4 | AL537042 |
| 203432_at | TMPO | AW272611 |
| 202433_at | SLC35B1 | NM_005827 |
| 204825_at | MELK | NM_014791 |
| 223054_at | DNAJB11 | BC001144.1 |
| 216640_s_at | | AK026926.1 |
| 208639_x_at | P5 | BC001312.1 |
| 207668_x_at | P5 | NM_005742 |
| 222411_s_at | SSR3 | AW087870 |
| 203594_at | RTCD1 | NM_003729 |
| 201532_at | PSMA3 | NM_002788 |
| 203857_s_at | PDIR | NM_006810 |
| 202345_s_at | FABP5 | NM_001444 |
| 229865_at | | AW058617 |
| 222435_s_at | UBE2J1 | AF161502.1 |
| 217825_s_at | UBE2J1 | AF151039.1 |
| 217826_s_at | UBE2J1 | NM_016021 |
| 201543_s_at | SARA1 | NM_020150 |
| 222231_s_at | PRO1855 | AK025328.1 |
| 217823_s_at | UBE2J1 | NM_016021.1 |
| 223325_at | LOC51061 | AF131780.1 |
| 209186_at | ATP2A2 | M23114.1 |
| 201281_at | ADRM1 | NM_007002 |
| 217824_at | UBE2J1 | NM_016021.1 |
| 214512_s_at | PC4 | NM_006713.1 |
| 226773_at | | AW290940 |
| 221867_s_at | FLJ31821 | BF436315 |
| 218927_s_at | C4S-2 | NM_018641 |
| 201714_at | TUBG1 | NM_001070 |
| 201516_at | SRM | NM_003132 |
| 218130_at | MGC4368 | NM_024510 |
| 203148_s_at | TRIM14 | NM_014788 |
| 203800_s_at | MRPS14 | NM_022100.1 |
| 201175_at | CGI-31 | NM_015959 |
| 203155_s_at | SETDB1 | NM_012432 |
| 201037_at | PFKP | NM_002627 |
| 204116_at | IL2RG | NM_000206 |
| 212733_at | KIAA0226 | AI798908 |
| 203281_s_at | UBE1L | NM_003335 |
| 202245_at | LSS | AW084510 |
| 218632_at | FLJ21156 | NM_024602 |
| 208676_s_at | | U87954.1 |
| 218059_at | LOC51123 | NM_016096 |
| 224333_s_at | MRPS5 | AB049940.1 |
| 222748_s_at | FLJ20511 | AW194729 |
| 207375_s_at | IL15RA | NM_002189 |
| 206576_s_at | CEACAM1 | NM_001712 |
| 208805_at | PSMA6 | BC002979.1 |
| 222631_at | PI4K2B | AI862887 |
| 200700_s_at | KDELR2 | NM_006854 |
| 222250_s_at | DKFZP434B168 | AK001363.1 |
| 208640_at | RAC1 | BG292367 |
| 208598_s_at | UREB1 | NM_005703 |
| 202474_s_at | HCFC1 | NM_005334 |
| 202854_at | HPRT1 | NM_000194 |
| 203573_s_at | RABGGTA | NM_004581 |
| 223163_s_at | HSPC216 | BC000190.1 |
| 202883_s_at | PPP2R1B | T79584 |
| 201068_s_at | PSMC2 | NM_002803 |
| 211762_s_at | KPNA2 | BC005978.1 |
| 223354_x_at | GL004 | BC003191.1 |
| 212250_at | | AI972475 |
| 202635_s_at | POLR2K | NM_005034 |
| 202511_s_at | APG5L | AK001899.1 |
| 214315_x_at | CALR | AI348935 |
| 212953_x_at | CALR | BE251303 |
| 213061_s_at | LOC123803 | AA643304 |
| 222805_at | FLJ12838 | AI587307 |
| 218048_at | BUP | NM_012071 |
| 209765_at | ADAM19 | Y13786.2 |
| 208815_x_at | HSPA4 | AB023420.1 |
| 223128_at | H17 | AL136923.1 |
| 221853_s_at | LOC283820 | N39536 |

TABLE 2B-continued

Table 2B

| Affymetrix ID | Common | Genbank |
|---|---|---|
| 227350_at | | AI807356 |
| 208808_s_at | HMGB2 | BC000903.1 |
| 201088_at | KPNA2 | NM_002266 |
| 204127_at | RFC3 | BC000149.2 |
| 224428_s_at | CDCA7 | AY029179.1 |
| 212020_s_at | MKI67 | BF001806 |
| 228069_at | | AL138828 |
| 213851_at | | BG031677 |
| 218447_at | DC13 | NM_020188 |
| 210927_x_at | JTB | BC004239.1 |
| 223991_s_at | GALNT2 | AF130059.1 |
| 230165_at | TRIPIN | N31731 |
| 228401_at | PRO2000 | AI656807 |
| 212053_at | KIAA0251 | AK025504.1 |
| 203033_x_at | FH | NM_000143 |
| 224745_x_at | DKFZp761A052 | AK026260.1 |
| 224405_at | IRTA2 | AF343663.1 |
| 206632_s_at | APOBEC3B | NM_004900 |
| 206486_at | LAG3 | NM_002286 |
| 226217_at | | AU152456 |
| 226025_at | KIAA0379 | AV740426 |
| 204563_at | SELL | NM_000655 |
| 201951_at | ALCAM | NM_001627.1 |
| 213116_at | NEK3 | AI191920 |
| 208979_at | NCOA6 | AF128458.1 |
| 201201_at | CSTB | NM_000100 |
| 210966_x_at | LARP | BC001460.1 |
| 202579_x_at | HMGN4 | NM_006353 |
| 209858_x_at | MPPE1 | BC002877.1 |
| 203688_at | PKD2 | NM_000297 |
| 208875_s_at | | AF092132.1 |
| 207167_at | IGSF2 | NM_004258 |
| 200988_s_at | PSME3 | NM_005789 |
| 209191_at | TUBB-5 | BC002654.1 |
| 235812_at | FLJ38101 | AI935115 |
| 212171_x_at | VEGF | H95344 |
| 204458_at | LYPLA3 | AL110209.1 |
| 212901_s_at | CSTF2T | BF732638 |
| 55692_at | ELMO2 | W22924 |
| 214414_x_at | HBA1 | T50399 |
| 227388_at | | AA479016 |
| 239582_at | | AW514654 |
| 209221_s_at | OSBPL2 | AI753638 |
| 206881_s_at | LILRA3 | NM_006865 |
| 244389_at | | AU145538 |
| 226759_at | ZNFN1A4 | BE793250 |
| 202359_s_at | SNX19 | NM_014758 |

Under- or over-expression of 371 (p<0.001) [or 844 (p<0.01)] (Table 2C) of the genes listed in Tables 2A and 2B are correlated with the severity of disease measured by SLE-DAI.

TABLE 2C

Table 2C

| Affy ID | Common | GenBank | p-value |
|---|---|---|---|
| 202446_s_at | PLSCR1 | AI825926 | P < 0.0001 |
| 223767_at | GPR84 | AF237762.1 | P < 0.0001 |
| 221485_at | B4GALT5 | NM_004776.1 | P < 0.0001 |
| 221050_s_at | GTPBP2 | NM_019096 | P < 0.0001 |
| 213361_at | PCTAIRE2BP | AW129593 | P < 0.0001 |
| 222154_s_at | DNAPTP6 | AK002064.1 | P < 0.0001 |
| 202145_at | LY6E | NM_002346 | P < 0.0001 |
| 221589_s_at | ALDH6A1 | AF130089.1 | P < 0.0001 |
| 202869_at | OAS1 | NM_016816 | P < 0.0001 |
| 225447_at | | AA613031 | P < 0.0001 |
| 205552_s_at | OAS1 | NM_002534 | P < 0.0001 |
| 209864_at | FRAT2 | AB045118.1 | P < 0.0001 |
| 227609_at | EPSTI1 | AA633203 | P < 0.0001 |

TABLE 2C-continued

Table 2C

| Affy ID | Common | GenBank | p-value |
|---|---|---|---|
| 225672_at | GOLGA2 | AL514295 | P < 0.0001 |
| 200815_s_at | PAFAH1B1 | L13386.1 | P < 0.0001 |
| 208901_s_at | TOP1 | J03250.1 | P < 0.0001 |
| 228230_at | PRIC285 | AL121829 | P < 0.0001 |
| 226968_at | KIF1B | AK023184.1 | P < 0.0001 |
| 209930_s_at | NFE2 | L13974.1 | P < 0.0001 |
| 204994_at | MX2 | NM_002463 | P < 0.0001 |
| 223220_s_at | BAL | AF307338.1 | P < 0.0001 |
| 206111_at | RNASE2 | NM_002934 | P < 0.0001 |
| 226702_at | LOC129607 | AI742057 | P < 0.0001 |
| 224009_x_at | RDHL | AF240697.1 | P < 0.0001 |
| 206157_at | PTX3 | NM_002852 | P < 0.0001 |
| 214453_s_at | IFI44 | NM_006417.1 | P < 0.0001 |
| 223952_x_at | RDHL | AF240698.1 | 0.0001 |
| 213607_x_at | FLJ13052 | BE551347 | 0.0001 |
| 222793_at | RIG-I | AK023661.1 | 0.0001 |
| 218883_s_at | FLJ23468 | NM_024629 | 0.0001 |
| 221484_at | B4GALT5 | NM_004776.1 | 0.0001 |
| 211883_x_at | CEACAM1 | M76742.1 | 0.0001 |
| 200999_s_at | CKAP4 | NM_006825 | 0.0001 |
| 201020_at | YWHAH | NM_003405 | 0.0001 |
| 210773_s_at | FPRL1 | U81501.1 | 0.0001 |
| 224707_at | ORF1-FL49 | AL522667 | 0.0001 |
| 208751_at | NAPA | BC001165.1 | 0.0002 |
| 214438_at | HLX1 | M60721.1 | 0.0002 |
| 204972_at | OAS2 | NM_016817 | 0.0002 |
| 202430_s_at | PLSCR1 | NM_021105 | 0.0002 |
| 202086_at | MX1 | NM_002462 | 0.0002 |
| 208918_s_at | FLJ13052 | BC001709.1 | 0.0002 |
| 207320_x_at | STAU | NM_004602 | 0.0002 |
| 204351_at | S100P | NM_005980 | 0.0002 |
| 207674_at | FCAR | NM_002000 | 0.0002 |
| 225834_at | | AL135396 | 0.0002 |
| 212020_s_at | MKI67 | BF001806 | 0.0002 |
| 203755_at | BUB1B | NM_001211 | 0.0002 |
| 230036_at | FLJ39885 | BE669858 | 0.0002 |
| 205698_s_at | MAP2K6 | NM_002758 | 0.0002 |
| 201926_s_at | DAF | BC001288.1 | 0.0002 |
| 209398_at | H1F2 | BC002649.1 | 0.0002 |
| 202068_s_at | LDLR | NM_000527 | 0.0002 |
| 206491_s_at | NAPA | NM_003827 | 0.0002 |
| 209498_at | CEACAM1 | X16354.1 | 0.0003 |
| 239988_at | | AA708470 | 0.0003 |
| 201193_at | IDH1 | NM_005896 | 0.0003 |
| 218660_at | DYSF | NM_003494 | 0.0003 |
| 218352_at | RCBTB1 | NM_018191 | 0.0003 |
| 208436_s_at | IRF7 | NM_004030 | 0.0003 |
| 233924_s_at | SEC15L | AK002113.1 | 0.0003 |
| 212602_at | ALFY | AI806395 | 0.0003 |
| 211456_x_at | | AF333388.1 | 0.0003 |
| 210772_at | FPRL1 | M88107.1 | 0.0003 |
| 204336_s_at | RGS19 | NM_005873 | 0.0003 |
| 219211_at | USP18 | NM_017414 | 0.0003 |
| 205863_at | S100A12 | NM_005621 | 0.0004 |
| 201315_x_at | IFITM2 | NM_006435 | 0.0004 |
| 44673_at | SN | N53555 | 0.0004 |
| 203761_at | SLA | NM_006748 | 0.0004 |
| 200998_s_at | CKAP4 | AW029619 | 0.0004 |
| 209616_s_at | CES1 | S73751.1 | 0.0004 |
| 211012_s_at | PML | BC000080.1 | 0.0004 |
| 214059_at | IFI44 | BE049439 | 0.0004 |
| 231688_at | | AW337833 | 0.0005 |
| 209417_s_at | IFI35 | BC001356.1 | 0.0005 |
| 236285_at | | AI631846 | 0.0005 |
| 207677_s_at | NCF4 | NM_013416 | 0.0006 |
| 206062_s_at | TNFAIP6 | NM_007115 | 0.0005 |
| 219356_s_at | HSPC177 | NM_016410 | 0.0005 |
| 202391_at | BASP1 | NM_006317 | 0.0005 |
| 216202_s_at | SPTLC2 | U15555.1 | 0.0005 |
| 241916_at | | AI984040 | 0.0005 |
| 222680_s_at | RAMP | AK001261.1 | 0.0005 |
| 203936_s_at | MMP9 | NM_004994 | 0.0005 |
| 210797_s_at | OASL | AF063612.1 | 0.0006 |
| 202530_at | MAPK14 | NM_001315 | 0.0006 |
| 222036_s_at | | AI859865 | 0.0006 |

TABLE 2C-continued

| Affy ID | Common | GenBank | p-value |
|---|---|---|---|
| 210101_x_at | SH3GLB1 | AF257318.1 | 0.0006 |
| 235568_at | LOC199675 | BF433657 | 0.0006 |
| 226603_at | FLJ39885 | BE966604 | 0.0006 |
| 211889_x_at | CEACAM1 | D12502.1 | 0.0006 |
| 228323_at | AF15Q14 | BF248364 | 0.0006 |
| 201118_at | PGD | NM_002631 | 0.0006 |
| 233072_at | KIAA1857 | AI348745 | 0.0006 |
| 204211_x_at | PRKR | NM_002759 | 0.0006 |
| 209091_s_at | SH3GLB1 | AF263293.1 | 0.0006 |
| 224701_at | KIAA1268 | AA056548 | 0.0007 |
| 204439_at | C1orf29 | NM_006820 | 0.0007 |
| 208864_s_at | TXN | AF313911.1 | 0.0007 |
| 218728_s_at | HSPC163 | NM_014184 | 0.0007 |
| 218403_at | HSPC132 | NM_016399 | 0.0007 |
| 202348_s_at | DYT1 | BC000674.1 | 0.0007 |
| 242760_x_at | | AA808203 | 0.0007 |
| 217995_at | SQRDL | NM_021199 | 0.0007 |
| 202794_at | INPP1 | NM_002194 | 0.0008 |
| 202411_at | IFI27 | NM_005532 | 0.0008 |
| 204714_s_at | F5 | NM_000130 | 0.0008 |
| 233587_s_at | | AK022852.1 | 0.0009 |
| 219283_at | C1GALT2 | NM_014158 | 0.0009 |
| 217977_at | SEPX1 | NM_016332 | 0.0009 |
| 226789_at | ARIH2 | W84421 | 0.0009 |
| 222662_at | LOC286044 | W60806 | 0.0009 |
| 222010_at | TCP1 | BF224073 | 0.0009 |
| 212531_at | LCN2 | NM_005564.1 | 0.001 |
| 203765_at | GCA | NM_012198 | 0.001 |
| 206515_at | CYP4F3 | NM_000896 | 0.001 |
| 201554_x_at | GYG | NM_004130 | 0.001 |
| 214290_s_at | HIST2H2AA | AA451996 | 0.001 |
| 200923_at | LGALS3BP | NM_005567 | 0.001 |
| 235816_s_at | Rgr | AI867408 | 0.001 |
| 212185_x_at | MT2A | NM_005953.1 | 0.0011 |
| 224414_s_at | CARD6 | AF356193.1 | 0.0011 |
| 228648_at | LRG | AA622495 | 0.0011 |
| 208886_at | H1F0 | BC000145.1 | 0.0011 |
| 205483_s_at | G1P2 | NM_005101 | 0.0012 |
| 203153_at | IFIT1 | NM_001548 | 0.0012 |
| 229770_at | FLJ31978 | AI041543 | 0.0013 |
| 212203_at | IFITM3 | BF338947 | 0.0013 |
| 201060_x_at | STOM | AI537887 | 0.0013 |
| 231455_at | | AA768888 | 0.0013 |
| 213532_at | LOC285148 | AI797833 | 0.0013 |
| 219863_at | CEB1 | NM_016323 | 0.0014 |
| 209593_s_at | TOR1B | AF317129.1 | 0.0014 |
| 213294_at | | AV755522 | 0.0014 |
| 205627_at | CDA | NM_001785 | 0.0014 |
| 200766_at | CTSD | NM_001909 | 0.0015 |
| 222986_s_at | SCOTIN | BC001463.1 | 0.0015 |
| 206177_s_at | ARG1 | NM_000045 | 0.0015 |
| 225468_at | FLJ36874 | AI761804 | 0.0016 |
| 206676_at | CEACAM8 | M33326.1 | 0.0016 |
| 227438_at | LAK | AI760166 | 0.0016 |
| 204174_at | ALOX5AP | NM_001629 | 0.0016 |
| 226448_at | | AI130705 | 0.0016 |
| 220947_s_at | DKFZP434P1750 | NM_015527 | 0.0016 |
| 201298_s_at | C2orf6 | BC003398.1 | 0.0017 |
| 225076_at | KIAA1404 | AA150460 | 0.0017 |
| 225032_at | FAD104 | AI141784 | 0.0017 |
| 226275_at | | AI188653 | 0.0018 |
| 210386_s_at | MTX1 | BC001906.1 | 0.0018 |
| 204923_at | CXorf9 | AL023653 | 0.0019 |
| 206025_s_at | TNFAIP6 | AW188198 | 0.0019 |
| 223375_at | FLJ20337 | BC002720.1 | 0.0019 |
| 201619_at | PRDX3 | NM_006793 | 0.0019 |
| 226077_at | FLJ31951 | AL553942 | 0.0019 |
| 228361_at | | AL561296 | 0.002 |
| 202441_at | KEO4 | AL568449 | 0.002 |
| 227833_s_at | MBD6 | AW207668 | 0.0021 |
| 212268_at | SERPINB1 | NM_030666.1 | 0.0021 |
| 219157_at | KLHL2 | NM_007246 | 0.0022 |
| 203397_s_at | GALNT3 | BF063271 | 0.0022 |
| 216041_x_at | GRN | AK023348.1 | 0.0023 |
| 205147_x_at | NCF4 | NM_000631 | 0.0023 |
| 200660_at | S100A11 | NM_005620 | 0.0023 |
| 201963_at | FACL2 | NM_021122 | 0.0023 |
| 229460_at | CED-6 | AI927605 | 0.0024 |
| 229450_at | | AI075407 | 0.0024 |
| 201061_s_at | STOM | M81635.1 | 0.0024 |
| 209369_at | ANXA3 | M63310.1 | 0.0025 |
| 231644_at | | AW016812 | 0.0025 |
| 200678_x_at | GRN | NM_002087 | 0.0025 |
| 220615_s_at | FLJ10462 | NM_018099 | 0.0025 |
| 211075_s_at | CD47 | Z25521.1 | 0.0025 |
| 207691_x_at | ENTPD1 | NM_001776 | 0.0028 |
| 238025_at | FLJ34389 | AA706818 | 0.0026 |
| 232517_s_at | PRIC285 | AL121829 | 0.0026 |
| 210449_x_at | MAPK14 | AF100544.1 | 0.0026 |
| 204043_at | TCN2 | NM_000355 | 0.0026 |
| 209408_at | KNSL6 | U63743.1 | 0.0027 |
| 213836_s_at | KIAA1001 | AW052084 | 0.0027 |
| 209396_s_at | CHI3L1 | M80927.1 | 0.0027 |
| 203725_at | GADD45A | NM_001924 | 0.0027 |
| 227807_at | | AI738416 | 0.0028 |
| 204026_s_at | ZWINT | NM_007057 | 0.0028 |
| 210176_at | TLR1 | AL050262.1 | 0.0028 |
| 201096_s_at | ARF4 | AL537042 | 0.0028 |
| 221036_s_at | PSFL | NM_031301 | 0.0029 |
| 229865_at | | AW058617 | 0.003 |
| 216565_x_at | | AL121994 | 0.003 |
| 206697_s_at | HP | NM_005143 | 0.0031 |
| 242625_at | cig5 | AW189843 | 0.0031 |
| 206682_at | HML2 | NM_006344 | 0.0031 |
| 226939_at | | AI202327 | 0.0032 |
| 205660_at | OASL | NM_003733 | 0.0032 |
| 200798_x_at | MCL1 | NM_021960 | 0.0032 |
| 228531_at | FLJ20073 | AA741307 | 0.0032 |
| 205513_at | TCN1 | NM_001062 | 0.0032 |
| 225056_at | | AB037810.1 | 0.0032 |
| 221345_at | GPR43 | NM_005306 | 0.0033 |
| 224790_at | DDEF1 | W03103 | 0.0033 |
| 219607_s_at | MS4A4A | NM_024021 | 0.0033 |
| 213476_x_at | TUBB4 | AL565749 | 0.0033 |
| 242020_s_at | | AI925506 | 0.0033 |
| 211284_s_at | GRN | BC000324.1 | 0.0034 |
| 224967_at | UGCG | W72338 | 0.0034 |
| 202934_at | HK2 | AI761561 | 0.0034 |
| 201951_at | ALCAM | NM_001627.1 | 0.0034 |
| 203140_at | BCL6 | NM_001706 | 0.0034 |
| 219492_at | CHIC2 | NM_012110 | 0.0034 |
| 227140_at | | AI343467 | 0.0035 |
| 220330_s_at | SAMSN1 | NM_022136 | 0.0035 |
| 228617_at | | AA142842 | 0.0035 |
| 208926_at | NEU1 | U84246.1 | 0.0035 |
| 205098_at | CCR1 | AI421071 | 0.0035 |
| 202708_s_at | HIST2H2BE | NM_003528 | 0.0036 |
| 203276_at | LMNB1 | NM_005573 | 0.0036 |
| 218472_s_at | PELO | NM_015946 | 0.0036 |
| 218059_at | LOC51123 | NM_016096 | 0.0036 |
| 225622_at | PAG | NM_018440.1 | 0.0037 |
| 202018_s_at | LTF | NM_002343 | 0.0038 |
| 218454_at | FLJ22662 | NM_024829 | 0.0038 |
| 218057_x_at | NOC4 | NM_006067 | 0.0038 |
| 230748_at | | AI873273 | 0.0038 |
| 204825_at | MELK | NM_014791 | 0.0039 |
| 201890_at | RRM2 | NM_001034.1 | 0.004 |
| 208881_x_at | IDI1 | BC005247.1 | 0.004 |
| 203371_s_at | NDUFB3 | NM_002491 | 0.0041 |
| 208919_s_at | FLJ13052 | BC001709.1 | 0.0041 |
| 202589_at | TYMS | NM_001071 | 0.0042 |
| 201292_at | TOP2A | NM_001067.1 | 0.0043 |
| 201015_s_at | JUP | NM_021991 | 0.0043 |
| 231769_at | FBXO6 | AF129536.1 | 0.0045 |
| 212606_at | ALFY | AI806395 | 0.0045 |
| 218599_at | REC8 | NM_005132 | 0.0046 |
| 218268_at | FLJ12085 | NM_022771 | 0.0046 |
| 242234_at | HSXIAPAF1 | AI859280 | 0.0047 |
| 211275_s_at | GYG | AF087942.1 | 0.0047 |
| 204308_s_at | KIAA0329 | NM_014844 | 0.0047 |

TABLE 2C-continued

Table 2C

| Affy ID | Common | GenBank | p-value |
|---|---|---|---|
| 208749_x_at | FLOT1 | AF085357.1 | 0.0047 |
| 204747_at | IFIT4 | NM_001549 | 0.0049 |
| 241812_at | | AV648669 | 0.0049 |
| 203127_at | SPTLC2 | BC005123.1 | 0.005 |
| 236172_at | | AW206817 | 0.0051 |
| 227236_at | TSPAN-2 | AK022144.1 | 0.0052 |
| 212051_at | | AK026913.1 | 0.0052 |
| 202197_at | MTMR3 | NM_021090 | 0.0052 |
| 200983_x_at | CD59 | NM_000611.1 | 0.0053 |
| 204615_x_at | IDI1 | NM_004508 | 0.0055 |
| 203021_at | SLPI | NM_003064 | 0.0055 |
| 202863_at | SP100 | NM_003113 | 0.0055 |
| 219259_at | FLJ12287 | NM_022367 | 0.0056 |
| 222981_s_at | RAB10 | BC000896.1 | 0.0056 |
| 204170_s_at | CKS2 | NM_001827 | 0.0057 |
| 239108_at | | H16791 | 0.0058 |
| 225095_at | | W81119 | 0.0058 |
| 201583_s_at | SEC23B | NM_006363 | 0.0059 |
| 203236_s_at | LGALS9 | NM_009587 | 0.006 |
| 223145_s_at | FLJ10342 | BC000764.1 | 0.0061 |
| 208805_at | PSMA6 | BC002979.1 | 0.0062 |
| 208977_x_at | TUBB2 | BC004188.1 | 0.0063 |
| 225160_x_at | MGC5370 | AI952357 | 0.0064 |
| 212639_x_at | K-ALPHA-1 | AL581768 | 0.0065 |
| 203432_at | TMPO | AW272611 | 0.0066 |
| 210244_at | CAMP | U19970.1 | 0.0067 |
| 220001_at | PADI4 | NM_012387 | 0.0067 |
| 221874_at | KIAA1324 | AB037745.1 | 0.0069 |
| 202084_s_at | SEC14L1 | NM_003003 | 0.0071 |
| 227219_x_at | MAP1LC3A | BE857601 | 0.0072 |
| 211404_s_at | APLP2 | BC004371.1 | 0.0072 |
| 227649_s_at | | AU144000 | 0.0073 |
| 238327_at | ECGF1 | AI962367 | 0.0073 |
| 200663_at | CD63 | NM_001780 | 0.0074 |
| 223423_at | GPCR1 | BC000181.2 | 0.0075 |
| 200039_s_at | PSMB2 | NM_002794 | 0.0075 |
| 204798_at | MYB | NM_005375 | 0.0077 |
| 203213_at | CDC2 | AL524035 | 0.0076 |
| 224829_at | KIAA1673 | AA772278 | 0.0077 |
| 208992_s_at | STAT3 | BC000627.1 | 0.0078 |
| 205099_s_at | CCR1 | NM_001295 | 0.0078 |
| 229305_at | | AA460299 | 0.008 |
| 203342_at | TIMM17B | NM_005834 | 0.008 |
| 201897_s_at | CKS1B | NM_001826 | 0.008 |
| 207375_s_at | IL15RA | NM_002189 | 0.0081 |
| 203094_at | CMT2 | NM_014628 | 0.0081 |
| 217794_at | DKFZP564J157 | NM_018457 | 0.0083 |
| 209221_s_at | OSBPL2 | AI753638 | 0.0083 |
| 202241_at | C8FW | NM_025195 | 0.0084 |
| 222498_at | FLJ21939 | AI809206 | 0.0084 |
| 208654_s_at | CD164 | AF299343.1 | 0.0085 |
| 211749_s_at | VAMP3 | BC005941.1 | 0.0085 |
| 232787_at | | AK023724.1 | 0.0086 |
| 204713_at | F5 | AA910306 | 0.0086 |
| 201601_x_at | IFITM1 | NM_003641 | 0.0087 |
| 219691_at | FLJ20073 | NM_017654 | 0.0088 |
| 242013_at | | BF445012 | 0.0089 |
| 228412_at | BAZ2B | AI991451 | 0.0089 |
| 228069_at | | AL138828 | 0.0089 |
| 219890_at | CLECSF5 | NM_013252 | 0.0091 |
| 201642_at | IFNGR2 | NM_005534 | 0.0091 |
| 235456_at | | AI810266 | 0.0092 |
| 208702_x_at | APLP2 | BC000373.1 | 0.0092 |
| 201453_x_at | RHEB2 | NM_005614 | 0.0092 |
| 201786_s_at | ADAR | NM_001111 | 0.0094 |
| 229521_at | FLJ36031 | BE466274 | 0.0094 |
| 203814_s_at | NQO2 | NM_000904 | 0.0096 |
| 209773_s_at | RRM2 | BC001886.1 | 0.0096 |
| 217835_x_at | C20orf24 | NM_018840 | 0.0097 |
| 204858_s_at | ECGF1 | NM_001953 | 0.0097 |
| 218559_s_at | MAFB | NM_005461 | 0.0098 |
| 218188_s_at | TIMM13 | NM_012458 | 0.0098 |
| 209911_x_at | H2BFB | BC002842.1 | 0.01 |
| 226883_at | | T89044 | 0.0099 |
| 241299_at | | AI651969 | 0.0099 |
| 212873_at | HA-1 | BE349017 | 0.0099 |
| 218496_at | RNASEH1 | BG534527 | 0.0098 |
| 218100_s_at | ESRRBL1 | NM_018010 | 0.0098 |
| 217256_x_at | dJ507I15.1 | Z98950 | 0.0098 |
| 243363_at | LEF1 | AA992805 | 0.0098 |
| 229874_x_at | | BE865517 | 0.0097 |
| 40255_at | DDX28 | AC004531 | 0.0095 |
| 220036_s_at | LIMR | NM_018113 | 0.0092 |
| 223444_at | SENP7 | AL136599.1 | 0.0091 |
| 202595_s_at | LEPROTL1 | AF161461.1 | 0.0089 |
| 212560_at | | AV728268 | 0.0089 |
| 204718_at | EPHB6 | NM_004445 | 0.0089 |
| 227077_at | | BF432238 | 0.0089 |
| 205376_at | INPP4B | NM_003866 | 0.0088 |
| 219765_at | FLJ12586 | NM_024620 | 0.0087 |
| 218531_at | FLJ21749 | NM_025124 | 0.0086 |
| 218142_s_at | LOC51185 | NM_016302 | 0.0086 |
| 90610_at | LRRN1 | AI654857 | 0.0085 |
| 205089_at | ZNF7 | NM_003416 | 0.0084 |
| 228049_x_at | | AA523172 | 0.0084 |
| 213377_at | C1S | AI799007 | 0.0084 |
| 213743_at | CCNT2 | BE674119 | 0.0083 |
| 217895_at | FLJ20758 | NM_017952 | 0.008 |
| 217549_at | | AW574933 | 0.008 |
| 235432_at | FLJ35693 | BE865779 | 0.0079 |
| 222895_s_at | BCL11B | AA918317 | 0.0079 |
| 224163_s_at | DMAP1 | AL136657.1 | 0.0079 |
| 213539_at | CD3D | NM_000732.1 | 0.0078 |
| 214527_s_at | PQBP1 | AB041836.1 | 0.0078 |
| 212936_at | DKFZP564D172 | AI927701 | 0.0077 |
| 201257_x_at | RPS3A | NM_001006 | 0.0076 |
| 216033_s_at | FYN | S74774.1 | 0.0075 |
| 214855_s_at | TULIP1 | AL050091.1 | 0.0074 |
| 201054_at | HNRPA0 | BE966599 | 0.0073 |
| 224664_at | | AK023981.1 | 0.0073 |
| 228239_at | C21orf51 | AA148789 | 0.0073 |
| 209153_s_at | TCF3 | M31523.1 | 0.007 |
| 209539_at | ARHGEF6 | D25304.1 | 0.0069 |
| 204773_at | IL11RA | NM_004512 | 0.0069 |
| 231798_at | NOG | AL575177 | 0.0068 |
| 231124_x_at | | AI524095 | 0.0068 |
| 224367_at | DJ79P11.1 | AF251053.1 | 0.0067 |
| 223231_at | CDA11 | AF212250.1 | 0.0067 |
| 224688_at | | BE962299 | 0.0067 |
| 210018_x_at | MALT1 | AB026118.1 | 0.0067 |
| 49111_at | | N80935 | 0.0066 |
| 207840_at | BY55 | NM_007053 | 0.0072 |
| 206267_s_at | MATK | NM_002378 | 0.0066 |
| 219335_at | FLJ12969 | NM_022838 | 0.0066 |
| 228662_at | | AI492369 | 0.0066 |
| 213035_at | KIAA0379 | AI081194 | 0.0066 |
| 224479_s_at | MRPL45 | BC006235.1 | 0.0065 |
| 214470_at | KLRB1 | NM_002258.1 | 0.0065 |
| 202746_at | ITM2A; E25A | AL021782 | 0.0065 |
| 221488_s_at | LOC51596 | AF230924.1 | 0.0065 |
| 216497_at | | AL390738 | 0.0065 |
| 227640_s_at | LOC222136 | AI492167 | 0.0064 |
| 228240_at | KIAA1337 | AW952320 | 0.0064 |
| 215440_s_at | FLJ10097 | AL523320 | 0.0064 |
| 200912_s_at | EIF4A2 | NM_001967 | 0.0064 |
| 225455_at | STAF42 | AI760812 | 0.0063 |
| 224968_at | MGC15407 | AL518311 | 0.0063 |
| 220942_x_at | E2IG5 | NM_014367 | 0.0062 |
| 202698_x_at | COX4I1 | NM_001861 | 0.0062 |
| 213830_at | TRD@ | AW007751 | 0.0062 |
| 200666_s_at | DNAJB1 | NM_006145 | 0.0062 |
| 221691_x_at | NPM1 | AB042278.1 | 0.0061 |
| 224935_at | EIF2S3 | BE252813 | 0.0061 |
| 221264_s_at | AF311304 | NM_031214 | 0.0061 |
| 211678_s_at | ZNF313 | AF090934.1 | 0.0061 |
| 242292_at | MGC34827 | H12084 | 0.006 |
| 213034_at | | AB023216.1 | 0.006 |
| 222279_at | | AI669379 | 0.0059 |
| 239300_at | | AI632214 | 0.0059 |
| 209323_at | PRKRIR | AF081567.1 | 0.0059 |

TABLE 2C-continued

Table 2C

| Affy ID | Common | GenBank | p-value |
|---|---|---|---|
| 204155_s_at | KIAA0999 | AA044154 | 0.0059 |
| 223092_at | ANKH | AF274753.1 | 0.0059 |
| 203932_at | HLA-DMB | NM_002118 | 0.0058 |
| 214800_x_at | BTF3 | R83000 | 0.0058 |
| 226718_at | KIAA1163 | AA001423 | 0.0058 |
| 212267_at | KIAA0261 | D87450.1 | 0.0057 |
| 212131_at | DKFZP434D1335 | AL117499.1 | 0.0057 |
| 240572_s_at | | BF436632 | 0.0056 |
| 210927_x_at | JTB | BC004239.1 | 0.0056 |
| 203581_at | RAB4A | BC002438.1 | 0.0056 |
| 205961_s_at | PSIP2 | NM_004682 | 0.0056 |
| 221493_at | TSPYL | AL136629.1 | 0.0055 |
| 212846_at | KIAA0179 | D80001.1 | 0.0055 |
| 225509_at | LOC56757 | AI862477 | 0.0055 |
| 203445_s_at | OS4 | NM_005730 | 0.0054 |
| 201665_x_at | RPS17 | NM_001021 | 0.0054 |
| 210502_s_at | PPIE | AF042386.1 | 0.0053 |
| 227878_s_at | MGC10974 | AI245026 | 0.0052 |
| 226816_s_at | KIAA1143 | AI745170 | 0.0052 |
| 212814_at | KIAA0828 | AB020635.1 | 0.0052 |
| 211761_s_at | SIP | BC005975.1 | 0.0051 |
| 211698_at | CRI1 | AF349444.1 | 0.0051 |
| 202741_at | PRKACB | AA130247 | 0.0051 |
| 212503_s_at | KIAA0934 | N31807 | 0.0051 |
| 200717_x_at | RPL7 | NM_000971 | 0.0051 |
| 243154_at | | AA215381 | 0.005 |
| 213588_x_at | RPL14 | AA838274 | 0.005 |
| 218592_s_at | CECR5 | NM_017829 | 0.0049 |
| 218263_s_at | LOC58486 | NM_021211 | 0.0049 |
| 227402_s_at | MGC14595 | AI056895 | 0.0049 |
| 212145_at | MRPS27 | D87453.1 | 0.0048 |
| 229264_at | | AI675152 | 0.0048 |
| 205005_s_at | NMT2 | AW293531 | 0.0048 |
| 200811_at | CIRBP | NM_001280 | 0.0048 |
| 222125_s_at | PH-4 | BC000580.1 | 0.0047 |
| 220952_s_at | PEPP2 | NM_019012 | 0.0047 |
| 204528_s_at | NAP1L1 | NM_004537 | 0.0047 |
| 214003_x_at | RPS20 | BF184532 | 0.0047 |
| 210017_at | MALT1 | AF070528.1 | 0.0047 |
| 52940_at | SIGIRR | AA085764 | 0.0046 |
| 206059_at | ZNF91 | NM_003430 | 0.0046 |
| 227567_at | | AL524467 | 0.0046 |
| 218437_s_at | LZTFL1 | NM_020347 | 0.0046 |
| 218039_at | ANKT | NM_016359 | 0.0046 |
| 208894_at | HLA-DRA | M60334.1 | 0.0046 |
| 203387_at | TBC1D4 | NM_014832 | 0.0045 |
| 230598_at | KIAA1387 | BF063821 | 0.0045 |
| 210653_s_at | BCKDHB | M55575.1 | 0.0045 |
| 243764_at | | AW085312 | 0.0045 |
| 202268_s_at | APPBP1 | NM_003905 | 0.0045 |
| 208745_at | ATP5L | AA917672 | 0.0044 |
| 216547_at | | AL353681 | 0.0044 |
| 223671_x_at | CGI-30 | AF248965.1 | 0.0043 |
| 218532_s_at | FLJ20152 | NM_019000 | 0.0043 |
| 218149_s_at | DKFZp434K1210 | NM_017606 | 0.0043 |
| 205259_at | NR3C2 | NM_000901 | 0.0042 |
| 227867_at | | AA005361 | 0.0042 |
| 227261_at | KLF12 | AA020010 | 0.0042 |
| 208657_s_at | MSF | AF142408.1 | 0.0041 |
| 206777_s_at | CRYBB2 | NM_000496 | 0.0041 |
| 202250_s_at | H326 | NM_015726 | 0.0041 |
| 211953_at | KPNB3 | NM_002271.1 | 0.0041 |
| 224734_at | HMGB1 | BF673940 | 0.0041 |
| 221523_s_at | RAGD | AL138717 | 0.004 |
| 212144_at | UNC84B | AL021707 | 0.004 |
| 227449_at | | AI799018 | 0.004 |
| 224841_x_at | | BF316352 | 0.004 |
| 215307_at | | AL109722.1 | 0.004 |
| 211005_at | LAT | AF036906.1 | 0.0039 |
| 223283_s_at | SDCCAG33 | AF039698.1 | 0.0039 |
| 204890_s_at | LCK | U07236.1 | 0.0039 |
| 212922_s_at | HSKM-B | AF070592.1 | 0.0038 |
| 231896_s_at | DENR | AF103800.1 | 0.0038 |
| 229614_at | LOC162967 | AI277652 | 0.0038 |
| 209471_s_at | FNTA | L00634.1 | 0.0037 |
| 225845_at | | BG253884 | 0.0037 |
| 212400_at | | AL043266 | 0.0037 |
| 214949_at | | AL050136.1 | 0.0037 |
| 228005_at | | BE677308 | 0.0037 |
| 203569_s_at | OFD1 | NM_003611 | 0.0037 |
| 216221_s_at | PUM2 | D87078.2 | 0.0037 |
| 207723_s_at | KLRC3 | NM_002261 | 0.004 |
| 219029_at | FLJ21657 | NM_022483 | 0.0036 |
| 221011_s_at | LBH | NM_030915 | 0.0036 |
| 217092_x_at | | AL031589 | 0.0035 |
| 218642_s_at | MGC2217 | NM_024300 | 0.0035 |
| 218314_s_at | FLJ10726 | NM_018195 | 0.0035 |
| 219093_at | FLJ20701 | NM_017933 | 0.0035 |
| 214317_x_at | RPS9 | BE348997 | 0.0034 |
| 214220_s_at | ALMS1 | AW003635 | 0.0034 |
| 225918_at | LOC146346 | AI742940 | 0.0034 |
| 213152_s_at | SRP46 | AI343248 | 0.0034 |
| 219599_at | PRO1843 | NM_018507 | 0.0033 |
| 219528_s_at | BCL11B | NM_022898 | 0.0033 |
| 205232_s_at | PAFAH2 | U89386.1 | 0.0032 |
| 230489_at | CD5 | AI797836 | 0.0032 |
| 212459_x_at | SUCLG2 | BF593940 | 0.0032 |
| 201877_s_at | PPP2R5C | NM_002719 | 0.0032 |
| 230224_at | | BF446577 | 0.0031 |
| 206542_s_at | SMARCA2 | AV725365 | 0.0031 |
| 214709_s_at | KTN1 | Z22551.1 | 0.0031 |
| 205255_x_at | TCF7 | NM_003202 | 0.0031 |
| 200763_s_at | RPLP1 | NM_001003 | 0.0031 |
| 216945_x_at | PASK | U79240.1 | 0.0031 |
| 238043_at | | AI913123 | 0.003 |
| 217950_at | NOSIP | NM_015953 | 0.003 |
| 222204_s_at | RRN3 | AL110238.1 | 0.0029 |
| 212675_s_at | KIAA0582 | AB011154.1 | 0.0029 |
| 202524_s_at | SPOCK2 | NM_014767 | 0.0028 |
| 235587_at | LOC202781 | BG400596 | 0.0027 |
| 210982_s_at | HLA-DRA | M60333.1 | 0.0027 |
| 213906_at | MYBL1 | AW592266 | 0.0027 |
| 41220_at | KIAA0991 | AB023208 | 0.0027 |
| 221596_s_at | DKFZP564O0523 | AL136619.1 | 0.0027 |
| 216191_s_at | TRA@ | X72501.1 | 0.0026 |
| 209112_at | CDKN1B | BC001971.1 | 0.0026 |
| 222824_at | SEC61A2 | AW237290 | 0.0025 |
| 215785_s_at | CYFIP2 | AL161999.1 | 0.0025 |
| 210212_x_at | MTCP1 | BC002600.1 | 0.0025 |
| 214482_at | ZNF46 | NM_006977.1 | 0.0024 |
| 202136_at | BS69 | BE250417 | 0.0024 |
| 225886_at | | AA156797 | 0.0024 |
| 205055_at | ITGAE | NM_002208 | 0.0024 |
| 212904_at | KIAA1185 | AB033011.1 | 0.0024 |
| 211796_s_at | TRB@ | AF043179.1 | 0.0024 |
| 217143_s_at | TRD@ | X06557.1 | 0.0024 |
| 205006_s_at | NMT2 | NM_004808 | 0.0023 |
| 228841_at | | AW299250 | 0.0023 |
| 228077_at | MGC3207 | AK026666.1 | 0.0022 |
| 209064_x_at | PAIP1 | AL136920.1 | 0.0022 |
| 209538_at | ZNF32 | U69645.1 | 0.0022 |
| 208667_s_at | ST13 | U17714.1 | 0.0022 |
| 205361_s_at | PFDN4 | AI718295 | 0.0022 |
| 209009_at | ESD | BC001169.1 | 0.0022 |
| 226143_at | RAI1 | BF984830 | 0.0022 |
| 202853_s_at | RYK | NM_002958 | 0.0022 |
| 203804_s_at | OA48-18 | NM_006107 | 0.0022 |
| 219762_s_at | RPL36 | NM_015414 | 0.0021 |
| 212205_at | H2AV | BF343852 | 0.0021 |
| 228007_at | | AL133101.1 | 0.0021 |
| 244189_at | | AI888657 | 0.002 |
| 212706_at | CAPRI | AB011110.2 | 0.002 |
| 201522_x_at | SNRPN | NM_003097 | 0.0019 |
| 213598_at | HSA9761 | W87688 | 0.0019 |
| 212893_at | DKFZP564I052 | AL080063.1 | 0.0019 |
| 209974_s_at | BUB3 | AF047473.1 | 0.0019 |
| 211929_at | | BE867771 | 0.0019 |
| 203386_at | TBC1D4 | AI650848 | 0.0018 |
| 229083_at | | AI672356 | 0.0018 |
| 201653_at | CNIH | NM_005776 | 0.0018 |

TABLE 2C-continued

| Affy ID | Common | GenBank | p-value |
|---|---|---|---|
| 211542_x_at | RPS10 | BC004334.1 | 0.0018 |
| 202968_s_at | DYRK2 | Y09216.1 | 0.0018 |
| 235199_at | | AI969697 | 0.0018 |
| 55616_at | CAB2 | AI703342 | 0.0018 |
| 227630_at | | AW274445 | 0.0018 |
| 212672_at | | U82828 | 0.0017 |
| 213193_x_at | TRB@ | AL559122 | 0.0017 |
| 227979_at | | AU152162 | 0.0017 |
| 225310_at | | AI928344 | 0.0017 |
| 203485_at | RTN1 | NM_021136 | 0.0017 |
| 212928_at | KIAA0721 | AL050331 | 0.0017 |
| 219155_at | RDGBB | NM_012417 | 0.0017 |
| 212313_at | MGC29816 | BC004344.1 | 0.0017 |
| 204153_s_at | MFNG | NM_002405 | 0.0016 |
| 227049_at | LOC147632 | N21127 | 0.0016 |
| 36553_at | CRIP2 | AA669799 | 0.0016 |
| 225457_s_at | DKFZP564I1171 | BF528646 | 0.0016 |
| 203366_at | POLG | NM_002693 | 0.0016 |
| 211989_at | SMARCE1 | NM_003079.1 | 0.0016 |
| 201106_at | GPX4 | NM_002085 | 0.0016 |
| 239401_at | | AI668672 | 0.0015 |
| 226656_at | CRTAP | AW024741 | 0.0015 |
| 200909_s_at | RPLP2 | NM_001004 | 0.0015 |
| 200005_at | EIF3S7 | NM_003753 | 0.0014 |
| 227844_at | WBP3 | AI089932 | 0.0014 |
| 208319_s_at | RBM3 | NM_006743 | 0.0015 |
| 236198_at | | AW292872 | 0.0014 |
| 210915_x_at | TRB@ | M15564.1 | 0.0013 |
| 210105_s_at | FYN | M14333.1 | 0.0013 |
| 212826_s_at | SLC25A6 | AI961224 | 0.0013 |
| 208662_s_at | TTC3 | D84294.1 | 0.0013 |
| 206989_s_at | SFRS2IP | NM_004719 | 0.0013 |
| 32541_at | calcineurin A | S46622 | 0.0012 |
| 212734_x_at | RPL13 | AI186735 | 0.0012 |
| 224838_at | FOXP1 | AK026898.1 | 0.0012 |
| 208630_at | HADHA | BG472176 | 0.0012 |
| 211105_s_at | NFATC1 | U80918.1 | 0.0012 |
| 212637_s_at | WWP1 | BF131791 | 0.0012 |
| 224709_s_at | | AF131831.1 | 0.0012 |
| 235124_at | | BE502930 | 0.0012 |
| 224060_s_at | CGI-30 | AF157319.1 | 0.0012 |
| 223162_s_at | | AF116707.1 | 0.0012 |
| 200826_at | SNRPD2 | NM_004597 | 0.0011 |
| 214081_at | TEM7 | AF070526.1 | 0.0011 |
| 202165_at | PPP1R2 | NM_006241.1 | 0.0011 |
| 219351_at | SEDL | NM_014563 | 0.0011 |
| 201326_at | CCT6A | BE737030 | 0.0011 |
| 223282_at | SDCCAG33 | W60810 | 0.001 |
| 217019_at | | AL137162 | 0.001 |
| 231817_at | KIAA1350 | H25097 | 0.001 |
| 213189_at | DKFZp667G2110 | AL574514 | 0.001 |
| 216177_at | RPL29 | AW582267 | 0.001 |
| 210949_s_at | EIF3S8 | BC000533.1 | 0.001 |
| 213416_at | ITGA4 | BG532690 | 0.001 |
| 225553_at | | AL042817 | 0.001 |
| 213762_x_at | RBMX | AI452524 | 0.001 |
| 218528_s_at | RNF38 | NM_022781 | 0.001 |
| 218131_s_at | p66alpha | NM_017660 | 0.001 |
| 202232_s_at | GA17 | NM_006360 | 0.001 |
| 228843_at | KIAA1337 | AI824171 | 0.0009 |
| 213019_at | RANBP6 | AI123233 | 0.0009 |
| 225478_at | | BE783723 | 0.0009 |
| 213567_at | | BF431965 | 0.0009 |
| 212399_at | KIAA0121 | D50911.2 | 0.0009 |
| 224711_at | | AK025731.1 | 0.0009 |
| 208740_at | SAP18 | NM_005870.2 | 0.0009 |
| 229544_at | | AI690169 | 0.0009 |
| 214835_s_at | SUCLG2 | AF131748.1 | 0.0009 |
| 218572_at | HSPC134 | NM_014169 | 0.0008 |
| 218237_s_at | SLC38A1 | NM_030674 | 0.0008 |
| 211954_at | KPNB3 | NM_002271.1 | 0.0008 |
| 212690_at | KIAA0725 | AB018268.1 | 0.0008 |
| 201022_s_at | DSTN | NM_006870 | 0.0008 |
| 228039_at | | AI765169 | 0.0008 |
| 208753_s_at | NAP1L1 | BC002387.1 | 0.0008 |
| 215963_x_at | | Z98200 | 0.0008 |
| 43511_s_at | | AI201594 | 0.0008 |
| 212537_x_at | RPL17 | BE733979 | 0.0008 |
| 229686_at | LOC286530 | AI436587 | 0.0008 |
| 207196_s_at | TNIP1 | NM_006058 | 0.0008 |
| 208051_s_at | PAIP1 | NM_006451 | 0.0009 |
| 202217_at | C21orf33 | NM_004649 | 0.0007 |
| 34210_at | CDW52 | N90866 | 0.0007 |
| 200674_s_at | RPL32 | NM_000994 | 0.0007 |
| 235046_at | | AA456099 | 0.0007 |
| 219293_s_at | PTD004 | NM_013341 | 0.0007 |
| 226496_at | FLJ22611 | BG291039 | 0.0007 |
| 218919_at | FLJ14007 | NM_024699 | 0.0007 |
| 226030_at | ACADSB | BE897866 | 0.0007 |
| 224196_x_at | CGI-30 | AF161492.1 | 0.0007 |
| 201513_at | TSN | NM_004622.1 | 0.0007 |
| 224741_x_at | | BG329175 | 0.0007 |
| 213564_x_at | LDHB | BE042354 | 0.0007 |
| 205324_s_at | FTSJ1 | NM_012280 | 0.0007 |
| 222557_at | STMN3 | AL353715 | 0.0007 |
| 200093_s_at | HINT1 | N32864 | 0.0007 |
| 221931_s_at | SEC13L | AV701173 | 0.0006 |
| 208848_at | ADH5 | M30471.1 | 0.0006 |
| 200631_s_at | SET | NM_003011 | 0.0006 |
| 228853_at | STYX | AI652546 | 0.0006 |
| 229064_s_at | DSCR1L2 | BE670097 | 0.0006 |
| 212352_s_at | TMP21 | BE780075 | 0.0006 |
| 213239_at | PIBF1 | NM_006346.1 | 0.0006 |
| 241859_at | | BF593050 | 0.0006 |
| 225112_at | | BF245400 | 0.0006 |
| 218802_at | FLJ20647 | NM_017918 | 0.0006 |
| 217906_at | KLHDC2 | NM_014315 | 0.0006 |
| 225274_at | | BF247054 | 0.0006 |
| 244798_at | | AA398139 | 0.0006 |
| 226611_s_at | p30 | AA722878 | 0.0006 |
| 213347_x_at | RPS4X | AW132023 | 0.0006 |
| 219700_at | TEM7 | NM_020405 | 0.0005 |
| 217726_at | COPZ1 | NM_016057 | 0.0005 |
| 204891_s_at | LCK | NM_005356 | 0.0005 |
| 201993_x_at | HNRPDL | NM_005463 | 0.0005 |
| 201406_at | RPL36A | NM_021029 | 0.0005 |
| 200949_x_at | RPS20 | NM_001023 | 0.0005 |
| 214271_x_at | RPL12 | AA281332 | 0.0005 |
| 201030_x_at | LDHB | NM_002300 | 0.0005 |
| 235014_at | LOC147727 | BF345728 | 0.0005 |
| 212716_at | M9 | AW083133 | 0.0005 |
| 201217_x_at | RPL3 | NM_000967 | 0.0005 |
| 226680_at | PEGASUS | BF056303 | 0.0005 |
| 203113_s_at | EEF1D | NM_001960 | 0.0005 |
| 228174_at | | AI832363 | 0.0005 |
| 202408_s_at | PRPF31 | NM_015629 | 0.0005 |
| 240344_x_at | | AA424065 | 0.0005 |
| 200725_x_at | RPL10 | NM_006013 | 0.0005 |
| 213047_x_at | SET | AI278616 | 0.0004 |
| 218495_at | UXT | NM_004182 | 0.0004 |
| 218092_s_at | HRB | NM_004504 | 0.0004 |
| 211734_s_at | FCER1A | BC005912.1 | 0.0004 |
| 201892_s_at | IMPDH2 | NM_000884 | 0.0004 |
| 213890_x_at | RPS16 | AI200589 | 0.0004 |
| 221816_s_at | NY-REN-34 | BF055474 | 0.0004 |
| 221452_s_at | MGC1223 | NM_030969 | 0.0004 |
| 215096_s_at | | AU145746 | 0.0004 |
| 214143_x_at | DPP7 | AI560573 | 0.0004 |
| 225982_at | UBTF | BG341575 | 0.0004 |
| 222448_s_at | UMP-CMPK | AF112216.1 | 0.0004 |
| 217266_at | | Z97353 | 0.0004 |
| 212508_at | MOAP1 | AK024029.1 | 0.0004 |
| 213958_at | CD6 | AW134823 | 0.0004 |
| 212433_x_at | RPS2 | AA630314 | 0.0004 |
| 229844_at | | AI699465 | 0.0004 |
| 205804_s_at | DJ434O14.3 | NM_025228 | 0.0004 |
| 213969_x_at | RPL29 | BF683426 | 0.0004 |
| 210501_x_at | | AF119846.1 | 0.0004 |
| 205571_at | LIPT1 | NM_015929 | 0.0004 |
| 219939_s_at | D1S155E | NM_007158 | 0.0004 |

TABLE 2C-continued

Table 2C

| Affy ID | Common | GenBank | p-value |
|---|---|---|---|
| 225958_at | M6PR | AI554106 | 0.0003 |
| 211727_s_at | COX11 | BC005895.1 | 0.0003 |
| 208929_x_at | RPL13 | BC004954.1 | 0.0003 |
| 200847_s_at | MGC8721 | NM_016127 | 0.0003 |
| 212085_at | SLC25A6 | AA916851 | 0.0003 |
| 220755_s_at | C6orf48 | NM_016947 | 0.0003 |
| 226062_x_at | FLJ11280 | AB037811.1 | 0.0003 |
| 37590_g_at | | AL109698 | 0.0003 |
| 218545_at | FLJ11088 | NM_018318 | 0.0003 |
| 218170_at | CGI-111 | NM_016048 | 0.0003 |
| 212406_s_at | MYT1 | AB028973.1 | 0.0003 |
| 229145_at | LOC119504 | AA541762 | 0.0003 |
| 234875_at | rpL7a | AJ224082 | 0.0003 |
| 209134_s_at | RPS6 | BC000524.1 | 0.0003 |
| 226272_at | | N25986 | 0.0003 |
| 213356_x_at | HNRPA1 | AL568186 | 0.0003 |
| 230479_at | | AI872374 | 0.0003 |
| 200823_x_at | RPL29 | NM_000992 | 0.0003 |
| 208796_s_at | CCNG1 | BC000196.1 | 0.0002 |
| 212270_x_at | RPL17 | BG168283 | 0.0002 |
| 213414_s_at | RPS19 | BE259729 | 0.0002 |
| 200802_at | SARS | NM_006513 | 0.0002 |
| 210463_x_at | FLJ20244 | BC002492.1 | 0.0002 |
| 229590_at | RPL13 | AI369389 | 0.0002 |
| 229253_at | CTMP | AI184512 | 0.0002 |
| 205987_at | CD1C | NM_001765 | 0.0002 |
| 201637_s_at | FXR1 | NM_005087 | 0.0002 |
| 201177_s_at | UBA2 | NM_005499 | 0.0002 |
| 212655_at | BDG-29 | AB011151.1 | 0.0002 |
| 210633_x_at | KRT10 | M19156.1 | 0.0002 |
| 226402_at | | AW055161 | 0.0002 |
| 209068_at | HNRPDL | D89678.1 | 0.0002 |
| 217379_at | bA209A2.1 | AL121934 | 0.0002 |
| 200888_s_at | RPL23 | NM_000978 | 0.0002 |
| 212191_x_at | RPL13 | AW574664 | 0.0002 |
| 200869_at | RPL18A | NM_000980 | 0.0002 |
| 224755_at | SMBP | BE621524 | 0.0002 |
| 201517_at | NCBP2 | BC001255.1 | 0.0001 |
| 212018_s_at | DKFZP564M182 | AK025446.1 | 0.0001 |
| 209422_at | C20orf104 | AL109965 | 0.0001 |
| 203314_at | PGPL | NM_012227 | 0.0001 |
| 211942_x_at | | BF979419 | 0.0001 |
| 212321_at | SGPL1 | AF144638.1 | 0.0001 |
| 212773_s_at | TOMM20 | BG165094 | 0.0001 |
| 214394_x_at | EEF1D | AI613383 | 0.0001 |
| 202231_at | GA17 | NM_006360 | 0.0001 |
| 228370_at | SNURF | BF114870 | 0.0001 |
| 200735_x_at | NACA | NM_005594 | 0.0001 |
| 226247_at | PLEKHA1 | AI346026 | 0.0001 |
| 202969_at | | Y09216.1 | 0.0001 |
| 214351_x_at | RPL13 | AA789278 | 0.0001 |
| 225391_at | LOC93622 | AL562398 | P < 0.0001 |
| 212594_at | PDCD4 | N92498 | P < 0.0001 |
| 221494_x_at | M9 | AF085358.1 | P < 0.0001 |
| 203285_s_at | HS2ST1 | NM_012262 | P < 0.0001 |
| 202649_x_at | RPS19 | NM_001022 | P < 0.0001 |
| 40189_at | set | M93651 | P < 0.0001 |
| 234873_x_at | rpL7a | AJ224080 | P < 0.0001 |
| 235725_at | | AW055351 | P < 0.0001 |
| 228416_at | | AI149508 | P < 0.0001 |
| 205849_s_at | UQCRB | NM_006294 | P < 0.0001 |
| 217286_s_at | | BC001805.1 | P < 0.0001 |
| 217870_s_at | UMP | NM_016308 | P < 0.0001 |
| 217747_s_at | RPS9 | NM_001013 | P < 0.0001 |
| 211073_x_at | RPL3 | BC006483.1 | P < 0.0001 |
| 200915_x_at | KTN1 | NM_004986 | P < 0.0001 |
| 200834_at | RPS21 | NM_001024 | P < 0.0001 |
| 200081_s_at | RPS6 | BE741754 | P < 0.0001 |
| 214167_s_at | RPLP0 | AA555113 | P < 0.0001 |
| 216342_x_at | | AL121916 | P < 0.0001 |
| 232004_at | | AK001846.1 | P < 0.0001 |
| 224910_at | LOC91012 | AL575747 | P < 0.0001 |
| 218645_at | ZNF277 | NM_021994 | P < 0.0001 |
| 218350_s_at | GMNN | NM_015895 | P < 0.0001 |
| 213581_at | PDCD2 | BF446180 | P < 0.0001 |
| 224763_at | | AL137450.1 | P < 0.0001 |
| 216505_x_at | | AL118502 | P < 0.0001 |
| 228959_at | | AI676241 | P < 0.0001 |
| 226116_at | | BF064224 | P < 0.0001 |
| 203582_s_at | RAB4A | NM_004578 | P < 0.0001 |
| 211345_x_at | EEF1G | AF119850.1 | P < 0.0001 |
| 200094_s_at | EEF2 | AI004246 | P < 0.0001 |
| 220960_s_at | RPL22 | NM_000983 | P < 0.0001 |
| 217988_at | HEI10 | NM_021178 | P < 0.0001 |
| 217740_x_at | RPL7A | NM_000972 | P < 0.0001 |
| 229588_at | ERdj5 | AA651899 | P < 0.0001 |
| 217846_at | QARS | NM_005051 | P < 0.0001 |
| 203413_at | NELL2 | NM_006159 | P < 0.0001 |
| 213941_x_at | RPS7 | AI970731 | P < 0.0001 |
| 211937_at | EIF4B | NM_001417.1 | P < 0.0001 |
| 201064_s_at | PABPC4 | NM_003819 | P < 0.0001 |
| 240806_at | | AI939308 | P < 0.0001 |
| 226336_at | PPIA | T62044 | P < 0.0001 |
| 201922_at | YR-29 | NM_014886 | P < 0.0001 |
| 200689_x_at | EEF1G | NM_001404 | P < 0.0001 |
| 206744_s_at | ZNF237 | NM_014242 | P < 0.0001 |
| 211710_x_at | RPL4 | BC005817.1 | P < 0.0001 |
| 216570_x_at | | AL096829 | P < 0.0001 |
| 211988_at | SMARCE1 | NM_003079.1 | P < 0.0001 |
| 208887_at | EIF3S4 | BC000733.1 | P < 0.0001 |
| 204102_s_at | EEF2 | NM_001961 | P < 0.0001 |
| 208635_x_at | NACA | BF976260 | P < 0.0001 |
| 208752_x_at | NAP1L1 | AI888672 | P < 0.0001 |
| 216032_x_at | SDBCAG84 | AF091085.1 | P < 0.0001 |
| 210027_s_at | APEX1 | M80261.1 | P < 0.0001 |
| 224719_at | LOC113246 | BG339653 | P < 0.0001 |
| 212039_x_at | RPL3 | BG339228 | P < 0.0001 |
| 200936_at | RPL8 | NM_000973 | P < 0.0001 |
| 201254_x_at | RPS6 | NM_001010 | P < 0.0001 |
| 221600_s_at | PTD015 | BC002752.1 | P < 0.0001 |
| 213750_at | | AA928506 | P < 0.0001 |
| 222229_at | | AL121821 | P < 0.0001 |
| 212063_at | CD44 | BE903880 | P < 0.0001 |
| 211955_at | KPNB3 | NM_002271.1 | P < 0.0001 |
| 208768_x_at | RPL22 | D17652.1 | P < 0.0001 |
| 238026_at | | AI458020 | P < 0.0001 |
| 208826_x_at | HINT1 | U27143.1 | P < 0.0001 |
| 201154_x_at | RPL4 | NM_000968 | P < 0.0001 |
| 217807_s_at | GLTSCR2 | NM_015710 | P < 0.0001 |
| 208646_at | RPS14 | AF116710.1 | P < 0.0001 |
| 200705_s_at | EEF1B2 | NM_001959 | P < 0.0001 |
| 201153_s_at | MBNL1 | NM_021038 | P < 0.0001 |
| 200651_at | GNB2L1 | NM_006098 | P < 0.0001 |
| 200715_x_at | RPL13A | BC000514.1 | P < 0.0001 |
| 217969_at | C11orf2 | NM_013265 | P < 0.0001 |
| 212042_x_at | RPL7 | BG389744 | P < 0.0001 |
| 213864_s_at | NAP1L1 | AI985751 | P < 0.0001 |
| 201812_s_at | TOM7 | NM_019059 | P < 0.0001 |
| 202365_at | MGC5139 | BC004815.1 | P < 0.0001 |
| 208754_s_at | NAP1L1 | AL162068.1 | P < 0.0001 |
| 216305_at | MRPL19 | AC005034 | P < 0.0001 |
| 212933_x_at | RPL13 | AA961748 | P < 0.0001 |
| 221475_s_at | RPL15 | NM_002948.1 | P < 0.0001 |
| 211927_x_at | | BE963164 | P < 0.0001 |
| 211938_at | PRO1843 | BF247371 | P < 0.0001 |
| 212967_x_at | NAP1L1 | AW148801 | P < 0.0001 |
| 211623_s_at | FBL | M30448.1 | P < 0.0001 |
| 228131_at | ASE-1 | BG111047 | P < 0.0001 |
| 234512_x_at | dJ486D24.1 | AL136226 | P < 0.0001 |
| 208697_s_at | EIF3S6 | BC000734.1 | P < 0.0001 |
| 207721_x_at | HINT1 | NM_005340 | P < 0.0001 |
| 211666_x_at | RPL3 | L22453.1 | P < 0.0001 |
| 213263_s_at | MAP3K12 | AW025150 | P < 0.0001 |
| 211939_x_at | BTF3 | X74070.1 | P < 0.0001 |
| 201592_at | EIF3S3 | NM_003756 | P < 0.0001 |
| 200036_s_at | RPL10A | NM_007104 | P < 0.0001 |
| 213687_s_at | RPL35A | BE968801 | P < 0.0001 |
| 213080_x_at | RPL5 | BF214492 | P < 0.0001 |
| 200858_s_at | RPS8 | NM_001012 | P < 0.0001 |
| 217719_at | EIF3S6IP | NM_016091 | P < 0.0001 |

TABLE 2C-continued

Table 2C

| Affy ID | Common | GenBank | p-value |
|---|---|---|---|
| 201258_at | RPS16 | NM_001020 | P < 0.0001 |
| 210908_s_at | PFDN5 | AB055804.1 | P < 0.0001 |
| 200089_s_at | RPL4 | AI953886 | P < 0.0001 |
| 214042_s_at | RPL22 | AW071997 | P < 0.0001 |
| 200937_s_at | RPL5 | NM_000969 | P < 0.0001 |
| 221476_s_at | RPL15 | AF279903.1 | P < 0.0001 |

The present invention includes a method for diagnosing systemic lupus erythematosus (SLE), by determining whether or not a mammal contains one or more cells that express at least 375 genes listed in Table 2A by at least 50% less, and/or in Table 2B to an extent at least two-fold more, than one or more controls; and diagnosing the mammal as having SLE if the mammal contains the one or more cells or diagnosing the mammal as not having SLE if the cell is not identified.

Based on more recently developed information due to the selection of potential SLE patients it was found that 2,626 of the 3004 genes were not previously identified by Baechler et al. or by the present inventors. Table 2D provides those new genes that are Unique to 3004 gene list. The 3004 genes were identified using the improved HG-U133 arrays, the previous papers used the HG-U95A array.

Table 2D. Unique to 3004 gene list.

TABLE 2D

Unique to 3004 genes list

| Affy ID | common | GenBank |
|---|---|---|
| 200902_at | 9-15 | NM_004261 |
| 204176_at | AB026190 | AA808694 |
| 203505_at | ABCA1 | AF285167.1 |
| 203505_s_at | ABCA1 | NM_005502 |
| 205142_x_at | ABCD1 | NM_000033 |
| 202366_at | ACADS | NM_000017 |
| 226030_at | ACADSB | BE897866 |
| 203839_s_at | ACK1 | NM_005781 |
| 207071_at | ACO1 | NM_002197 |
| 201630_s_at | ACP1 | NM_004300 |
| 204638_at | ACP5 | NM_001611 |
| 204393_s_at | ACPP | NM_001099 |
| 223717_s_at | ACRBP | AB051833.1 |
| 202135_s_at | ACTR1B | NM_005735 |
| 227511_at | ACTR2 | BE963280 |
| 206833_s_at | ACYP2 | NM_001108 |
| 209765_s_at | ADAM19 | Y13786.2 |
| 205882_x_at | ADD3 | AI818488 |
| 201753_s_at | ADD3 | NM_019903 |
| 201752_s_at | ADD3 | AI763123 |
| 208848_at | ADH5 | M30471.1 |
| 204120_s_at | ADK | NM_001123 |
| 201281_at | ADRM1 | NM_007002 |
| 202144_s_at | ADSL | NM_000026 |
| 218735_s_at | AF020591 | AA349848 |
| 228323_at | AF15Q14 | BF248364 |
| 221264_s_at | AF311304 | NM_031214 |
| 204333_s_at | AGA | NM_000027 |
| 32836_at | AGPAT1 | U56417 |
| 225440_at | AGPAT3 | BE737251 |
| 200850_s_at | AHCYL1 | NM_006621 |
| 201782_s_at | AIP | NM_003977 |
| 201781_s_at | AIP | AL558532 |
| 244481_at | AK2 | BF196523 |
| 231029_at | AK2 | AI740541 |
| 224151_s_at | AK3L1 | AF183419.1 |
| 210625_s_at | AKAP1 | U34074.1 |
| 222024_s_at | AKAP13 | AK022014.1 |
| 221718_s_at | AKAP13 | M90360.1 |
| 208325_s_at | AKAP13 | NM_006738 |
| 227546_x_at | AKIP | AI738987 |
| 201272_at | AKR1B1 | NM_001628 |
| 204151_x_at | AKR1C1 | NM_001353 |
| 209160_at | AKR1C3 | AB018580.1 |
| 214259_s_at | AKR7A2 | AW074911 |
| 202139_at | AKR7A2 | NM_003689 |
| 201951_at | ALCAM | NM_001627.1 |
| 212224_at | ALDH1A1 | NM_000689.1 |
| 221589_s_at | ALDH6A1 | AF130089.1 |
| 221588_s_at | ALDH6A1 | AF130089.1 |
| 204290_s_at | ALDH6A1 | NM_005589 |
| 201612_at | ALDH9A1 | NM_000696 |
| 212606_at | ALFY | AI806395 |
| 212602_at | ALFY | AI806395 |
| 214220_s_at | ALMS1 | AW003635 |
| 223266_at | ALS2CR2 | AB038950.1 |
| 203043_at | ALTE | NM_004729 |
| 225554_s_at | ANAPC7 | AA131793 |
| 223092_at | ANKH | AF274753.1 |
| 218039_at | ANKT | NM_016359 |
| 222608_s_at | ANLN | AK023208.1 |
| 208103_s_at | ANP32E | NM_030920 |
| 201012_at | ANXA1 | NM_000700 |
| 213503_x_at | ANXA2 | BE908217 |
| 210427_x_at | ANXA2 | BC001388.1 |
| 201590_x_at | ANXA2 | NM_004039 |
| 209369_at | ANXA3 | M63310.1 |
| 201302_at | ANXA4 | NM_001153 |
| 201301_s_at | ANXA4 | BC000182.1 |
| 200782_at | ANXA5 | NM_001154 |
| 209174_s_at | ANXA6 | BC000978.2 |
| 201366_at | ANXA7 | NM_004034 |
| 222715_s_at | AP1GBP1 | BE856321 |
| 203300_x_at | AP1S2 | NM_003916 |
| 234068_at | AP2A1 | AC006942 |
| 203142_s_at | AP3B1 | NM_003664 |
| 222517_at | AP3M1 | AA700485 |
| 203526_s_at | APC | M74088.1 |
| 207845_s_at | APC10 | NM_014885 |
| 210027_s_at | APEX1 | M80261.1 |
| 221492_s_at | APG3 | AF202092.1 |
| 202511_s_at | APG5L | AK001899.1 |
| 32042_at | APK1 antigen | S72904 |
| 214875_x_at | APLP2 | AW001847 |
| 211404_s_at | APLP2 | BC004371.1 |
| 208702_x_at | APLP2 | BC000373.1 |
| 210873_x_at | APOBEC3A | U03891.2 |
| 221087_s_at | APOL3 | NM_014349 |
| 202268_s_at | APPBP1 | NM_003905 |
| 203025_at | ARD1 | NM_003491 |
| 201097_s_at | ARF4 | NM_001660 |
| 201096_s_at | ARF4 | AL537042 |
| 214182_at | ARF6 | AA243143 |
| 206177_s_at | ARG1 | NM_000045 |
| 219045_at | ARHF | NM_019034 |
| 203175_at | ARHG | NM_001665 |
| 211716_x_at | ARHGDIA | BC005851.1 |
| 201168_x_at | ARHGDIA | NM_004309 |
| 209539_at | ARHGEF6 | D25304.1 |
| 226789_at | ARIH2 | W84421 |
| 205020_s_at | ARL4 | NM_005738 |
| 218150_at | ARL5 | NM_012097 |
| 202208_s_at | ARL7 | BC001051.1 |
| 200950_at | ARPC1A | NM_006409 |
| 209788_s_at | ARTS-1 | AF183569.1 |
| 228131_at | ASE-1 | BG111047 |
| 222103_at | ATF1 | AI434345 |
| 210858_x_at | ATM | U26455.1 |
| 208442_s_at | ATM | NM_000051 |
| 212536_at | ATP11B | AB023173.1 |
| 209186_at | ATP2A2 | M23114.1 |
| 217801_at | ATP5E | NM_006886 |
| 208745_at | ATP5L | AA917672 |

TABLE 2D-continued

Unique to 3004 genes list

| Affy ID | common | GenBank |
|---|---|---|
| 216954_x_at | ATP5O | S77356.1 |
| 207809_s_at | ATP6IP1 | NM_001183 |
| 212383_at | ATP6V0A1 | AL096733.1 |
| 201172_x_at | ATP6V0E | NM_003945 |
| 214594_x_at | ATP8B1 | BG252666 |
| 36994_at | ATPL | M62762 |
| 37549_g_at | B1 | U87408 |
| 228760_at | B2M | AV725947 |
| 221485_at | B4GALT5 | NM_004776.1 |
| 221484_at | B4GALT5 | NM_004776.1 |
| 53076_at | B4GALT7 | AI040029 |
| 219079_at | b5 + b5R | NM_016230 |
| 217379_at | bA209A2.1 | AL121934 |
| 212768_s_at | bA209J19.1 | AL390736 |
| 227173_s_at | BACH2 | AW450901 |
| 202387_at | BAG1 | NM_004323 |
| 223220_s_at | BAL | AF307338.1 |
| 233186_s_at | BANP | AK001039.1 |
| 200041_s_at | BAT1 | NM_004640 |
| 225472_at | BAT4 | AF129756 |
| 228412_at | BAZ2B | AI991451 |
| 202331_at | BCKDHA | NM_000709 |
| 210653_s_at | BCKDHB | M55575.1 |
| 222891_s_at | BCL11A | AI912275 |
| 222895_s_at | BCL11B | AA918317 |
| 219528_s_at | BCL11B | NM_022898 |
| 205681_at | BCL2A1 | NM_004049 |
| 202518_at | BCL7B | NM_001707 |
| 219433_at | BCoR | NM_017745 |
| 202201_at | BLVRB | NM_000713 |
| 218050_at | BM-002 | NM_016617 |
| 232103_at | BPNT1 | AI439695 |
| 215460_x_at | BRD1 | AL080149.1 |
| 204520_x_at | BRD1 | NM_014577 |
| 203825_at | BRD3 | NM_007371 |
| 202227_s_at | BRD8 | NM_006696 |
| 219177_at | BRIX | NM_018321 |
| 204481_at | BRPF1 | NM_004634 |
| 202136_at | BS69 | BE250417 |
| 208677_s_at | BSG | AL550657 |
| 207722_s_at | BTBD2 | NM_017797 |
| 214800_x_at | BTF3 | R83000 |
| 211939_x_at | BTF3 | X74070.1 |
| 209846_s_at | BTN3A2 | BC002832.1 |
| 204820_s_at | BTN3A3 | NM_006994 |
| 203755_at | BUB1B | NM_001211 |
| 218048_at | BUP | NM_012071 |
| 207840_at | BY55 | NM_007053 |
| 205839_s_at | BZRAP1 | NM_004758 |
| 202096_s_at | BZRP | NM_000714 |
| 201725_at | C10orf7 | NM_006023 |
| 219953_s_at | C11orf17 | NM_020642 |
| 217969_at | C11orf2 | NM_013265 |
| 217928_s_at | C11orf23 | NM_018312 |
| 218220_at | C12orf10 | NM_021640 |
| 201216_at | C12orf8 | NM_006817 |
| 219164_s_at | C14orf103 | NM_018036 |
| 230790_x_at | C14orf116 | AI589978 |
| 222494_at | C14orf116 | AW051527 |
| 235369_at | C14orf28 | BF435952 |
| 234970_at | C14orf47 | AI741469 |
| 238523_at | C16orf44 | BF941204 |
| 227319_at | C16orf44 | AI693862 |
| 203437_at | C17orf35 | NM_003876 |
| 209574_s_at | C18orf1 | AI349506 |
| 207996_s_at | C18orf1 | NM_004338 |
| 219283_at | C1GALT2 | NM_014158 |
| 221210_s_at | C1orf13 | NM_030769 |
| 201794_s_at | C1orf16 | NM_014837 |
| 207571_x_at | C1orf38 | NM_004848 |
| 200620_at | C1orf8 | NM_004872 |
| 213377_x_at | C1S | AI799007 |
| 209422_at | C20orf104 | AL109965 |
| 219443_at | C20orf13 | NM_017714 |
| 233571_x_at | C20orf149 | AL121829 |
| 217835_x_at | C20orf24 | NM_018840 |
| 50314_i_at | C20orf27 | AI761506 |
| 217851_s_at | CGI-107 | NM_016045 |
| 225890_at | C20orf72 | AI678096 |
| 202217_at | C21orf33 | NM_004649 |
| 228239_at | C21orf51 | AA148789 |
| 228909_at | C21orf86 | AW131553 |
| 218018_at | C21orf97 | NM_021941.1 |
| 201299_s_at | C2orf6 | NM_018221 |
| 201298_s_at | C2orf6 | BC003398.1 |
| 218927_s_at | C4S-2 | NM_018641 |
| 218518_at | C5orf5 | NM_016603 |
| 229436_x_at | C6.1A | AI672084 |
| 224973_at | C6orf37; FLJ20037 | AL078599 |
| 221766_s_at | C6orf37; FLJ20037 | AL078599 |
| 220755_s_at | C6orf48 | NM_016947 |
| 202241_at | C8FW | NM_025195 |
| 200767_s_at | C9orf10 | NM_014612 |
| 223006_s_at | C9orf5 | BG402553 |
| 205950_s_at | CA1 | NM_001738 |
| 55616_at | CAB2 | AI703342 |
| 229908_s_at | CAB56184 | BF338332 |
| 32541_at | calcineurin A catalytic subunit, calmodulin-dependent protein phosphatase catalytic subunit, CaM-PrP catalytic subunit | S46622 |
| 200622_x_at | CALM3 | AV685208 |
| 214315_x_at | CALR | AI348935 |
| 212953_x_at | CALR | BE251303 |
| 200757_s_at | CALU | NM_001219 |
| 241871_at | CAMK4 | AL529104 |
| 210349_at | CAMK4 | L24959.1 |
| 201850_at | CAPG | NM_001747 |
| 208683_at | CAPN2 | M23254.1 |
| 236077_at | CAPN3 | AI671238 |
| 200001_at | CAPNS1 | NM_001749 |
| 212706_at | CAPRI | AB011110.2 |
| 220066_at | CARD15 | NM_022162 |
| 224414_s_at | CARD6 | AF356193.1 |
| 218929_at | CARF | NM_017632 |
| 211208_s_at | CASK | AB039327.2 |
| 209970_x_at | CASP1 | M87507.1 |
| 207467_x_at | CAST | NM_001750 |
| 216903_s_at | CBARA1 | AK022697.1 |
| 203341_at | CBF2 | NM_005760 |
| 201518_at | CBX1 | NM_006807 |
| 227558_at | CBX4 | AI570531 |
| 213743_at | CCNT2 | BE674119 |
| 206983_at | CCR6 | NM_004367 |
| 207445_s_at | CCR9 | AF145439.1 |
| 201946_s_at | CCT2 | AL545982 |
| 201327_s_at | CCT6A | NM_001762 |
| 201326_at | CCT6A | BE737030 |
| 208654_s_at | CD164 | AF299343.1 |
| 205831_at | CD2 | NM_001767 |
| 220307_at | CD244 | NM_016382 |
| 206545_at | CD28 | NM_006139 |
| 213539_at | CD3D | NM_000732.1 |
| 230489_at | CD5 | AI797836 |
| 243931_at | CD58 | R64696 |
| 205173_x_at | CD58 | NM_001779 |
| 200985_s_at | CD59 | NM_000611 |
| 200983_x_at | CD59 | NM_000611.1 |
| 213958_at | CD6 | AW134823 |
| 200663_at | CD63 | NM_001780 |
| 214049_x_at | CD7 | AI829961 |
| 205627_at | CDA | NM_001785 |
| 221449_s_at | CDA08 | NM_030790 |
| 223231_at | CDA11 | AF212250.1 |

TABLE 2D-continued

Unique to 3004 genes list

| Affy ID | common | GenBank |
|---|---|---|
| 228516_at | CDAN1 | AI122852 |
| 213151_s_at | CDC10 | AU157515 |
| 203213_at | CDC2 | AL524035 |
| 212540_at | CDC34 | BG476661 |
| 209056_s_at | CDC5L | AW268817 |
| 224428_s_at | CDCA7 | AY029179.1 |
| 210622_x_at | CDK10 | AF153430.1 |
| 204252_at | CDK2 | M68520.1 |
| 204995_at | CDK5R1 | AL567411 |
| 202284_s_at | CDKN1A | NM_000389 |
| 209714_s_at | CDKN3 | AF213033.1 |
| 34210_at | CDW52 | N90866 |
| 224596_at | CDW92 | NM_022109.1 |
| 211657_at | CEACAM6 | M18728.1 |
| 203757_s_at | CEACAM6 | BC005008.1 |
| 219863_at | CEB1 | NM_016323 |
| 219505_at | CECR1 | NM_017424 |
| 218592_s_at | CECR5 | NM_017829 |
| 229460_at | CED-6 | AI927605 |
| 90265_at | CENTA1 | AW050627 |
| 213618_at | CENTD1 | AB011152.1 |
| 218421_at | CERK | NM_022766 |
| 209616_s_at | CES1 | S73751.1 |
| 203166_at | CFDP1 | NM_006324 |
| 202259_s_at | CG005 | NM_014887 |
| 202194_at | CGI-100 | AL117354 |
| 214658_at | CGI-109 | BG286537 |
| 218170_at | CGI-111 | NM_016048 |
| 203259_s_at | CGI-130 | BC001671.1 |
| 224196_x_at | CGI-30 | AF161492.1 |
| 224060_s_at | CGI-30 | AF157319.1 |
| 223671_x_at | CGI-30 | AF248965.1 |
| 201175_at | CGI-31 | NM_015959 |
| 217748_at | CGI-45 | NM_015999 |
| 226758_at | CGI-59 | AA043552 |
| 227551_at | CGI-67 | BE856596 |
| 223649_s_at | CGI-69 | AF317711.1 |
| 204605_at | CGR19 | NM_006568 |
| 206499_s_at | CHC1 | NM_001269 |
| 208807_s_at | CHD3 | U91543.1 |
| 209396_s_at | CHI3L1 | M80927.1 |
| 219492_at | CHIC2 | NM_012110 |
| 221675_s_at | CHPT1 | AF195624.1 |
| 203518_at | CHS1 | NM_000081 |
| 201897_s_at | CKS1B | NM_001826 |
| 219890_at | CLECSF5 | NM_013252 |
| 222934_s_at | CLECSF9 | BC000715.1 |
| 219529_at | CLIC3 | NM_004669 |
| 210859_x_at | CLN3 | AF077973.1 |
| 214252_at | CLN5 | AV700514 |
| 209143_s_at | CLNS1A | AF005422.1 |
| 201561_s_at | CLSTN1 | NM_014944 |
| 204050_s_at | CLTA | NM_001833 |
| 200960_x_at | CLTA | NM_007096 |
| 225439_at | CML66 | BC000967.2 |
| 203094_at | CMT2 | NM_014628 |
| 201653_at | CNIH | NM_005776 |
| 229143_at | CNOT3 | AW449353 |
| 226153_s_at | CNOT6L | AW514857 |
| 202163_s_at | CNOT8 | NM_004779 |
| 208912_s_at | CNP | BC001362.1 |
| 202757_at | COBRA1 | NM_015456 |
| 203073_at | COG2 | NM_007357 |
| 222391_at | COL12A1; BA209D8.1; DJ234P15.1 | AL080250 |
| 217726_at | COPZ1 | NM_016057 |
| 221676_s_at | CORO1C | BC002342.1 |
| 202698_x_at | COX4I1 | NM_001861 |
| 201119_s_at | COX8 | NM_004074 |
| 225129_at | CPNE2 | AW170571 |
| 202119_s_at | CPNE3 | NM_003909 |
| 239205_s_at | CR1L | BE552138 |
| 201988_s_at | CREBL2 | NM_001310.1 |
| 201200_at | CREG | NM_003851 |
| 211698_at | CRI1 | AF349444.1 |
| 208669_s_at | CRI1 | AF109873.1 |
| 36553_at | CRIP2 | AA669799 |
| 205474_at | CRLF3 | NM_015986 |
| 204349_at | CRSP9 | BC005250.1 |
| 209674_at | CRY1 | D83702.1 |
| 206777_s_at | CRYBB2 | NM_000496 |
| 219767_s_at | CRYZL1 | NM_005111 |
| 201160_s_at | CSDA | AL556190 |
| 202573_at | CSNK1G2 | AL530441 |
| 203575_at | CSNK2A2 | NM_001896 |
| 201360_at | CST3 | NM_000099 |
| 201201_at | CSTB | NM_000100 |
| 212905_at | CSTF2T | BF732638 |
| 212901_s_at | CSTF2T | BF732638 |
| 232233_at | CT2; OKB1; FLIPT2; dJ261K5.1 | AL050350 |
| 220957_at | CTAGE-1 | NM_022663 |
| 213979_s_at | CTBP1 | AA053830 |
| 218924_s_at | CTBS | NM_004388 |
| 202521_at | CTCF | NM_006565 |
| 229253_at | CTMP | AI184512 |
| 200765_x_at | CTNNA1 | NM_001903 |
| 200839_at | CTSB | NM_001908 |
| 200766_at | CTSD | NM_001909 |
| 202901_x_at | CTSS | BC002642.1 |
| 207614_s_at | CUL1 | NM_003592 |
| 203078_at | CUL2 | U83410.1 |
| 201424_s_at | CUL4A | NM_003589 |
| 215997_s_at | CUL4B | AV694732 |
| 210257_x_at | CUL4B | AF212995.1 |
| 202213_s_at | CUL4B | AI650819 |
| 204470_at | CXCL1 | NM_001511 |
| 204533_at | CXCL10 | NM_001565 |
| 209774_x_at | CXCL2 | M57731.1 |
| 201634_s_at | CXorf9 | AL023653 |
| 215785_s_at | CYB5-M | NM_030579 |
| 206515_at | CYFIP2 | AL161999.1 |
| 219573_s_at | CYP4F3 | NM_000896 |
| 218443_s_at | D1S155E | NM_007158 |
| 214334_x_at | DAZAP1 | NM_018959 |
| 218981_at | DAZAP2 | N34846 |
| 218447_at | DC11 | NM_020186 |
| 221434_s_at | DC13 | NM_020188 |
| 218482_at | DC50 | NM_031210 |
| 219678_x_at | DC6 | NM_020189 |
| 201894_s_at | DCLRE1C | NM_022487 |
| 201082_s_at | DCN | NM_001920 |
| 224791_at | DCTN1 | NM_004082 |
| 224790_at | DDEF1 | W03103 |
| 208895_s_at | DDEF1 | W03103 |
| 40255_at | DDX18 | BC003360.1 |
| 222875_at | DDX28 | AC004531 |
| 223140_s_at | DDX33 | AI720923 |
| 212107_s_at | DDX36 | AF217190.1 |
| 202447_at | DDX9 | BE910323 |
| 231896_s_at | DECR1 | NM_001359 |
| 221509_at | DENR | AF103800.1 |
| 223518_at | DENR | AB014731.1 |
| 203277_at | DFFA | AF087573.1 |
| 239342_at | DFFA | NM_004401 |
| 207556_s_at | DGKZ | AI567554 |
| 205726_at | DGKZ | NM_003646 |
| 216260_at | DIAPH2 | NM_006729 |
| 214779_s_at | DICER1 | AK001827.1 |
| 227712_at | DJ1042K10.2 | R51077 |
| 221311_x_at | DJ122O8.2 | AV682940 |
| 222235_s_at | DJ122O8.2 | NM_020466 |
| 205804_s_at | dJ19N1.1 | AL139812 |
| 225876_at | DJ434O14.3 | NM_025228 |
| 234512_x_at | DJ462O23.2 | T84558 |
| 217256_x_at | dJ486D24.1 | AL136226 |
| 224367_at | dJ507I15.1 | Z98950 |
| | DJ79P11.1 | AF251053.1 |

TABLE 2D-continued

Unique to 3004 genes list

| Affy ID | common | GenBank |
|---|---|---|
| 217336_at | dJ858M22.1 | AL118510 |
| 226688_at | DKFZp313N0621 | AW003508 |
| 229949_at | DKFZP434A0131 | AA554827 |
| 227580_s_at | DKFZP434B0335 | BE616972 |
| 222250_s_at | DKFZP434B168 | AK001363.1 |
| 212886_at | DKFZP434C171 | AL080169.1 |
| 225487_at | DKFZp434C1714 | AI720705 |
| 222099_s_at | DKFZP434D1335 | AW593859 |
| 212132_at | DKFZP434D1335 | AL117499.1 |
| 212131_at | DKFZP434D1335 | AL117499.1 |
| 226224_at | DKFZp434D1428 | AI798846 |
| 227197_at | DKFZP434D146 | AI989530 |
| 229584_at | DKFZp434H2111 | AK026776.1 |
| 228171_s_at | DKFZp434I216 | AI056683 |
| 218149_s_at | DKFZp434K1210 | NM_017606 |
| 226071_at | DKFZP434K1772 | AF217974.1 |
| 220947_s_at | DKFZP434P1750 | NM_015527 |
| 207283_at | DKFZp547I014 | NM_020217 |
| 220985_s_at | DKFZP564A022 | NM_030954 |
| 222154_s_at | DNAPTP6 | AK002064.1 |
| 216028_at | DKFZP564C152 | AL049980.1 |
| 226665_at | DKFZp564C236 | AI986239 |
| 223155_at | DKFZP564D1378 | AL136681.1 |
| 212936_at | DKFZP564D172 | AI927701 |
| 212893_at | DKFZP564I052 | AL080063.1 |
| 225458_at | DKFZP564I1171 | BF528646 |
| 225457_s_at | DKFZP564I1171 | BF528646 |
| 217794_at | DKFZP564J157 | NM_018457 |
| 212018_at | DKFZP564M182 | AK025446.1 |
| 232661_s_at | DKFZP564O0523 | AF161422.1 |
| 221596_s_at | DKFZP564O0523 | AL136619.1 |
| 202537_s_at | DKFZP564O123 | AF151842.1 |
| 227375_at | DKFZP566D1346 | AA152232 |
| 205087_at | DKFZP566K023 | NM_015485 |
| 213497_at | DKFZP586C1619 | AL050374.1 |
| 213861_s_at | DKFZP586D0919 | N67741 |
| 223031_at | DKFZp586I021 | AL136921.1 |
| 221214_s_at | DKFZP586J1624 | NM_015537 |
| 213189_at | DKFZp667G2110 | AL574514 |
| 225117_at | DKFZP727C091 | AL137317.1 |
| 224745_x_at | DKFZp761A052 | AK026260.1 |
| 224593_at | DKFZp761B128 | BE965646 |
| 223228_at | DKFZp761O17121 | AL136553.1 |
| 235085_at | DKFZp761P0423 | BF739767 |
| 223983_at | DKFZP762D096 | BC004957.1 |
| 224578_at | DKFZp762N0610 | AB040903.1 |
| 225405_at | DKFZp762N1910 | AI151434 |
| 224163_s_at | DMAP1 | AL136657.1 |
| 200666_s_at | DNAJB1 | NM_006145 |
| 200664_s_at | DNAJB1 | BG537255 |
| 223054_at | DNAJB11 | BC001144.1 |
| 213919_at | DNAJC4 | AW024467 |
| 208873_s_at | DP1 | BC000232.1 |
| 208872_s_at | DP1 | AA814140 |
| 214143_x_at | DPP7 | AI560573 |
| 34689_at | drn3 | AJ243797 |
| 229064_s_at | DSCR1L2 | BE670097 |
| 201022_s_at | DSTN | NM_006870 |
| 213079_at | DT1P1A10 | AA223871 |
| 202703_at | DUSP11 | NM_003584 |
| 218660_at | DYSF | NM_003494 |
| 202348_s_at | DYT1 | BC000674.1 |
| 220942_x_at | E2IG5 | NM_014367 |
| 205419_at | EBI2 | NM_004951 |
| 220048_at | EDAR | NM_022336 |
| 203279_at | EDEM | NM_014674 |
| 230464_at | EDG8 | AI814092 |
| 204905_s_at | EEF1E1 | NM_004280 |
| 211345_x_at | EEF1G | AF119850.1 |
| 200689_x_at | EEF1G | NM_001404 |
| 204102_s_at | EEF2 | NM_001961 |
| 200094_s_at | EEF2 | AI004246 |
| 213113_s_at | EEG1 | AI630178 |
| 225159_s_at | EG1 | AW614072 |
| 206254_at | EGF | NM_001963 |
| 212830_at | EGFL5 | BF110421 |
| 227404_s_at | EGR1 | AI459194 |
| 201694_s_at | EGR1 | NM_001964 |
| 205249_at | EGR2 | NM_000399 |
| 208289_s_at | EI24 | NM_004879 |
| 201017_at | EIF1A | BE542684 |
| 225164_s_at | EIF2AK4 | AB037759.1 |
| 202461_at | EIF2B2 | NM_014239 |
| 215482_s_at | EIF2B4 | AJ011307 |
| 218287_s_at | EIF2C1 | NM_012199 |
| 201143_s_at | EIF2S1 | BC002513.1 |
| 208264_s_at | EIF3S1 | NM_003758 |
| 200597_at | EIF3S10 | BE614908 |
| 201592_at | EIF3S3 | NM_003756 |
| 208887_at | EIF3S4 | BC000733.1 |
| 208697_s_at | EIF3S6 | BC000734.1 |
| 217719_at | EIF3S6IP | NM_016091 |
| 200005_at | EIF3S7 | NM_003753 |
| 210949_s_at | EIF3S8 | BC000533.1 |
| 200592_at | EIF4A2 | NM_001967 |
| 211937_at | EIF4B | NM_001417.1 |
| 201437_s_at | EIF4E | NM_001968 |
| 224653_at | EIF4EBP2 | BG106477 |
| 224645_at | EIF4EBP2 | BG106477 |
| 208625_s_at | EIF4G1 | AF104913.1 |
| 208705_s_at | EIF5 | AL080102.1 |
| 225184_at | ELD/OSA1 | AK000921.1 |
| 225181_at | ELD/OSA1 | AK000921.1 |
| 201677_at | ELF3 | AI937543 |
| 55692_at | ELMO2 | W22924 |
| 231713_s_at | ELP2 | NM_018255.1 |
| 226115_at | ELYS | AI138934 |
| 203729_at | EMP3 | NM_001425 |
| 203370_s_at | ENIGMA | NM_005451 |
| 207691_x_at | ENTPD1 | NM_001776 |
| 234969_s_at | EPC1 | AK024117.1 |
| 204718_at | EPHB6 | NM_004445 |
| 226133_s_at | EPI64 | AW628835 |
| 235276_at | EPSTI1 | AA781795 |
| 227609_at | EPSTI1 | AA633203 |
| 219672_at | ERAF | NM_016633 |
| 225344_at | ERAP140 | AL035689 |
| 229588_at | ERdj5 | AA651899 |
| 218100_s_at | ESRRBL1 | NM_018010 |
| 224833_at | ETS1 | BE218980 |
| 204328_at | EVER1 | NM_007267 |
| 214958_s_at | EVIN1 | AK021738.1 |
| 212034_s_at | EXO70 | BE646386 |
| 50376_at | EZF-2 | AI278629 |
| 202345_s_at | FABP5 | NM_001444 |
| 207275_s_at | FACL1 | NM_001995 |
| 225032_at | FAD104 | AI141784 |
| 219253_at | FAM11B | NM_024121 |
| 217047_s_at | FAM13A1 | AK027138.1 |
| 202973_x_at | FAM13A1 | NM_014883 |
| 203974_at | FAM16AX | NM_012080 |
| 203420_at | FAM8A1 | NM_016255 |
| 205189_s_at | FANCC | NM_000136 |
| 203184_at | FBN2 | NM_001999 |
| 218539_at | FBXO34 | NM_017943 |
| 231769_at | FBXO6 | AF129536.1 |
| 201178_at | FBXO7 | NM_012179 |
| 212991_at | FBXO9 | AL137520.1 |
| 210638_s_at | FBXO9 | AF176704.1 |
| 223050_s_at | FBXW5 | BC000850.1 |
| 222729_at | FBXW7 | BE551877 |
| 205237_at | FCN1 | NM_002003 |
| 243968_x_at | FCRH1 | AI572979 |
| 224800_at | FENS-1 | AK022888.1 |
| 201798_s_at | FER1L3 | NM_013451 |
| 227811_at | FGD3 | AK000004.1 |
| 203033_x_at | FH | NM_000143 |
| 202041_s_at | FIBP | NM_004214 |
| 200709_at | FKBP1A | NM_000801 |
| 218003_s_at | FKBP3 | NM_002013 |

TABLE 2D-continued

Unique to 3004 genes list

| Affy ID | common | GenBank |
|---|---|---|
| 40850_at | FKBP38 | L37033 |
| 222848_at | FKSG14 | BC005400.1 |
| 208588_at | FKSG2 | NM_021631 |
| 212025_s_at | FLII | U80184 |
| 228497_at | FLIPT1 | AI279062 |
| 225180_at | FLJ00166 | W73788 |
| 205510_s_at | FLJ10038 | NM_017976 |
| 218008_at | FLJ10099 | NM_017994 |
| 227701_at | FLJ10188 | AK024739.1 |
| 217900_at | FLJ10326 | NM_018060 |
| 227854_at | FLJ10335 | BE620258 |
| 218397_at | FLJ10335 | NM_018062 |
| 223145_s_at | FLJ10342 | BC000764.1 |
| 234672_s_at | FLJ10407 | AL354612.1 |
| 218570_at | FLJ10450 | NM_018095 |
| 220071_x_at | FLJ10460 | NM_018097 |
| 220615_at | FLJ10462 | NM_018099 |
| 218155_x_at | FLJ10534 | AK026565.1 |
| 201917_s_at | FLJ10618 | AI694452 |
| 218314_s_at | FLJ10726 | NM_018195 |
| 211068_x_at | FLJ10824 | BC006456.1 |
| 218568_at | FLJ10842 | NM_018238 |
| 201307_at | FLJ10849 | AL534972 |
| 224849_at | FLJ10890 | AK023161.1 |
| 222690_s_at | FLJ10902 | AA194996 |
| 218999_at | FLJ11000 | NM_018295 |
| 219392_x_at | FLJ11029 | NM_018304 |
| 218545_at | FLJ11088 | NM_018318 |
| 202577_s_at | FLJ11126 | BC005162.1 |
| 221103_s_at | FLJ11142 | NM_018338 |
| 218610_s_at | FLJ11151 | NM_018340 |
| 223824_at | FLJ11218 | BC005364.1 |
| 222790_s_at | FLJ11220 | BE888593 |
| 222789_at | FLJ11220 | BE888593 |
| 223431_at | FLJ11230 | BC001818.1 |
| 226529_at | FLJ11273 | BF513060 |
| 226062_x_at | FLJ11280 | AB037811.1 |
| 211433_x_at | FLJ11560 | AL583909.1 |
| 220252_x_at | FLJ11577 | NM_025159 |
| 219056_at | FLJ11712 | NM_024570 |
| 218165_at | FLJ11730 | NM_022756 |
| 213064_at | FLJ11806 | N64802 |
| 213063_at | FLJ11806 | N64802 |
| 218268_at | FLJ12085 | NM_022771 |
| 219259_at | FLJ12287 | NM_022367 |
| 220576_at | FLJ12377 | NM_024989 |
| 224721_at | FLJ12519 | AI917328 |
| 224186_s_at | FLJ12565 | AL136729.1 |
| 219765_at | FLJ12586 | NM_024620 |
| 219627_at | FLJ12700 | NM_024910 |
| 222805_at | FLJ12838 | AI587307 |
| 219335_at | FLJ12969 | NM_022838 |
| 213607_x_at | FLJ13052 | BE551347 |
| 208919_at | FLJ13052 | BC001709.1 |
| 208918_s_at | FLJ13052 | BC001709.1 |
| 64899_at | FLJ13055 | AA209463 |
| 234947_s_at | FLJ13188 | AK026630.1 |
| 222151_s_at | FLJ13386 | AK023738.1 |
| 218395_at | FLJ13433 | NM_022496 |
| 225350_s_at | FLJ13456 | AV701229 |
| 218674_at | FLJ13611 | NM_024941 |
| 230509_at | FLJ13952 | BF528605 |
| 218919_at | FLJ14007 | NM_024699 |
| 79005_at | FLJ14251 | AA504646 |
| 220760_x_at | FLJ14345 | NM_024733 |
| 49329_at | FLJ14360 | N38751 |
| 235729_at | FLJ14457 | T93113 |
| 227585_at | FLJ14600 | AI359136 |
| 229063_s_at | FLJ14642 | AI912238 |
| 225226_at | FLJ14743 | AB051548.1 |
| 213031_s_at | FLJ14888 | AF161382.1 |
| 218986_s_at | FLJ20035 | NM_017631 |
| 230793_at | FLJ20048 | BE671038 |
| 228531_at | FLJ20073 | AA741307 |
| 219691_at | FLJ20073 | NM_017654 |
| 219163_at | FLJ20079 | NM_017656 |
| 234294_x_at | FLJ20085 | AL390164.1 |
| 38710_at | FLJ20113 | AL096714 |
| 218532_s_at | FLJ20152 | NM_019000 |
| 226811_at | FLJ20202 | AL046017 |
| 210463_x_at | FLJ20244 | BC002492.1 |
| 222496_s_at | FLJ20273 | AW241742 |
| 222816_s_at | FLJ20281 | BE676543 |
| 219062_s_at | FLJ20281 | NM_017742 |
| 52731_at | FLJ20294 | AI359466 |
| 223076_s_at | FLJ20303 | BC001041.1 |
| 223375_at | FLJ20337 | BC002720.1 |
| 219256_s_at | FLJ20356 | NM_018986 |
| 222547_at | FLJ20373 | AL561281 |
| 222654_at | FLJ20421 | AW295105 |
| 239598_x_at | FLJ20481 | AA789296 |
| 222887_s_at | FLJ20507 | AA034018 |
| 222748_s_at | FLJ20511 | AW194729 |
| 218905_at | FLJ20530 | NM_017864 |
| 217961_at | FLJ20551 | NM_017875 |
| 222244_s_at | FLJ20618 | AK000749.1 |
| 219352_at | FLJ20637 | NM_017912 |
| 218802_at | FLJ20647 | NM_017918 |
| 205684_s_at | FLJ20686 | NM_017925 |
| 207730_x_at | FLJ20700 | NM_017932 |
| 219093_at | FLJ20701 | NM_017933 |
| 223117_s_at | FLJ20727 | AW025093 |
| 217895_at | FLJ20758 | NM_017952 |
| 214749_s_at | FLJ20811 | AK000818.1 |
| 51200_at | FLJ20850 | AI744084 |
| 219315_s_at | FLJ20898 | NM_024600 |
| 212297_at | FLJ20986 | BF218804 |
| 224898_at | FLJ21016 | AA482548 |
| 218632_at | FLJ21156 | NM_024602 |
| 204665_at | FLJ21168 | NM_025073.1 |
| 229872_s_at | FLJ21308 | AA532655 |
| 219029_at | FLJ21657 | NM_022483 |
| 218531_at | FLJ21749 | NM_025124 |
| 225688_s_at | FLJ21791 | AK025444.1 |
| 65635_at | FLJ21865 | AL044097 |
| 220349_s_at | FLJ21865 | NM_022759 |
| 202809_s_at | FLJ21919 | NM_023015 |
| 223846_at | FLJ21939 | BC001139.1 |
| 222498_at | FLJ21939 | AI809206 |
| 220721_at | FLJ21941 | NM_025040 |
| 212918_at | FLJ22028 | BF219234 |
| 212917_x_at | FLJ22028 | BF219234 |
| 218277_s_at | FLJ22060 | NM_024612 |
| 64438_at | FLJ22222 | W19668 |
| 222143_s_at | FLJ22405 | AY007098.1 |
| 219100_at | FLJ22559 | NM_024928 |
| 223553_s_at | FLJ22570 | BC004564.1 |
| 220320_at | FLJ22570 | NM_024872 |
| 226496_s_at | FLJ22611 | BG291039 |
| 218454_at | FLJ22662 | NM_024829 |
| 218543_s_at | FLJ22693 | NM_022750 |
| 219698_s_at | FLJ23017 | NM_022840 |
| 220206_at | FLJ23151 | NM_024772 |
| 219506_at | FLJ23221 | NM_024579 |
| 218776_s_at | FLJ23375 | NM_024956 |
| 218883_s_at | FLJ23468 | NM_024629 |
| 229025_s_at | FLJ25059 | AW008627 |
| 229903_x_at | FLJ25070 | AI632212 |
| 227224_at | FLJ25604 | AW003297 |
| 225619_at | FLJ30046 | AV730849 |
| 217627_at | FLJ30921 | BE515346 |
| 228152_s_at | FLJ31033 | AK023743.1 |
| 230490_x_at | FLJ31034 | AI866717 |
| 235054_at | FLJ31265 | BF941983 |
| 221867_at | FLJ31821 | BF436315 |
| 226077_at | FLJ31951 | AL553942 |
| 229770_at | FLJ31978 | AI041543 |
| 223443_s_at | FLJ32065 | BC003669.1 |
| 213474_at | FLJ32069 | AI890903 |
| 225753_at | FLJ32203 | AW003280 |

TABLE 2D-continued

Unique to 3004 genes list

| Affy ID | common | GenBank |
|---|---|---|
| 228916_at | FLJ32343 | BE857467 |
| 238692_at | FLJ33957 | AL040935 |
| 227796_at | FLJ34231 | AW157773 |
| 235170_at | FLJ34299 | T52999 |
| 238025_at | FLJ34389 | AA706818 |
| 235432_at | FLJ35693 | BE865779 |
| 228961_at | FLJ35954 | R66534 |
| 229521_at | FLJ36031 | BE466274 |
| 226449_at | FLJ36090 | AI392933 |
| 217608_at | FLJ36754 | AW408767 |
| 235234_at | FLJ36874 | AA359612 |
| 225468_at | FLJ36874 | AI761804 |
| 225466_at | FLJ36874 | AI761804 |
| 235812_at | FLJ38101 | AI935115 |
| 223477_s_at | FLJ38663 | AF061733.1 |
| 230036_at | FLJ39885 | BE669858 |
| 226603_at | FLJ39885 | BE966604 |
| 36564_at | FLJ90005 | W27419 |
| 227410_at | FLJ90022 | AW264102 |
| 35254_at | fln29 | AB007447 |
| 243196_s_at | FLN29 | BF223703 |
| 207876_s_at | FLNC | NM_001458 |
| 201350_at | FLOT2 | NM_004475 |
| 204789_at | FMNL | NM_005892 |
| 202709_at | FMOD | NM_002023 |
| 219806_s_at | FN5 | NM_020179 |
| 213329_at | FNBP2 | AA742261 |
| 209471_s_at | FNTA | L00634.1 |
| 209189_at | FOS | BC004490.1 |
| 202768_at | FOSB | NM_006732 |
| 202724_s_at | FOXO1A | NM_002015 |
| 224838_at | FOXP1 | AK026898.1 |
| 223936_s_at | FOXP1 | BC005055.1 |
| 223287_s_at | FOXP1 | AF146696.1 |
| 205119_s_at | FPR1 | NM_002029 |
| 227948_at | FRABIN | AI949549 |
| 209864_s_at | FRAT2 | AB045118.1 |
| 235372_at | FREB | AW575245 |
| 218373_at | FTS | NM_022476 |
| 205324_s_at | FTSJ1 | NM_012280 |
| 200959_at | FUS | NM_004960 |
| 201637_s_at | FXR1 | NM_005087 |
| 201635_s_at | FXR1 | AI990766 |
| 207434_s_at | FXYD2 | NM_021603 |
| 202488_s_at | FXYD3 | NM_005971 |
| 217897_at | FXYD6 | NM_022003 |
| 216033_s_at | FYN | S74774.1 |
| 210105_s_at | FYN | M14333.1 |
| 200792_at | G22P1 | NM_001469 |
| 202275_at | G6PD | NM_000402 |
| 202232_s_at | GA17 | NM_006360 |
| 202231_at | GA17 | NM_006360 |
| 226002_at | GAB1 | AK022142.1 |
| 37028_at | GADD34 | U83981 |
| 203725_at | GADD45A | NM_001924 |
| 40225_at | GAK | D88435 |
| 202281_at | GAK | NM_005255 |
| 203066_at | GALNAC4S-6ST | NM_014863 |
| 218871_x_at | GALNACT-2 | NM_018590 |
| 206335_at | GALNS | NM_000512 |
| 223991_s_at | GALNT2 | AF130059.1 |
| 203397_s_at | GALNT3 | BF063271 |
| 203179_at | GALT | NM_000155 |
| AFFX-HUMGAPDH/M33197_M_at | GAPD | M33197 |
| 213453_x_at | GAPD | BF689355 |
| 218911_at | GAS41 | NM_006530 |
| 204793_at | GASP | NM_014710 |
| 235175_at | GBP4 | BG260886 |
| 202832_at | GCC185 | NM_014635 |
| 202922_at | GCLC | BF676980 |
| 202592_at | GCN5L1 | NM_001487 |
| 202182_at | GCN5L2 | NM_021078 |
| 208296_x_at | GG2-1 | NM_014350 |
| 219571_s_at | GIOT-3 | NM_016265 |

TABLE 2D-continued

Unique to 3004 genes list

| Affy ID | common | GenBank |
|---|---|---|
| 218030_at | GIT1 | NM_014030 |
| 229312_s_at | GKAP42 | BF434321 |
| 223354_x_at | GL004 | BC003191.1 |
| 201576_s_at | GLB1 | NM_000404 |
| 207972_at | GLRA1 | NM_000171 |
| 217807_s_at | GLTSCR2 | NM_015710 |
| 212737_at | GM2A | AL513583 |
| 222251_s_at | GMEB2 | AL133646.1 |
| 218350_s_at | GMNN | NM_015895 |
| 224681_at | GNA12 | BG028884 |
| 200651_at | GNB2L1 | NM_006098 |
| 204000_at | GNB5 | NM_016194 |
| 205042_at | GNE | NM_005476 |
| 207157_s_at | GNG5 | NM_005274 |
| 205495_s_at | GNLY | NM_006433 |
| 225853_at | GNPNAT1 | BE789346 |
| 225672_at | GOLGA2 | AL514295 |
| 215690_x_at | GPAA1 | AL157437.1 |
| 211060_x_at | GPAA1 | BC006383.1 |
| 201618_x_at | GPAA1 | NM_003801 |
| 223423_at | GPCR1 | BC000181.2 |
| 210279_at | GPR18 | AF261135.1 |
| 227769_at | GPR27 | AI703476 |
| 221345_at | GPR43 | NM_005306 |
| 223767_at | GPR84 | AF237762.1 |
| 202848_s_at | GPRK6 | BG423052 |
| 201106_at | GPX4 | NM_002085 |
| 209409_at | GRB10 | D86962.1 |
| 212244_at | GRINL1A | AI632774 |
| 202479_s_at | GS3955 | BC002637.1 |
| 215438_x_at | GSPT1 | BE906054 |
| 205541_s_at | GSPT2 | NM_018094 |
| 202554_s_at | GSTM3 | AL527430 |
| 201470_at | GSTTLp28 | NM_004832 |
| 202355_s_at | GTF2F1 | BC000120.1 |
| 221050_s_at | GTPBP2 | NM_019096 |
| 211275_s_at | GYG | AF087942.1 |
| 201554_x_at | GYG | NM_004130 |
| 223128_at | H17 | AL136923.1 |
| 209398_at | H1F2 | BC002649.1 |
| 204805_s_at | H1FX | NM_006026 |
| 225245_s_at | H2AFJ | BG386566 |
| 224301_x_at | H2AFJ | BC003602.1 |
| 207168_s_at | H2AFY | NM_004893 |
| 212205_at | H2AV | BF343852 |
| 209911_x_at | H2BFB | BC002842.1 |
| 202250_s_at | H326 | NM_015726 |
| 212873_at | HA-1 | BE349017 |
| 208630_at | HADHA | BG472176 |
| 208629_s_at | HADHA | BG472176 |
| 201036_s_at | HADHSC | NM_005327 |
| 221744_at | HAN11 | AK026008.1 |
| 219343_at | HARC | NM_017913 |
| 202042_at | HARS | NM_002109 |
| 214414_x_at | HBA1 | T50399 |
| 204848_x_at | HBG1 | NM_000559 |
| 213515_x_at | HBG2 | AI133353 |
| 204419_x_at | HBG2 | NM_000184 |
| 218423_x_at | HCC8 | NM_016516 |
| 202474_s_at | HCFC1 | NM_005334 |
| 215985_at | HCGVIII-1 | X92110.1 |
| 201209_at | HDAC1 | NM_004964 |
| 201833_at | HDAC2 | NM_001527 |
| 217988_at | HEI10 | NM_021178 |
| 33304_at | HEM45 | U88964 |
| 206087_x_at | HFE | NM_000410 |
| 206910_x_at | HFL3 | NM_005666 |
| 228071_at | hIAN7 | AA858297 |
| 59999_at | HIF1AN | W37897 |
| 232024_at | HIMAP2 | AI431931 |
| 208826_x_at | HINT1 | U27143.1 |
| 207721_x_at | HINT1 | NM_005340 |
| 200093_s_at | HINT1 | N32864 |
| 212641_at | HIVEP2 | AL023584 |
| 202934_at | HK2 | AI761561 |

TABLE 2D-continued

Unique to 3004 genes list

| Affy ID | common | GenBank |
|---|---|---|
| 205936_s_at | HK3 | NM_002115 |
| 203932_at | HLA-DMB | NM_002118 |
| 210982_s_at | HLA-DRA | M60333.1 |
| 208894_at | HLA-DRA | M60334.1 |
| 217456_x_at | HLA-E | M31183.1 |
| 210514_x_at | HLA-G | AF226990.2 |
| 214438_at | HLX1 | M60721.1 |
| 224734_at | HMGB1 | BF673940 |
| 202579_x_at | HMGN4 | NM_006353 |
| 218120_s_at | HMOX2 | D21243.1 |
| 201055_s_at | HNRPA0 | NM_006805 |
| 201054_at | HNRPA0 | BE966599 |
| 213356_x_at | HNRPA1 | AL568186 |
| 212626_x_at | HNRPC | AA664258 |
| 200751_s_at | HNRPC | BE898861 |
| 209330_s_at | HNRPD | D55674.1 |
| 235603_at | HNRPU | N95466 |
| 229204_at | HP1-BP74 | BE218428 |
| 212552_at | HPCAL1 | BE617588 |
| 214177_s_at | HPIP | AI935162 |
| 212259_s_at | HPIP | BF344265 |
| 216111_x_at | hPMSR3 | U38979 |
| 202854_at | HPRT1 | NM_000194 |
| 222881_at | HPSE | AF155510.1 |
| 219403_s_at | HPSE | NM_006665 |
| 203203_s_at | HRB2 | NM_007043 |
| 221170_at | HRH4 | AF312230.1 |
| 217736_s_at | HRI | NM_014413 |
| 209971_x_at | HRI | AI928526 |
| 224786_at | HRIHFB2072 | AL133580.1 |
| 228725_x_at | HRMT1L1 | BF003112 |
| 228722_at | HRMT1L1 | AI928367 |
| 221564_at | HRMT1L1 | AL570294 |
| 206445_s_at | HRMT1L2 | NM_001536 |
| 203285_s_at | HS2ST1 | NM_012262 |
| 227361_at | HS3ST3B1 | AA780067 |
| 217978_at | HSA243666 | NM_017582 |
| 222779_s_at | HSA277841 | AA706815 |
| 213598_at | HSA9761 | W87688 |
| 213540_at | HSD17B8 | AL031228 |
| 209657_s_at | HSF2 | M65217.1 |
| 212922_s_at | HSKM-B | AF070592.1 |
| 227026_at | HSMPP8 | AI016714 |
| 208815_x_at | HSPA4 | AB023420.1 |
| 221891_at | HSPA8 | AA704004 |
| 210338_s_at | HSPA8 | AB034951.1 |
| 208687_x_at | HSPA8 | AF352832.1 |
| 226148_at | HSPC063 | AU144305 |
| 218565_at | HSPC109 | BG223334 |
| 219006_at | HSPC125 | NM_014165 |
| 222438_at | HSPC126 | AK001934.1 |
| 217843_s_at | HSPC126 | NM_014166 |
| 218403_at | HSPC132 | NM_016399 |
| 218572_at | HSPC134 | NM_014169 |
| 221046_s_at | HSPC135 | NM_014170 |
| 226188_at | HSPC159 | AK025603.1 |
| 218728_s_at | HSPC163 | NM_014184 |
| 219356_s_at | HSPC177 | NM_016410 |
| 218085_at | HSPC177 | NM_015961 |
| 224516_s_at | HSPC195 | BC006428.1 |
| 223163_s_at | HSPC216 | BC000190.1 |
| 206976_s_at | HSPH1 | NM_006644 |
| 229574_at | HSU53209 | AI268231 |
| 204521_at | HSU79274 | NM_013300 |
| 226987_at | HUMAGCGB | W68720 |
| 213708_s_at | HUMGT198A | N40555 |
| 210970_s_at | IBTK | AF235049.1 |
| 211633_x_at | ICAP-1A | M24668.1 |
| 210785_s_at | ICB-1 | AB035482.1 |
| 201611_s_at | ICMT | NM_012405 |
| 201193_at | IDH1 | NM_005896 |
| 202069_s_at | IDH3A | AI826060 |
| 210418_s_at | IDH3B | AF023265.1 |
| 201509_at | IDH3B | NM_006899 |
| 208881_x_at | IDI1 | BC005247.1 |
| 204615_x_at | IDI1 | NM_004508 |
| 202439_s_at | IDS | NM_000202 |
| 201025_at | IF2 | NM_015904.1 |
| 202411_at | IFI27 | NM_005532 |
| 201315_x_at | IFITM2 | NM_006435 |
| 211676_s_at | IFNGR1 | AF056979.1 |
| 202105_at | IGBP1 | NM_001551 |
| 216401_x_at | IGKV | AJ408433 |
| 216207_x_at | IGKV1D-13 | AW408194 |
| 216517_at | IGKV1D-8; L24; L24a; IGKV1D8 IGKV1OR15-118; IGKVP2; IGKV1OR118; IGKV1/OR-118; IGKV1/OR15-118 | Z00008 |
| 217480_x_at |  | M20812 |
| 234764_x_at | IGL@ | U96394.1 |
| 234366_x_at | IGL@ | AF103591.1 |
| 224342_x_at | IGL@ | L14452.1 |
| 217227_x_at | IGL@ | X93006.1 |
| 217179_x_at | IGL@ | X79782.1 |
| 207167_at | IGSF2 | NM_004258 |
| 202491_s_at | IKBKAP | NM_003640 |
| 205992_s_at | IL15 | NM_000585 |
| 209827_s_at | IL16 | NM_004513.1 |
| 220054_at | IL23A | NM_016584 |
| 204116_at | IL2RG | NM_000206 |
| 217805_at | ILF3 | NM_004516 |
| 201234_at | ILK | NM_004517 |
| 225244_at | IMAGE3451454 | AA019893 |
| 218637_at | IMPACT | NM_018439 |
| 201892_s_at | IMPDH2 | NM_000884 |
| 223871_x_at | ING5 | BC005370.1 |
| 202794_at | INPP1 | NM_002194 |
| 205376_at | INPP4B | NM_003866 |
| 223309_x_at | IPLA2(GAMMA) | BG025248 |
| 218617_at | IPT | NM_017646 |
| 214666_x_at | IREB2 | AI204981 |
| 224405_at | IRTA2 | AF343663.1 |
| 203882_at | ISGF3G | NM_006084 |
| 213416_at | ITGA4 | BG532690 |
| 205055_at | ITGAE | NM_002208 |
| 205786_s_at | ITGAM | NM_000632 |
| 205176_s_at | ITGB3BP | NM_014288 |
| 236267_at | JAZ | BG178775 |
| 221508_at | JIK | AF181985.1 |
| 220761_s_at | JIK | NM_016281 |
| 214037_s_at | JM1 | BF224247 |
| 210927_x_at | JTB | BC004239.1 |
| 203751_x_at | JUND | NM_005354.2 |
| 201015_s_at | JUP | NM_021991 |
| 212639_x_at | K-ALPHA-1 | AL581768 |
| 231513_at | KCNJ2 | BF111326 |
| 200922_at | KDELR1 | NM_006801 |
| 200700_s_at | KDELR2 | NM_006854 |
| 202441_at | KEO4 | AL568449 |
| 201488_x_at | KHDRBS1 | BC000717.1 |
| 214662_at | KIAA0007 | D26488.1 |
| 212896_at | KIAA0052 | D29641.2 |
| 203494_s_at | KIAA0092 | NM_014679 |
| 212399_s_at | KIAA0121 | D50911.2 |
| 213000_at | KIAA0136 | AP000693 |
| 212846_at | KIAA0179 | D80001.1 |
| 201462_at | KIAA0193 | NM_014766 |
| 212733_at | KIAA0226 | AI798908 |
| 38892_at | KIAA0240 | D87077 |
| 38487_at | KIAA0246 | D87433 |
| 212053_at | KIAA0251 | AK025504.1 |
| 212302_at | KIAA0252 | D87440.1 |
| 212267_at | KIAA0261 | D87450.1 |
| 204308_s_at | KIAA0329 | NM_014844 |
| 204291_at | KIAA0335 | NM_014803 |
| 41386_i_at | KIAA0346 | AB002344 |
| 226025_at | KIAA0379 | AV740426 |
| 213035_at | KIAA0379 | AI081194 |

TABLE 2D-continued

Unique to 3004 genes list

| Affy ID | common | GenBank |
|---|---|---|
| 212601_at | KIAA0399 | AB007859.2 |
| 201855_s_at | KIAA0431 | NM_015251 |
| 202255_s_at | KIAA0440 | NM_015556 |
| 203958_at | KIAA0478 | AI557467 |
| 213340_s_at | KIAA0495 | AB007964.1 |
| 212443_at | KIAA0540 | AB011112.2 |
| 213109_at | KIAA0551 | N25621 |
| 204075_s_at | KIAA0562 | NM_014704 |
| 212946_at | KIAA0564 | AK025432.1 |
| 212675_s_at | KIAA0582 | AB011154.1 |
| 212370_x_at | KIAA0592 | AL080183.1 |
| 212577_at | KIAA0650 | AA868754 |
| 212052_s_at | KIAA0676 | AB014576.1 |
| 212467_at | KIAA0678 | AB014578.1 |
| 212928_at | KIAA0721 | AL050331 |
| 212690_at | KIAA0725 | AB018268.1 |
| 203907_s_at | KIAA0763 | NM_014869 |
| 212814_at | KIAA0828 | AB020635.1 |
| 203321_s_at | KIAA0863 | NM_014913.1 |
| 212197_x_at | KIAA0864 | AB020671.1 |
| 212975_at | KIAA0870 | AB020677.2 |
| 212492_s_at | KIAA0876 | AW237172 |
| 217118_s_at | KIAA0930 | AK025608.1 |
| 212503_s_at | KIAA0934 | N31807 |
| 203051_at | KIAA0945 | NM_014952 |
| 41220_at | KIAA0991 | AB023208 |
| 214672_at | KIAA0998 | AB023215.1 |
| 204155_s_at | KIAA0999 | AA044154 |
| 213836_s_at | KIAA1001 | AW052084 |
| 212795_at | KIAA1033 | AL137753.1 |
| 215146_s_at | KIAA1043 | AB028966.1 |
| 212845_at | KIAA1053 | AB028976.1 |
| 226144_at | KIAA1138 | AB032964.1 |
| 226816_s_at | KIAA1143 | AI745170 |
| 226718_at | KIAA1163 | AA001423 |
| 212904_at | KIAA1185 | AB033011.1 |
| 224900_at | KIAA1255 | AK025960.1 |
| 225295_at | KIAA1265 | AB033091.1 |
| 224701_at | KIAA1268 | AA056548 |
| 221874_at | KIAA1324 | AB037745.1 |
| 228843_at | KIAA1337 | AI824171 |
| 228240_at | KIAA1337 | AW952320 |
| 227150_at | KIAA1337 | N46867 |
| 231817_at | KIAA1350 | H25097 |
| 225847_at | KIAA1363 | AB037784.1 |
| 230598_at | KIAA1387 | BF063821 |
| 225076_s_at | KIAA1404 | AA150460 |
| 226254_s_at | KIAA1430 | AI912523 |
| 230492_s_at | KIAA1434 | BE328402 |
| 223392_s_at | KIAA1474 | BF510588 |
| 225629_s_at | KIAA1538 | AI669498 |
| 227624_at | KIAA1546 | AB046766.1 |
| 233880_at | KIAA1554 | AL161961.1 |
| 225931_s_at | KIAA1554 | AI954660 |
| 225929_s_at | KIAA1554 | AI954660 |
| 226155_at | KIAA1600 | AB046820.1 |
| 231940_at | KIAA1615 | AI369933 |
| 227638_at | KIAA1632 | AI393091 |
| 224829_at | KIAA1673 | AA772278 |
| 231850_x_at | KIAA1712 | AB051499.1 |
| 228334_x_at | KIAA1712 | AI633734 |
| 225717_at | KIAA1715 | AI814587 |
| 228754_at | KIAA1719 | BG150485 |
| 226909_at | KIAA1729 | AW270138 |
| 233914_s_at | KIAA1766 | AK022478.1 |
| 233072_at | KIAA1857 | AI348745 |
| 224789_at | KIAA1892 | AL555107 |
| 225760_at | KIAA1915 | AI302244 |
| 44040_at | KIAA1940 | AA524093 |
| 228029_at | KIAA1982 | AW513477 |
| 228446_at | KIAA2026 | BF062203 |
| 226968_at | KIF1B | AK023184.1 |
| 209234_at | KIF1B | BF939474 |
| 202183_s_at | KIF22 | NM_007317 |
| 225205_at | KIF3B | AI819734 |
| 227261_at | KLF12 | AA020010 |
| 226646_at | KLF2 | AI831932 |
| 217906_at | KLHDC2 | NM_014315 |
| 219157_at | KLHL2 | NM_007246 |
| 226874_at | KLHL8 | BF591270 |
| 203723_at | ITPKB | NM_002221 |
| 235024_at | Jade-1 | AI868315 |
| 218517_at | Jade-1 | NM_024900 |
| 206785_s_at | KLRC2 | NM_002260 |
| 207723_s_at | KLRC3 | NM_002261 |
| 220646_s_at | KLRF1 | NM_016523 |
| 212878_at | KNS2 | AA284075 |
| 209408_at | KNSL6 | U63743.1 |
| 211762_s_at | KPNA2 | BC005978.1 |
| 201088_at | KPNA2 | NM_002266 |
| 225268_at | KPNA4 | AK021602.1 |
| 213573_at | KPNB1 | AA861608 |
| 213507_s_at | KPNB1 | BG249565 |
| 211955_at | KPNB3 | NM_002271.1 |
| 211954_s_at | KPNB3 | NM_002271.1 |
| 211953_s_at | KPNB3 | NM_002271.1 |
| 210633_x_at | KRT10 | M19156.1 |
| 207023_x_at | KRT10 | NM_000421 |
| 213287_s_at | KRT10; K10; KPP | X14487 |
| 234631_at | KRTAP4-8 | AJ406940.1 |
| 214709_s_at | KTN1 | Z22551.1 |
| 200915_x_at | KTN1 | NM_004986 |
| 206486_at | LAG3 | NM_002286 |
| 227438_at | LAK | AI760166 |
| 226280_at | LAMB1 | AA133277 |
| 212408_at | LAP1B | AK023204.1 |
| 217933_s_at | LAP3 | NM_015907 |
| 217810_x_at | LARS | NM_020117 |
| 211005_at | LAT | AF036906.1 |
| 207734_at | LAX | NM_017773 |
| 221011_s_at | LBH | NM_030915 |
| 200650_s_at | LDHA | NM_005566 |
| 243363_at | LEF1 | AA992805 |
| 221558_s_at | LEF1 | AF288571.1 |
| 220750_s_at | LEPRE1 | NM_022356 |
| 202595_s_at | LEPROTL1 | AF161461.1 |
| 202594_at | LEPROTL1 | NM_015344 |
| 201105_at | LGALS1 | NM_002305 |
| 203236_s_at | LGALS9 | NM_009587 |
| 218253_s_at | LGTN | NM_006893 |
| 206881_s_at | LILRA3 | NM_006865 |
| 211681_s_at | LIM | AF116705.1 |
| 203243_s_at | LIM | NM_006457 |
| 202193_at | LIMK2 | NM_005569 |
| 220036_s_at | LIMR | NM_018113 |
| 205571_at | LIPT1 | NM_015929 |
| 202089_s_at | LIV-1 | NM_012319 |
| 203713_s_at | LLGL2 | NM_004524 |
| 204249_s_at | LMO2 | NM_005574 |
| 226548_at | LOC112868 | AI935915 |
| 224719_s_at | LOC113246 | BG339653 |
| 229861_at | LOC117584 | N66669 |
| 229145_at | LOC119504 | AA541762 |
| 235802_at | LOC122618 | BE676703 |
| 213061_s_at | LOC123803 | AA643304 |
| 224981_at | LOC124446 | AL520900 |
| 226702_at | LOC129607 | AI742057 |
| 224643_at | LOC133619 | AL524045 |
| 230721_at | LOC146174 | BF436957 |
| 225918_at | LOC146346 | AI742940 |
| 227049_at | LOC147632 | N21127 |
| 235014_at | LOC147727 | BF345728 |
| 225633_at | LOC147991 | BF057717 |
| 226845_s_at | LOC150678 | AL036350 |
| 225415_at | LOC151636 | AA577672 |
| 213372_at | LOC152559 | AW173157 |
| 225956_at | LOC153222 | AL565238 |
| 225361_x_at | LOC159090 | AI341165 |
| 222673_x_at | LOC159090 | AI582192 |
| 213285_at | LOC161291 | AV691491 |

TABLE 2D-continued

Unique to 3004 genes list

| Affy ID | common | GenBank |
|---|---|---|
| 212697_at | LOC162427 | AL515874 |
| 229614_at | LOC162967 | AI277652 |
| 235568_at | LOC199675 | BF433657 |
| 241525_at | LOC200772 | AV700191 |
| 212640_at | LOC201562 | AV712602 |
| 235587_at | LOC202781 | BG400596 |
| 226760_at | LOC203411 | BF666325 |
| 227640_s_at | LOC222136 | AI492167 |
| 227035_x_at | LOC222136 | BE670798 |
| 225782_at | LOC253827 | BG171064 |
| 226169_at | LOC283105 | AW276572 |
| 221853_s_at | LOC283820 | N39536 |
| 213725_x_at | LOC283824 | AI693140 |
| 227680_at | LOC284695 | AI057121 |
| 225376_at | LOC284734 | BG480592 |
| 225661_at | LOC284829 | BF794958 |
| 213532_at | LOC285148 | AI797833 |
| 222662_at | LOC286044 | W60806 |
| 59433_at | LOC286434 | N32185 |
| 229686_at | LOC286530 | AI436587 |
| 223325_at | LOC51061 | AF131780.1 |
| 226910_at | LOC51122 | AW008502 |
| 218059_at | LOC51123 | NM_016096 |
| 218142_s_at | LOC51185 | NM_016302 |
| 223043_at | LOC51234 | AF151018.1 |
| 64432_at | LOC51275 | W05463 |
| 221488_s_at | LOC51596 | AF230924.1 |
| 225206_s_at | LOC54516 | NM_019041.1 |
| 217882_at | LOC55831 | NM_018447 |
| 219125_s_at | LOC55974 | NM_018845 |
| 227748_at | LOC56267 | AI971694 |
| 225509_at | LOC56757 | AI862477 |
| 208424_s_at | LOC57019 | NM_020313 |
| 218263_s_at | LOC58486 | NM_021211 |
| 225346_at | LOC80298 | NM_025198.1 |
| 225341_at | LOC80298 | NM_025198.1 |
| 223248_at | LOC83693 | AK025626.1 |
| 223773_s_at | LOC85028 | AF277181.1 |
| 227172_at | LOC89894 | BC000282.1 |
| 225320_at | LOC90550 | AA579630 |
| 224951_at | LOC91012 | BE348305 |
| 224910_at | LOC91012 | AL575747 |
| 225030_at | LOC91272 | AA824341 |
| 225795_at | LOC91689 | AV751709 |
| 213119_at | LOC91974 | AW058600 |
| 225391_at | LOC93622 | AL562398 |
| 228648_at | LRG | AA622495 |
| 201186_at | LRPAP1 | NM_002337 |
| 90610_at | LRRN1 | AI654857 |
| 209841_s_at | LRRN3 | AL442092.1 |
| 211747_s_at | LSM5 | BC005938.1 |
| 204559_s_at | LSM7 | NM_016199 |
| 235470_at | LSM8 | AI766279 |
| 203523_at | LSP1 | NM_002339 |
| 229891_x_at | LSR7 | AI630799 |
| 202245_at | LSS | AW084510 |
| 207339_s_at | LTB | NM_002341 |
| 206584_at | LY96 | NM_015364 |
| 210754_s_at | LYN | M79321.1 |
| 202626_s_at | LYN | NM_002350 |
| 204458_at | LYPLA3 | AL110209.1 |
| 218437_s_at | LZTFL1 | NM_020347 |
| 225958_at | M6PR | AI554106 |
| 221494_x_at | M9 | AF085358.1 |
| 212716_s_at | M9 | AW083133 |
| 204857_at | MAD1L1 | NM_003550 |
| 203077_s_at | MADH2 | NM_005901 |
| 205398_s_at | MADH3 | NM_005902 |
| 202526_at | MADH4 | U44378.1 |
| 207922_s_at | MAEA | NM_005882 |
| 222670_s_at | MAFB | AW135013 |
| 218559_s_at | MAFB | NM_005461 |
| 209536_s_at | MAGED2 | AF320070.1 |
| 218573_at | MAGEH1 | NM_014061 |
| 223218_s_at | MAIL | AB037925.1 |
| 218918_at | MAN1C1 | NM_020379 |
| 227219_x_at | MAP1LC3A | BE857601 |
| 215498_s_at | MAP2K3 | AA780381 |
| 205698_s_at | MAP2K6 | NM_002758 |
| 213263_s_at | MAP3K12 | AW025150 |
| 205192_at | MAP3K14 | NM_003954 |
| 243_g_at | MAP4 | M64571 |
| 203552_at | MAP4K5 | AW298170 |
| 224621_at | MAPK1 | AA129773 |
| 217956_s_at | MASA | NM_021204 |
| 207041_at | MASP2 | NM_006610 |
| 227833_at | MBD6 | AW207668 |
| 218411_s_at | MBIP | NM_016586 |
| 201151_s_at | MBNL | NM_021038.1 |
| 201153_s_at | MBNL1 | NM_021038 |
| 239264_at | MCCC2 | AW973078 |
| 200798_x_at | MCL1 | NM_021960 |
| 200797_s_at | MCL1 | NM_021960.1 |
| 202107_s_at | MCM2 | NM_004526 |
| 230110_at | MCOLN2 | AV713773 |
| 219209_at | MDA5 | NM_022168 |
| 236814_at | MDM4 | AA745971 |
| 218992_at | MDS030 | NM_018465 |
| 214684_at | MEF2A | X63381.1 |
| 208819_at | MEL | BC002977.1 |
| 204825_at | MELK | NM_014791 |
| 212673_at | METAP1 | D42084.1 |
| 201155_s_at | MFN2 | NM_014874 |
| 204153_s_at | MFNG | NM_002405 |
| 205740_s_at | MGC10433 | NM_024321 |
| 208094_s_at | MGC10471 | NM_030818 |
| 223303_at | MGC10966 | BC004347.1 |
| 227878_s_at | MGC10974 | AI245026 |
| 223318_s_at | MGC10974 | BC004393.1 |
| 221452_s_at | MGC1223 | NM_030969 |
| 229070_at | MGC12335 | AA470369 |
| 227814_at | MGC12928 | AA789329 |
| 224452_s_at | MGC12966 | BC006110.1 |
| 224518_s_at | MGC13105 | BC006436.1 |
| 231241_at | MGC13114 | AW469714 |
| 57516_at | MGC13138 | AA746290 |
| 227402_s_at | MGC14595 | AI056895 |
| 225501_at | MGC14797 | AK027039.1 |
| 224968_at | MGC15407 | AL518311 |
| 227686_at | MGC15763 | BE465433 |
| 227935_at | MGC16202 | AA522681 |
| 225889_at | MGC17922 | BF475280 |
| 224759_s_at | MGC17943 | AK001731.1 |
| 225330_at | MGC18216 | AL044092 |
| 221893_s_at | MGC20727 | N32831 |
| 214061_at | MGC21654 | AI017564 |
| 218642_s_at | MGC2217 | NM_024300 |
| 238439_at | MGC22805 | AI925518 |
| 244716_x_at | MGC23244 | AI817976 |
| 223177_at | MGC24302 | AL515061 |
| 219812_at | MGC2463 | NM_024070 |
| 228856_at | MGC2474 | AV698149 |
| 221515_s_at | MGC2488 | BC000229.1 |
| 223252_at | MGC2641 | BC000755.1 |
| 227726_at | MGC2647 | BF057084 |
| 204985_s_at | MGC2650 | NM_024108 |
| 238077_at | MGC27385 | T75480 |
| 219111_s_at | MGC2835 | NM_024072 |
| 226466_s_at | MGC29729 | AL544688 |
| 212313_at | MGC29816 | BC004344.1 |
| 222129_at | MGC3035 | AK026155.1 |
| 221253_s_at | MGC3178 | NM_030810 |
| 228089_x_at | MGC3196 | H72927 |
| 223269_at | MGC3200 | BC004355.1 |
| 228077_at | MGC3207 | AK026666.1 |
| 217795_s_at | MGC3222 | W74580 |
| 226464_at | MGC33365 | BE348597 |
| 242292_at | MGC34827 | H12084 |
| 225941_at | MGC39820 | BE465037 |
| 225940_at | MGC39820 | BE465037 |

TABLE 2D-continued

Unique to 3004 genes list

| Affy ID | common | GenBank |
|---|---|---|
| 225065_x_at | MGC40157 | AI826279 |
| 227313_at | MGC40499 | AI870866 |
| 212959_s_at | MGC4170 | AK001821.1 |
| 214214_at | MGC4189 | AU151801 |
| 228099_at | MGC41917 | AI805301 |
| 228155_at | MGC4248 | BF512388 |
| 224435_at | MGC4248 | BC005871.1 |
| 222483_at | MGC4342 | AW664179 |
| 218130_at | MGC4368 | NM_024510 |
| 227379_at | MGC44669 | AI734993 |
| 225314_at | MGC45416 | BG291649 |
| 235005_at | MGC4562 | AA192361 |
| 207786_at | MGC4663 | NM_024514 |
| 202365_at | MGC5139 | BC004815.1 |
| 209702_at | MGC5149 | U79260.1 |
| 220949_s_at | MGC5242 | NM_024033 |
| 225160_x_at | MGC5370 | AI952357 |
| 242463_x_at | MGC5384 | AI620827 |
| 208137_x_at | MGC5384 | NM_030972 |
| 200847_at | MGC8721 | NM_016127 |
| 227158_at | MGC9912 | AU149257 |
| 212020_s_at | MKI67 | BF001806 |
| 222530_s_at | MKKS | AF275813.1 |
| 209467_s_at | MKNK1 | BC002755.1 |
| 209845_at | MKRN1 | AF117233.1 |
| 201285_at | MKRN1 | NM_013446 |
| 231974_at | MLL2 | AI742164 |
| 227528_s_at | MLL2 | AI394529 |
| 227527_at | MLL2 | AI394529 |
| 226100_at | MLL5 | AI762876 |
| 223189_x_at | MLL5 | AW082219 |
| 205408_at | MLLT10 | NM_004641 |
| 204918_at | MLLT3 | NM_004529 |
| 204917_s_at | MLLT3 | AV756536 |
| 225628_s_at | MLLT6 | BE677453 |
| 207329_at | MMP8 | NM_002424 |
| 212462_at | MORF | AF113514.1 |
| 223849_s_at | MOV10 | BC002548.1 |
| 202974_at | MPP1 | NM_002436 |
| 209858_x_at | MPPE1 | BC002877.1 |
| 204387_x_at | MRP63 | NM_024026 |
| 223154_at | MRPL1 MRPL19; RLX1; RPML15; MRP-L15; KIAA0104; MGC20675; RPML15 | AF212225.1 |
| 216305_s_at | KIAA0104 | AC005034 |
| 224331_s_at | MRPL36 | AB049654.1 |
| 222466_s_at | MRPL42 | AL136659.1 |
| 224479_s_at | MRPL45 | BC006235.1 |
| 203801_at | MRPS14 | NM_022100.1 |
| 203800_s_at | MRPS14 | NM_022100.1 |
| 221693_s_at | MRPS18A | AB049952.1 |
| 228019_s_at | MRPS18C | AV758614 |
| 218001_at | MRPS2 | NM_016034 |
| 223448_x_at | MRPS22 | AF063603.1 |
| 225477_s_at | MRPS25 | AL138444 |
| 212145_at | MRPS27 | D87453.1 |
| 224333_s_at | MRPS5 | AB049940.1 |
| 224919_at | MRPS6 | AL555227 |
| 218538_s_at | MRS2L | NM_020662 |
| 219607_s_at | MS4A4A | NM_024021 |
| 231078_at | MSCP | H69701 |
| 221920_s_at | MSCP | BE677761 |
| 208657_s_at | MSF | AF142408.1 |
| 209421_at | MSH2 | U04045.1 |
| 218499_at | MST4 | NM_016542 |
| 212859_x_at | MT1E | BF217861 |
| 217165_at | MT1F | M10943 |
| 204745_at | MT1G | NM_005950 |
| 204326_x_at | MT1L | NM_002450 |
| 216862_s_at | MTCP1 | Z24459 |
| 210212_x_at | MTCP1 | BC002600.1 |
| 202197_at | MTMR3 | NM_021090 |

| Affy ID | common | GenBank |
|---|---|---|
| 210386_s_at | MTX1 | BC001906.1 |
| 225294_s_at | MUM2 | BG340967 |
| 204798_at | MYB | NM_005375 |
| 213906_at | MYBL1 | AW592266 |
| 221820_s_at | MYST1 | AK024102.1 |
| 212406_at | MYT1 | AB028973.1 |
| 214775_at | N4BP3 | AW139448 |
| 208635_x_at | NACA | BF976260 |
| 200735_x_at | NACA | NM_005594 |
| 202926_at | NAG | NM_015909 |
| 218064_s_at | NAKAP95 | NM_014371 |
| 47530_at | NAP1 | AA748492 |
| 208751_at | NAPA | BC001165.1 |
| 206491_s_at | NAPA | NM_003827 |
| 221207_s_at | NBEA | NM_015678 |
| 202906_s_at | NBS1 | AI796269 |
| 211685_s_at | NCALD | AF251061.1 |
| 201517_at | NCBP2 | BC001255.1 |
| 214084_x_at | NCF1 | AW072388 |
| 204961_s_at | NCF1 | NM_000265 |
| 209106_at | NCOA1 | U19179.1 |
| 208979_at | NCOA6 | AF128458.1 |
| 202000_at | NDUFA6 | BC002772.1 |
| 218201_at | NDUFB2 | NM_004546 |
| 203371_s_at | NDUFB3 | NM_002491 |
| 213116_at | NEK3 | AI191920 |
| 203413_at | NELL2 | NM_006159 |
| 217979_at | NET-6 | NM_014399 |
| 222774_s_at | NETO2 | AI335263 |
| 208926_at | NEU1 | U84246.1 |
| 226103_at | nexilin | AF114264.1 |
| 243099_at | NFAM1 | AW271350 |
| 230322_at | NFAM1 | AI492017 |
| 224984_at | NFAT5 | W61007 |
| 211105_s_at | NFATC1 | U80918.1 |
| 210162_s_at | NFATC1 | U08015.1 |
| 210555_s_at | NFATC3 | U85430.1 |
| 203574_at | NFIL3 | NM_005384 |
| 209636_at | NFKB2 | BC002844.1 |
| 224716_at | NFKBIE | BG163267 |
| 206968_s_at | NFRKB | NM_006165 |
| 218129_s_at | NFYB | NM_006166 |
| 218127_at | NFYB | AI804118 |
| 201377_at | NICE-4 | NM_014847 |
| 39729_at | NKEFB | L19185 |
| 201268_at | NME2 | NM_002512 |
| 218057_x_at | NOC4 | NM_006067 |
| 231798_at | NOG | AL575177 |
| 217950_at | NOSIP | NM_015953 |
| 221499_s_at | NPEPL1 | AF008936.1 |
| 221691_x_at | NPM1 | AB042278.1 |
| 203814_s_at | NQO2 | NM_000904 |
| 225768_at | NR1D2 | AI761621 |
| 216321_s_at | NR3C1 | X03348.1 |
| 208709_s_at | NRD1 | U64898.1 |
| 204081_at | NRGN | NM_006176 |
| 209025_s_at | NSAP1 | AF037448.1 |
| 223298_s_at | NT5C3 | AF312735.1 |
| 203939_at | NT5E | NM_002526 |
| 203718_at | NTE | NM_006702 |
| 207152_at | NTRK2 | NM_006180 |
| 200649_at | NUCB1 | BC002356.1 |
| 226880_at | NUCKS | AL035851 |
| 217802_s_at | NUCKS | NM_022731 |
| 210574_s_at | NUDC | AF241788.1 |
| 230219_at | NUDE1 | AI831952 |
| 241596_at | NUDT10 | AL045306 |
| 229803_s_at | NUDT3 | AI347000 |
| 218375_at | NUDT9 | NM_024047 |
| 212709_at | NUP160 | D83781.1 |
| 204435_at | NUPL1 | NM_014778 |
| 222512_at | NYREN18 | AF300717.1 |
| 213815_x_at | NY-REN-24 | AI913329 |
| 221816_s_at | NY-REN-34 | BF055474 |
| 219644_at | NY-REN-58 | NM_016122 |

TABLE 2D-continued

Unique to 3004 genes list

| Affy ID | common | GenBank |
|---|---|---|
| 203804_s_at | OA48-18 | NM_006107 |
| 232666_at | OAS3 | R13458 |
| 218400_at | OAS3 | NM_006187 |
| 229854_at | OBSCN | AW614056 |
| 208503_s_at | ODAG | NM_021167 |
| 200790_at | ODC1 | NM_002539 |
| 203569_s_at | OFD1 | NM_003611 |
| 215136_s_at | OIP2 | AL050353.1 |
| 225291_at | OLD35 | AI967971 |
| 224392_s_at | OPN3 | AF303588.1 |
| 224707_at | ORF1-FL49 | AL522667 |
| 203445_s_at | OS4 | NM_005730 |
| 215399_s_at | OS-9 | AI683900 |
| 200714_x_at | OS-9 | NM_006812 |
| 209221_s_at | OSBPL2 | AI753638 |
| 227645_at | P101-PI3K | BF892532 |
| 226611_s_at | p30 | AA722878 |
| 200654_at | P4HB | J02783.1 |
| 208639_x_at | P5 | BC001312.1 |
| 207668_x_at | P5 | NM_005742 |
| 218131_s_at | p66alpha | NM_017660 |
| 201544_x_at | PABPN1 | BF675004 |
| 223565_at | PACAP | AF151024.1 |
| 220001_at | PADI4 | NM_012387 |
| 200815_s_at | PAFAH1B1 | L13386.1 |
| 205232_s_at | PAFAH2 | U89386.1 |
| 225622_at | PAG | NM_018440.1 |
| 209064_x_at | PAIP1 | AL136920.1 |
| 208051_s_at | PAIP1 | NM_006451 |
| 218271_s_at | PARL | NM_018622 |
| 37965_at | PARVB | AA181053 |
| 216945_x_at | PASK | U79240.1 |
| 213534_s_at | PASK | D50925.1 |
| 226223_at | PAWR | AI189509 |
| 221969_at | PAX5 | BF510692 |
| 217738_at | PBEF | BF575514 |
| 232349_x_at | PC326 | BF671187 |
| 214512_s_at | PC4 | NM_006713.1 |
| 238792_at | PCNX | BF209668 |
| 213581_at | PDCD2 | BF446180 |
| 228993_s_at | PDCD4 | AV728606 |
| 212594_at | PDCD4 | N92498 |
| 219275_at | PDCD5 | NM_004708 |
| 204449_at | PDCL | NM_005388 |
| 222317_at | PDE3B | AA888858 |
| 214582_at | PDE3B | NM_000753.1 |
| 208591_s_at | PDE3B | NM_000922 |
| 206792_x_at | PDE4C | NM_000923 |
| 218718_at | PDGFC | NM_016205 |
| 203857_s_at | PDIR | NM_006810 |
| 226452_at | PDK1 | AU146532 |
| 202671_s_at | PDXK | NM_003681 |
| 203097_s_at | PDZ-GEF1 | NM_014247 |
| 218025_s_at | PECI | NM_006117 |
| 226680_at | PEGASUS | BF056303 |
| 218472_s_at | PELO | NM_015946 |
| 220952_s_at | PEPP2 | NM_019012 |
| 49878_at | PEX16 | AA523441 |
| 205361_s_at | PFDN4 | AI718295 |
| 228499_at | PFKFB4 | AL038787 |
| 201037_at | PFKP | NM_002627 |
| 204992_s_at | PFN2 | NM_002628 |
| 200886_s_at | PGAM1 | NM_002629 |
| 201118_at | PGD | NM_002631 |
| 203314_at | PGPL | NM_012227 |
| 201701_s_at | PGRMC2 | NM_006320 |
| 222125_s_at | PH-4 | BC000580.1 |
| 231812_x_at | PHAX | AK023255.1 |
| 217952_x_at | PHF3 | AW189430 |
| 215718_s_at | PHF3 | AI949220 |
| 222631_at | PI4K2B | AI862887 |
| 212881_at | PIASY | NM_015897.1 |
| 213239_at | PIBF1 | NM_006346.1 |
| 212506_at | PICALM | AL135735 |
| 214151_s_at | PIGB | AU144243 |
| 216593_s_at | PIGCP1 | AB000359 |
| 207105_s_at | PIK3R2 | NM_005027 |
| 210417_s_at | PIK4CB | U81802.1 |
| 218773_s_at | PILB | NM_012228 |
| 228972_at | PITPN | AI028602 |
| 218667_at | PJA1 | NM_022368 |
| 222468_at | PKD1-like | W58365 |
| 203688_at | PKD2 | NM_000297 |
| 202732_at | PKIG | NM_007066 |
| 201251_at | PKM2 | NM_002654 |
| 205372_at | PLAG1 | NM_002655 |
| 204613_at | PLCG2 | NM_002661 |
| 205934_at | PLCL1 | NM_006226 |
| 216218_s_at | PLCL2 | AK023546.1 |
| 201050_at | PLD3 | NM_012268 |
| 222826_at | PLDN | BC004819.1 |
| 203471_s_at | PLEK | NM_002664 |
| 226247_at | PLEKHA1 | AI346026 |
| 201136_at | PLP2 | NM_002668 |
| 211012_s_at | PML | BC000080.1 |
| 203366_at | POLG | NM_002693 |
| 220113_x_at | POLR1B | NM_019014 |
| 202635_s_at | POLR2K | NM_005034 |
| 201876_at | PON2 | NM_000305 |
| 204839_at | POP5 | NM_015918 |
| 212200_at | POU2F1 | AB014592.1 |
| 204436_at | PP1628 | NM_025201 |
| 205661_s_at | PP591 | NM_025207 |
| 227447_at | PPAP2A | AA525163 |
| 203497_at | PPARBP | NM_004774 |
| 200661_at | PPGB | NM_000308 |
| 226336_at | PPIA | T62044 |
| 217602_at | PPIA | AI191118 |
| 210502_s_at | PPIE | AF042386.1 |
| 201489_at | PPIF | BC005020.1 |
| 208995_s_at | PPIG | U40763.1 |
| 228788_at | PPIL2 | AA425358 |
| 224364_s_at | PPIL3 | AF251049.1 |
| 235113_at | PPIL5 | AA742244 |
| 204788_s_at | PPOX | NM_000309 |
| 202014_at | PPP1R15A | NM_014330 |
| 202165_at | PPP1R2 | NM_006241.1 |
| 202883_s_at | PPP2R1B | T79584 |
| 202313_at | PPP2R2A | NM_002717 |
| 201877_s_at | PPP2R5C | NM_002719 |
| 229322_at | PPP2R5E | BF529715 |
| 32540_at | PPP3CC | AI762547 |
| 207000_s_at | PPP3CC | NM_005605 |
| 201594_s_at | PPP4R1 | NM_005134 |
| 225426_at | PPP6C | BF240782 |
| 214527_s_at | PQBP1 | AB041836.1 |
| 207769_s_at | PQBP1 | NM_005710 |
| 205277_at | PRDM2 | NM_012231 |
| 203057_s_at | PRDM2 | NM_015866.1 |
| 208680_at | PRDX1 | L19184.1 |
| 201619_at | PRDX3 | NM_006793 |
| 201923_at | PRDX4 | NM_006406 |
| 200845_s_at | PRDX6 | NM_004905 |
| 224909_s_at | PRex1 | BF308645 |
| 201858_s_at | PRG1 | J03223.1 |
| 232517_s_at | PRIC285 | AL121829 |
| 228230_at | PRIC285 | AL121829 |
| 202742_s_at | PRKACB | NM_002731 |
| 202741_at | PRKACB | AA130247 |
| 201805_at | PRKAG1 | NM_002733 |
| 213052_at | PRKAR2A | BF246917 |
| 218764_at | PRKCH | NM_024064 |
| 206099_at | PRKCH | NM_006255 |
| 210039_s_at | PRKCQ | L01087.1 |
| 209323_at | PRKRIR | AF081567.1 |
| 222231_s_at | PRO1855 | AK025328.1 |
| 225517_at | PRO1914 | AW236976 |
| 228401_at | PRO2000 | AI656807 |
| 202408_s_at | PRPF31 | NM_015629 |
| 228253_at | PRSS25 | AI917716 |

TABLE 2D-continued

Unique to 3004 genes list

| Affy ID | common | GenBank |
|---|---|---|
| 219669_at | PRV1 | NM_020406 |
| 202880_s_at | PSCD1 | NM_004762 |
| 221036_s_at | PSFL | NM_031301 |
| 205961_s_at | PSIP2 | NM_004682 |
| 201532_at | PSMA3 | NM_002788 |
| 216088_s_at | PSMA7 | AL078633 |
| 200039_s_at | PSMB2 | NM_002794 |
| 228204_at | PSMB4 | AA630330 |
| 209040_s_at | PSMB8 | U17496.1 |
| 201068_s_at | PSMC2 | NM_002803 |
| 200814_at | PSME1 | NM_006263 |
| 209853_s_at | PSME3 | BC002684.1 |
| 200988_s_at | PSME3 | NM_005789 |
| 200987_x_at | PSME3 | AA758755 |
| 218371_s_at | PSPC1 | NM_018282 |
| 219938_s_at | PSTPIP2 | NM_024430 |
| 219293_s_at | PTD004 | NM_013341 |
| 221600_s_at | PTD015 | BC002752.1 |
| 200773_x_at | PTMA | NM_002823 |
| 205171_at | PTPN4 | NM_002830 |
| 202897_at | PTPNS1 | AB023430.1 |
| 203554_x_at | PTTG1 | NM_004219 |
| 200677_at | PTTG1IP | NM_004339 |
| 216221_s_at | PUM2 | D87078.2 |
| 201606_s_at | PWP1 | BE796924 |
| 217846_at | QARS | NM_005051 |
| 212262_at | QKI | AF142419.1 |
| 201482_at | QSCN6 | NM_002826 |
| 222981_s_at | RAB10 | BC000896.1 |
| 200863_s_at | RAB11A | AI215102 |
| 208724_s_at | RAB1A | BC000905.1 |
| 203885_at | RAB21 | NM_014999 |
| 225074_at | RAB2B | AA531016 |
| 202372_at | RAB3-GAP150 | BF240652 |
| 230274_s_at | RAB5EP | BF589088 |
| 211961_s_at | RAB7 | AK000826.1 |
| 218700_s_at | RAB7L1 | BC002585.1 |
| 218699_at | RAB7L1 | BG338251 |
| 203573_s_at | RABGGTA | NM_004581 |
| 208640_at | RAC1 | BG292367 |
| 200608_s_at | RAD21 | NM_006265 |
| 238656_at | RAD50 | AA877043 |
| 37793_r_at | RAD51D | AF034956 |
| 221523_s_at | RAGD | AL138717 |
| 226143_at | RAI1 | BF984830 |
| 214435_x_at | RALA | NM_005402.1 |
| 222680_s_at | RAMP | AK001261.1 |
| 213019_at | RANBP6 | AI123233 |
| 210097_s_at | RARG-1 | AF130102.1 |
| 214369_at | RASGRP2 | AI688812 |
| 208206_s_at | RASGRP2 | NM_005825 |
| 240862_at | RASGRP4 | AA923524 |
| 211950_at | RBAF600 | AB007931.1 |
| 212783_at | RBBP6 | AK026954.1 |
| 212781_at | RBBP6 | AK026954.1 |
| 201092_at | RBBP7 | NM_002893 |
| 203344_s_at | RBBP8 | NM_002894 |
| 212168_at | RBM12 | AB018308.1 |
| 208319_s_at | RBM3 | NM_006743 |
| 213762_x_at | RBMX | AI452524 |
| 218117_at | RBX1 | NM_014248 |
| 212820_at | RC3 | AB020663.1 |
| 218352_at | RCBTB1 | NM_018191 |
| 201486_at | RCN2 | NM_002902 |
| 219155_at | RDGBB | NM_012417 |
| 217776_at | RDH11 | AF167438.1 |
| 217775_s_at | RDH11 | NM_016026 |
| 224009_x_at | RDHL | AF240697.1 |
| 223952_x_at | RDHL | AF240698.1 |
| 212397_at | RDX | AL137751.1 |
| 218599_at | REC8 | NM_005132 |
| 210568_s_at | RECQL | BC001052.1 |
| 206036_s_at | REL | NM_002908 |
| 220570_at | RETN | NM_020415 |
| 218428_s_at | REV1L | NM_016316 |
| 204127_at | RFC3 | BC000149.2 |
| 235816_s_at | Rgr | AI867408 |
| 204336_s_at | RGS19 | NM_005873 |
| 201453_x_at | RHEB2 | NM_005614 |
| 216049_at | RHOBTB3 | AK023621.1 |
| 222793_at | RIG-I | AK023661.1 |
| 218943_s_at | RIG-I | NM_014314 |
| 209684_at | RIN2 | AL136924.1 |
| 219041_s_at | RIP60 | NM_014374 |
| 218217_at | RISC | NM_021626 |
| 214519_s_at | RLN2 | NM_005059.1 |
| 201788_s_at | RNAHP | NM_007372 |
| 218496_at | RNASEH1 | BG534527 |
| 208632_at | RNF10 | AL578551 |
| 218528_s_at | RNF38 | NM_022781 |
| 202683_s_at | RNMT | NM_003799 |
| 212430_at | RNPC1 | AL109955 |
| 208270_s_at | RNPEP | NM_020216 |
| 239049_at | ROCK1 | BF514509 |
| 213637_at | ROK1 | BE503392 |
| 212834_at | ROK1 | AK001652.1 |
| 212774_at | RP58 | AJ223321 |
| 222490_at | RPC5 | AK023160.1 |
| 210573_s_at | RPC62 | BC004424.1 |
| 209382_at | RPC62 | U93867.1 |
| 225039_at | RPE | AV699857 |
| 200725_x_at | RPL10 | NM_006013 |
| 200036_s_at | RPL10A | NM_007104 |
| 214271_x_at | RPL12 | AA281332 |
| 229590_at | RPL13 | AI369389 |
| 214351_x_at | RPL13 | AA789278 |
| 212933_x_at | RPL13 | AA961748 |
| 212734_x_at | RPL13 | AI186735 |
| 212191_x_at | RPL13 | AW574664 |
| 208929_x_at | RPL13 | BC004954.1 |
| 200716_x_at | RPL13A | NM_012423 |
| 200715_x_at | RPL13A | BC000514.1 |
| 213588_x_at | RPL14 | AA838274 |
| 221476_s_at | RPL15 | AF279903.1 |
| 221475_s_at | RPL15 | NM_002948.1 |
| 212537_x_at | RPL17 | BE733979 |
| 212270_x_at | RPL17 | BG168283 |
| 222297_x_at | RPL18 | AV738806 |
| 200869_at | RPL18A | NM_000980 |
| 221775_x_at | RPL22 | BG152979 |
| 221726_at | RPL22 | BE250348 |
| 220960_x_at | RPL22 | NM_000983 |
| 214042_s_at | RPL22 | AW071997 |
| 208768_x_at | RPL22 | D17652.1 |
| 200888_s_at | RPL23 | NM_000978 |
| 216177_at | RPL29 | AW582267 |
| 213969_x_at | RPL29 | BF683426 |
| 200823_x_at | RPL29 | NM_000992 |
| 212039_x_at | RPL3 | BG339228 |
| 211666_x_at | RPL3 | L22453.1 |
| 211073_x_at | RPL3 | BC006483.1 |
| 201217_x_at | RPL3 | NM_000967 |
| 200674_s_at | RPL32 | NM_000994 |
| 213687_s_at | RPL35A | BE968801 |
| 219762_s_at | RPL36 | NM_015414 |
| 201406_at | RPL36A | NM_021029 |
| 214041_x_at | RPL37A | BE857772 |
| 211710_x_at | RPL4 | BC005817.1 |
| 201154_x_at | RPL4 | NM_000968 |
| 200089_s_at | RPL4 | AI953886 |
| 213080_x_at | RPL5 | BF214492 |
| 200937_s_at | RPL5 | NM_000969 |
| 212042_x_at | RPL7 | BG389744 |
| 200717_x_at | RPL7 | NM_000971 |
| 234875_x_at | rpL7a | AJ224082 |
| 234873_x_at | rpL7a | AJ224080 |
| 217740_x_at | RPL7A | NM_000972 |
| 200936_at | RPL8 | NM_000973 |
| 214167_s_at | RPLP0 | AA555113 |
| 200763_s_at | RPLP1 | NM_001003 |

TABLE 2D-continued

Unique to 3004 genes list

| Affy ID | common | GenBank |
|---|---|---|
| 201426_s_at | RPLP2 | AI922599 |
| 200909_s_at | RPLP2 | NM_001004 |
| 205562_at | RPP38 | NM_006414 |
| 211542_x_at | RPS10 | BC004334.1 |
| 208646_at | RPS14 | AF116710.1 |
| 200781_s_at | RPS15A | NM_001019 |
| 213890_x_at | RPS16 | AI200589 |
| 201258_at | RPS16 | NM_001020 |
| 212578_x_at | RPS17 | BF026595 |
| 201665_x_at | RPS17 | NM_001021 |
| 213414_s_at | RPS19 | BE259729 |
| 202649_s_at | RPS19 | NM_001022 |
| 212433_x_at | RPS2 | AA630314 |
| 214003_x_at | RPS20 | BF184532 |
| 200949_x_at | RPS20 | NM_001023 |
| 214097_at | RPS21 | AW024383 |
| 200834_s_at | RPS21 | NM_001024 |
| 200926_at | RPS23 | NM_001025 |
| 200741_s_at | RPS27 | NM_001030 |
| 242214_at | RPS27A | AU152194 |
| 212391_x_at | RPS3A | AI925635 |
| 201257_x_at | RPS3A | NM_001006 |
| 213347_x_at | RPS4X | AW132023 |
| 209134_s_at | RPS6 | BC000524.1 |
| 201254_x_at | RPS6 | NM_001010 |
| 200081_s_at | RPS6 | BE741754 |
| 204635_at | RPS6KA5 | NM_004755 |
| 203777_s_at | RPS6KB2 | NM_003952 |
| 218909_at | RPS6KC1 | NM_012424 |
| 213941_x_at | RPS7 | AI970731 |
| 200858_s_at | RPS8 | NM_001012 |
| 217747_s_at | RPS9 | NM_001013 |
| 214317_x_at | RPS9 | BE348997 |
| 212590_at | RRAS2 | BG168858 |
| 209773_s_at | RRM2 | BC001886.1 |
| 201890_at | RRM2 | NM_001034.1 |
| 222204_s_at | RRN3 | AL110238.1 |
| 203594_at | RTCD1 | NM_003729 |
| 203485_at | RTN1 | NM_021136 |
| 211509_s_at | RTN4 | AB015639.1 |
| 210968_s_at | RTN4 | AF333336.1 |
| 202426_s_at | RXRA | NM_002957.2 |
| 202853_s_at | RYK | NM_002958 |
| 200660_at | S100A11 | NM_005620 |
| 208540_x_at | S100A11P | NM_021039 |
| 217728_s_at | S100A6 | NM_014624 |
| 217946_s_at | SAE1 | NM_016402 |
| 201748_s_at | SAFB | NM_002967 |
| 235964_x_at | SAMHD1 | AA603344 |
| 235529_s_at | SAMHD1 | BF437747 |
| 220330_s_at | SAMSN1 | NM_022136 |
| 208740_at | SAP18 | NM_005870.2 |
| 201543_s_at | SARA1 | NM_020150 |
| 200802_at | SARS | NM_006513 |
| 213988_s_at | SAT | BE971383 |
| 203455_s_at | SAT | NM_002970 |
| 203408_s_at | SATB1 | NM_002971 |
| 204516_at | SCA7 | BG390306 |
| 212416_at | SCAMP1 | BF058944 |
| 205790_at | SCAP1 | NM_003726 |
| 219304_s_at | SCDGF-B | NM_025208 |
| 220791_s_at | SCN11A | NM_014139 |
| 222986_s_at | SCOTIN | BC001463.1 |
| 221514_at | SDCCAG16 | BC001149.1 |
| 223283_s_at | SDCCAG33 | AF039698.1 |
| 223282_at | SDCCAG33 | W60810 |
| 202228_s_at | SDFR1 | NM_017455 |
| 210131_x_at | SDHC | D49737.1 |
| 202004_x_at | SDHC | NM_003001 |
| 221931_s_at | SEC13L | AV701173 |
| 202084_s_at | SEC14L1 | NM_003003 |
| 233924_s_at | SEC15L | AK002113.1 |
| 201583_s_at | SEC23B | NM_006363 |
| 222824_at | SEC61A2 | AW237290 |
| 219351_at | SEDL | NM_014563 |
| 209751_s_at | SEDLP | AF291676.1 |
| 204563_at | SELL | NM_000655 |
| 206049_at | SELP | NM_003005 |
| 225561_at | SELT | BF692332 |
| 203788_s_at | SEMA3C | AI962897 |
| 46665_at | SEMA4C | AI949392 |
| 223444_at | SENP7 | AL136599.1 |
| 217977_at | SEPX1 | NM_016332 |
| 212190_at | SERPINE2 | AL541302 |
| 40189_at | set | M93651 |
| 213047_x_at | SET | AI278616 |
| 200631_s_at | SET | NM_003011 |
| 203155_at | SETDB1 | NM_012432 |
| 203818_s_at | SF3A3 | NM_006802 |
| 213370_s_at | SFMBT | BF057298 |
| 232392_at | SFRS3 | BE927772 |
| 203380_x_at | SFRS5 | NM_006925 |
| 202774_s_at | SFRS8 | AI023864 |
| 212321_at | SGPL1 | AF144638.1 |
| 221268_s_at | SGPP1 | NM_030791 |
| 202060_at | SH2BP1 | NM_014633 |
| 210101_x_at | SH3GLB1 | AF257318.1 |
| 209091_s_at | SH3GLB1 | AF263293.1 |
| 221519_at | SHFM3 | AF281859.1 |
| 221834_at | SIAH1 | U70056 |
| 209339_at | SIAH2 | U76248.1 |
| 209899_s_at | SIAHBP1 | AF217197.1 |
| 52940_at | SIGIRR | AA085764 |
| 211761_s_at | SIP | BC005975.1 |
| 210691_s_at | SIP | AF275803.1 |
| 201381_x_at | SIP | AF057356.1 |
| 206934_at | SIRPB1 | NM_006065 |
| 202782_s_at | SKIP | NM_016532 |
| 210567_s_at | SKP2 | BC001441.1 |
| 230452_at | SLC20A1 | AI939400 |
| 232167_at | SLC2A11 | BE675356 |
| 222088_s_at | SLC2A14, | AA778684 |
| 202499_s_at | SLC2A3 | NM_006931 |
| 204430_s_at | SLC2A5 | NM_003039 |
| 202433_at | SLC35B1 | NM_005827 |
| 218237_s_at | SLC38A1 | NM_030674 |
| 218682_s_at | SLC4A1AP | NM_018158 |
| 202111_at | SLC4A2 | NM_003040 |
| 241752_at | SLC8A1 | AA094434 |
| 221423_s_at | SMAP-5 | NM_030799 |
| 203874_s_at | SMARCA1 | NM_003069 |
| 217707_x_at | SMARCA2 | AI535683 |
| 206542_s_at | SMARCA2 | AV725365 |
| 202983_at | SMARCA3 | AI760760 |
| 213720_s_at | SMARCA4 | AI831675 |
| 211989_at | SMARCE1 | NM_003079.1 |
| 211988_at | SMARCE1 | NM_003079.1 |
| 224755_at | SMBP | BE621524 |
| 213879_at | SMT3H2 | AI971724 |
| 208738_x_at | SMT3H2 | AK024823.1 |
| 230820_at | SMURF2 | BF111169 |
| 44673_at | SN | N53555 |
| 209130_at | SNAP23 | BC003686.1 |
| 211546_x_at | SNCA | L36674.1 |
| 207827_x_at | SNCA | L36675.1 |
| 204466_s_at | SNCA | BG260394 |
| 215722_s_at | SNRPA1 | AJ130971.1 |
| 201342_at | SNRPC | NM_003093 |
| 203316_s_at | SNRPE | NM_003094 |
| 201522_x_at | SNRPN | NM_003097 |
| 228370_at | SNURF | BF114870 |
| 206042_x_at | SNURF | NM_022804 |
| 202359_s_at | SNX19 | NM_014758 |
| 223027_at | SNX9 | BF972871 |
| 208127_s_at | SOCS5 | NM_014011 |
| 201563_at | SORD | L29008.1 |
| 203509_at | SORL1 | NM_003105 |
| 212807_s_at | SORT1 | BE742268 |
| 212468_at | SPAG9 | AB011088.1 |
| 205312_at | SPI1 | NM_003120 |

TABLE 2D-continued

Unique to 3004 genes list

| Affy ID | common | GenBank |
|---|---|---|
| 222431_at | SPIN | AL136719.1 |
| 202524_s_at | SPOCK2 | NM_014767 |
| 209436_at | SPON1 | AB018305.1 |
| 218638_s_at | SPON2 | NM_012445 |
| 226353_at | SPPL2A | AI674647 |
| 224640_at | SPPL3 | AL514199 |
| 217995_at | SQRDL | NM_021199 |
| 224130_s_at | SRA1 | AF293026.1 |
| 201516_at | SRM | NM_003132 |
| 203182_s_at | SRPK2 | NM_003138 |
| 218283_at | SS18L2 | NM_016305 |
| 201139_s_at | SSB | NM_003142 |
| 202591_s_at | SSBP1 | NM_003143 |
| 200652_at | SSR2 | NM_003145 |
| 222411_s_at | SSR3 | AW087870 |
| 200957_s_at | SSRP1 | NM_003146 |
| 208667_s_at | ST13 | U17714.1 |
| 207040_s_at | ST13 | NM_003932 |
| 225455_at | STAF42 | AI760812 |
| 201837_s_at | STAF65(gamma) | AF197954.1 |
| 203544_s_at | STAM | NM_003473 |
| 226390_at | STARD4 | AA628398 |
| 225636_at | STAT2 | H98105 |
| 208992_s_at | STAT3 | BC000627.1 |
| 206118_at | STAT4 | NM_003151 |
| 213037_x_at | STAU | AJ132258.1 |
| 207320_x_at | STAU | NM_004602 |
| 225250_at | STIM2 | AB040915.1 |
| 202693_s_at | STK17A | NM_004760.1 |
| 222557_at | STMN3 | AL353715 |
| 217903_at | STRN4 | NM_013403 |
| 210190_at | STX11 | AF071504.1 |
| 209367_at | STXBP2 | AB002559.1 |
| 203310_at | STXBP3 | NM_007269 |
| 228853_at | STYX | AI652546 |
| 202130_at | SUDD | AW006290 |
| 203615_x_at | SULT1A1 | NM_001055 |
| 211385_x_at | SULT1A2 | U28169.1 |
| 207122_x_at | SULT1A2 | NM_001054 |
| 210580_x_at | SULT1A3 | L25275.1 |
| 201484_at | SUPT4H1 | NM_003168 |
| 237333_at | SYNCOILIN | T90771 |
| 201260_s_at | SYPL | NM_006754 |
| 206761_at | TACTILE | NM_005816 |
| 213090_s_at | TAF4 | AI744029 |
| 201463_at | TALDO1 | NM_006755 |
| 230052_s_at | TA-NFKBH | AA004799 |
| 208829_at | TAPBP | AF029750.1 |
| 213786_at | TAX1BP1 | AI935415 |
| 200977_s_at | TAX1BP1 | AF090891.1 |
| 203387_s_at | TBC1D4 | NM_014832 |
| 203386_at | TBC1D4 | AI650848 |
| 218520_at | TBK1 | NM_013254 |
| 216241_s_at | TCEA1 | X57718.1 |
| 204045_at | TCEAL1 | NM_004780 |
| 215511_at | TCF20 | U19345.1 |
| 212931_at | TCF20 | AB006630.1 |
| 222146_s_at | TCF4 | AK026674.1 |
| 203753_at | TCF4 | NM_003199 |
| 202261_at | TCFL1 | NM_005997 |
| 217909_s_at | TCFL4 | BF056105 |
| 204043_at | TCN2 | NM_000355 |
| 222010_at | TCP1 | BF224073 |
| 203303_at | TCTE1L | NM_006520 |
| 201999_s_at | TCTEL1 | NM_006519 |
| 208089_s_at | TDRD3 | NM_030794 |
| 201737_s_at | TEB4 | NM_005885 |
| 200627_at | TEBP | BC003005.1 |
| 219025_at | TEM1 | NM_020404 |
| 217853_at | TEM6 | NM_022748 |
| 219700_at | TEM7 | NM_020405 |
| 214081_at | TEM7 | AF070526.1 |
| 203449_s_at | TERF1 | NM_017489 |
| 227637_at | TFCP2 | AV712694 |
| 209338_at | TFCP2 | U03494.1 |
| 207627_s_at | TFCP2 | NM_005653 |
| 242538_at | TFDP1 | AW007021 |
| 212330_at | TFDP1 | R60866 |
| 226157_at | TFDP2 | AI569747 |
| 212457_at | TFE3 | AL161985.1 |
| 221866_at | TFEB | AL035588 |
| 217839_at | TFG | NM_006070 |
| 208691_at | TFRC | BC001188.1 |
| 207332_s_at | TFRC | NM_003234 |
| 203085_s_at | TGFB1 | BC000125.1 |
| 208944_at | TGFBR2 | D50683.1 |
| 222122_s_at | THOC2 | BG403671 |
| 218491_s_at | THY28 | NM_014174 |
| 228259_s_at | TIGA1 | AW590155 |
| 218188_s_at | TIMM13 | NM_012458 |
| 203342_at | TIMM17B | NM_005834 |
| 201666_at | TIMP1 | NM_003254 |
| 203167_at | TIMP2 | NM_003255 |
| 206472_s_at | TLE3 | NM_005078 |
| 203254_s_at | TLN1 | NM_006289 |
| 220146_at | TLR7 | NM_016562 |
| 209263_x_at | TM4SF7 | BC000389.1 |
| 201078_at | TM9SF2 | NM_004800 |
| 208184_s_at | TMEM1 | NM_003274 |
| 212352_s_at | TMP21 | BE780075 |
| 223482_at | TMPIT | AF327923.1 |
| 203432_at | TMPO | AW272611 |
| 206026_s_at | TNFAIP6 | NM_007115 |
| 206025_s_at | TNFAIP6 | AW188198 |
| 223502_s_at | TNFSF13B | AF134715.1 |
| 207196_s_at | TNIP1 | NM_006058 |
| 228369_at | TNRC5 | AI262560 |
| 222243_s_at | TOB2 | AB051450.1 |
| 217930_s_at | TOLLIP | NM_019009 |
| 201812_s_at | TOM7 | NM_019059 |
| 212773_s_at | TOMM20-PENDING | BG165094 |
| 202264_s_at | TOMM40 | NM_006114 |
| 201292_at | TOP2A | NM_001067.1 |
| 203375_s_at | TPP2 | NM_003291 |
| 216520_s_at | TPT1 | AF072098 |
| 211943_s_at | TPT1 | AL565449 |
| 205875_s_at | TREX1 | NM_016381 |
| 218425_at | TRIAD3 | BC000787.1 |
| 210705_s_at | TRIM5 | AF220028.1 |
| 221897_at | TRIM52 | AA205660 |
| 230165_at | TRIPIN | N31731 |
| 234351_x_at | TRPS1 | AK000948.1 |
| 226339_at | TRUB1 | AW500239 |
| 201758_at | TSG101 | NM_006292 |
| 201513_at | TSN | NM_004622.1 |
| 203983_at | TSNAX | NM_005999 |
| 221493_at | TSPYL | AL136629.1 |
| 204772_s_at | TTF1 | NM_007344 |
| 212705_x_at | TTS-2.2 | BF570210 |
| 209251_x_at | TUBA6 | BC004949.1 |
| 209191_at | TUBB-5 | BC002654.1 |
| 231853_at | TUBD1 | AK022771.1 |
| 201714_at | TUBG1 | NM_001070 |
| 214855_s_at | TULIP1 | AL050050.1 |
| 206828_at | TXK | NM_003328 |
| 201177_s_at | UBA2 | NM_005499 |
| 221490_at | UBAP1 | AL136733.1 |
| 217144_at | UBBP1 | X04801 |
| 200964_at | UBE1 | NM_003334 |
| 203281_s_at | UBE1L | NM_003335 |
| 201898_s_at | UBE2A | AI126625 |
| 201345_s_at | UBE2D2 | NM_003339 |
| 201344_at | UBE2D2 | NM_003339.1 |
| 201343_at | UBE2D2 | NM_003339.1 |
| 229355_at | UBE2D3 | AU150386 |
| 209096_at | UBE2V2 | U62136.2 |
| 225982_at | UBTF | BG341575 |
| 202692_s_at | UBTF | NM_014233 |
| 220083_x_at | UCHL5 | NM_016017 |

TABLE 2D-continued

Unique to 3004 genes list

| Affy ID | common | GenBank |
|---|---|---|
| 209712_at | UGTREL7 | N80922 |
| 209711_at | UGTREL7 | N80922 |
| 203790_s_at | UK114 | N54448 |
| 222448_at | UMP-CMPK | AF112216.1 |
| 217870_s_at | UMP-CMPK | NM_016308 |
| 212144_at | UNC84B; SUN2; KIAA0668 | AL021707 |
| 220998_s_at | UNC93B1 | NM_030930 |
| 203234_at | UP | NM_003364 |
| 209066_x_at | UQCRB | M26700.1 |
| 205849_s_at | UQCRB | NM_006294 |
| 201903_at | UQCRC1 | NM_003365 |
| 200883_at | UQCRC2 | NM_003366 |
| 208598_s_at | UREB1 | NM_005703 |
| 208971_at | UROD | M14016.1 |
| 213327_s_at | USP12 | AI820101 |
| 210681_s_at | USP15 | AF153604.1 |
| 219211_at | USP18 | NM_017414 |
| 214674_at | USP19 | AW451502 |
| 223167_s_at | USP25 | AF170562.1 |
| 229501_s_at | USP8 | AI393759 |
| 205139_s_at | UST | NM_005715 |
| 203241_at | UVRAG | NM_003369 |
| 225583_at | UXS1 | AL573637 |
| 218495_at | UXT | NM_004182 |
| 211749_s_at | VAMP3 | BC005941.1 |
| 218522_s_at | VCY2IP1 | NM_018174 |
| 204255_s_at | VDR | NM_000376.1 |
| 223302_s_at | VIK | BC004288.1 |
| 205844_at | VNN1 | NM_004666 |
| 212090_at | VPS28 | AL571424 |
| 221593_s_at | VRP | BC001663.1 |
| 222734_at | WARS2 | BF515963 |
| 209117_at | WBP2 | U79458.1 |
| 238823_at | WBP3 | AA481044 |
| 227844_at | WBP3 | AI089932 |
| 206621_s_at | WBSCR1 | NM_022170 |
| 224076_s_at | WHSC1L1 | AF255649.1 |
| 219628_at | WIG1 | NM_022470 |
| 205926_at | WSX1 | NM_004843 |
| 221786_s_at | XAP135 | AF055030.1 |
| 209375_at | XPC | D21089.1 |
| 212160_at | XPOT | AI984005 |
| 201922_at | YR-29 | NM_014886 |
| 210996_s_at | YWHAE | U43430.1 |
| 210317_s_at | YWHAE | U28936.1 |
| 214032_at | ZAP70 | AI817942 |
| 208087_s_at | ZBP1 | NM_030776 |
| 222731_at | ZDHHC2 | AI814257 |
| 222730_at | ZDHHC2 | AI814257 |
| 224858_at | ZDHHC5 | AB051535.1 |
| 202978_s_at | ZF | NM_021212.1 |
| 201531_at | ZFP36 | NM_003407 |
| 211962_s_at | ZFP36L1 | X79067.1 |
| 226111_s_at | ZFP385 | BF525395 |
| 214678_x_at | ZFX | R51161 |
| 212538_at | zizimin1 | AL576253 |
| 202939_at | ZMPSTE24 | NM_005857 |
| 225916_at | ZNF131 | AA789302 |
| 221842_s_at | ZNF131 | BE972394 |
| 244743_x_at | ZNF138 | AA114243 |
| 219854_at | ZNF14 | NM_021030 |
| 209565_at | ZNF183 | BC000832.1 |
| 204327_s_at | ZNF202 | N91520 |
| 244024_at | ZNF21 | T67481 |
| 210275_s_at | ZNF216 | AF062347.1 |
| 218005_at | ZNF22 | AA744771 |
| 219603_s_at | ZNF226 | NM_015919 |
| 215948_x_at | ZNF237 | AI522311 |
| 206014_at | ZNF237 | NM_014242 |
| 206900_x_at | ZNF253 | NM_021047 |
| 203707_at | ZNF263 | NM_005741 |
| 211009_s_at | ZNF271 | AF159567.1 |
| 218645_at | ZNF277 | NM_021994 |
| 209431_s_at | ZNF278 | AF254083.1 |

TABLE 2D-continued

Unique to 3004 genes list

| Affy ID | common | GenBank |
|---|---|---|
| 218490_s_at | ZNF302 | NM_018443 |
| 211678_s_at | ZNF313 | AF090934.1 |
| 209538_at | ZNF32 | U69645.1 |
| 78330_at | ZNF335 | AA845577 |
| 235300_x_at | ZNF363 | AW236209 |
| 215359_x_at | ZNF44 | AI758888 |
| 222028_at | ZNF45 | AI967981 |
| 228988_at | ZNF6 | AU157017 |
| 205089_at | ZNF7 | NM_003416 |
| 227670_at | ZNF75A | N74222 |
| 221645_s_at | ZNF83 | M27877.1 |
| 206158_s_at | ZNF9 | NM_003418 |
| 206059_at | ZNF91 | NM_003430 |
| 226255_at | ZNF-kaiso | BE302089 |
| 226759_at | ZNFN1A4 | BE793250 |
| 244534_at | ZRF1 | AI695743 |
| 215706_x_at | ZYX | BC002323.1 |
| 200808_s_at | ZYX | NM_003461 |
| 230703_at | | AA001543 |
| 241365_at | | AA002140 |
| 227867_at | | AA005361 |
| 226413_at | | AA044705 |
| 228590_at | | AA045257 |
| 235309_at | | AA126311 |
| 227087_at | | AA126419 |
| 217713_x_at | | AA126763 |
| 236742_at | | AA132172 |
| 228617_at | | AA142842 |
| 225276_at | | AA143579 |
| 228987_at | | AA156238 |
| 225886_at | | AA156797 |
| 226085_at | | AA181060 |
| 243154_at | | AA215381 |
| 238534_at | | AA262583 |
| 236583_at | | AA286867 |
| 227937_at | | AA307731 |
| 242943_at | | AA352113 |
| 204552_at | | AA355179 |
| 244798_at | | AA398139 |
| 235427_at | | AA418074 |
| 240344_x_at | | AA424065 |
| 235046_at | | AA456099 |
| 229305_at | | AA460299 |
| 239780_at | | AA468422 |
| 227388_at | | AA479016 |
| 230350_at | | AA503360 |
| 228049_x_at | | AA523172 |
| 225447_at | | AA613031 |
| 237006_at | | AA703523 |
| 239988_at | | AA708470 |
| 243601_at | | AA744124 |
| 244660_at | | AA746320 |
| 229483_at | | AA760738 |
| 231455_at | | AA768888 |
| 239287_at | | AA769410 |
| 242035_at | | AA805681 |
| 242760_x_at | | AA808203 |
| 235885_at | | AA810452 |
| 238649_at | | AA815089 |
| 227547_at | | AA824321 |
| 242104_at | | AA826288 |
| 229429_x_at | | AA863228 |
| 241692_at | | AA868729 |
| 213750_at | | AA928506 |
| 213034_at | | AB023216.1 |
| 225056_at | | AB037810.1 |
| 234921_at | | AC007228 |
| 213241_at | | AF035307.1 |
| 210829_s_at | | AF077048.1 |
| 210524_x_at | | AF078844.1 |
| 208875_s_at | | AF092132.1 |
| 221681_s_at | | AF094508.1 |
| 216576_x_at | | AF103529.1 |
| 223162_s_at | | AF116707.1 |
| 210501_x_at | | AF119846.1 |

TABLE 2D-continued

Unique to 3004 genes list

| Affy ID | common | GenBank |
|---|---|---|
| 223797_at | | AF130079.1 |
| 224709_s_at | | AF131831.1 |
| 211456_x_at | | AF333388.1 |
| 202663_at | | AI005043 |
| 226924_at | | AI016355 |
| 224783_at | | AI024869 |
| 235695_at | | AI051236 |
| 244313_at | | AI052659 |
| 229450_at | | AI075407 |
| 226692_at | | AI092931 |
| 227001_at | | AI096706 |
| 226448_at | | AI130705 |
| 228416_at | | AI149508 |
| 226275_at | | AI188653 |
| 244548_at | | AI189587 |
| 230739_at | | AI192379 |
| 43511_s_at | | AI201594 |
| 226939_at | | AI202327 |
| 227181_at | | AI203021 |
| 230580_at | | AI222805 |
| 226201_at | | AI224128 |
| 236280_at | | AI225238 |
| 240336_at | | AI242749 |
| 229220_x_at | | AI249173 |
| 212099_at | | AI263909 |
| 227639_at | | AI275605 |
| 241837_at | | AI289774 |
| 240015_at | | AI299467 |
| 240830_at | | AI300126 |
| 228585_at | | AI301948 |
| 241962_at | | AI332476 |
| 242865_at | | AI332638 |
| 227562_at | | AI335267 |
| 230376_at | | AI339915 |
| 227140_at | | AI343467 |
| 200962_at | | AI348010 |
| 225716_at | | AI357639 |
| 240118_at | | AI401105 |
| 228822_s_at | | AI435036 |
| 238026_at | | AI458020 |
| 231929_at | | AI458439 |
| 242403_at | | AI459177 |
| 238722_x_at | | AI460037 |
| 239278_at | | AI471969 |
| 64418_at | | AI472320 |
| 238788_at | | AI475803 |
| 228628_at | | AI478268 |
| 228549_at | | AI491983 |
| 228662_at | | AI492369 |
| 231124_x_at | | AI524095 |
| 232375_at | | AI539443 |
| 239277_at | | AI559696 |
| 244811_at | | AI561173 |
| 231225_at | | AI568622 |
| 227100_at | | AI569766 |
| 226527_at | | AI569785 |
| 244219_at | | AI613089 |
| 236285_at | | AI631846 |
| 239300_at | | AI632214 |
| 238155_at | | AI638235 |
| 235536_at | | AI640483 |
| 228607_at | | AI651594 |
| 241299_at | | AI651969 |
| 211984_at | | AI653730 |
| 229410_at | | AI659219 |
| 239401_at | | AI668672 |
| 222279_at | | AI669379 |
| 226550_at | | AI672159 |
| 229083_at | | AI672356 |
| 229264_at | | AI675152 |
| 228959_at | | AI676241 |
| 217679_x_at | | AI683552 |
| 229544_at | | AI690169 |
| 229844_at | | AI699465 |
| 227696_at | | AI701408 |
| 225897_at | | AI709406 |
| 227807_at | | AI738416 |
| 226951_at | | AI741415 |
| 227981_at | | AI741458 |
| 226885_at | | AI743880 |
| 228039_at | | AI765169 |
| 235457_at | | AI769569 |
| 235956_at | | AI797063 |
| 227449_at | | AI799018 |
| 213461_at | | AI800983 |
| 228604_at | | AI805069 |
| 228291_s_at | | AI806322 |
| 239467_at | | AI806747 |
| 227350_at | | AI807356 |
| 235456_at | | AI810266 |
| 229097_at | | AI813331 |
| 228974_at | | AI816281 |
| 230386_at | | AI819394 |
| 217704_x_at | | AI820796 |
| 242390_at | | AI821925 |
| 240413_at | | AI827431 |
| 228174_at | | AI832363 |
| 222036_s_at | | AI859865 |
| 230479_at | | AI872374 |
| 230748_at | | AI873273 |
| 235258_at | | AI873425 |
| 228495_at | | AI880633 |
| 226392_at | | AI888503 |
| 244189_at | | AI888657 |
| 237262_at | | AI912190 |
| 228109_at | | AI912976 |
| 238043_at | | AI913123 |
| 235680_at | | AI914925 |
| 222000_at | | AI915947 |
| 242471_at | | AI916641 |
| 229629_at | | AI923633 |
| 242020_s_at | | AI925506 |
| 225396_at | | AI928212 |
| 225310_at | | AI928344 |
| 235385_at | | AI935334 |
| 240806_at | | AI939308 |
| 235479_at | | AI948598 |
| 229101_at | | AI963142 |
| 235199_at | | AI969697 |
| 212250_at | | AI972475 |
| 241916_at | | AI984040 |
| 228685_at | | AI990349 |
| 227877_at | annexin II receptor | AI991103 |
| 231840_x_at | | AK000803.1 |
| 232004_at | | AK001846.1 |
| 233779_x_at | | AK022046.1 |
| 233605_x_at | | AK022050.1 |
| 233587_s_at | | AK022852.1 |
| 233068_at | | AK023264.1 |
| 232520_s_at | | AK023585.1 |
| 225635_s_at | | AK023696.1 |
| 232787_at | | AK023724.1 |
| 215375_x_at | | AK023938.1 |
| 224664_at | | AK023981.1 |
| 217052_x_at | | AK024108.1 |
| 224580_at | | AK024263.1 |
| 224579_at | | AK024263.1 |
| 216751_at | | AK024879.1 |
| 216437_at | | AK024949.1 |
| 224871_at | | AK025464.1 |
| 232161_x_at | | AK025546.1 |
| 226274_at | | AK025562.1 |
| 221648_s_at | | AK025651.1 |
| 224604_at | | AK025703.1 |
| 224718_at | | AK025731.1 |
| 224711_at | | AK025731.1 |
| 234192_s_at | | AK026487.1 |
| 212051_at | | AK026913.1 |
| 216640_s_at | | AK026926.1 |
| 212528_at | | AL023553 |

TABLE 2D-continued

Unique to 3004 genes list

| Affy ID | common | GenBank |
|---|---|---|
| 217340_at | | AL024509 |
| 217322_x_at | | AL024509 |
| 217092_x_at | | AL031589 |
| 216336_x_at | | AL031602 |
| 209733_at | | AL034399 |
| 243495_s_at | | AL036450 |
| 201648_at | | AL039831 |
| 225899_x_at | | AL040396 |
| 225553_at | | AL042817 |
| 212400_at | | AL043266 |
| 221748_s_at | | AL046979 |
| 216348_at | | AL049693 |
| 214857_at | | AL050035.1 |
| 214949_at | | AL050136.1 |
| 213929_at | | AL050204.1 |
| 216559_x_at | | AL050348 |
| 217446_x_at | | AL080160.1 |
| 214902_x_at | | AL080232.1 |
| 215766_at | | AL096729.1 |
| 216570_x_at | | AL096829 |
| 37590_g_at | | AL109698 |
| 226269_at | | AL110252.1 |
| 232034_at | | AL117607.1 |
| 216505_x_at | | AL118502 |
| 226664_at | | AL121747 |
| 222229_x_at | | AL121871 |
| 234807_x_at | | AL121916 |
| 216342_x_at | | AL121916 |
| 216565_x_at | | AL121994 |
| 228007_at | | AL133101.1 |
| 225834_at | | AL135396 |
| 210038_at | | AL137145 |
| 217019_at | | AL137162 |
| 226959_at | | AL137430.1 |
| 233732_at | | AL137445.1 |
| 224763_at | | AL137450.1 |
| 233224_at | | AL137645.1 |
| 228069_at | | AL138828 |
| 212828_at | | AL157424.1 |
| 216547_at | | AL353681 |
| 215063_x_at | | AL390149.1 |
| 216497_at | | AL390738 |
| 227567_at | | AL524467 |
| 225409_at | | AL529672 |
| 228361_at | | AL561296 |
| 226532_at | | AL563613 |
| 226878_at | | AL581873 |
| 225893_at | | AL589593 |
| 228548_at | | AU126086 |
| 227649_s_at | | AU144000 |
| 233019_at | | AU145061 |
| 222164_at | | AU145411 |
| 244389_at | | AU145538 |
| 215617_at | | AU145711 |
| 243819_at | | AU146329 |
| 225732_at | | AU146850 |
| 232909_s_at | | AU146870 |
| 232614_at | | AU146963 |
| 233425_at | | AU147903 |
| 227929_at | | AU151342 |
| 227979_at | | AU152162 |
| 226217_at | | AU152456 |
| 222833_at | | AU154202 |
| 233011_at | | AU155094 |
| 226350_at | | AU155565 |
| 226641_at | | AU157224 |
| 233433_at | | AU158871 |
| 232537_x_at | | AU159474 |
| 225816_at | | AV646599 |
| 241812_at | | AV648669 |
| 212920_at | | AV682285 |
| 231234_at | | AV699565 |
| 243158_at | | AV700081 |
| 227754_at | | AV700815 |
| 222303_at | | AV700891 |
| 229725_at | | AV705292 |
| 228477_at | | AV707196 |
| 213251_at | | AV712064 |
| 235421_at | | AV713062 |
| 228381_at | | AV716964 |
| 204651_at | | AW003022 |
| 227129_x_at | | AW006934 |
| 230314_at | | AW014557 |
| 231644_at | | AW016812 |
| 227199_at | | AW027812 |
| 227722_at | | AW043594 |
| 226402_at | | AW055161 |
| 235725_at | | AW055351 |
| 240038_at | | AW057518 |
| 229865_at | | AW058617 |
| 229907_at | | AW058634 |
| 236243_at | | AW070776 |
| 228846_at | | AW071793 |
| 241801_at | | AW084937 |
| 243764_at | | AW085312 |
| 227198_at | | AW085505 |
| 243934_at | | AW139261 |
| 229373_at | | AW139719 |
| 223501_at | | AW151360 |
| 239896_at | | AW190479 |
| 232001_at | | AW193600 |
| 244312_at | | AW195572 |
| 238156_at | | AW205632 |
| 236172_at | | AW206817 |
| 230085_at | | AW263542 |
| 223358_s_at | | AW269834 |
| 227630_at | | AW274445 |
| 228108_at | | AW274846 |
| 226773_at | | AW290940 |
| 235508_at | | AW291023 |
| 236198_at | | AW292872 |
| 227884_at | | AW296067 |
| 237143_at | | AW296162 |
| 228841_at | | AW299250 |
| 231688_at | | AW337833 |
| 228680_at | | AW340096 |
| 242558_at | | AW362945 |
| 244358_at | | AW372457 |
| 239379_at | | AW449624 |
| 243095_at | | AW451624 |
| 237753_at | | AW504569 |
| 239582_at | | AW514654 |
| 217549_at | | AW574933 |
| 225522_at | | AW628987 |
| 235222_x_at | | AW675725 |
| 230003_at | | AW779917 |
| 235361_at | | AW842975 |
| 239331_at | | AW954199 |
| 235592_at | | AW960145 |
| 215275_at | | AW963138 |
| 222315_at | | AW972855 |
| 236155_at | | AW974609 |
| 238883_at | | AW975051 |
| 217286_s_at | | BC001805.1 |
| 210679_x_at | | BC002629.1 |
| 224482_s_at | | BC006240.1 |
| 229384_at | | BE044193 |
| 244443_at | | BE247450 |
| 227984_at | | BE464483 |
| 239231_at | | BE464819 |
| 227590_at | | BE501980 |
| 235124_at | | BE502930 |
| 214751_at | | BE541042 |
| 234975_at | | BE544748 |
| 241845_at | | BE550501 |
| 228380_at | | BE551193 |
| 224806_at | | BE563152 |
| 224818_at | | BE622952 |
| 238761_at | | BE645241 |
| 239979_at | | BE645480 |

TABLE 2D-continued

Unique to 3004 genes list

| Affy ID | common | GenBank |
|---|---|---|
| 230178_s_at | | BE672676 |
| 230248_x_at | | BE673759 |
| 228005_at | | BE677308 |
| 225478_at | | BE783723 |
| 241027_at | | BE858373 |
| 229874_x_at | | BE865517 |
| 235292_at | | BE875232 |
| 225584_at | | BE880820 |
| 225123_at | | BE883841 |
| 224891_at | | BE888885 |
| 228710_at | | BE905157 |
| 241893_at | | BE927766 |
| 224688_at | | BE962299 |
| 211927_x_at | | BE963164 |
| 228571_at | | BE963438 |
| 212472_at | | BE965029 |
| 225750_at | | BE966748 |
| 227665_at | | BE968576 |
| 221963_x_at | | BE999967 |
| 213145_at | | BF001666 |
| 228324_at | | BF031819 |
| 242878_at | | BF061275 |
| 244026_at | | BF063657 |
| 226116_at | | BF064224 |
| 235847_at | | BF111312 |
| 235459_at | | BF114745 |
| 235882_at | | BF115777 |
| 225549_at | | BF129093 |
| 226712_at | | BF206389 |
| 225112_at | | BF245400 |
| 225274_at | | BF247054 |
| 224841_x_at | | BF316352 |
| 224983_at | | BF339821 |
| 244492_at | | BF357738 |
| 213567_at | | BF431965 |
| 227077_at | | BF432238 |
| 225240_s_at | | BF435123 |
| 227964_at | | BF435621 |
| 240572_s_at | | BF436632 |
| 225892_at | | BF438417 |
| 238952_x_at | | BF439163 |
| 242013_at | | BF445012 |
| 227446_s_at | | BF445127 |
| 230224_at | | BF446577 |
| 236001_at | | BF446940 |
| 226352_at | | BF447037 |
| 227451_s_at | | BF507383 |
| 227184_at | | BF508702 |
| 228393_s_at | | BF508739 |
| 228392_at | | BF508739 |
| 225856_at | | BF512028 |
| 227991_x_at | | BF516567 |
| 243261_at | | BF530486 |
| 229893_at | | BF589413 |
| 241859_at | | BF593050 |
| 230779_at | | BF594371 |
| 231927_at | | BF671883 |
| 225967_s_at | | BF683512 |
| 238520_at | | BF724270 |
| 238513_at | | BF905445 |
| 238311_at | | BF940192 |
| 225036_at | | BF969806 |
| 215082_at | | BF973387 |
| 238768_at | | BF976290 |
| 211942_x_at | | BF979419 |
| 213851_at | | BG031677 |
| 215088_s_at | | BG110532 |
| 229814_at | | BG149337 |
| 225116_at | | BG166310 |
| 226635_at | | BG170478 |
| 224606_at | | BG250721 |
| 225845_at | | BG253884 |
| 212995_x_at | | BG255188 |
| 221507_at | | BG258639 |
| 224916_at | | BG286973 |
| 235028_at | | BG288330 |
| 224741_x_at | | BG329175 |
| 213166_x_at | | BG332462 |
| 225155_at | | BG339050 |
| 224569_s_at | | BG388615 |
| 224754_at | | BG431266 |
| 225494_at | | BG478726 |
| 227616_at | | BG481877 |
| 232744_x_at | | BG485129 |
| 226936_at | | BG492359 |
| 223455_at | | BG493862 |
| 225492_at | | BG500396 |
| 227636_at | | BG500677 |
| 239108_at | | H16791 |
| 217506_at | | H49382 |
| 211628_x_at | | J04755.1 |
| 234884_x_at | | L21961.1 |
| 217466_x_at | | L48784 |
| 214058_at | | M19720 |
| 210592_s_at | | M55580.1 |
| 212239_at | | M61906.1 |
| 212486_s_at | | N20923 |
| 226272_at | | N25986 |
| 238929_at | | N30132 |
| 229348_at | | N30416 |
| 227221_at | | N36085 |
| 229200_at | | N40199 |
| 235694_at | | N49233 |
| 226577_at | | N49844 |
| 226179_at | | N63920 |
| 235424_at | | N66727 |
| 49111_at | | N80935 |
| 229905_at | | N92500 |
| 228891_at | | N93399 |
| 201417_at | | NM_003107.1 |
| 201416_at | | NM_003107.1 |
| 208760_at | | NM_003345.1 |
| 217833_at | | NM_006372.1 |
| 221419_s_at | | NM_013307 |
| 219731_at | | NM_024343 |
| 220712_at | | NM_024984 |
| 239876_at | | R37337 |
| 231109_at | | R44974 |
| 204831_at | | R59697 |
| 243973_at | | R67076 |
| 226883_at | | T89044 |
| 239725_at | | T90703 |
| 217202_s_at | | U08626 |
| 216383_at | | U52111 |
| 215057_at | | U66046.1 |
| 215283_at | | U79248.1 |
| 212607_at | | U79271.1 |
| 214848_at | | U79277.1 |
| 212672_at | | U82828 |
| 208676_s_at | | U87954.1 |
| 215009_s_at | | U92014.1 |
| 238431_at | | W68845 |
| 225095_at | | W81119 |
| 212605_s_at | | W85912 |
| 239555_at | | W87626 |
| 202969_at | | Y09216.1 |
| 217347_at | | Z82202 |
| 217266_at | | Z97353 |
| 215963_x_at | | Z98200 |

The expression of a gene in Table 2A could be at least 75% less, at least 80% less, at least 90% less or at least 95% less in a SLE subject as compared to one or more controls. The expression of a gene in Table 2B could be at least four-fold, at least five-fold, or at least ten-fold greater in a SLE subject as compared to one or more controls. Also, in preferred embodiments, the method includes determining the relative levels of expression of at least 400, 450, 500, 550, 600, 650, 700, 750, 800, 850, 850, 900, 950, or at least 1000 genes in Table 2A and/or 2B as compared to one or more controls. In one embodiment, the determining step measures the level of mRNA expressed.

As an alternative to comparing the level of expression of genes listed in Table 2A, 2B and/or 2C in a mammalian subject with the expression levels in one or more controls, the level of expression in the subject can be compared to a plurality of reference profiles associated with the presence or absence of SLE, and optionally, the severity of SLE. Accordingly, the invention provides a method for diagnosing systemic lupus erythematosus (SLE), by providing a plurality of reference expression profiles, each representing the level of expression of at least 375 genes listed in Table 2A and/or Table 2B and associated with the presence or absence of SLE, and optionally with the severity of SLE; providing a subject expression profile generated from one or more cells or other sample from a mammalian subject and representing the level of expression of at least 10 genes listed in Table 2A and/or Table 2B; and selecting the reference profile most similar to the subject expression profile, to thereby diagnose the presence or absence of SLE in the subject, and optionally the severity of SLE in the subject.

The reference expression profile represents the level of expression of at least 400, at least 450, at least 500, at least 550, at least 600, at least 650, at least 700, at least 750, at least 800, at least 850, at least 900, at least 950, or at least 1000 genes listed in Table 2A and/or Table 2B. Preferably the subject expression profiles represents the level of expression of at least 20, at least 30, at least 40, at least 50, at least 75, at least 100, at least 150, at least 200, at least 250, at least 300, at least 350, at least 375, at least 400, at least 450, at least 500, at least 550, at least 600, at least 650, at least 700, at least 750, at least 800, at least 850, at least 900, at least 950, or at least 1000 genes listed in Table 2A and/or Table 2B.

The inventors have identified 45 genes that discriminate SLE patients from patients with influenza and healthy patients. Table 3A lists 27 genes which are under-expressed in SLE patients as compared to influenza and healthy patients. Table 3B lists 18 genes which are over-expressed in SLE patients as compared to influenza and healthy patients.

Table 3A. Genes under-expressed in SLE patients as compared to healthy patients and/or patients infected with influenza.

TABLE 3A

| Affymetrix ID | Common | Genbank ID |
|---|---|---|
| 227616_at | | BG481877 |
| 229312_s_at | GKAP42 | BF434321 |
| 210031_at | CD3Z | J04132.1 |
| 202479_s_at | GS3955 | BC002637.1 |
| 225628_s_at | MLLT6 | BE677453 |
| 213109_at | KIAA0551 | N25621 |
| 201748_s_at | SAFB | NM_002967 |
| 222122_s_at | THOC2 | BG403671 |
| 237333_at | SYNCOILIN | T90771 |
| 216111_x_at | hPMSR3 | U38979 |
| 221264_s_at | AF311304 | NM_031214 |
| 201416_at | | NM_003107.1 |
| 201417_at | | NM_003107.1 |
| 235014_at | LOC147727 | BF345728 |
| 221214_s_at | DKFZP586J1624 | NM_015537 |
| 226611_s_at | p30 | AA722878 |
| 205005_s_at | NMT2 | AW293531 |
| 215440_s_at | FLJ10097 | AL523320 |
| 214081_at | TEM7 | AF070526.1 |
| 214857_at | | AL050035.1 |
| 200767_s_at | C9orf10 | NM_014612 |
| 212107_s_at | DDX9 | BE910323 |

TABLE 3A-continued

| Affymetrix ID | Common | Genbank ID |
|---|---|---|
| 201917_s_at | FLJ10618 | AI694452 |
| 227712_at | DJ122O8.2 | AV682940 |
| 225184_at | ELD/OSA1 | AK000921.1 |
| 227722_at | | AW043594 |
| 205839_s_at | BZRAP1 | NM_004758 |

Table 3B. Genes over-expressed in SLE patients as compared to healthy patients and/or patients infected with influenza.

TABLE 3B

| Affymetrix ID | Common | Genbank ID |
|---|---|---|
| 202568_s_at | MARK3 | AI745639 |
| 210681_s_at | USP15 | AF153604.1 |
| 230110_at | MCOLN2 | AV713773 |
| 218048_at | BUP | NM_012071 |
| 208683_at | CAPN2 | M23254.1 |
| 209593_s_at | TOR1B | AF317129.1 |
| 217995_at | SQRDL | NM_021199 |
| 201576_s_at | GLB1 | NM_000404 |
| 200677_at | PTTG1IP | NM_004339 |
| 211509_s_at | RTN4 | AB015639.1 |
| 217763_s_at | RAB31 | NM_006868 |
| 201012_at | ANXA1 | NM_000700 |
| 212268_at | SERPINB1 | NM_030666.1 |
| 204714_s_at | F5 | NM_000130 |
| 227769_at | GPR27 | AI703476 |
| 225633_at | LOC147991 | BF057717 |
| 204780_s_at | TNFRSF6 | AA164751 |
| 219253_at | FAM11B | NM_024121 |

In one aspect, the human patient suffering from SLE expresses at least 2, 3, 4, 5, 10, 15, 20, 25, 30, or at least 40 genes, preferably 45 genes in Table 3A and/or Table 3B, wherein the patient expresses genes in Table 3A to an extent at least 50% less than the control, and expresses genes in Table 3B to extent at least two-fold more than the control. The level of expression in SLE patients can be at least 50%, 60%, 70%, 80%, 90% or at least 95% less than the level of expression of a gene in Table 3A as compared to the control. The level of expression in SLE patients can be at least two-fold, three-fold, four-fold or at least five-fold more than the control. In a yet further aspect, the one or more gene is expressed in a peripheral blood mononuclear cell. In one embodiment, the determining step measures the level of mRNA expressed.

In another embodiment, the invention provides a method for diagnosing systemic lupus erythematosus (SLE), by providing a plurality of reference expression profiles, each associated with the presence or absence of SLE, and optionally with the severity of SLE; providing a subject expression profile generated from one or more cells or other sample from a mammalian subject; and selecting the reference expression profile most similar to the subject expression profile, to thereby diagnose the presence or absence of SLE in the subject, and optionally the severity of SLE in the subject; wherein, the subject expression profile and the reference profiles represent the level of expression of at least 1 gene listed in Table 3A and/or Table 3B.

The reference expression profile contains the levels of expression of at least 2, 3, 4, 5, 6, 7, 8, 9, 10, 15, 20, 25, 30, 35, 40, or at least 45 genes listed in Table 3A and/or Table 3B. The subject expression profile may include the levels of expression of at least 2, 3, 4, 5, 6, 7, 8, 9, 10, 15, 20, 25, 30, 35, 40, or at least 45 genes listed in Table 3A and/or Table 3B.

The 3004 transcripts shown in Tables 2A and 2B (supra) were identified that are differentially expressed in pediatric SLE as compared to healthy controls. A p<0.0001 with parametric or non-parametric t-test Analysis of a greater number of probe sets in the analysis confirmed expression signatures 255 of the 374 genes was identified by the present inventors (Bennett et al. (2003) J Exp Med 197:711-723). 263 of the 3004 differentially regulated transcripts are type I IFN-regulated. Transcripts were considered to be IFN-regulated if they were at least 2-fold up or down in two healthy donor PBMCs incubated with recombinant IFN-α for 6 hours compared to both the median of the healthy controls and to healthy PBMCs incubated with autologous serum. According to these criteria, 2,741 of the 3004 transcripts are not regulated by IFN. Because of the possibility that some of these 2,741 transcripts could be up- or down-regulated by type I interferon at different time-points, these probes were used to search the Gene Ontology (GO) database. No further type I interferon-regulated transcripts were identified. Table 3C shows 50 probe sets with the most significant p-values from a parametric analysis with Welch correction. It was found that, 37/50 of transcripts are type I IFN-regulated, 13 are not regulated by IFN.

Table 3C. A 50 probe set with the most significant p-values from a parametric analysis with Welch correction.

TABLE 3C

| Affymetrix ID | Common name | Genbank ID |
|---|---|---|
| 214453_s_at | IFI44 | NM_006417.1 |
| 218400_at | OAS3 | NM_006187 |
| 202086_at | MX1 | NM_002462 |
| 242625_at | cig5 | AW189843 |
| 219863_at | CEB1 | NM_016323 |
| 204994_at | MX2 | NM_002463 |
| 222154_s_at | DKFZP564A2416 | AK002064.1 |
| 213294_at | IMAGE: 4074138 | AV755522 |
| 229450_at | cig41 | AI075407 |
| 44673_at | SN | N53555 |
| 213797_at | cig5 | AI337069 |
| 204747_at | IFIT4 | NM_001549 |
| 227609_at | EPSTI1 | AA633203 |
| 202145_at | LY6E | NM_002346 |
| 202411_at | IFI27 | NM_005532 |
| 208436_s_at | IRF7 | NM_004030 |
| 204439_at | C1orf29 | NM_006820 |
| 226702_at | LOC129607 | AI742057 |
| 205483_s_at | G1P2 | NM_005101 |
| 202869_at | OAS1 | NM_016816 |
| 228607_at | IMAGE: 2304958 | AI651594 |
| 204972_at | OAS2 | NM_016817 |
| 227807_at | FLJ35310 | AI738416 |
| 214042_s_at | RPL22 | AW071997 |
| 211938_at | PRO1843 | BF247371 |
| 218660_at | DYSF | NM_003494 |
| 219352_at | FLJ20637 | NM_017912 |
| 210797_s_at | OASL | AF063612.1 |
| 242234_at | HSXIAPAF1 | AI859280 |
| 226757_at | IFIT2 | AA131041 |
| 221726_at | RPL22 | BE250348 |
| 236285_at | ESTs | AI631846 |
| 206111_at | RNASE2 | NM_002934 |
| 231798_at | NOG | AL575177 |
| 202446_s_at | PLSCR1 | AI825926 |
| 200705_s_at | EEF1B2 | NM_001959 |
| 216177_at | RPL29 | AW582267 |
| 229305_at | IMAGE: 4303245 | AA460299 |
| 205660_at | OASL | NM_003733 |
| 201786_s_at | ADAR | NM_001111 |
| 207157_s_at | GNG5 | NM_005274 |
| 228617_at | FLJ34480 | AA142842 |
| 203236_s_at | LGALS9 | NM_009587 |
| 217340_at | RP3-522P13 | AL024509 |
| 225344_at | ERAP140 | AL035689 |

TABLE 3C-continued

| Affymetrix ID | Common name | Genbank ID |
|---|---|---|
| 228152_s_at | FLJ31033 | AK023743.1 |
| 208886_at | H1F0 | BC000145.1 |
| 201154_x_at | RPL4 | NM_000968 |
| 233880_at | KIAA1554 | AL161961.1 |
| 223220_s_at | BAL | AF307338.1 |

In another aspect, the inventors have identified 6 genes listed in Table 4, in which expression is correlated directly with the SLEDAI index, which indicates the severity of SLE. The level of expression of these genes indicates the presence and severity of SLE, and can be used to monitor disease progression or remission, and the efficacy of therapy.

TABLE 4

SLE-associated human genes highly correlated with SLEDAI index

| Accession No. | Database | Gene |
|---|---|---|
| NM_019096 | GenBank | GTPBP2 |
| AK002064.1 | GenBank | DNAPTP6 |
| AF237762 | GenBank | GPR84 |
| NM_004776.1 | GenBank | B4GALT5 |
| AB045118.1 | GenBank | FRAT2 |
| L13386.1 | GenBank | PAFAH1B1 |

Thus, in one embodiment, the invention provides a method of diagnosing system lupus erythematosus (SLE), by determining whether a mammal contains one or more cells that express at least one gene selected from Table 4 to an extent at least two-fold greater than one or more controls; and diagnosing the mammal as having SLE if the mammal contains the one or more cells, or as not having SLE if the cell is not identified.

In another embodiment, the invention provides a method of determining the severity of SLE, by determining the extent to which one or more cells from a mammal suffering from SLE over-express one or more genes selected from Table 4 as compared to one or more controls; and correlating the severity of the disease with the extent of over-expression. The level of expression of 2, 3, 4 or 5 genes in Table 4 is determined. Rather than comparing the expression of the genes in Table 4 in SLE patients and controls, the levels in SLE patients can be compared to a reference profile which correlates level of expression with an index of disease severity, such as, but not limited to SLEDAI. Thus, the invention provides a method for diagnosing systemic lupus erythematosus (SLE) and/or determining the severity thereof by providing a plurality of reference expression profiles, each associated with the presence or absence of SLE, and optionally with the severity of SLE; providing a subject expression profile generated from one or more cells or other sample from a mammalian subject; and selecting the reference expression profile most similar to the subject expression profile, to thereby diagnose the presence or absence of SLE in the subject, and optionally the severity of SLE in the subject; wherein, the subject expression profile and the reference expression profiles represent the level of expression of at least 1 gene listed in Table 4. The reference expression profiles represent the levels of expression of 2, 3, 4 or 5 genes in Table 4, and/or the subject expression profile represents the levels of expression of 2, 3, 4, or 5 genes in Table 4.

The level of expression of genes in Table 4 can also be used to monitor disease progression or remission, or the efficacy of a therapeutic treatment. Thus, the invention provides a method for monitoring disease state in an adult subject having systemic lupus erythematosus, by comparing the level of expression of at least one gene selected from Table 4 in one or more cells or sample isolated from the patient at a first time point to the level of expression in one or more cells or sample isolated at a second time point; and correlating a decrease in the degree of expression of genes in Table 4 at the second time point as compared to the first time point with an improvement in the patient's disease state, and/or correlating an increase in the degree of expression of genes in Table 4 at the second time point as compared to the first time point with an increase in the severity of the disease state.

In the above methods, preferably the relative levels of expression of at least two, three, four or five of the genes listed in Table 4 is determined. By relative level is meant that the extent of expression in one or more cells of an SLE patient or possible SLE patient is compared to the level of expression in one or more controls, or is compared to a reference profile.

This invention also includes a diagnostic array that includes at least 10 polynucleotides that hybridize under stringent conditions to a different polynucleotide of Table 1A and/or Table 1B; at least 375 polynucleotides that hybridize under stringent conditions to a different nucleic acid molecule identified in Table 2A and/or Table 2B; at least 10 polynucleotides that hybridize under stringent conditions to a different polynucleotide of Table 3A and/or Table 3B; and/or at least 2 polynucleotides that hybridize under stringent conditions to a different polynucleotide of Table 4; wherein the nucleic acids may include at least 40% of the polynucleotides in the composition. Generally, the nucleic acids include at least 50%, at least 60%, at least 70%, at least 80%, at least 90% or 100% of the polynucleotides in the array.

In another aspect, the invention provides a method for detecting a systemic lupus erythematosus (SLE) profile in a suitable sample by contacting the suitable sample with the above diagnostic composition under conditions that are favorable to the recognition of one or more nucleic acids identified in Table 1A, 1B, 2A, 2B, 2C, 3A, 3B or 4, by the polynucleotides and detecting the location and identity of nucleic acids recognized by the polynucleotides, thereby detecting the presence or absence of an SLE profile.

The method may further include correlating the profile with a diagnostic and/or control profile. For example, the control diagnostic or control profile can be selected from the group of indications consisting of a normal healthy control, an influenza infection, SLE subjects with renal involvement, and SLE subjects without renal involvement. In one embodiment, the control is from the profile determined for a subject prior to therapeutic intervention. Examples of therapeutic interventions include, but are not limited to a candidate therapeutic agent, interferon alpha (IFN-α) inhibitors, corticosteroids, nonsteroidal immune suppressants, antimalarials, nonsteroidal anti-inflammatory drugs and the like. In a further embodiment, the diagnostic nucleic acids are attached to a substrate, e.g., glass, silicon or a device, e.g., a charge-coupled device. In another embodiment, the invention provides a kit including one or more arrays, and instructions for determining the identity of each polynucleotide and its location in the array.

In one embodiment, the agents are polynucleotide probes or amplification primers (e.g., polymerase chain reaction (PCR) primers) and/or detectable markers. In one aspect, the detectable markers are quantitative. Examples of detectable markers include, e.g., a radiolabel, a fluorescent dye molecule or biotin markers. This invention also includes a method of manufacture, or kit with one or more arrays described above and instructions for determining the identity of each nucleic acid and its location in the array. The methods and compositions of the invention are useful to diagnose, prognose and monitor SLE subjects, and to determine whether SLE patients are likely to develop renal involvement. In one embodiment, the control is from the profile determined for a subject prior to therapeutic intervention. Such therapeutic interventions include, but are not limited to a candidate therapeutic agent, interferon alpha (IFN-α) therapy, corticosteroids, nonsteroidal immune suppressants, antimalarials, and nonsteroidal anti-inflamatory drugs.

Further provided by this invention are nucleic acid arrays for use in the methods described herein. The nucleic acid array may include at least 10 nucleic acid molecules, wherein each of the at least 10 nucleic acid molecules has a different nucleic acid sequence, and wherein at least 25 percent of the nucleic acid molecules of the array comprise sequences that specifically hybridize to genes listed in Tables 1A, 1B, 2A, 2B, 2C, 3A, 3B or 4, alone or in combination. The nucleic acid array may include at least 20, at least 30, at least 40, at least 50, at least 60, at least 70, at least 80, at least 90, at least 100, at least 150, at least 200, at least 250, at least 300, at least 350, at least 375, or at least 400 nucleic acid molecules that specifically hybridize to genes listed in the Tables. Generally, at least 50 percent, at least 75% or 100% of the nucleic acid molecules of the array specifically hybridize to genes listed in the Tables.

Diagnostic Methods. As noted above, this invention provides various methods for the diagnosis, prognosis and disease monitoring of a subject. The methods involve determining the level of expression of at least one gene identified in the Table 1A, 1B, 2A, 2B, 2C, 3A, 3B and/or Table 4 in a subject as compared to one or more controls or reference profiles. The level of expression can be measured at the RNA or protein level. Detection can be by any appropriate method, including, e.g., detecting the quantity of mRNA transcribed from the gene or the quantity of nucleic acids derived from the mRNA transcripts. Examples of nucleic acids derived from an mRNA include a cDNA produced from the reverse transcription of the mRNA, an RNA transcribed from the cDNA, a DNA amplified from the cDNA, an RNA transcribed from the amplified cDNA, and the like. In order to detect the level of mRNA expression, the amount of the derived nucleic acid should be proportional to the amount of the mRNA transcript from which it is derived. Detection of the level of gene expression can also include detecting the quantity of the polypeptide or protein encoded by the gene. Methods of detecting polypeptides are known to those of skill in the art. In one embodiment, antibodies specific for polypeptide products of the genes in the Tables herein, or of allelic variants or homologs thereof, are used to quantitate the level of gene expression.

In one embodiment, the level of mRNA expression is detected by hybridization of the mRNA or cDNA by hybridization to a probe. In another embodiment, the probe is immobilized, e.g., on a substrate. These methods may be performed on a sample by sample basis or modified for high throughput analysis. Such methods are known to those of skill in the art. For example, the methods of detecting gene expression are disclosed at the Affymetrix.com website, relevant portions incorporated herein by reference. Additionally, databases with quantitative full or partial transcripts or protein sequences isolated from a cell sample can be searched and analyzed for the presence and amount of transcript or expressed gene product. In one aspect, the database contains at least one of the sequences shown in any one or more of Table 1A, 1B, 2A. 2B, 3A, 3B and Table 4, alone or in combination, and/or at least the sequence of an expression product of the gene.

The level of gene expression in one or more cells, tissues or extracellular samples can be determined. Cells, tissue samples and extracellular samples used for this invention encompass body fluid, solid tissue samples, tissue cultures or cells derived there from and the progeny thereof and sections or smears prepared from any of these sources or any other samples that may contain an expression product (e.g., a secreted protein) of a gene listed in the Tables herein, or an allelic variant or homolog thereof. Cells may be obtained from blood, e.g., peripheral blood mononuclear cells (PBMCs), monocytes, dendritic cells, immature neutrophils (IN) mature neutrophils (MN), granulocytes, B cells and T cells. However, any cells obtained from a patient may be used with the present invention. Levels of secreted polypeptides can be measured in order to determine whether a cell differentially expresses a gene. As a non-limiting example, secreted polypeptides can be found in blood, plasma, serum, urine, sputum and other bodily fluids.

In assaying for an alteration in mRNA level, nucleic acid in the samples can be measured in situ or in extracts, according to standard methods in the art. Methods for isolating total mRNA are known to those of skill in the art. See Chapter 3 of Laboratory Techniques in Biochemistry ad Molecular Biology: Hybridization with Nucleic Acid Probes, Theory and Nucleic Acid Preparation, Tijssen, ed. Elsevier, N.Y. (1993); Sambrook et al., Molecular Cloning: A Laboratory Manual (latest edition), Cold Spring Harbor Laboratory; and Current Protocols in Molecular Biology, Ausubel, et al., ed. Greene Publishing and Wiley-Interscience, New York (1987). For instance, mRNA can be isolated using various lytic enzymes or chemical solutions according to the procedures set forth in Sambrook, et al. (1989) supra or extracted by nucleic-acid-binding resins following the accompanying instructions provided by manufacturers. The mRNA expression level of a gene of Table 1A, 1B, 2A, 2B, 2C, 3A, 3B or 4, contained in the sample can be detected by any method, including hybridization (e.g., nucleic acid arrays, Northern blot analysis, etc.) and/or amplification procedures according to methods widely known in the art or based on the methods exemplified herein. In a preferred embodiment, the level of mRNA is detected by hybridization to a nucleic acid array. Nucleic acid arrays are commonly used to simultaneously detect and/or quantify the expression of one or a multitude of genes. Such methods are known to those of skill in the art. See U.S. Pat. Nos. 6,040,138 and 6,391,550, the contents of which are incorporated by reference. For example, the RNA in or from a sample can be detected directly or after amplification. Any suitable method of amplification may be used. In one embodiment, cDNA is reversed transcribed from RNA, and then optionally amplified, for example, by PCR.

Nucleic acid molecules having at least 10 nucleotides and exhibiting sequence complementarity or homology to at least one polynucleotide encoding a peptide identified in Table 1A, 1B, 2A, 2B, 2C, 3A, 3B or 4, may be used as hybridization and amplification probes. It is known in the art that a "perfectly matched" probe is not needed for a specific hybridization or amplification. Minor changes in probe sequence achieved by substitution, deletion or insertion of a small number of bases do not affect the hybridization specificity. In general, as much as 20% base-pair mismatch (when optimally aligned) can be tolerated. A probe useful for detecting mRNA is at least about 80% identical to the homologous region of comparable size contained in the genes or polynucleotides encoding the peptides identified in Table 1A, 1B, 2A, 2B, 2C, 3A, 3B or 4, and to allelic variants and homologs thereof. In one aspect, the probe is 85% identical to the corresponding polynucleotide sequence after alignment of the homologous region or, alternatively, it exhibits 90% identity. These probes can be used in nucleic acid arrays, as amplification primers, in radioassays (e.g., Southern and Northern blot analysis), etc., to detect, prognose, diagnose or monitor various conditions resulting from differential expression of a polynucleotide of interest, e.g., SLE. The total size of fragment, as well as the size of the complementary stretches, will depend on the intended use or application of the particular nucleic acid segment. Smaller fragments derived from the known sequences will generally find use in hybridization embodiments, wherein the length of the complementary region may be varied, such as between about 10 and about 100 nucleotides or even full-length according to the complementary sequences one wishes to detect.

In one aspect, nucleotide probes having complementary sequences over stretches greater than about 10 nucleotides in length are used, so as to increase stability and selectivity of the hybrid and, thereby, improving the specificity of particular hybrid molecules obtained. Alternatively, the user can design nucleic acid molecules having gene-complementary stretches of more than about 25 or alternatively more than about 50 nucleotides in length or even longer where desired. Such fragments may be readily prepared by, for example, directly synthesizing the fragment chemically, by application of nucleic acid reproduction technology, such as the PCR technology with two or more priming oligonucleotides as described in U.S. Pat. No. 4,603,102 (relevant portions incorporated herein by reference) or by introducing selected sequences into recombinant vectors for recombinant production. In one aspect, a probe is about 50 to about 75, nucleotides or, alternatively, about 50 to about 100 nucleotides in length. These probes can be designed from the sequence of full length genes.

In certain embodiments, it will be advantageous to employ nucleic acid sequences as described herein in combination with an appropriate label for detecting hybridization and/or complementary sequences. A wide variety of appropriate labels, markers and/or reporters are known in the art, including fluorescent, radioactive, enzymatic or other ligands, such as avidin/biotin, which are capable of giving a detectable signal. One can employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a signal that is visible to the human eye or spectrophotometrically, to identify specific hybridization with complementary nucleic acid-containing samples. In one embodiment of the invention, a detectable label is incorporated into a cDNA copy of an mRNA, and then the labeled cDNA is hybridized to an immobilized probe, e.g., to a probe immobilized on a substrate that is formed as a microarray.

Hybridization reactions can be performed under conditions of different "stringency". Relevant conditions include temperature, ionic strength, time of incubation, the presence of additional solutes in the reaction mixture such as formamide and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, Sambrook, et al. (1989) supra.

The nucleotide probes of the present invention can also be used as primers and detection of genes or gene transcripts that are differentially expressed in certain body tissues. Additionally, a primer useful for detecting the aforementioned differentially expressed mRNA is at least about 80% identical to the homologous region of comparable size contained in the previously identified sequences encoding the peptides identified in Table 1A, 1B, 2A, 2B, 2C, 3A, 3B or 4. For the purpose of this invention, "amplification" refers to any method employing a primer-dependent polymerase capable of replicating a target sequence with reasonable fidelity. Amplification may be carried out by natural or recombinant DNA-polymerases such as, but not limited to, T7 DNA polymerase, Klenow fragment of *E. coli* DNA polymerase and reverse transcriptase.

A known amplification method is PCR, MacPherson et al., PCR: A PRACTICAL APPROACH, (IRL Press at Oxford University Press (1991)). However, PCR conditions used for each application reaction are empirically determined. A number of parameters influence the success of a reaction. Among them are annealing temperature and time, extension time, Mg2+ ATP concentration, pH and the relative concentration of primers, templates and deoxyribonucleotides.

After amplification, the resulting DNA fragments can be detected by agarose gel electrophoresis followed by visualization with ethidium bromide staining and ultraviolet illumination. A specific amplification of differentially expressed genes of interest can be verified by demonstrating that the amplified DNA fragment has the predicted size, exhibits the predicated restriction digestion pattern and/or hybridizes to the correct cloned DNA sequence.

The probes also can be attached to a solid support for use in high throughput screening assays using methods known in the art. PCT WO 97/10365 and U.S. Pat. Nos. 5,405,783; 5,412,087 and 5,445,934; for example, disclose the construction of high density oligonucleotide chips which can contain one or more of the sequences disclosed herein. Using the methods disclosed in U.S. Pat. Nos. 5,405,783; 5,412,087 and 5,445,934; the probes of this invention are synthesized on a derivatized glass surface. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

The expression level of a gene can also be determined through exposure of a nucleic acid sample to a probe-modified chip. Extracted nucleic acid is labeled, for example, with a fluorescent tag, during an amplification step. Hybridization of the labeled sample is performed at an appropriate stringency level. The degree of probe-nucleic acid hybridization is quantitatively measured using a detection device, such as a confocal microscope. See, U.S. Pat. Nos. 5,578,832 and 5,631,734. The obtained measurement is directly correlated with gene expression level.

The probes and high density oligonucleotide probe arrays also provide an effective way to monitor expression of a gene or protein identified in Table 1A, 1B, 2A, 2B, 2C, 3A, 3B or 4. They are also useful to screen for compositions that up-regulate or down-regulate the expression of one or more of these genes and their expression products. In another embodiment, the methods of this invention are used to monitor expression of at least one gene of Table 1A, 1B, 2A, 2B, 2C, 3A, 3B or 4, or an allelic variant or homolog thereof which specifically hybridizes to the probes of this invention in response to defined stimuli, such as an exposure of a cell or subject to a drug.

In another embodiment, the hybridized nucleic acids are detected using one or more labels attached to the sample nucleic acids. The labels may be incorporated by any of a number of methods known to those of skill in the art. In one embodiment, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g., fluorescein-labeled UTP, GTP, ATP and/or CTP) incorporates a label into the transcribed nucleic acids. Methods for detecting amplification products, such as PCR products are known to those of skill in the art. Alternatively, a label may be added directly to the original nucleic acid sample (e.g., mRNA, polyA, mRNA, cDNA, etc.) or to the amplification product after the amplification is completed. Methods for attaching labels to nucleic acids are known to those of skill in the art and include, for example nick translation or end-labeling (e.g., with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical detection methods. Useful labels in the present invention include biotin for staining with labeled streptavidin conjugate, magnetic beads (e.g., Dynabeads™), fluorescent dyes (e.g., fluorescein, Texas red, rhodamine, green fluorescent protein and the like), radiolabels (e.g., 3H, 125I, 35S, 14C or 32P) enzymes (e.g., horseradish peroxidase, alkaline phosphatase and others commonly used in an ELISA) and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, relevant portions incorporated herein by reference. Methods of detecting such labels are known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate and colorimetric labels are detected by simply visualizing the colored label.

As described in more detail in WO 97/10365 (relevant portions incorporated herein by reference), the label may be added to the target (sample) nucleic acid(s) prior to or after the hybridization. These are detectable labels that are directly attached to or incorporated into the target (sample) nucleic acid prior to hybridization. In contrast, "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids; see, Laboratory Techniques In Biochemistry And Molecular Biology, Vol. 24: Hybridization with Nucleic Acid Probes, P. Tijssen, ed. Elsevier, N.Y. (1993). The nucleic acid sample also may be modified prior to hybridization to the high density probe array in order to reduce sample complexity thereby decreasing background signal and improving sensitivity of the measurement using methods known in the art, e.g., the methods disclosed in WO 97/10365.

Results from the chip assay are typically analyzed using a computer software program which are described in the literature (see, for example, EP 0717 113 A2 and WO 95/20681) or commercially available from a vendor such as Affymetrix (Santa Clara, Calif.). See the Affymetrix web site (www.affymetrix.com), which contains detailed protocols, as well as links to the sequences of the probes contained in the HG-U133A and HG-U133B arrays used in the examples. The hybridization data can be read into the program, which calculates the expression level of the targeted gene(s) i.e., the genes identified in Table 1A, 1B, 2A, 2B, 2C, 3A, 3B or 4. This figure is compared against existing data sets of gene expression levels for SLE patients, and healthy individuals, fibromyalgia patients, flu patients, SLE patients known to have later developed renal involvement, and the like. A correlation between the obtained data and that of a set of SLE patients with known outcomes indicates SLE in a subject patient, the likelihood that that patient will develop renal disease and the efficacy of therapeutic intervention.

Alternatively, gene expression profiles can be determined by sequencing mRNA in a sample. Briefly, multiple RNAs can be isolated from cell or tissue samples using methods known in the art and described for example, in Sambrook et al. (1989) supra. Optionally, the gene transcripts can be converted to cDNA. A sampling of the gene transcripts are subjected to sequence-specific analysis and quantified. These gene transcript sequence abundances are compared against reference database sequence abundances including normal data sets for SLE patients and healthy patients. The likelihood that an SLE patient will develop renal disease can be predicted by correlation with the over expression and/or under expression of the transcripts identified herein.

Differential expression can also be determined by examining the protein product. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays and PAGE-SDS. One method to determine protein level involves (a) providing a biological sample containing polypeptides; and (b) measuring the amount of any immunospecific binding that occurs between an antibody reactive to the expression product of a gene of interest and a component in the sample, in which the amount of immunospecific binding indicates the level of the expressed proteins.

Antibodies that specifically recognize and bind to the protein products of these genes are required for these immunoassays. These may be purchased from commercial vendors or generated and screened using methods well known in the art. See, Harlow and Lane (1988) supra and Sambrook et al. (1989) supra. Alternatively, polyclonal or monoclonal antibodies that specifically recognize and bind the protein product of a gene of interest can be made and isolated using known methods.

In diagnosing abnormalities or pathologies characterized by a differential expression of genes, one typically conducts a comparative analysis of the subject and appropriate controls. Preferably, a diagnostic test includes a control sample derived from a subject (hereinafter "positive control"), that exhibits the predicted change in expression of a gene of interest and clinical characteristics of SLE. Alternatively, a diagnosis also includes a control sample derived from a subject (hereinafter "negative control"), that lacks the clinical characteristics of interest and whose expression level of the gene at question is within a normal range. A positive correlation between the subject and the positive control with respect to the identified alterations indicates the likelihood of the presence of or a predisposition to the abnormality of interest. A lack of correlation between the subject and the negative control can confirm the diagnosis.

Screening Assays. The present invention also provides a screen for identifying leads, drugs, therapeutic biologics and methods for treating SLE and related pathologies. In one aspect, the screen identifies lead compounds or biological agents which are useful for the treatment of an abnormality such as SLE and which is characterized by differential expression of a polynucleotide of Table 1A, 1B, 2A, 2B, 2C, 3A, 3B or 4. Thus, one way to practice the method in vitro, suitable cell cultures or tissue cultures are first provided. The cell can be a cultured cell or a genetically modified cell which differentially expresses at least one gene identified in Table 1A, 1B, 2A, 2B, 2C, 3A, 3B or 4. Alternatively, the cells can be from one or more subjects. Preferably the cell is a PBMC. It also is desirable to maintain an additional separate cell culture; one which does not receive the agent being tested as a control.

As is apparent to one of skill in the art, the method can be modified for high throughput analysis and suitable cells may be cultured in microtiter plates and several agents may be assayed at the same time by noting genotypic changes, phenotypic changes and/or cell death. As is apparent to those skilled in the art, an "effective" amount must be added which can be empirically determined.

The screen involves contacting the agent with a test cell characterized by differential expression of gene of interest and then assaying the cell for the level of expression. In some aspects, it may be necessary to determine the level of gene expression prior to the assay. This provides a base line to compare expression after administration of the agent to the cell culture. In another embodiment, the test cell is a cultured cell from an established cell line that differentially expresses a gene of interest. An agent is a possible therapeutic agent if gene expression is returned (reduced or increased) to a level that is present in a cell in a normal or healthy state, or the cell selectively dies, or exhibits reduced rate of growth. In yet another aspect, the test cell or tissue sample is isolated from the subject to be treated and one or more potential agents are screened to determine the optimal therapeutic and/or course of treatment for that individual patient.

For the purposes of this invention, an "agent" is intended to include, but not be limited to a biological or chemical compound such as a simple or complex organic or inorganic molecule, a peptide, a protein, antibody, an oligonucleotide, and the like. A vast array of compounds can be synthesized, for example oligomers, such as oligopeptides and oligonucleotides and synthetic organic compounds based on various core structures; these compounds are also included in the term "agent". In addition, various natural sources can provide compounds for screening, such as plant or animal extracts and the like. It should be understood, although not always explicitly stated that the agent is used alone or in combination with another agent, having the same or different biological activity as the agents identified by the inventive screen. The agents and methods also are intended to be combined with other therapies.

When the agent is a nucleic acid, it can be added to the cell cultures by methods known in the art, which includes, but is not limited to calcium phosphate precipitation, microinjection or electroporation. Alternatively or additionally, the nucleic acid can be incorporated into an expression or insertion vector for incorporation into the cells. Vectors that contain both a promoter and a cloning site into which a polynucleotide can be operatively linked are well known in the art and briefly described infra.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other methods are well-known and available in the art.

One can determine if the object of the method has been achieved by a return to "normal" gene expression levels. Kits containing the agents and instructions necessary to perform the screen and in vitro method as described herein also are claimed. When the subject is an animal such as a rat or mouse, the method provides a convenient animal model system which can be used prior to clinical testing of the therapeutic agent or alternatively, for lead optimization. In this system, a candidate agent is a potential drug if gene expression is returned to a normal level or if symptoms associated or correlated to the presence of cells containing differential expression of a gene of interest are ameliorated, each as compared to untreated, animal suffering from SLE or an associated condition. It also can be useful to have a separate negative control group of cells or animals which are healthy and not treated, which provides a basis for comparison.

The following materials and methods are intended to illustrate, but not limit this invention and to illustrate how to make and use the inventions described above.

Messenger RNA Samples. After informed consent, blood was obtained from 53 pediatric patients who satisfied diagnostic criteria of the American College of Rheumatology (ACR) for SLE (pedSLE) and 11 adult SLE patients (ASLE), as well as 10 adult fibromyalgia patients (AFIB) were recruited from rheumatology clinics. All the clinical and laboratory data pertaining to these patients were thoroughly accrued. The clinicians evaluated all the entry points from pediatric and adult patients to determine the disease activity index (SLEDAI) and determined the day of the blood draw. The controls were 12 pediatric subjects (children visiting the clinic for reasons other than autoimmunity or infectious disease) and 9 healthy adults. Blood leukocytes were isolated on Ficoll gradient and immediately processed for RNA extraction using the RNeasy™ kit (QIAGEN) according to the manufacturer's instructions.

Flow Cytometry. A fraction of patients cells was retained for flow cytometry analysis including the determination of T cells, B cells, plasmablasts (CD20-CD19 low CD38 high), monocytes as described by Arce et al. (2001) J Immunol 167:2361-2369, and DCs (DC kit; Beckton Dickinson). Leukocytes from healthy adults were cultured in RPMI enriched with 5% fetal calf serum for 6 hour with or without 1000 U/ml Interferon a2b (Intron A; Schering-Plough).

Staining of PBMCs and Sorted Granular Cells: PBMCs were stained with anti-CD14 PE (BD Biosciences) and sorted (FACS-Vantage™; Becton Dickinson) based on granularity (high forward side scatter/side light scatter) and lack of CD14 expression. Both unsorted PBMCs and sorted cells were allowed to adhere for 1 hour on slides previously coated with 0.1 mg/ml of poly-L-lysine (Sigma-Aldrich) for 1 hour at room temperature and fixed with 4% paraformaldehyde. After quenching with PBS-glycine (50 mM), cells were permeabilized with Triton X-100 (0.1%) for 10 minutes. They were subsequently washed with PBS-saponin (0.2%) and quenched with PBS-BSA-gelatin fish before staining with FITC-conjugated mouse anti-human myleoperoxidase (DakoCytomation). Cytospins of unsorted and sorted cells were stained with Giemsa or treated with p-phenylenediamine and catechol to detect cytoplasmic myeloperoxidase according to the method described by Hanker et al. (1978 Histochemistry 58:241-252). Fluorescence labeled cells were mounted in fluoromount mounting medium (Southern Biotechnology Associates, Inc.) for confocal microscopy. All micrographs were recorded using a confocal microscopy equipped with three Ar488, Kr568 and HeNe633 lasers (TCS-SP; Leica) as well as spectrophotometers using the objectives 63× or 100× PL APO with zoom 2.

Microarray Procedures. Global gene expression analysis was carried out using the Affymetrix HG-U133A and HG-U133B GeneChips (Affymetrix, Santa Clara, Calif.). The HG-U133 set contains almost 45,000 probe sets representing more than 39,000 transcripts derived from approximately 33,000 well substantiated human genes. The oligonucleotide probes used in the HG-U133 microarray are 25 nucleotides in length and hybridize to antisense of the transcript (e.g., the probes hybridize to a cDNA reverse transcribed from mRNA). 5 μg of total RNA extracted from samples was used to prepare anti-sense biotinylated RNA. Briefly, single-stranded complementary DNA (cDNA) and double-stranded cDNA were synthesized as described in U.S. patent publication number US 2004/0033498 (see paragraph 0045). In vitro transcription was carried out using biotinylated ribonucleotides (Enzo, Farmingdale, N.Y.). Biotinylated RNA was hybridized to the GeneChips at 45° C. for 16 hours. Staining, washing and scanning procedures were carried out according to Affymetrix protocols. Scanned GeneChips were individually inspected for abnormalities irregularities.

Data Analysis. Intensity values were scaled to 500 using global scaling in MAS 5.0 and data were exported in MS Excel for import into GeneSpring software (Silicon Genetics) for gene expression analyses. No "per chip" normalization was applied in GeneSpring as global scaling had already been applied in MAS 5.0. Global scaling adjusts for chip-to chip variations in hybridization intensities. For each probe set, normalization was carried out to either the median intensity of each probe set across all samples or to the median of a set of control samples depending on the purpose of the analysis. Subsequent analyses were performed from 22,664 probe sets on the microarrays that had a control signal of 50 or above (above the background intensity) and that were identified as "present" according to MAS 5.0 in 10 (15%) of 65 samples. Statistical comparisons were performed in GeneSpring using both parametric (Welch's approximate t-test) and non-parametric (Mann-Whitney U-test) methods. Unsupervised hierarchical clustering was performed using Standard correlation, Pearson correlation or Euclidian distance.

The Class Predictor algorithm in GeneSpring and Prediction Analysis of Microarrays (PAM) were used to find genes whose behavior is related to a given parameter. The class predictor algorithm is a supervised learning algorithm based on Fisher's exact test combined with k-nearest neighbors clustering method. PAM uses a "nearest shrunken centroid" method which is an enhancement of the simple nearest prototype (centroid) classifier.

Identification of genes associated with the likelihood of progression to renal disease. Two groups of patients were compared: Ten patients had renal disease at the time of blood draw (NN) and no renal involvement to date; Seven patients had no renal disease at the time of blood draw but have developed renal disease since (NY). To identify transcripts that showed altered transcription between those two groups parametric and non-parametric analyses were carried out as described previously. 345 transcripts were differentially expressed between the two groups. 185 transcripts were increased and 160 decreased in patients who developed nephritis compared to those who did not.

A supervised analysis using Prediction Analysis of Microarrays (PAM) was also used to classify and predict the diagnostic category (either NN or NY) for the patient samples based on gene expression profiles. We started from 345 probe sets that were differentially expressed between SLE patients that have no renal disease to date (NN) and those that developed renal disease some time after the date of blood draw (NY), PAM identified a minimum of 99 probe sets that distinguished between the two groups with 100% accuracy. A minimum of 37 probe sets predicted those patients who have not developed renal disease with 100% accuracy as well as those patients who have developed renal disease with 86% accuracy.

The development of renal disease was diagnosed by increase levels of creatine and protein in the urine. Most of these patients had type III or type IV nephritis. Type II=4; Type III=8; Type III/V=2; Type IV=7; Type V=3. Genes which are down-regulated in patients likely to develop renal disease are shown in Table 1A, supra. Genes which are up-regulated in patients likely to develop renal disease are shown in Table 1B, supra.

All Adult SLE Patients Tested Display Similar IFN and Granulopoiesis Signatures to Pediatric SLE Patients. Studies using blood from adult SLE patients have reported a type I IFN signature only in approximately 50% of patients. Differences in gene expression in our cohort of adult SLE patients compared to the pediatric patients were also examined. A set of 21 adult patients who were positive for antinuclear-antibodies (ANA) were collected. Eleven patients were diagnosed as having adult SLE (ASLE) and 10 Fibromyalgia (AFIB).

Unsupervised hierarchical clustering of both probe sets and patient samples using 3004 genes differentially expressed in pediatric SLE patients was determined (not shown). Apart from two pedSLE outliers that branch off first, the patients form two clusters based on molecular signatures: clusters A and B. Cluster B contains 28 patients (22 pedSLE and 6 ASLE), the majority of whom have more active disease: 20/28 (71%) have a SLEDAI≧10. Cluster A contains a mixture of healthy, AFIB and SLE patients. Cluster A separates into two sub-clusters, Clusters A1 and A2. Cluster A1 contains all the healthy patients plus 8/10 AFIB patients, as well as two inactive pedSLE. Of the two pediatric SLE patients that fell within a healthy/AFIB cluster, one has been in complete remission for up to at least 5 years (OS), the other (SLE 62) was very inactive, and has a SLEDAI of 4. Cluster A2 contains 27 pediatric SLE patients and 5 ASLE patients, 23 (68%) of whom have a SLEDAI of <8. It was found that, expression of PLSCR1, GTPBP2, PCTAIRE2BP, DNAPTP6, GPR84, B4GALT5, FRAT2 and PAFAH1B in adult SLE do NOT correlate with SLEDAI in those patients.

Figure 2:
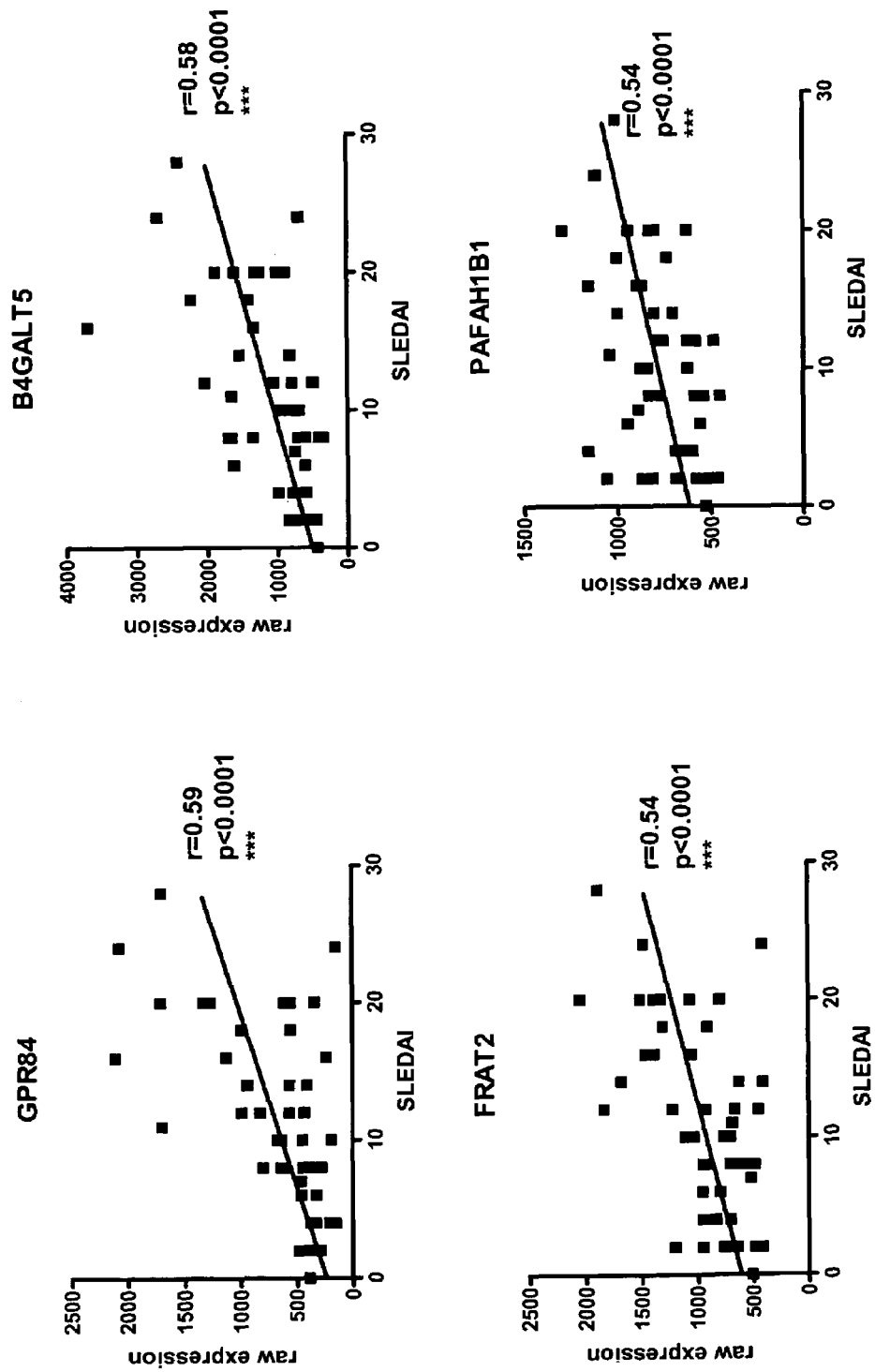
FIG. 2 shows the correlation between SLEDAI index and the level of expression of four non IFN-regulated genes newly associated with SLE: GPR84, B4GALT5, FRAT2 and PAFAH1B.

When only the type I IFN-regulated probes were used for clustering, two pedSLE outliers branch off first, then 2 major clusters were generated with all healthy controls plus all AFIB falling into cluster C and all ASLE plus 47/53 pediatric SLE falling into cluster D (data not shown). All adult SLE patients as well as 50/53 (94%) of pediatric SLE display a gene expression pattern consistent with exposure of PBMCs to type I interferon, whereas none of the adult fibromyalgia (AFIB) patients show an interferon signature. FIG. 1 shows the direct correlation between levels of expression of the IFN-regulated genes GTPBP2 and DNAPTP6 with respect to SLEDAI score in pediatric SLE patients. FIG. 2 shows the direct correlation between levels of expression of the non-IFN-regulated genes GPR84, B4GALT5, FRAT2 and PAFAH1B with respect to SLEDAI score in pediatric SLE patients. The genes in FIGS. 1 and 2 are listed in Table 4, supra.

Forty-Five Genes Discriminate SLE From Influenza And Healthy. As viral infection induces an interferon response similar to SLE, the minimum set of transcripts that discriminate SLE from flu as well as from healthy was examined. A supervised learning algorithm based on Fisher's exact test combined with k-nearest neighbors clustering method was applied to identify the minimum number of transcripts that discriminate SLE from flu and healthy both by supervised learning and hierarchical clustering. Tables 3A and 3B, supra, list the identity of 45 transcripts that discriminate SLE from flu and healthy samples. Genes listed in Table 3A are down-regulated in SLE patients, while genes listed in Table 3B are up-regulated in SLE patients. Patient samples separate into two major clusters: cluster M and cluster N (not shown). Using the present invention it was found that 53/53 (100%) of SLE patients fall into cluster N, while all health and 14/15 flu patients segregate into cluster M. Only one of the flu patient's samples (INF095) clustered with SLE patient samples in cluster N.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of diagnosing pediatric systemic U pus erythematosus in a pediatric individual comprising assaying a blood sample from the pediatric individual for an increase in the mRNA level of each of the genes GTPBP2, PCTAIRE2BP, DNAPTP6, GPR84, B4GALT5, FRAT2 and PAFAH1B, wherein the increase in the mRNA level of each of the genes indicates that the pediatric individual has systemic lupus erythematosus (SLE) and wherein the mRNA level is increased relative to the mRNA level in a normal control.

2. The method of claim 1, wherein the sample comprises cells obtained from the blood.

3. The method of claim 1, wherein the increase is at least two fold relative to a normal pediatric control.

4. The method of claim 1, wherein the normal control comprise normal pediatric healthy individuals.

5. A method for diagnosing systemic lupus erythematosus (SLE) in a pediatric human individual comprising the steps of:
   obtaining a peripheral blood mononuclear cell (PBMC) sample from the pediatric human individual; and
   assaying the sample for an increase in the mRNA level of GTPBP2, PCTAIRE2BP, DNAPTP6, GPR84, B4GALT5, FRAT2 and PAFAH1B relative to a PBMC normal control, wherein the increase in the mRNA level of GTPBP2, PCTAIRE2BP, DNAPTP6, GPR84, B4GALT5, FRAT2 and PAFAH1B indicates that the pediatric human individual has systemic lupus erythematosus.

6. The method of claim 5, wherein the increase in the mRNA level of GTPBP2, PCTAIRE2BP, DNAPTP6, GPR84, B4GALT5, FRAT2 and PAFAH1B is at least two fold relative to the mRNA level in a PBMC normal pediatric control.

7. The method of claim 5, wherein the PBMC normal control comprise normal pediatric healthy individuals.

8. A method of identifying a pediatric human individual at risk for systemic lupus erythematosus comprising the steps of:
   obtaining a peripheral blood mononuclear cell (PBMC) sample from the pediatric human individual; and
   assaying the sample for an increase in the mRNA level of GTPBP2, PCTAIRE2BP, DNAPTP6, GPR84, B4GALT5, FRAT2 and PAFAH1B relative to a PBMC normal control, wherein said increase in the mRNA level of GTPBP2, PCTAIRE2BP, DNAPTP6, GPR84, B4GALT5, FRAT2 and PAFAH1B indicates that the pediatric individual is at risk for systemic lupus erythematosus.

9. The method of claim 8, wherein the increase in the mRNA level of GTPBP2, PCTAIRE2BP, DNAPTP6, GPR84, B4GALT5, FRAT2 and PAFAH1B is at least two fold relative to the mRNA level in a PBMC normal control.

10. The method of claim 8, wherein the peripheral blood mononuclear cell normal control comprise mRNA level of normal pediatric healthy individuals.

11. A method for diagnosing systemic lupus erythematosus (SLE) in a pediatric human individual comprising the steps of:
   obtaining mRNA from a peripheral blood mononuclear cell (PBMC) sample from the pediatric human individual;
   hybridizing the mRNA from the sample with a microarray; and
   detecting if there is an increase in the mRNA level, relative to a normal control, of each of the genes of GTPBP2, PCTAIRE2BP, DNAPTP6, GPR84, B4GALT5, FRAT2 and PAFAH1B, wherein an increase in the mRNA level of each of the genes signifies the presence of SLE.

12. The method of claim 11, wherein the increase is at least two fold relative to the normal control.

13. The method of claim 11, wherein the normal control comprise mRNA level of normal pediatric healthy individuals.

14. The method of claim 11, further comprising obtaining the peripheral blood mononuclear cell sample from the pediatric human individual prior to administering a therapeutic intervention.

15. The method of claim 14, wherein the therapeutic intervention comprise a candidate therapeutic agent selected from interferon alpha inhibitors, corticosteroids, nonsteroidal immune suppressants, antimalarials, and nonsteroidal anti-inflammatory drugs.

* * * * *

UNITED STATES PATENT AND TRADEMARK OFFICE
CERTIFICATE OF CORRECTION

PATENT NO. : 7,608,395 B2  Page 1 of 1
APPLICATION NO. : 11/228586
DATED : October 27, 2009
INVENTOR(S) : Pascual et al.

It is certified that error appears in the above-identified patent and that said Letters Patent is hereby corrected as shown below:

Column 123, line 15
Replace "pediatric systemic U pus erythe-" with --pediatric systemic lupus erythe- --

Signed and Sealed this

Ninth Day of February, 2010

David J. Kappos
*Director of the United States Patent and Trademark Office*